(12) United States Patent
McKerracher et al.

(10) Patent No.: US 7,795,218 B2
(45) Date of Patent: Sep. 14, 2010

(54) ADP-RIBOSYL TRANSFERASE FUSION VARIANT PROTEINS

(75) Inventors: Lisa McKerracher, Montreal (CA); Jon Scott Munzer, Pointe-Claire (CA)

(73) Assignee: Bioaxone Therapeutique Inc., Montréal (CA)

( * ) Notice: Subject to any disclaimer, the term of this patent is extended or adjusted under 35 U.S.C. 154(b) by 178 days.

(21) Appl. No.: 11/808,773

(22) Filed: Jun. 12, 2007

(65) Prior Publication Data

US 2008/0269120 A1 Oct. 30, 2008

Related U.S. Application Data

(63) Continuation-in-part of application No. 11/643,940, filed on Dec. 22, 2006, now abandoned, which is a continuation-in-part of application No. 10/902,878, filed on Aug. 2, 2004, now abandoned, and a continuation-in-part of application No. 10/902,959, filed on Aug. 2, 2004, now Pat. No. 7,442,686.

(60) Provisional application No. 60/506,162, filed on Sep. 29, 2003.

(51) Int. Cl.
| | |
|---|---|
| A61K 38/00 | (2006.01) |
| C07K 17/00 | (2006.01) |
| C07K 14/00 | (2006.01) |
| C08H 1/00 | (2006.01) |
| C07H 21/02 | (2006.01) |

(52) U.S. Cl. .................. 514/12; 530/325; 530/350; 530/402; 530/345; 514/13; 536/23.1

(58) Field of Classification Search .................. None
See application file for complete search history.

(56) References Cited

U.S. PATENT DOCUMENTS

| 5,194,596 A | * | 3/1993 | Tischer et al. ............... 530/399 |
| 5,350,836 A | * | 9/1994 | Kopchick et al. ........... 530/399 |
| 2005/0059595 A1 | | 3/2005 | Lasko et al. |

FOREIGN PATENT DOCUMENTS

| CA | 2300878 | 2/1999 |
| CA | 2304981 | 5/1999 |
| WO | WO 2005/030248 | 7/2005 |

OTHER PUBLICATIONS

Benjamin et al., (1998, Development 125:1591-1598).*
Vukicevic et al. (1996, PNAS USA 93:9021-9026).*
Massague (1987, Cell 49:437-8).*
Pilbeam et al., (1993, Bone 14:717-720).*
Skolnick et al. (2000, Trends in Biotech. 18:34-39).*
Bork (2000, Genome Research 10:398-400).*
Doerks et al. (1998, Trends in Genetics 14:248-250).*
Smith et al. (1997, Nature Biotechnology 15:1222-1223).*
Brenner (1999, Trends in Genetics 15:132-133).*
Bork et al. (1996, Trends in Genetics 12:425-427).*
U.S. Appl. No. 11/643,940.
Int.Search Report, Jul. 3, 2008.

* cited by examiner

*Primary Examiner*—Cherie M Woodward
(74) *Attorney, Agent, or Firm*—Ogilvy Renault LLP

(57) ABSTRACT

The present invention relates to novel chimeric C3-like Rho antagonists and their use for promoting repair and neuron survival in injured mammalian central and peripheral nervous system and for treating or preventing cancer.

29 Claims, 40 Drawing Sheets

```
                                                    ↓
WT C3       MKGLRKSILC LVLSAGVIAP VTSGMIQSPQ KCYAYSINQK AYS NTYQEFTNID  53
SEQ ID NO: 44                     MSRVALQACN AYSINQK AYS NTYQEFTNID    30
SEQ ID NO: 10                                MS AYS NTYQEFTNID         15
```
Fig. 2A
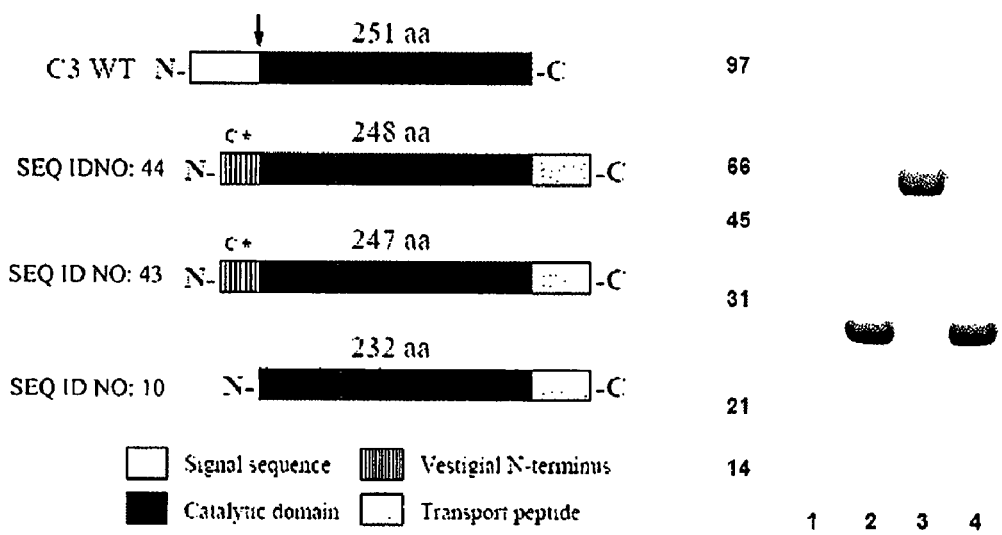
Fig. 2B
Fig. 2C
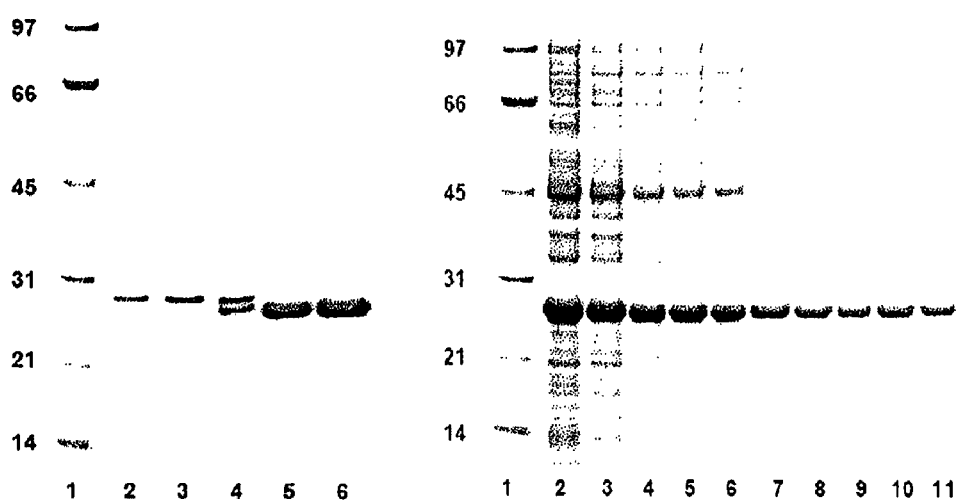
Fig. 2D
Fig. 2E

| | | |
|---|---|---|
| SEQ ID NO: 13 | MSAYSNTYQE FTNIDQAKAW GNAQYKKYGL SKSEKEAIVS YTKSASEING KLRQNKGVIN | 60 |
| SEQ ID NO: 14 | MSAYSNTYQE FTNIDQAKAW GNAQYKKYGL SKSEKEAIVS YTKSASEING KLRQNKGVIN | 60 |
| SEQ ID NO: 15 | MSAYSNTYQE FTNIDQAKAW GNAQYKKYGL SKSEKEAIVS YTKSASEING KLRQNKGVIN | 60 |
| SEQ ID NO: 16 | MSAYSNTYQE FTNIDQAKAW GNAQYKKYGL SKSEKEAIVS YTKSASEING KLRQNKGVIN | 60 |
| SEQ ID NO: 17 | MSAYSNTYQE FTNIDQAKAW GNAQYKKYGL SKSEKEAIVS YTKSASEING KLRQNKGVIN | 60 |
| SEQ ID NO: 18 | MSAYSNTYQE FTNIDQAKAW GNAQYKKYGL SKSEKEAIVS YTKSASEING KLRQNKGVIN<br>GFPSNLIKQV ELLDKSFNKM KTPENIMLFR GDDPAYLGTE FQNTLLNSNG TINKTAFEKA | 60<br>120 |
| SEQ ID NO: 19 | MSAYSNTYQE FTNIDQAKAW GNAQYKKYGL SKSEKEAIVS YTKSASEING KLRQNKGVIN<br>GFPSNLIKQV ELLDKSFNKM KTPENIMLFR GDDPAYLGTE FQNTLLNSNG TINKTAFEKA | 60<br>120 |
| SEQ ID NO: 20 | RHSTYHIDDM RLSSDGKQII ITATMMGTAI NPKEFVMNPA NAQGRHTPGT RL | 232 |
| SEQ ID NO: 21 | RHSTYHIDDM RLSSDGKQII ITATMMGTAI NPKEFVMNPA NAQGRHTPGT RL | 232 |
| SEQ ID NO: 22 | RHSTYHIDDM RLSSDGKQII ITATMMGTAI NPKEFVMNPA NAQGRHTPGT RL | 232 |

Fig. 3

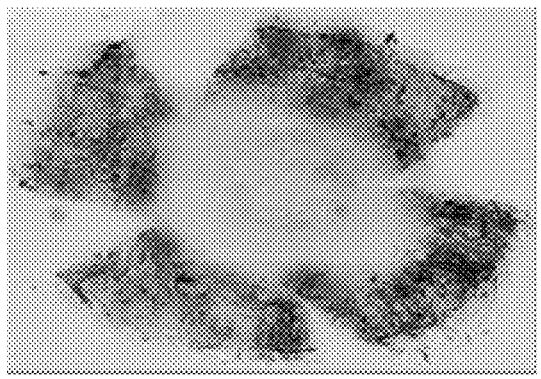
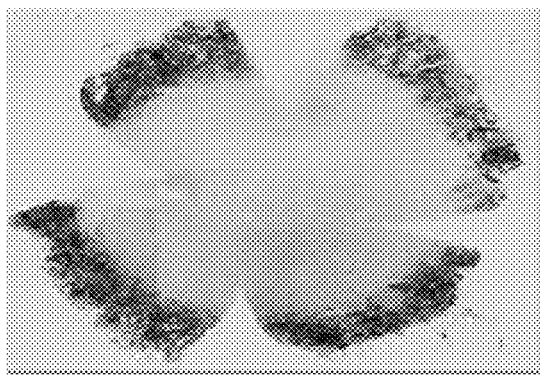
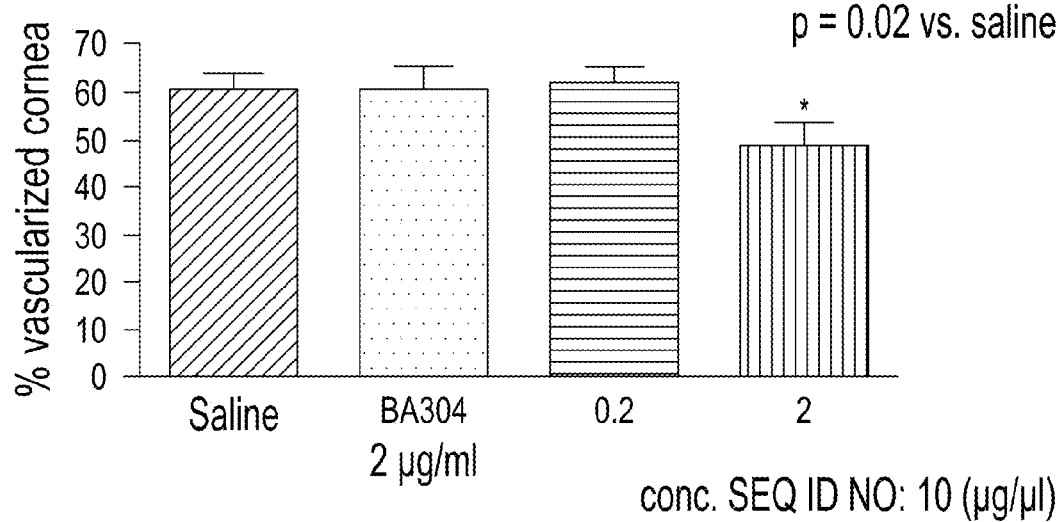
Fig. 11

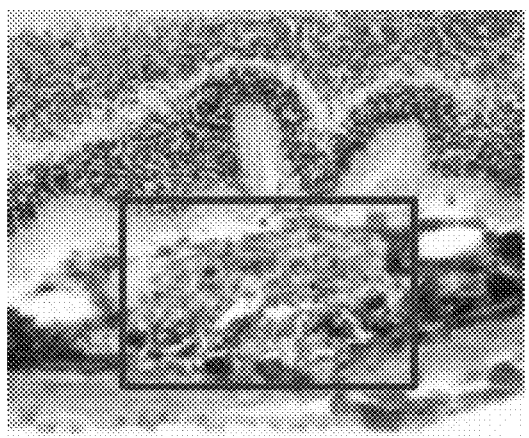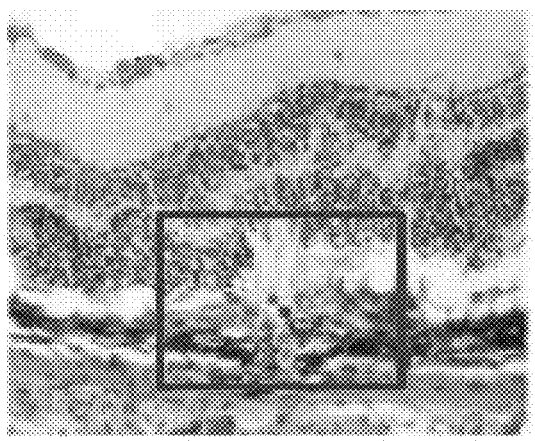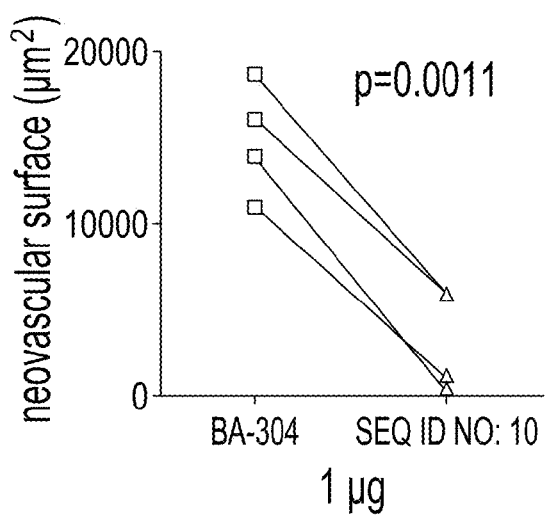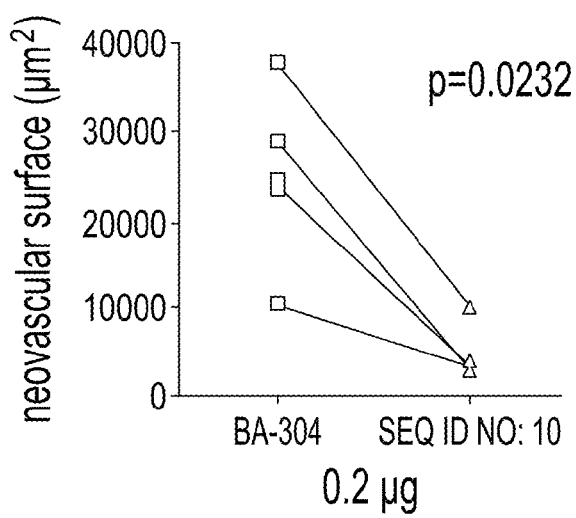
Fig. 12

Fig. 18

ADP-RIBOSYL TRANSFERASE FUSION VARIANT PROTEINS

CROSS-REFERENCE TO RELATED APPLICATIONS

This application is a continuation-in-part of U.S. application Ser. No. 11/643,940 filed Dec. 22, 2006, now abandoned which is a continuation-in-part of U.S. application Ser. No. 10/902,878 filed Aug. 2, 2004, now abandoned and of application Ser. No. 10/902,959 filed Aug. 2, 2004, now U.S. Pat. No. 7,442,686 both applications claiming priority to Canadian Application Nos 2,342,970, 2,362,004, and 2,367,636, filed Apr. 12, 2001, Nov. 13, 2001 and Jan. 15, 2002, respectively, and further claiming priority to U.S. provisional application No. 60/506,162 filed Sep. 29, 2003. The entire content of these applications is hereby incorporated by reference.

FIELD OF THE INVENTION

The present invention relates to novel chimeric C3-like Rho antagonists and their use for promoting repair and neuron survival in injured mammalian central nervous system, including the retina, and for the inhibition of the proliferation of cancer cells.

BACKGROUND

Traumatic injury of the spinal cord results in permanent functional impairment. Most of the deficits associated with spinal cord injury result from the loss of axons that are damaged in the central nervous system (CNS). Similarly, other diseases of the CNS are associated with axonal loss and retraction, such as stroke, human immunodeficiency virus (HIV), dementia, prion diseases, Parkinson's disease, Alzheimer's disease, multiple sclerosis, traumatic brain injury, macular degeneration and glaucoma. Common to all of these CNS diseases, including many of the eye diseases, is the loss of axonal connections with their targets, and cell death. The ability to stimulate growth of axons from the affected or diseased neuronal population would improve recovery of lost neurological functions, and protection from cell death can limit the extent of damage. For example, following a white matter stroke, axons are damaged and lost, even though the neuronal cell bodies are alive, and stroke in grey matter kills many neurons and non-neuronal (glial) cells. Treatments that are effective in eliciting sprouting from injured axons are equally effective in treating some types of stroke (Chen et al., 2002, PNAS 99:9031-9036). Neuroprotective agents are often tested as potential compounds that can limit damage after stroke. Compounds which show both growth-promotion and neuroprotection are especially good candidates for treatment of stroke and neurodegenerative diseases.

It has been proposed to use various Rho antagonists as agents to stimulate regeneration of (cut) axons, i.e. nerve lesions; please see, for example, Canadian Patent application Nos 2,304,981 (McKerracher et al.) and 2,300,878 (Strittmatter). These patent application documents propose the use of known Rho antagonists such as, for example, the chimeric C3 proteins as well as substances selected from among known trans-4-amino (alkyl)-1-pyridylcarbamoylcyclohexane compounds or Rho kinase inhibitors for use in the regeneration of axons. C3 inactivates Rho by ADP-ribosylation and is fairly non-toxic to cells (Dillon and Feig, 1995, Methods in Enzymology: Small GTPases and their regulators Part. B, 256: 174-184).

Treatment with Rho antagonists would also be used to enhance the rate of axon growth of peripheral nerves and thereby be effective for repair of peripheral nerves after surgery, for example after reattaching severed limbs. In addition, Rho is an important target for treatment of cancer and metastasis (Clark et al., 2000, Nature, 406: 532-535), and hypertension (Uehata et al., 1997, Nature, 389: 990) and RhoA is reported to have a cardioprotective role (Lee et al., FASEB J., 15: 1886-1884).

Targeting intracellular signaling mechanisms involving Rho and the Rho kinase for promoting axon regeneration has been proposed (Canadian Patent application No 2,304,981). *Clostridium botulinum* C3 exotransferase (hereinafter simply referred to as C3) can stimulate regeneration and sprouting of injured axons; C3 is a toxin purified from *Clostridium botulinum* (Wilde et al., 2000, J. Biol. Chem., 275: 16478). Compounds of the C3 family from *Clostridium botulinum* inactivate Rho by ADP-ribosylation and thus act as antagonists of Rho effect or function (Rho antagonists).

While the C3 protein can effectively promote regeneration, it has been noted that C3 does not easily penetrate into cells, and high doses must therefore be applied for it to be effective. The high dose of recombinant C3 needed to promote functional recovery presents a practical constraint or limitation on the use of C3 in vivo to promote regeneration. In tissue culture studies, it has been determined that the minimum amount of C3 that can be used to induce growth on inhibitory substrates is 25 μg/ml (Lehmann et al., 1999, J. Neurosci. 19: 7537-7547). If the cells are not triturated, even this dose is ineffective. It has been estimated that at least 40 μg of C3 per 20 g of mouse needs to be applied to injured mouse spinal cord or rat optic nerve (Canadian patent application No 2,325,842). Calculating doses that would be required to treat an adult human with an equivalent dose per weight (scaling up from the dose used for rat and mice experiments) it would be necessary to apply 120 mg/kg of C3 to the injured human spinal cord. The large amount of recombinant C3 protein needed creates significant problems for manufacturing, due to the large-scale protein purification and cost. It also limits the dose ranges that can be tested because of the large amount of protein needed for minimal effective doses.

Another related limitation with respect to the use of C3 to promote repair in the injured CNS is that it does not easily penetrate the plasma membrane of living cells. In tissue culture studies where C3's biological effects have been tested, it was microinjected directly into the cell (Ridley and Hall, 1992, Cell, 70: 389-399), or applied by trituration of the cells to break the plasma membrane (Lehmann et al., 1999, J. Neurosci., 19: 7537-7547). In the case of axon injury in vivo, the C3 protein is likely able to enter the cell because injured axons readily take up substances from their environment. After incomplete spinal cord injury (SCI), there is plasticity of motor systems attributed to cortical and subcortical levels, including spinal cord circuitry. This plasticity may be attributed to axonal or dendritic sprouting of collaterals and synaptic strengthening or weakening. Additionally, it has been shown that sparing of a few ventrolateral fibers may translate into significant differences in locomotor performance since these fibers are important in the initiation and control of locomotor pattern through spinal central pattern generators. It is well documented that reorganization of spared collateral cortical spinal fibers occurs after spinal cord injury and this contributes to functional recovery. The process of reorganization and sprouting of spared fibers would be enhanced by treatment with C3-like proteins able to enter non-injured neurons. This would enhance spontaneous plasticity of axons and dendritic remodeling known to help functional recovery.

Other methods of delivery of C3 in vitro include making a recombinant protein that can be taken up by a receptor-mediated mechanism (Boquet et al., 1995, Meth. Enzymol., 256: 297-306). The disadvantage of this method is that the cells needing treatment must express the necessary receptor. Lastly, addition of a C2II binding protein to the tissue culture medium, along with a C21N-C3 fusion toxin allows uptake of C3 by receptor-mediated endocytosis (Barthe et al., 1998, Infection and Immunity, 66: 1364). The disadvantage of this system is that much of the C3 in the cell will be restrained within a membrane compartment. More importantly, two different proteins must be added separately for transport to occur, which makes this system difficult to apply to treatment of disease in vivo.

Currently, there is a need to find a therapy that can stop degenerative progression in people who have eye diseases. The neurons of the retina are derived from the CNS, and also are expected to respond to treatments effective in other regions of the CNS, for example, age-related macular degeneration (AMD). Most experimental forms of treatment known to date address the wet form of AMD, and target specifically neovascularization. Laser photocoagulation of the subretinal neovascular membranes that occur in 10-15% of affected patients can benefit individuals with macular degeneration who develop acute, extrafoveal choroidal neovascularization. For dry AMD, high daily doses of antioxidants such vitamin C (500 mg), vitamin E (400 IU), beta carotene (15 mg), as well as zinc oxide (80 mg; high concentrations of zinc occur in ocular tissues, particularly the retina, pigment epithelium and choroid) may modestly reduce risk of progression of those who have intermediate-sized drusen, large drusen, or non-central geographic atrophy, or advanced macular degeneration in one eye. There is current need of therapy to treat such eye diseases with compounds that protect the retinal neurons. There is also a current need of therapy for persons with acute ocular ischemic disease. Ocular ischemic disease, or stroke of the optic nerve results in irreversible death of retinal neurons, leading to permanent visual impairment. This disease is not expected to respond to current therapies for AMD. C3-like proteins may reduce the cell death and progression of the disease.

Therefore, the new C3-like proteins are expected to be useful for a variety of diseases where inhibition of Rho activity is required. Thus, there is a need for compounds, methods of treatment and formulations to treat or prevent diseases where inhibition of Rho activity is required. It would also be desirable to be provided with C3-like protein compositions having the ability to penetrate inside tumor cells and inactivate rapidly Rho at lower doses.

SUMMARY OF THE INVENTION

The present invention relates to novel chimeric C3-like Rho antagonists and their use for promoting repair and neuron survival in injured mammalian central nervous system, including the retina, and for the inhibition of the proliferation of cancer cells. In one aspect, polypeptides corresponding to novel chimeric C3-like Rho antagonists are provided, as well as compositions comprising the polypeptides. In other aspects, therapeutic methods using the polypeptides and compositions of the invention are provided, as well as use of the polypeptides and compositions of the invention.

In one aspect, the polypeptides of the invention include conjugate or fusion type proteins (polypeptides) comprising, for example, C3-like fusion proteins, and C3 chimeric fusion proteins. Exemplary polypeptides of the invention include SEQ ID NO:4, SEQ ID NO:6, SEQ ID NO:14, SEQ ID NO:18, SEQ ID NO: 20, SEQ ID NO:25, SEQ ID NO:30, SEQ ID NO:35, SEQ ID NO:37, and SEQ ID NO:10, and analogues or variants thereof. In another aspect, the polypeptides of the invention include SEQ ID NO.: 4, SEQ ID NO:6, SEQ ID NO:14, SEQ ID NO:18, SEQ ID NO: 20, SEQ ID NO:25, SEQ ID NO:30, SEQ ID NO:35, SEQ ID NO:37, and SEQ ID NO:10, wherein the polypeptides are truncated by 20 amino acids at their N-terminus, or the polypeptides are truncated by 10 amino acids at their C-terminus, or the polypeptides are truncated by both 20 amino acids at their N-terminus and 10 amino acids at their C-terminus. In another aspect, the polypeptides of the invention include any of the polypeptides disclosed herein. In another aspect, the polypeptides of the invention are PEGylated.

In another aspect, polypeptides of the invention include those in SEQ ID NO: 1, SEQ ID NO: 2, SEQ ID NO: 6, SEQ ID NO: 8, SEQ ID NO: 10, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 43, SEQ ID NO: 44, SEQ ID NO: 78 and SEQ ID NO: 79.

In a further aspect, a polypeptide of the invention is covalently linked to an amino acid sequence of a transport agent, which facilitates uptake of the polypeptide by a receptor-independent or receptor-dependent mechanism. In one aspect, the amino acid sequence of the transport agent is the polypeptide of SEQ ID NO: 3, SEQ ID NO: 4, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76 and/or SEQ ID NO: 77. In a further aspect, the polypeptide of the invention is a cell-permeable fusion protein conjugate comprising a polypeptidic cell-membrane transport moiety, and the pharmaceutical compositions of the invention may include a cell-permeable fusion protein conjugate comprising a polypeptidic cell-membrane transport moiety and a substantially purified polypeptide of the invention. In another aspect, a polypeptidic cell-membrane transport moiety comprising a peptide having from about 5 to about 50 amino acids is provided.

The invention also relates to pharmaceutical compositions comprising the polypeptides of the invention. In an aspect, the pharmaceutical compositions include a pharmaceutically acceptable carrier. In an aspect, the pharmaceutical composition is sterile, sterilizable or sterilized. In a further aspect, the pharmaceutical composition is in a vial in a unit dosage amount or in an integral multiple of a unit dosage amount. In yet another aspect, the pharmaceutical composition is dried or lyophilized or comprises a dehydrated matrix, or comprises a fusion protein in a lyophilized matrix. In addition, pharmaceutical compositions of the invention may include a tissue adhesive, and/or fibrin, which may be a fibrin sealant such as, for example, Tisseel®.

Non-limiting examples of pharmaceutically acceptable carriers to be used in the compositions of the invention include poly(ethylene-co-vinyl acetate), PVA, partially hydrolyzed poly(ethylene-co-vinyl acetate), poly(ethylene-co-vinyl acetate-co-vinyl alcohol), a cross-linked poly(ethylene-co-vinyl acetate), a cross-linked partially hydrolyzed poly(ethylene-co-vinyl acetate), a cross-linked poly(ethylene-co-vinyl acetate-co-vinyl alcohol), poly-D,L-lactic acid, poly-L-lactic acid, polyglycolic acid, PGA, copolymers of lactic acid and glycolic acid (PLGA), polycaprolactone, polyvalerolactone, poly(anhydrides), copolymers of polycaprolactone with polyethylene glycol, copolymers of polylactic acid with polyethylene glycol, polyethylene glycol; and combinations and blends thereof.

In another aspect, the pharmaceutically acceptable carrier is an aqueous gelatin, an aqueous protein, a polymeric carrier, a cross-linking agent, or a combination thereof. In another aspect, the pharmaceutically acceptable carrier is a matrix. In yet another aspect, the pharmaceutically acceptable carrier includes water, a pharmaceutically acceptable buffer salt, a pharmaceutically acceptable buffer solution, a pharmaceutically acceptable antioxidant, ascorbic acid, one or more low molecular weight pharmaceutically acceptable polypeptides, a peptide comprising about 2 to about 10 amino acid residues, one or more pharmaceutically acceptable proteins, one or more pharmaceutically acceptable amino acids, an essential-to-human amino acid, one or more pharmaceutically acceptable carbohydrates, one or more pharmaceutically acceptable carbohydrate-derived materials, a non-reducing sugar, glucose, sucrose, sorbitol, trehalose, mannitol, maltodextrin, dextrins, cyclodextrin, a pharmaceutically acceptable chelating agent, EDTA, DTPA, a chelating agent for a divalent metal ion, a chelating agent for a trivalent metal ion, glutathione, pharmaceutically acceptable nonspecific serum albumin, and/or combinations thereof.

The invention also relates to therapeutic methods comprising administering to a subject the polypeptides or compositions of the invention. In one aspect, a therapeutically effective amount of polypeptide or composition is administered. In another aspect, the subject is in need of such treatment. The subject may be a mammal, particularly a human, in certain aspects of the invention. In an aspect, polypeptides and compositions of the invention may be administered by topical application. In another aspect, polypeptides and compositions of the invention may be administered by injection.

In an aspect, the invention pertains to the field of mammalian nervous system repair (e.g. repair of a central nervous system (CNS) lesion site, repair of damaged retina, or a peripheral nervous system (PNS) lesion site), axon regeneration and axon sprouting, neurite growth, neuroprotective activity, protection from neurodegeneration and ischemic damage, and/or treatment of traumatically damaged nervous systems. One aspect of the present invention is to promote regeneration of the nerve axons in the injured region in the case of lesions to the spinal cord, and to stimulate nerve growth in other diseases of the peripheral and central nervous system. Another aspect of the present invention is to promote neuronal regeneration of the peripheral nervous system.

The following therapeutic methods are provided: a method of treating macular degeneration in a subject; a method of inhibiting or reducing the rate of subretinal neovascularization and/or proliferation of neovascular tissue associated with macular degeneration in the eye in a subject; a method of protecting retinal photoreceptors from cell death associated with macular degeneration in the eye in a subject; a method of protecting retinal photoreceptors from cell death associated with macular degeneration in the eye in a subject; and/or a method of prevention or inhibition of uncontrolled proliferation or spreading or migration of a metastatic neoplastic cell of a cancer in a subject. In another aspect, the invention relates to a method of prevention or inhibition of uncontrolled proliferation or spreading or migration, within a resection margin of a host tissue proximal to the site of excision of a tumor of a cancer in a subject, or of a metastatic neoplastic cell residing in the resection margin. Administration may be directly on to the surface of the resection margin or below the surface of the resection margin or into the tissue proximal to the resection margin which remains in the subject, and the administration may be in a time interval prior to or subsequent to, or both prior to and subsequent to, excision or removal of the tumor.

In a further aspect, a method of prevention of growth of a tumor from a malignant cell in a host tissue in a subject is provided. The polypeptide, fusion protein or composition of the invention may simultaneously prevent or inhibit at least two of malignant cell migration, malignant cell proliferation, angiogenesis or tubular structure formation or capillary network growth proximal to the malignant cell, and secretion of an active metalloproteinase from the malignant cell. A method of prevention of growth within a resection margin of a host tissue proximal to a site of excision or removal of a first tumor of a cancer in a subject, of a second tumor comprising a residual tumor cell of the cancer is also provided. Administration may be directly on to the surface of the resection margin or below the surface of the resection margin or into the tissue proximal to the resection margin which remains in the subject, and may be in a time interval prior to or subsequent to, or both prior to and subsequent to, excision or removal of the first tumor, wherein the fusion protein simultaneously prevents or inhibits at least two of residual tumor cell migration, residual tumor cell proliferation, angiogenesis or tubular structure formation or capillary network growth proximal to the residual tumor cell, and secretion of an active metalloproteinase from the residual tumor cell. In an aspect, the cancer is breast, brain, colon, skin, kidney, or hepatic cancer. In another aspect, the cancer is a brain tumor such as, for example, a glial tumor, a neuron tumor, a pineal gland tumor, a menigeal tumor, a tumor of nerve sheath, a lymphoma, a malformative tumor, and a metastatic tumor located in the brain derived from tumors of the lung, breast, melanoma, kidney, or gastrointestinal tract. In a further aspect, the cancer is a brain tumor selected from the group consisting of anaplastic astrocytoma, glioblastoma multiform, pilocytic astrocytoma, oligodendroglioma, ependymoma, myxopapillary ependymoma, subependymoma, choroid plexus papilloma, neuroblastoma, ganglioneuroblastoma, ganglioneuroma, and medulloblastoma, pineoblastoma and pineocytoma, meningioma, meningeal hemangiopericytoma, meningeal sarcoma, Schwannoma (neurolemmoma) and neurofibroma, Hodgkin's lymphoma, non-Hodgkin's lymphoma, primary and secondary subtypes of Hodgkin's lymphoma, primary and secondary subtypes of non-Hodgkin's lymphoma, craniopharyngioma, epidermoid cysts, dermoid cysts and colloid cysts.

In one aspect, a therapeutically effective amount is about 0.001 micrograms per cc to about 50 micrograms per cc of tissue, or about 0.0001 micrograms of fusion protein per cubic centimeter (cc) of tissue to about 100 micrograms per cubic centimeter of tissue, or about 1 micrograms per milliliter to about 10 micrograms per milliliter to about 50 micrograms per milliliter. Administration may be by injection, by topical application, or by implantation. In an aspect, administration is intrarticular, intraocular, intranasal, intraneural, intradermal, intraosteal, sublingual, oral, topical, intravesical, intrathecal, intravenous, intraperitoneal, intracranial, intramuscular, subcutaneous, inhalation, by atomization and inhalation, by application directly into a tumor, by application directly into a disease site, by application directly on or into the margins remaining after resection of a tumor, enteral, enteral together with a gastroscopic procedure, and/or ECRP.

In another aspect, a method of treating spinal cord injury in a subject is provided, as well as a method of preventing or treating macular degeneration and/or a method of preventing or treating cancer.

The invention also relates to the use of polypeptides and compositions of the invention for e.g. treatment of spinal cord injury, macular degeneration, and/or cancer (e.g. breast, brain, colon, skin, kidney, or hepatic cancer). In an aspect, axon or neurite regeneration or growth in a subject is promoted. In another aspect, the invention relates to the use of polypeptides and compositions of the invention in the manufacture of a medicament for e.g. treatment of spinal cord injury, macular degeneration, and/or cancer (e.g. breast, brain, colon, skin, kidney, or hepatic cancer).

In one aspect, a subject may have a neurological or neurodegenerative disease. Non-limiting examples of such diseases include Stargardt disease, Lebers Congenital Amaurosis, Best disease, Choroideremia, Retinoschisis, Bardet-Biedl syndrome, Anterior ischemic optic neuropathy, Purtscher's retinopathy, Optic neuritis, Optic disc edema, Coats' disease and/or Leber's miliary aneurysm, immune and peripheral neuropathy, multiple sclerosis, Parkinson's, amyotrophic lateral sclerosis, Alzheimer's, Charcot-Marie-Tooth disease, Giant axonal neuropathy, trigeminal neuralgia, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, acrylamides, gamma-diketones (glue-sniffer's neuropathy), carbon disulfide, dapsone, ticks, porphyria, Gullain-Barre syndrome, Huntington's chorea, human immunodeficiency virus (HIV) dementia, prion diseases and glaucoma. In another aspect, a subject has nerve system damage resulting from stroke, surgery, infarction, infection, exposure to toxic agents, malignancy or paraneoplastic syndromes.

These and other aspects of the present invention will become evident upon reference to the associated detailed description and attached figures.

BRIEF DESCRIPTION OF THE FIGURES

Reference will now be made to the accompanying drawings, which show by way of illustration, one embodiment thereof, and in which:

FIG. 2 illustrates in (A) an alignment of N-termini of WT C3 exoenzyme, SEQ ID NO: 10 and SEQ ID NO: 43 wherein the amino acid residues indicated in italics represent the endogenously cleaved signal peptide of WT C3 exoenzyme, while those in bold have been engineered; in (B) a schematic representation of variants; in (C) a gradient gel showing dimerization of SEQ ID NO: 44; in (D) a gradient gel showing enhanced stability of SEQ ID NO: 10; and in (E) a gradient gel showing representative purification of variant (SEQ ID NO: 44);

FIG. 3 illustrates the deleted sequences of truncated SEQ ID NO: 10 variants (SEQ ID NO: 13-22), wherein the highlighted portions in peptide sequences illustrate the amino acid stretches that were deleted to generate the new truncated SEQ ID NO: 10 variants, wherein the amino acids highlighted in gray represent the sequences that were deleted from the N- or C-terminus of SEQ ID NO: 10, and wherein the underlined amino acids indicate the membrane transport sequence;

FIG. 4A illustrates a NuPAGE gels showing a molecular weight standard (lane 1), purified PEG-BA-220 variant (lane 3), PEG-BA-225 variant (lane 4), PEG-BA-230 variant (lane 5), PEG-BA-231 variant (lanes 6 and 7); and wherein

FIG. 9A illustrates a histogram representing the total number of TUNNEL labeled photoreceptors in 100 micron lengths, whereas

FIG. 11 illustrates that topical application of SEQ ID NO: 10 decreased pathological angiogenesis in the mouse cornea;

FIG. 12 illustrates that intravitreous injection of SEQ ID NO: 10 decreased laser induced subretinal neovascularization in mice;

FIG. 18 illustrates a time course of SEQ ID NO: 10 vs. BA-231 (PEGylated variant of SEQ ID NO: 10) retinal residence after intravitreal injection;

DETAILED DESCRIPTION

Figure 1:
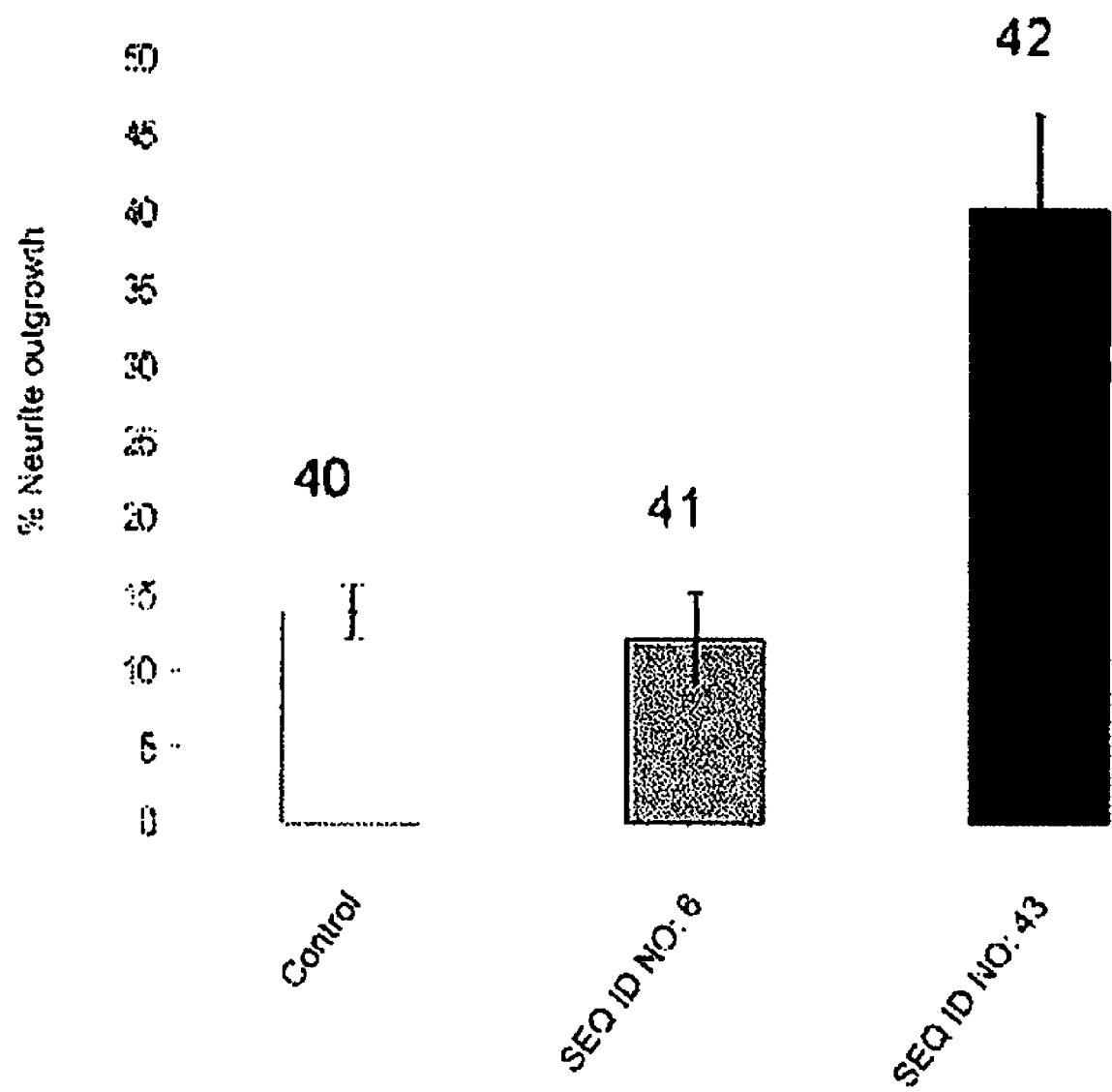
FIG. 1 illustrates the activity of a fusion protein of the invention, SEQ ID NO: 43, and lack of activity of an inactive mutant of SEQ ID NO: 43, SEQ ID NO: 6, as assayed by bioassay with NG-108 cells; wherein NG-108 cells cultured with SEQ ID NO: 43 exhibit accelerated neurite outgrowth (bar 42, which shows approximately 40% neurite outgrowth); and wherein neurite outgrowth of NG-108 cells treated with SEQ ID NO: 6 (bar 41, which shows approximately 12% neurite outgrowth) is similar to that of the control (bar 40, which shows approximately 14% neurite outgrowth) of untreated cells demonstrating that protein SEQ ID NO: 6 is not active as a fusion protein to induce accelerated neurite outgrowth.

The present invention relates to conjugate or fusion type proteins (polypeptides) comprising, for example, C3-like fusion proteins, and C3 chimeric fusion proteins. The fusion-type proteins of the present invention will be particularly discussed in relation to the use to facilitate regeneration of axons and neuroprotection and as anti-tumor compounds. It is to be understood that the fusion proteins may be exploited in other contexts as well.

The present invention pertains in particular to the field of mammalian nervous system repair (e.g. repair of a central nervous system (CNS) lesion site, repair of damaged retina, or a peripheral nervous system (PNS) lesion site), axon regeneration and axon sprouting, neurite growth, neuroprotective activity and protection from neurodegeneration and ischemic damage.

The present invention is useful for treatment in traumatically damaged nervous systems. In particular, the methods and compositions of the present invention can be useful in treating damage associated with branch and central vein/artery occlusion, trauma, macular edema, angle-closure glaucoma, open-angle glaucoma, age related macular degeneration, retinitis pigmentosa, retinal detachments, damage associated with laser therapy (including photodynamic therapy), diabetic retinopathy, and surgical light-induced iatrogenic retinopathy. In another embodiment, the methods and compositions of the invention are used to treat damage associated with Stargardt disease, Lebers Congenital Amaurosis, Best disease, Choroideremia, Retinoschisis, Bardet-Biedl syndrome, Anterior ischemic optic neuropathy, Purtscher's retinopathy, Optic neuritis, Optic disc edema, Coats' disease and/or Leber's miliary aneurysm. The present invention is useful to treat diseases or conditions such as spinal cord injury, immune and peripheral neuropathy, multiple sclerosis, Parkinson's, amyotrophic lateral sclerosis, Alzheimer's, traumatic brain injury, Charcot-Marie-Tooth disease, Giant axonal neuropathy, trigeminal neuralgia, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, acrylamides, gamma-diketones (glue-sniffer's neuropathy), carbon disulfide, dapsone, ticks, porphyria, Gullain-Barre syndrome, Huntington's chorea and other diseases associated with axonal loss and retraction, such as stroke, human immunodeficiency virus (HIV) dementia, prion diseases and glaucoma.

Glaucoma is the second leading cause of blindness worldwide, after cataract. It has been estimated that more than 50 million persons are affected by glaucoma, with over 7 million people presenting bilateral (both eyes) blindness caused by this disease (Quigley H A. Glaucoma: Macrocosm to Microcosm The Friedenwald Lecture. Invest. Opthalmol. Vis. Sci. 2005; 46: 2663-2670). Glaucoma is a group of diseases characterized by progressive optic nerve degeneration that leads to visual field loss and irreversible blindness. There are several types of glaucoma, including primary open angle, angle-closure and congenital glaucoma. A common characteristic of all types of glaucoma is the death of retinal ganglion cells (RGCs). When there is substantial loss of RGCs, the patient experiences gradual and progressively worsening vision, usually more in one eye than the other. Visual loss usually starts in the periphery and advances to involve the central vision. In the later stages of the disease, the patient may also notice increasing difficulty with night vision.

Elevated intraocular pressure is another key risk factor for developing glaucoma. Open angle and angle-closure glaucoma, the most common forms of the disease, are often associated with high intraocular pressure. The current standard therapy for glaucoma is to lower eye pressure by medication (e.g. prostaglandin therapy) and/or surgery. However, there are risks and adverse side effects associated with these treatments (Lee D A, Higginbotham E J. Glaucoma and its treatment: a review. Am. J. Health-Syst. Pharm. 2005; 62: 691-600). A significant proportion of patients continue to experience visual loss in spite of responding well to pressure lowering medications. Moreover, approximately 25% to 30% of patients in North America suffer from "normal tension glaucoma" in which there is optic nerve degeneration in the absence of high intraocular pressure (Anderson D R. Collaborative Normal Tension Glaucoma Study. Curr. Opin. Opthalmol. 2003; 14: 86-90). Thus, current therapeutic strategies for glaucoma are insufficient and new approaches to slow disease progression are urgently needed.

In another embodiment, the compositions and methods of the invention are used to treat glaucoma, including without limitation open-angle, angle-closure and congenital glaucoma.

The present invention is useful for treatment of spinal cord injury. The spinal cord and the brain form the central nervous system (CNS) in vertebrates. The spinal cord extends along the longitudinal axis of the body and is surrounded by the spinal canal. In human beings, the spinal cord is divided into eight cervical segments, twelve thoracic segments, five lumbar segments, five sacral segments and one or two coccygeal segments. The central gray substance, with its lateral projections (the anterior horn and the posterior horn), is formed by the cytosomes of the nerve cells, while the peripheral white substance is formed by the medullated nerve fiber bundles. The afferent (ascending or sensory) neural pathways and efferent (descending or effector) neural pathways run in the white substance. The efferent pathways in the spinal cord are either pyramidal (for voluntary movements) or extrapyramidal (for involuntary movements and for the distribution of the muscular tone). The majority of the pyramidal fibers run with a cross-over in the lateral pyramidal tract of the opposite side, and to a smaller extent without a cross-over in the anterior pyramidal tract to the cells in the anterior horn and the posterior horn in the various segments of the spinal cord.

The spinal cord and the brain are formed by cells of two types: the nerve cells or neurons and glial cells. The glial cells can be either oligodendrocytes or astrocytes. The oligodendrocytes form the myelin sheath of the nerve axons, while the astrocytes supply the nerve cells or neurons with nourishment, absorb the neurotransmitters secreted, and form the blood-brain barrier. Myelin is the fatty insulating sheath that surrounds the nerves in a helical form. This coating ensures the trouble-free conduction of electrical impulses along the nerve.

The myelin sheath is attacked and destroyed in numerous diseases, such as: multiple sclerosis, encephalitis periaxialis, diffuse sclerosis, acute disseminated encephalomyelitis, neuromyelitis optica, SMON (subacute myelo-optical neuropathy), congenital demyelinization disorders (such as leukodystrophy), and the generally immune-mediated inflammatory diseases of the nervous system, such as neurologic Behcet syndrome and Kawasaki syndrome. This damage leads to an electrical conduction blockade and neurologic symptoms, with the loss of numerous important functions. Injury to the spinal cord, e.g. as a result of an accident, leads to a lasting abolition of the conduction function of the nerve fibers affected. Paralysis caused by the complete abolition of at least one segment is called transverse lesion of the spinal cord with paraplegia. This means the loss of sensory functions (e.g. temperature, pain or pressure sensations), motor functions (voluntary and involuntary movements) and vegetative functions (e.g. bladder and intestinal function) for all areas that lie under the affected segment. Owing to the poor regenerative capability of the nerve fibers, the paralysis of the voluntary movements and the complete loss of sensation are permanent.

In an embodiment, the present invention can be used in regimens where an increase in neurite extension, growth, or regeneration is desired, e.g., in patients with nervous system damage. In another embodiment, treatment of patients suffering from traumatic disorders (including but not limited to spinal cord injuries, spinal cord lesions, or other CNS pathway lesions), surgical nerve lesions, damage secondary to infarction, infection, exposure to toxic agents, malignancy, paraneoplastic syndromes, or patients with various types of degenerative disorders of the central nervous system are encompassed. Examples of such disorders include but are not limited to amyotrophic lateral sclerosis, progressive supranuclear palsy and other dementias.

One embodiment of the present invention is to promote regeneration of the nerve axons in the injured region in the case of lesions to the spinal cord, and to stimulate nerve growth in other diseases of the peripheral and central nervous system.

One embodiment of the present invention is to promote neuronal regeneration of the peripheral nervous system. The peripheral nervous system consists of the nerves and neurons that reside or extend outside the central nervous system (the brain quad spinal cord) to serve the limbs and organs. Unlike the central nervous system, however, the PNS is not protected by bone or the blood-brain barrier, leaving it exposed to toxins and mechanical injuries. The peripheral nervous system is divided into the somatic nervous system and the autonomic nervous system.

The present invention is also useful for treatment of eye diseases such as retinal pigmentosa, macular degeneration, ocular ischemic neuropathy. Degeneration of components of the retina can lead to partial or total blindness. Macular degeneration is a degeneration of the macular region of the retina in the eye. Degeneration of the macula causes a decrease in acute vision and can lead to eventual loss of acute vision. The wet form of macular degeneration is related to abnormal growth of blood vessels in the retina that can leak blood and can cause damage to photoreceptor cells.

Age-related macular degeneration (AMD) is a collection of clinically recognizable ocular symptoms that can lead to blindness.

Macular degeneration includes a group of diseases that affect the central retina, or macula. There are two basic types of macular degeneration: "wet" and "dry". In wet macular degeneration, there is an abnormal growth of new blood vessels. These new blood vessels break and leak fluid, causing damage to the central retina. This form of macular degeneration is often associated with aging. Approximately 90% of macular degeneration cases are dry macular degeneration. In dry macular degeneration, vision loss can result from the accumulation of deposits in the retina called drusen, and from the death of photoreceptor cells. This process can lead to thinning and drying of the retina.

The symptoms of AMD include the presence of drusen, retinal pigment epithelial disturbance, including pigment clumping and/or dropout, retinal pigment epithelial detachment, geographic atrophy, subretinal neovascularization and disciform scar. Age-related macular degeneration is a leading cause of presently incurable blindness, particularly in persons over 55 years of age. Approximately one in four persons age 65 or over have signs of age-related maculopathy and about 7% of persons age 75 or over have advanced macular degeneration with vision loss. A patient who has drusen and who suffers complications in one eye may suffer no complications in the other eye. Complications may comprise one or more conditions selected from the group consisting of retina pigment epithelium atrophy, choroid neovascularization, retina detachment serous, and retina detachment hemorrhagic. Drusen may affect contrast sensitivity, and may reduce the eye's ability to see adequately to allow a person to read in dim light or to see sufficient detail to permit a person to drive an automobile safely at night. Not all these manifestations are needed for AMD to be considered present, and drusen alone are not directly associated with vision loss. While the exact causes of macular degeneration are not known, contributing factors have been identified. The collective result of the contributing factors is a disturbance between the photoreceptor cells and the tissues under the retina which nourish the photoreceptor cells, including the retinal pigment epithelium, which directly underlies and supports the photoreceptor cells, and the choroid, which underlies and nourishes the retinal pigment epithelium.

The retina and macula may be subjected to oxidative damage by oxidants such as free-radicals and singlet oxygen. The macula contains polyunsaturated fatty acids and is exposed to light, including in the visible and near ultraviolet light spectrum high-energy blue light, which can photosensitize the conversion of triplet oxygen to singlet oxygen, an oxidizing agent capable of damaging the polyunsaturated fatty acids, DNA, proteins, lipids, and carbohydrates in the macula. Reaction products resulting from oxidative interactions between components of the retina and oxidizing agents may accumulate in the retinal pigment epithelium and contribute to macular degeneration. Certain antioxidant nutrients may reduce the risk of developing macular degeneration by reducing the formation of radicals and reactive oxygen, thereby preventing cell death. Another factor which may be involved in the pathology of macular degeneration comprises an elevated serum concentration of low density cholesterol lipoprotein (LDL). Low density lipoprotein cholesterol can be oxidized by an oxidizing agent to form oxidized LDL, which is found in atherosclerotic plaques. These oxidized products may accumulate as deposits in healthy retinal pigment epithelium and cause necrosis or death of functioning tissue. LDL cholesterol may also form atherosclerotic plaques in the blood vessels of the retinal and subretinal tissue, inducing hypoxia in the tissue, resulting in neovascularization. Postmenopausal women given unopposed estrogen replacement therapy can have a reduced risk of neovascular age-related macular degeneration. Estrogen can increase the amount of high density lipoprotein cholesterol (HDL) in the blood, which may produce changes in the transport and metabolism of lipid-soluble antioxidants, and limit the accumulation of oxidized LDL cholesterol in the retinal and subretinal tissues and blood vessels.

A contributing and indicating factor of advanced macular degeneration is neovascularization of the choroid tissue underlying the photoreceptor cells in the macula. Healthy mature ocular vasculature is normally quiescent and exists in a state of homeostasis in which a balance is maintained between positive and negative mediators of angiogenisis in development of new vasculature. Macular degeneration, particularly in its advanced stages, is characterized by the pathological growth of new blood vessels in the choroid underlying the macula. Angiogenic blood vessels in the subretinal choroid can leak vision obscuring fluids, leading to blindness.

In one aspect, diseases of the eye which exhibit neovascularization proximal to the retina such as wet macular degeneration can be treated to reduce the rate of neovascularization by administration of a composition of this invention comprising a fusion protein of this invention having angiogenesis inhibiting activity.

In another aspect, diseases of the eye which exhibit neovascularization proximal to the retina such as wet macular degeneration can be treated to prevent or reduce the rate of photoreceptor cell death by administration of a composition of this invention comprising a fusion protein of this invention.

Neovascularization proximal to the retina as a result of a disease, especially neovascularization proximal to the macula, can lead to photoreceptor cell death in the retina of a patient. Photoreceptor cell death in the retina can be produced as a consequence of a disease of the retina as a result of neovascularization as well as other mechanisms of cell death.

Advanced dry macular degeneration comprises the deposition of drusen and death of photoreceptor cells. The mechanism of drusen deposition is unknown, but exocytosis from cells is one likely mechanism of release into the extracellular space. Another embodiment of the present invention comprises the inhibition of drusen deposition and prevention of photoreceptor cell death by a cell-permeable fusion protein conjugate comprising a polypeptide comprising an amino acid sequence of a transport agent covalently linked to an amino acid sequence of an active agent, said amino acid sequence of said active agent consisting of ADP-ribosyl transferase C3 or a fragment thereof retaining an ADP-ribosyl transferase activity, said amino acid sequence of said transport agent facilitating cellular uptake of the active agent, for example a fusion protein such as C3APLT. In one aspect, the functional analog of a *Clostridium botulinum* C3 exotransferase unit comprises a protein exhibiting an ADP-ribosyl transferase activity in the range of 50% to 500% of the ADP-ribosyl transferase activity of *Clostridium botulinum* C3 exotransferase. Inactivation of Rho in a cell by a fusion protein of this invention after penetration of the cell membrane can block or inhibit exocytosis and thereby block or inhibit the release from the cell of cellular debris or cellular-derived material that can form drusen. A fusion protein of this invention can also prevent injury-induced cell death of a cell in the CNS.

Angiogenesis in neovascularization is the complex process of blood vessel formation. The process involves both biochemical and cellular events, including (1) activation of endothelial cells (ECs) by an angiogenic stimulus; (2) degradation of the extracellular matrix, invasion of the activated endothelial cells into the surrounding tissues, and migration toward the source of the angiogenic stimulus; and (3) proliferation and differentiation of endothelial cells to form new blood vessels. Angiogenisis in the choroid can be induced by the presence of cytokine growth factors such as basic fibroblast growth factor (bFGF). Hypoxia of retinal cells may induce the expression of such growth factors, wherein the hypoxia may be induced by cellular debris or drusen accumulated in the retinal pigment epithelium, by oxidative damage of retinal and subretinal tissue, or by deposits of oxidized LDL cholesterol.

The control of angiogenesis is a highly regulated process involving angiogenic stimulators and inhibitors. In healthy humans and animals, angiogenesis occurs under specific, restricted situations. For example, angiogenesis is normally observed in fetal and embryonal development, development and growth of normal tissues and organs, wound healing, and the formation of the corpus luteum, endometrium and placenta. Another embodiment of the present invention comprises the inhibition of angiogenesis by a cell-permeable fusion protein conjugate comprising a polypeptide comprising an amino acid sequence of a transport agent covalently linked to an amino acid sequence of an active agent, said amino acid sequence of said active agent consisting of ADP-ribosyl transferase C3 or a fragment thereof retaining an ADP-ribosyl transferase activity, said amino acid sequence of said transport agent facilitating cellular uptake of the active agent, for example a fusion protein such as SEQ ID NO: 8. In one aspect, the functional analog of a *Clostridium botulinum* C3 exotransferase unit comprises a protein exhibiting an ADP-ribosyl transferase activity in the range of 50% to 500% or more of the ADP-ribosyl transferase activity of *Clostridium botulinum* C3 exotransferase.

Rho family proteins have been investigated in relation to cancer. Ras (and RhoB as a secondary target) are targets for metastasis by molecules that inhibit posttranslational modification. However, these therapeutics investigations focus on Ras and are limited to RhoB among Rho family members.

Increased protein levels of RhoA and RhoB are found in colon, breast and lung tumors. RhoA and RhoB levels have been found in 5 µm sections from head and neck squamous cell carcinomas using polyclonal antibodies directed against these proteins, followed by visualization using a VectaStain kit (Vector Labs) and image analysis. Nearby "normeoplastic" areas were used as controls. Although RhoA protein levels increased with tumor progression, RhoB levels decreased in invasive tumors compared to carcinomas in situ and well-differentiated tumors.

Overexpression of RhoA and RhoB may occur in breast and lung adenocarcinomas compared to normal tissue, whereas expression of Rho proteins is decreased in astrocytic tumors and inversely related to grade II to IV malignancy.

Rho is involved in regulation of cell migration and motility. MM1 rat hepatoma cells transfected with Rho A mutant constructs (Val$^{14}$ or Val$^{14}$ or Val$^{14}$Ile$^{41}$) result in constitutively activated Rho. In an in vitro invasion assay, the percent of seeded cells capable of infiltration into a mesothelial cell layer was correlated with the level of expression of transfected RhoA Val 4. When these activated Rho-transfected cells were used in an in vivo assay in the peritoneal cavity, 6 of 10 implants resulted in tumor nodules compared with 2 of 8 for mock transfectants. These results indicate that active Rho is correlated with tumorigenicity.

A comprehensive study of gene expression compared two metastatic melanoma model systems, one human and one mouse, and comparison of at the shared similarities in gene expression by microarray concluded that RhoC expression was altered in increasing levels of metastasis (Clark et al., 2000, Nature, 406: 532-535). Furthermore, when gene expression was manipulated experimentally, RhoC overexpression induced a human melanoma cell line to switch from low metastatic potential to high metastatic potential.

Although RhoA was not observed to be overexpressed, a dominant negative mutation (N19RhoA) diminished metastatic potential.

A set of 70 genes whose expression correlated with propensity for metastasis in human breast cancer was identified (van't Veer et al., 2002, Nature, 415:530-536). Although Rho genes were not found, the value of a disease marker as a prognostic indicator is not necessarily related to its value as a target for therapy. In the case of Rho family signaling, there is complex regulation of enzymatic activity and protein-protein interactions which is not apparent from measurements of transcription levels alone.

Mechanisms to control cell proliferation are dysregulated in cancer. An increased apoptosis in EL4 Murine T lymphoma cells occurs after Rho inactivation by recombinant C3 exoenzyme. In NIH3t3 cells, treatment with the Rho kinase inhibitor Y-27632 significantly inhibited anchorage-independent growth. In one embodiment, inactivation of Rho can prevent tumour cell proliferation, and the present invention comprises the reduction or arrest of cell proliferation or induction of apoptosis by a cell-permeable fusion protein conjugate comprising a polypeptidic cell-membrane transport moiety and a *Clostridium botulinum* C3 exotransferase unit, or a functional analog thereof. In another embodiment, the present invention comprises the reduction or arrest of cell proliferation or induction of apoptosis by an effective amount of a pharmaceutical composition comprising a cell-permeable fusion protein conjugate comprising a polypeptidic cell-membrane transport moiety and a *Clostridium botulinum* C3 exotransferase unit, or a functional analog thereof.

Metastatic cancer cells are highly migratory. Inactivation of Rho can prevent cell migration in certain cell types. C3 transferase and the Rho kinase inhibitor Y-27632 block cellular invasion by HT29 human colon cancer cells. In a v-Crk-inducible rat fibroblast 3Y1 cell line, C3 and Y-27632 inhibited v-Crk, resulting in decreased cell motility. Decreased apoptosis in RhoB−/− cells in Rho B+/− or RhoB−/− MEF cells treated with doxorubicin, radiation or Taxol results from the lack of RhoB protein. In another embodiment, antagonism of Rho can reduce cell migration and metastasis. In one aspect, the present invention comprises the inhibition of cell migration by a cell-permeable fusion protein conjugate comprising a polypeptidic cell-membrane transport moiety and a *Clostridium botulinum* C3 exotransferase unit, or a functional analog thereof.

Invasive tumour cells have the property of being able to degrade the extracellular matrix that surrounds them by secreting proteases that degrade the extracellular matrix. One important class of proteases that are secreted by tumour cells is the matrix metalloproteinases (MMPs). These enzymes open up paths in the matrix through which the cancer cells can invade and spread. Tumour cells can produce different types of MMPs, and MMP are often made as pro-enzymes that are cleaved and released upon activation. MMP1 cleaves collagen matrix. MMP-2 may play an important role invasion of lung cancer cells. MMP-9 has also been implicated in tumour cell invasion. In another embodiment, the present invention comprises the inhibition of MMP expression, MMP processing or MMP secretion from a tumor cell, the inhibition by a cell-permeable fusion protein conjugate comprising a polypeptidic cell-membrane transport moiety and a *Clostridium botulinum* C3 exotransferase unit, or a functional analog thereof.

The brain is highly functionally localized: i.e., each specific anatomical region is specialized to carry out a specific function. The location of a cancer in the brain of a patient (and brain pathology) can be more important than the type of tissue or tumor type. A relatively small tumor or lesion in a key area of the brain can be far more devastating than a much larger lesion in a relatively less important area of the brain. A lesion on the surface of the brain may be relatively easy to resect surgically, while a tumor of comparable size but located deep in the brain may not be relatively easy to resect surgically because access to the deep tumor could require disruption of intervening tissue such as by cutting through many vital structures to reach or access and remove the deep tumor. In addition, benign tumors in the brain can be dangerous to a patient. A benign tumor may grow in a key area and cause significant damage to surrounding brain tissue and function. Although a benign tumor can be cured by surgical resection, removal of the tumor from deep tissue may not be possible. If left unchecked a benign tumor can grow, increase in volume, and cause increased intracranial pressure. If such a condition is left untreated, vital structures in the brain can be compressed, and death of the patient can result. The incidence of CNS (central nervous system) malignancies is about 8 to 16 cases per 100,000 people. The prognosis of a primary malignancy of the brain is dismal, with a median survival of less than one year, even following surgical resection. Brain tumors, especially gliomas, are predominantly a local disease which can recur within about 2 centimeters of the original focus of disease after surgical removal.

Representative examples of brain tumors which may be treated utilizing the compositions and methods described herein include glial tumors such as anaplastic astrocytoma, glioblastoma multiform, pilocytic astrocytoma, oligodendroglioma, ependymoma, myxopapillary ependymoma, subependymoma, choroid plexus papilloma; neuron tumors such as neuroblastoma, ganglioneuroblastoma, ganglioneuroma, and medulloblastoma; pineal gland tumors such as pineoblastoma and pineocytoma; menigeal tumors such as meningioma, meningeal hemangiopericytoma, meningeal sarcoma; tumors of nerve sheath cells such as Schwannoma (neurolemmoma) and neurofibroma; lymphomas such as Hodgkin's lymphoma and non-Hodgkin's lymphoma, primary and secondary subtypes of Hodgkin's lymphoma, primary and secondary subtypes of non-Hodgkin's lymphoma (and including numerous subtypes of these, both primary and secondary); malformative tumors such as craniopharyngioma, epidermoid cysts, dermoid cysts and colloid cysts; and metastatic tumors located in the brain which can be derived from virtually any tumor, the most common being derived from tumors of the lung, breast, melanoma, kidney, and gastrointestinal tract.

Examples of administration techniques of the pharmaceutical composition of the present invention have been disclosed for administration of drugs to the eye including the posterior region of the eye. For example, U.S. Pat. No. 5,707,643 relates to a biodegradable scleral plug that is inserted through an incision in the sclera into the vitreous body. For administration of a drug to the eye, the plug releases a drug into the vitreous body for treating the retina by diffusion through the vitreous body.

Another technique for administration of a drug to the eye is disclosed in U.S. Pat. No. 5,443,505 which discloses implants which can be placed in the suprachoroidal space over an avascular region of the eye such as the pars plana or a surgically induced avascular region. Another embodiment involves forming a partial thickness scleral flap over an avascular region, inserting an implant onto the remaining scleral bed, optionally with holes therein, and suturing closed the flap. The drug can diffuse into the vitreous region and the intraocular structure.

Figure 4A:
Figure 4B:
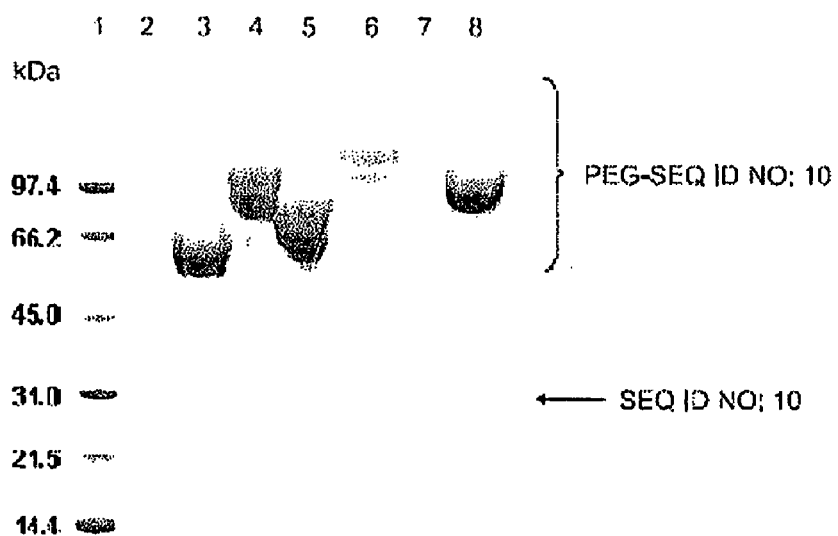
FIG. 4B illustrates a NuPAGE gels showing a molecular weight standard (lane 1), purified PEG-BA-230 variant (lane 3), PEG-BA-231 variant (lane 4), PEG-BA-235 variant (lane 5), PEG-BA-236 variant (lane 6) and PEG-BA-240 variant (lane 8)

Another delivery approach for administration of a drug to the eye is by transfecting the retinal neurons with a cDNA encoding the drug protein sequence. Such form of administration is disclosed by Fischer et al. (J. Neuroscience, 2004, 24:8726-2740) who transfected C3 into retinal ganglion cell neurons and found increased cell survival and increased regeneration of retinal ganglion cell axons. Another embodiment would be to transfect cells with the truncated fragments or variants reported in FIG. 4 of this application.

Another delivery approach for administration of a drug to the eye is direct injection. For the posterior segment of the eye, an intravitreal injection has been used to deliver drugs into the vitreous body. In this regard, U.S. Pat. No. 5,632,984 relates to a treatment of macular degeneration with various drugs by intraocular injection. For administration of a drug to the eye, drugs are preferably injected as microcapsules. Intraocular injection into the posterior segment of the eye can allow diffusion of the drug throughout the vitreous, the entire retina, the choroid and the opposing sclera. Additionally, U.S. Pat. No. 5,770,589 relates to treating macular degeneration by intravitreally injecting an anti-inflammatory into the vitreous humor for administration of a drug to the eye. Injections can be administered through the pars plana in order to minimize the damage to the eye while drug is delivered to the posterior segment.

Another delivery approach is by surgical procedure. For example, U.S. Pat. No. 5,767,079 relates to the treatment of ophthalmic disorders including macular holes and macular degeneration, by administration of TGF-β for example by placing an effective amount of the growth factor on the ophthalmic abnormality. In treating the macula and retina, for administration of a drug to the eye a surgical procedure involving a core vitrectomy or a complete pars plana vitrectomy is performed before the growth factor can be directly applied, presumably by administration to the sclera on the anterior segment of the eye at an avascular region or by administration to the sclera behind the retina via a surgical procedure through the vitreous body, retina, and choroids, a dramatic, highly invasive, technique usually suitable only where partial vision loss has already occurred or was imminently threatened.

Another delivery approach for administration of a drug to the eye is by use of a device and a cannula. For example, U.S. Pat. No. 5,273,530 relates to the intraretinal delivery and withdrawal of samples and a device therefor. Unlike direct intraocular injection techniques, the method disclosed in this patent avoids the use of a pars plana incision and instead uses an insertion path around the exterior of the orbit. The device, having a curved handle and a tip with collar, allows a cannula to be inserted through the posterior sclera and down into the subretinal space without passing through the vitreous body. The collar is stated to regulate the penetration to the desired depth. The device is taught to be adjustable to any part of the eye including the scleral area, the choroidal area, the subretinal area, the retinal area and the vitreous area.

Another delivery approach for administration of a drug to the eye is by intrascleral injection. For example, U.S. Pat. No. 6,397,849 discloses a method of intrascleral injection which comprises injecting into the scleral layer of an eye through a location on the exterior surface of the sclera which overlies retinal tissue an effective amount of a therapeutic or diagnostic material. Depending on the injection conditions, the material can form a deposit within the scleral layer and diffuse into the underlying tissue layers such as the choroid and/or retina, and/or the material can be propelled through the scleral layer and into the underlying layers. Because the sclera moves with the entire eye including the retina, the site of deposit on the sclera remains constant relative to a point on the underlying retina, even as the eye moves within the eye socket to permit site specific delivery by depositing material into the sclera at a site overlying the macula, thereby allowing material to be delivered to the macula and surrounding tissues. The injection procedure employs a cannula or needle as well as needle-less particle/solution techniques. In a preferred embodiment, a cannula is inserted into the sclera in a rotational direction relative to the eye and not orthogonal to the surface of the sclera.

Another delivery approach for administration of a drug to the eye is disclosed in U.S. Pat. No. 6,299,895 which discloses a method for delivering a biologically active molecule to the eye comprising implanting a capsule periocularly in the sub-Tenon's space, the capsule comprising a core containing a cellular source of the biologically active molecule and a surrounding biocompatible jacket, the jacket permitting diffusion of the biologically active molecule into the eye, wherein the dosage of the biologically active molecule delivered is between 50 pg and 1000 ng per eye per patient per day. The biologically active molecule can be an anti-angiogenic factor, and a second biologically active molecule or peptide can be co-delivered from the capsule to the eye. The method is disclosed to be useful treating ophthalmic disorders including macular degeneration.

Other delivery approaches for administration of a drug to the eye which can be useful with compositions of the current invention are well known in the art. For example, U.S. Pat. No. 5,399,163 discloses a method of providing a jet injection by pressurizing a fluid injectant; U.S. Pat. No. 5,383,851 discloses a needleless injection device; U.S. Pat. No. 5,312,335 discloses a needleless injection system; U.S. Pat. No. 5,064,413 discloses an injection device; U.S. Pat. No. 4,941,880 discloses an ampule for non-invasive injecting of a medication; U.S. Pat. No. 4,790,824 discloses a non-invasive hypodermic injection device; U.S. Pat. No. 4,596,556 discloses a pressure-operated hypodermic injection apparatus; U.S. Pat. No. 4,487,603 discloses an implantable micro-infusion pump for dispensing medication at a controlled rate; U.S. Pat. No. 4,486,194 discloses a therapeutic device for administering medicants through the skin; U.S. Pat. No. 4,447,233 discloses a medication infusion pump for delivering medication at a precise infusion rate; U.S. Pat. No. 4,447,224 discloses a variable flow implantable infusion apparatus for continuous drug delivery; U.S. Pat. No. 4,439,196 discloses an osmotic drug delivery system having multi-chamber compartments; and U.S. Pat. No. 4,475,196 discloses an osmotic drug delivery system.

Another delivery approach for administration of a drug to regions of tumour ressection includes injection of the drug at the surgical site, or delivery in a fibrin matrix into the lesion cavity following surgical removal of the tumour.

The term "Rho antagonists" as used herein includes, but is not restricted to, C3 proteins, including C3-like proteins.

The term "C3 protein" refers to ADP-ribosyl transferase C3 isolated from *Clostridium botulinum, Bacillus cereus* or *Staphylococcus aureus* or a recombinant ADP-ribosyl transferase.

The terms "C3-like protein", "ADP-ribosyl transferase C3-like protein", "ADP-ribosyl transferase C3 analogue", "C3-like transferase" or "C3 chimeric proteins" as used herein refers to any protein or polypeptide having a biological activity similar (e.g., the same, substantially similar) to ADP-ribosyl transferase C3. Examples of C3-like proteins include, but are not restricted to, SEQ ID NO: 1, SEQ ID NO: 8, SEQ ID NO: 10, SEQ ID NO: 13, SEQ ID NO: 14, SEQ ID NO: 15, SEQ ID NO: 16, SEQ. ID NO: 17, SEQ ID NO: 18, SEQ ID NO: 19, SEQ ID NO: 20, SEQ ID NO: 21, SEQ ID NO: 22, SEQ ID NO: 43, SEQ ID NO: 44, SEQ ID NO: 78 and SEQ ID NO: 79.

The term "nerve injury site" refers to a site of traumatic nerve injury or nerve injury caused by disease. The nerve injury site may be a single nerve (e.g. sciatic nerve or optic nerve) or a nerve tract comprised of many nerves (e.g. damaged region of the spinal cord). The nerve injury site may be in the central nervous system or peripheral nervous system or in any region needing repair. The nerve injury site may form as a result of damage caused by stroke in the CNS, including the brain and the optic nerve. The nerve injury site may be in the brain as a result of surgery, brain tumour removal or therapy following a cancerous lesion. The nerve injury site may result from stroke, Parkinson's disease, Alzheimer's disease, amyotrophic lateral sclerosis (ALS), diabetes or any other type of neurodegenerative disease.

As used herein, the term "substantially purified" means a preparation having better than 80% purity, preferably more than 90% purity and more preferably greater than 95% purity. More specifically, the term "substantially purified" means substantially free of contaminants which are associated with the protein in its native environment.

As used herein, the term "pegylation or PEG-variant relates to a variant where a PEG moeity is covalently attached to the C3 fusion protein to increase the retention of the drug in the tissue. The C3 fusion protein that is pegylated may include SEQ ID NO: 10, or truncated variants described in this application. Examples include PEG variants with different molecular weights from variation in the length of the C3 fusion construct, and differences in the molecular weight of the PEG used.

As used herein, the term "delivery agent" relates to an agent comprising a cargo moiety and a transport moiety. Examples of cargo moiety include ADP-ribosyl transferase C3 and ADP-ribosyl transferase C3 analogues. Examples of transport moiety comprise for example SEQ ID NO: 2 and analogues thereof.

"Polynucleotide" generally refers to any polyribonucleotide or polydeoxyribonucleotide, which may be unmodified RNA or DNA, or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus "polynucleotide" embraces chemically, enzymatically or metabolically modified forms of polynucleotides as typically found in nature, as well as the chemical forms of DNA and RNA characteristic of viruses and cells. "Polynucleotide" includes but is not limited to linear and end-closed molecules. "Polynucleotide" also embraces oligonucleotides.

"Polypeptides" refers to any peptide or protein comprising two or more amino acids joined to each other by peptide bonds or modified peptide bonds (i.e., peptide isosteres).

"Polypeptide" refers to both short chains, commonly referred as peptides, oligopeptides or oligomers, and to longer chains generally referred to as proteins. As described above, polypeptides may contain amino acids other than the 20 gene-encoded amino acids.

A cell membrane transport-enhancing peptide (also referred to as "transport moiety" or "transport agent") of a composition of this invention can comprise one or more than one proline-rich regions, each of which can be the same or different sequence of amino acids, and each of which is covalently linked together by a peptide bond or by the peptide bonds comprising one or more non-proline-rich amino-acid sequences which may each be the same or different when the non-proline-rich amino-acid sequence comprises more than 10 amino acids.

As used herein the term "to help neuron(s) make new connections with other cells" or "helping neurons to make new cell connection(s)" means that upon treatment of cells (e.g., neuron(s)) or tissue with a drug delivery construct, a conjugate, a fusion-protein, a polypeptide or a pharmaceutical composition of the present invention, neurons may grow (develop) for example new dendrite(s), new axon(s) or new neurite(s) (i.e., cell bud(s)), or already existing dendrite(s), axon(s) or neurite(s) (i.e., cell bud(s)) are induced to grow to a greater extent.

As used herein, the term "vector" refers to an autonomously replicating DNA or RNA molecule into which foreign DNA or RNA fragments are inserted and then propagated in a host cell for either expression or amplification of the foreign DNA or RNA molecule. The term "vector" comprises and is not limited to a plasmid (e.g., linearized or not) that can be used to transfer DNA sequences from one organism to another.

The terms "pharmaceutically acceptable carrier" and "adjuvant" and "physiologically acceptable vehicle" and the like are to be understood as referring to an acceptable carrier or adjuvant that may be administered to a patient, together with a compound of this invention, and which does not destroy the pharmacological activity thereof. Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

As used herein, "pharmaceutical composition" means therapeutically effective amounts (dose) of the agent together with pharmaceutically acceptable diluents, preservatives, solubilizers, emulsifiers, adjuvants and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, and detergents (e.g., Tween 20, Tween 80, Pluronic F68, bile acid salts). The pharmaceutical composition of the present invention can comprise pharmaceutically acceptable solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral routes. In one embodiment the pharmaceutical composition is administered parenterally, paracancerally, transmucosally, transdermally, intramuscularly, intravenously, intradermally, subcutaneously, intraperitonealy, intraventricularly, intracranially intratumorally or more preferably, directly at a central nervous system (CNS) lesion site or a peripheral nervous system (PNS) lesion site.

In addition, the term "pharmaceutically effective amount" or "therapeutically effective amount" refers to an amount (dose) effective in treating a patient, having, for example, a nerve injury. It is also to be understood herein that a "pharmaceutically effective amount" may be interpreted as an amount giving a desired therapeutic effect, either taken in one dose or in any dosage or route, taken alone or in combination with other therapeutic agents. In the case of the present invention, a "pharmaceutically effective amount" may be understood as an amount of ADP-ribosyl transferase C3 or ADP-ribosyl transferase C3 analogues (e.g., fusion proteins) of the present invention which may for example, suppress (e.g., totally or partially) the inhibition of neuronal axon growth, facilitate axon growth, prevent cell apoptosis, suppress Rho activity, help regenerate injured axons, or which may help neurons to make new connections with other cells.

A therapeutically effective amount or dosage of an active agent, e.g. a C3 or C3 analogue protein, may range from about 0.001 to 30 mg/kg body weight, with other ranges of the invention including about 0.01 to 25 mg/kg body weight, about 0.025 to 10 mg/kg body weight, about 0.3 to 20 mg/kg body weight, about 0.1 to 20 mg/kg body weight, about 1 to 10 mg/kg body weight, 2 to 9 mg/kg body weight, 3 to 8 mg/kg body weight, 4 to 7 mg/kg body weight, 5 to 6 mg/kg body weight, and 20 to 50 mg/kg body weight. In other embodiments, a therapeutically effective amount or dosage of an active agent may range from about 0.001 to 50 mg total, with other ranges of the invention including about 0.01 to 10 mg, about 0.3 to 3 mg, about 3 to 10 mg, about 6 mg, about 9 mg, about 10 to 20 mg, about 20-30 mg, about 30 to 40 mg, and about 40 to 50 ing.

In addition, a skilled artisan will appreciate that the pharmaceutical compositions of the present invention may also be formulated for intravenous or subcutaneous administration. For example, single-dose vials can be produced containing about 25, about 40, about 60, about 100, about 150, about 200, about 300, or about 500 micrograms of active agent.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an active compound can include a single treatment or a series of treatments. In one example, a subject is treated with an active compound in the range of between about 0.3 to 10 mg, one time per week for between about 1 to 10 weeks, alternatively between 2 to 8 weeks, between about 3 to 7 weeks, or for about 4, 5, or 6 weeks. It will also be appreciated that the effective dosage of an active compound used for treatment may increase or decrease over the course of a particular treatment.

As used herein, the term "subject" means a patient in need of a treatment. In one embodiment, a subject is a mammal. In another embodiment, a subject is a human.

In addition, a transport agent such as for example, a subdomain of HIV Tat protein, and a homeodomain of Antennapedia may be repeated more than one time in a polypeptide comprising the ADP-ribosyl transferase C3 or ADP-ribosyl transferase C3 analogues. The transport agent region may be either at the amino-terminal region of an ADP-ribosyl transferase C3 or ADP-ribosyl transferase C3 analogues or at its carboxy-terminal region or at both regions. The repetition of a transport agent region may affect (e.g., increase) the uptake of the ADP-ribosyl transferase C3 or ADP-ribosyl transferase C3 analogues by a desired cell.

Heterologous fusion includes new polypeptides made by the fusion of polypeptides of the present invention with heterologous polypeptides. Such polypeptides may include but are not limited to bacterial polypeptides (e.g., betalactamase, glutathione-S-transferase, or an enzyme encoded by the *E. coli* trp locus), yeast protein, viral proteins, phage proteins, bovine serum albumin, chemotactic polypeptides, immunoglobulin constant region (or other immunoglobulin regions), albumin, or ferritin.

Proteins and polypeptides having at least 50% identity, as determined by methods known to those skilled in the art (for example, the methods described by Smith and Waterman, 1981, Ad. Appl. Math., 2:482-489; or Needleman and Wunsch, 1970, J. Mol. Biol., 48: 443-453), to the polypeptides of the invention described herein, are included in the invention. In one embodiment, a polypeptide of the invention has at least about 50%, at least about 55%, preferably at least about 60%, at least about 65%, at least about 70%, at least about 75%, more preferably at least about 80%, at least about 85%, at least about 90%, or at least about 95% identity to the polypeptides described herein. In an embodiment, the identity extends over a region of at least 5, or at least 20, contiguous amino acids.

Unless otherwise indicated, the recombinant DNA techniques utilized in the present invention are standard procedures, known to those skilled in the art. Example of such techniques are explained in the literature in sources such as Perbal, A Practical Guide to Molecular Cloning, John Wiley and Sons (1984); Sambrook et al., Molecular Cloning: A Laboratory Manual, Cold Spring Harbor Laboratory Press (1989); and Ausubel et al. (editors), Current Protocols in Molecular Biology, Greene Pub. Associates and Wiley-Interscience (1988, including all updates until present) and are incorporated herein by reference.

Rho GTPases include members of the Rho, Rac and Cdc42 family of proteins. The present invention concerns Rho family members of the Rho class. Rho proteins consist of different variants encoded by different genes. For example, PC-12 cells (Pheocbromocytom cell line) express RhoA, RhoB and RhoC. To inactivate Rho proteins inside cells, Rho antagonists of the C3 family type are effective because they inactivate all forms of Rho (e.g. RhoA, Rho B etc). In contrast, gene therapy techniques, such as introduction of a dominant negative RhoA family member into a diseased cell, will only inactivate that specific RboA family member.

Recombinant C3 proteins or C3 proteins that retain the ribosylation activity are also effective in the disclosed delivery system and are covered by this invention. In addition, Rho kinase is a well-known target for active Rho, and inactivating Rho kinase has the same effect as inactivating Rho, at least in terms of neurite or axon growth.

The proteins of the present invention may be prepared from bacterial cell extracts, or through the use of recombinant techniques. In general, C3 proteins according to the invention can be produced by transformation (transfection, transduction, or infection) of a host cell with all or part of a C3-encoding DNA fragment in a suitable expression vehicle. Suitable expression vehicles are known in the art and non-limiting examples include, for example: plasmids, viral particles, and phages. For insect cells, baculovirus expression vectors are suitable. The entire expression vehicle, or a part thereof, can be integrated into the host cell genome. In some circumstances, it is desirable to employ an inducible expression vector.

The host cells harboring the expression vehicle can be cultured in conventional nutrient media adapted as need for activation of a chosen gene, repression of a chosen gene, selection of transform ants, or amplification of a chosen gene. One expression system is the mouse 3T3 fibroblast host cell transfected with a pMAMneo expression vector (Clontech, Palo Alto, Calif.).

Those skilled in the field of molecular biology will understand that any of a wide variety of expression systems can be used to provide the recombinant protein. The precise host cell used is not critical to the invention. The C3 and C3-like proteins may be produced in a prokaryotic host (e.g., *E. coli* or *B. subtilis*) or in a eukaryotic host (e.g., *Saccharomyces* or *Pichia*; mammalian cells, e.g., COS, NIH 3T3, CHO, BHK, 293, or HeLa cells; or insect cells).

Proteins and polypeptides may also be produced by plant cells. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.). The methods of transformation or transfection and the choice of expression vehicle will depend on the host system selected.

C3 polypeptides can be produced as fusion proteins. For example, expression vectors may be used to create lacZ fusion proteins. The pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety. Another strategy to make fusion proteins is to use the His tag system.

In an insect cell expression system, *Autographa calfornica* nuclear polyhedrosis virus AcNPV), which grows in *Spodoptera frugiperda* cells, is used as a vector to express foreign genes. A C3 coding sequence can be cloned individually into non-essential regions (for example the polyhedrin gene) of the virus and placed under control of an AcNPV promoter, e.g., the polyhedrin promoter. Successful insertion of a gene encoding a C3 or C3-like protein (polypeptide) will result in inactivation of the polyhedrin gene and production of non-occluded recombinant virus (i.e., virus lacking the proteinaceous coat encoded by the polyhedrin gene). These recombinant viruses are then used to infect *Spodoptera frugiperda* cells in which the inserted gene is expressed.

In mammalian host cells, a number of viral-based expression systems can be utilized. In cases where an adenovirus is used as an expression vector, the C3 nucleic acid sequence can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing a C3 gene product in infected hosts.

Specific initiation signals may also be required for efficient translation of inserted nucleic acid sequences. These signals include the ATG initiation codon and adjacent sequences. These exogenous translational control signals and initiation codons can be of a variety of origins, both natural and synthetic. The efficiency of expression may be enhanced by the inclusion of e.g. appropriate transcription enhancer elements, or transcription terminator, etc.

In addition, a host cell may be chosen which modulates the expression of the inserted sequences, or modifies and processes the gene product in a specific, desired fashion. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used.

Alternatively, a C3 protein can be produced by a stably-transfected mammalian cell line. A number of vectors suitable for stable transfection of mammalian cells are available to the public; methods for constructing such cell lines are also publicly available. In one example, cDNA encoding the C3 protein may be cloned into an expression vector that includes the dihydrofolate reductase (DHFR) gene. Integration of the plasmid and, therefore, the C3 or C3-like protein-encoding gene into the host cell chromosome is selected for by including 0.01-300 µM (micromole) methotrexate in the cell culture medium (as described in Ausubel et al., supra). This dominant selection can be accomplished in most cell types. Recombinant protein expression may be increased by DHFR-mediated amplification of the transfected gene. Methods for selecting cell lines bearing gene amplifications are known in the art; such methods generally involve extended culture in medium containing gradually increasing levels of methotrexate. DHFR-containing expression vectors commonly used for this purpose include pCVSEII-DHFR and pAdD26SV(A). Any of the host cells described above or, preferably, a DHFR-deficient CHO cell line (e.g., CHO DHFR cells, ATCC Accession No. CRL 9096) are among the host cells preferred for DHFR selection of a stably-transfected cell line or DHFR-mediated gene amplification.

A number of other selection systems may be used, including but not limited to the herpes simplex virus thymidine kinase, hypoxanthine-guanine phosphoribosyltransferase, and adenine phosphoribosyltransferase genes, which can be employed in tk, hgprt, or aprt cells, respectively. In addition, gpt, which confers resistance to mycophenolic acid; neo, which confers resistance to the aminoglycoside G-418; and hygro, which confers resistance to hygromycin may be used.

Alternatively, any fusion protein can be readily purified by utilizing an antibody specific for the fusion protein being expressed. For example, a system described in Janknecht et al. (1981) Proc. Natl. Acad. Sci., USA 88, 8972, allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, C3, C3-like protein or a portion (fragment) thereof, can be fused to an immunoglobulin Fc domain. Such a fusion protein can be readily purified using a protein A column.

To determine the relative and effective Rho antagonist activity of the compositions of this invention, a tissue culture bioassay system can be used. For example, a fusion protein such as SEQ ID No: 8 at a concentration range of from about 0.01 to about 10 µg/ml (microgram per milligram) is useful and is not toxic to cells.

A compound can be confirmed as a Rho antagonist in for example, one of the following ways:
 a. Cells are cultured on a growth inhibitory substrate as above, and exposed to the candidate Rho antagonist;
 b. Cells of step a) are homogenized and a pull-down assay is performed. This assay is based on the capability of GST-Rhotektin to bind to GTP-bound Rho. Recombinant GST-Rhotektin or GST rhotektin binding domain (GST-RBD) is added to the cell homogenate made from cells cultured as in a). It has been found that inhibitory substrates activate Rho, and that this activated Rho is pulled down by GST-RBD. Rho antagonists will block activation of Rho, and therefore, an effective Rho antagonist will block the detection of Rho when cells are cultured as described by a) above; or
 c. An alternate method for this pull-down assay would be to use the GTPase activating protein, Rho-GAP as bait in the assay to pull down activated Rho.

Another method to confirm that a compound is a Rho antagonist is as follows: when added to living cells antagonists that inactivate Rho by ADP-ribosylation of the effector domain can be identified by detecting a molecular weight shift in Rho. The molecular weight shift can be detected after treatment of cells with Rho antagonist by homogenizing the cells, separating the proteins in the cellular homogenate by SDS polyacrylamide gel electrophoresis. The proteins are transferred to nitrocellulose paper, then Rho is detected with Rho-specific antibodies by a Western blotting technique.

Other transport agents which may be used in conjugates of the present invention are known in the art. For example, the polypeptides of the present invention may include a transport agent such as a subdomain of HIV Tat protein, or a homeodomain of Antennapedia. The transport sequence may include a region consisting of basic amino acids, such as a polyarginine sequence. The transport agent may be repeated more than once in a polypeptide. The transport agent may be located at the amino-terminal region or at the carboxy-terminal region or at both regions in the conjugate. Duplication of a transport agent may affect (e.g., increase) the uptake of the conjugate by a cell.

In an embodiment, a transport agent facilitates uptake of an active agent by a receptor-independent mechanism. In another embodiment, examples of transport sequences include, but are not limited to, SEQ ID NOs: 45-51. Other transport agents encompassed by the present invention include, without limitation: the third helix of the homeodomain of Antennapedia protein (Penetratin™; SEQ ID NO: 52); TAT (SEQ ID NO: 53); Silaproline conjugates; gamma-amino-L-proline oligomers; polyarginine (SEQ ID NO: 54); Transportan (SEQ ID NOs: 55-56); Pep-1 (SEQ ID NO: 57); $S4_{13}$-PV (SEQ ID NO: 58); VP22 protein; MAO (Model sunthic peptide; SEQ ID NO: 59); SynB1 (SEQ ID NO: 60); SynB3 (SEQ ID NO: 61); SynB5 (SEQ ID NO: 62); b-FGF; FGF-4 signal sequence (SEQ ID NO: 63); pVEC (SEQ ID NO: 64); SAP sweet arrow peptide; hCT(9-32)-br human calcitonin derived peptide; bPrPp (prion protein N-term; SEQ ID NO: 65); BagP peptide; *Mycobacterium* cell entry protein (Mce1A); Synthetic peptides YTA2 and YTA4; SEQ ID NO: 66; C105Y (corresponding to amino acids 359-374 of alpha1-antitrypsin; SEQ ID NO: 67), TP10; dynorphins A and B; and Diatos peptide vectors (Vectocell®; SEQ ID NOs: 68-77).

Other transport sequences that have been tested in other contexts, (i.e., to show that they work through the use of reporter sequences), are known. One transport peptide, a 12 mer, AAVLLPVLLAAP (SEQ ID NO: 3), is rich in proline. It was made as a GST-MTS fusion protein and is derived from the h region of the Kaposi FGF signal sequence. Another example is the sperm fertiline alpha peptide, HPI-QIAAFLARIPPISSIGTCILK (SEQ ID NO: 4). It must be noted however that the alpha helix-breaking propensity of proline (Pro) residues is not a general rule, since the putative fusion peptide of sperm fertilin alpha displays a high alpha helical content in the presence of liposomes. However, the Pro-Pro sequence is required for efficient fusion properties of fertilin. The SEQ ID No: 8 fusion protein that was tested fits the requirement of having two prolines for making an effective transport peptide. Therefore, proline-rich sequences and random sequences that have helix-breaking propensity that act as effective transporters would also be effective if fused to C3.

Referring to FIG. 1, the intentional inactivity of a mutant of the SEQ ID No: 43 fusion protein, i.e., inactive SEQ ID NO: 6 (nucleotide sequence corresponds to SEQ ID NO: 5), as assayed by a bioassay with NG-108 cells is illustrated. NG-108 cells cultured with an active fusion protein of this invention, SEQ ID NO: 43, exhibit accelerated neurite outgrowth, which neurite-outgrowth is the result of the presence of SEQ ID NO: 43. However, neurite outgrowth of cells treated with intentionally inactive mutant SEQ ID NO: 6 is similar to that of the control cells which are not treated with additional protein. The similarity to the control group demonstrates that the intentionally inactive mutant protein SEQ ID NO: 6 is inactive with respect to stimulation of neurite outgrowth.

An injection of a fusion protein of this invention, SEQ ID NO: 43, can prevent (substantially reduce the observed rate of) death of retinal ganglion cells (RGCs) induced by crush of the optic nerve following a single injection. After axotomy or axotomy of the optic nerve with injection of vehicle (phosphate buffered saline), cells die. When SEQ ID NO: 6, an intentionally inactive mutant of SEQ ID NO: 43, is injected into the eye it is not able to prevent death of the RGCs. A single injection of SEQ ID NO: 43 prevents cell death and the number of surviving cells is similar to that in control, non-axotomized retinas. The results demonstrate that SEQ ID NO: 43 as a fusion protein of this invention can prevent death of retinal neurons; the neuroprotective activity of SEQ ID NO: 43 requires that the enzymatic activity of the C3 fusion protein is retained.

Administration of a pharmaceutical composition comprising a fusion protein of the invention to a patient in need of treatment for macular degeneration, can substantially reduce or prevent angiogenesis associated with subretinal neovascularization, choroid neovascularization underlying the macula, and a proliferation of neovascular tissue in the subretinal choroid proximal to the macula in an eye in a mammalian host. In one aspect, the invention relates to a method of treatment of macular degeneration. In another aspect, the compositions of the invention are useful for inhibiting or substantially reducing the rate of subretinal neovascularization and proliferation of neovascular tissue related to macular degeneration. The method can be useful as a prophylactic treatment to prevent further onset or progression of macular degeneration in an eye. In another aspect, the method can be useful as a prophylactic treatment to prevent the deposition of drusen and the death of cells in the macula. In another aspect, the method can prevent the death of photoreceptor cells (which photoreceptor cells are also herein referred to as photoreceptors) in the eye of a patient by acting on intracellular mechanisms of the regulation of cell death. The method can also be useful to prevent onset or progression of macular degeneration in an eye that does not exhibit vision-obscuring symptoms of macular degeneration, especially in an eye of a patient whose other eye does exhibit vision-obscuring symptoms of macular degeneration.

In another aspect of the invention, a method of treatment of macular degeneration, comprises administration such as by injection or implantation into tissue proximal to the eye of a therapeutically effective amount of a polypeptide of the invention. In addition, the invention comprises administration of a sterile pharmaceutical composition of the invention suitable for injectable administration and comprising a polypeptide of the invention and a carrier suitable for injectable use (e.g., sterile, sterilizable, and isotonic with blood), which polypeptide or pharmaceutical composition can prevent or delay the onset of angiogenesis associated with the group consisting of subretinal neovascularization, choroid neovascularization underlying the macula, and a proliferation of neovascular tissue in the subretinal choroid proximal to the macula in an eye of an average patient in a statistically relevant population of patients to produce a mean delay in the onset of vision loss. Delay in the onset of vision loss can result from said angiogenesis, and the mean delay of onset being measured relative to the mean time of onset of vision loss that occurs in an average patient in the statistically relevant population of patients in the absence of said amount of polypeptide, the mean delay in the onset of vision loss comprising a period of at least 1 month, and more preferably a period of at least 6 months, and most preferably a period of greater than 6 months.

Inhibition of angiogenesis by a pharmaceutical composition comprising a fusion protein of this invention such as SEQ ID NO: 8 (corresponding nucleotide sequence corresponds to SEQ ID NO: 7) can be evaluated in an in vitro system that can also be useful for the study of angiogenesis in the growth of a tumor, i.e., a system comprising cultivation of endothelial cells in the presence of an extract of basement membrane (MATRIGEL®) as a model for angiogenesis and for neovascularization and proliferation of neovascular tissue in the eye of a mammal. Under experimental conditions, capillary-like structures or tubules associated with angiogenesis or blood vessel capillary formation can be viewed under a microscope. The inhibitory effect of a fusion protein of this invention such as SEQ ID NO: 8 on the progress of angiogenesis or on the formation of a tubular capillary network or on the disruption of the process or progress of tumor-associated angiogenesis can be observed by following the disappearance of tubular structures in a MATRIGEL® assay.

MATRIGEL® Matrix (BD Biosciences) is a solubulized basement membrane preparation extracted from Engelbreth-Holm-Swarm (EHS) mouse sarcoma, a tumor rich in extracellular matrix (ECM) proteins. Its major components are laminin, collagen IV, heparan sulfate proteoglycans, and entactin. At room temperature, BD MATRIGEL® Matrix polymerizes to produce biologically active matrix material which can mimic mammalian cellular basement membrane, wherein cells can behave in vitro in a manner similar to in vivo conditions. MATRIGEL® Matrix can provide a physiologically relevant environment for studies of cell morphology, biochemical function, migration or invasion, and gene expression.

In a MATRIGEL® assay, MATRIGEL® (about 12.5 mg/mL) is thawed at about 4° C. The matrix (about 50 microliters (uL)) is added to each well of a 96 well plate and allowed to solidify for about 10 min at about 37° C. The wells containing solid MATRIGEL® are incubated for about 30 minutes with human umbilical vein endothelial cells (HUVEC cells) at a concentration of about 15,000 cells per well. When the cells are adhered, medium is removed and replaced by fresh medium supplemented with a fusion protein of this invention such as SEQ ID NO: 8 and incubated at 37° C. for about 6 to about 8 hours. Control wells are incubated with medium alone. To analyze the growth, tube formation can be visualized by microscopy at, for example, about 50× magnification. The relative mean length, Yx, of an angiogenesis-derived capillary network observed in an evaluation of a pharmaceutical composition comprising a fusion protein, x, of this invention can be quantified using Northern Eclipse software according to the instructions.

Construction of SEQ ID NO: 10, a Truncated Variant of SEQ ID NO: 43

SEQ ID NO: 10, with the corresponding nucleotide sequence of SEQ ID NO: 9, is a derivative of SEQ ID NO: 43 (FIG. 2). SEQ ID NO: 43 is a derivative of SEQ ID NO: 8, lacking the GST sequence.

C3 exoenzyme does not possess the specific receptor-binding and translocation domains typical of other bacterial toxins. Hence, cellular uptake is slow and non specific, being mainly driven by pinocytosis. SEQ ID NO: 44 is a fusion protein that is obtained by linking C3 exoenzyme to a proline-rich transport sequence that facilitates crossing of the plasma membrane in a receptor-independent fashion. This engineered fusion protein is shown to be >100 fold more efficient than C3 when tested in vitro by neurite outgrowth assay.

In order to improve the purity and yield of C3 preparations, SEQ ID NO: 44 is removed from the GST fusion protein pGEX-4T vector and transferred into a pET vector. The resulting fusion protein, SEQ ID NO: 43, is purified by fast-protein liquid chromatography (FPLC) using standard chromatography steps. The purified protein is >95% pure, low in endotoxin (<2 units/mg), stable at −70° C. for >2 years and presented equivalent of higher glycohydrolase and neurite outgrowth activities compared to SEQ ID NO: 44.

To stabilize the final product for cGMP manufacturing an additional variant, SEQ ID NO: 10, is constructed. A sequence of 15 amino acids, comprising 8 residues of the native C3 signal sequence and 7 amino acids derived from a vestigial multiple cloning site, are removed from the N-terminus of SEQ ID NO: 44. The N-terminus of the resulting SEQ ID NO: 10 is nearly identical to that of the WT enzyme following endogenous cleavage of the native signal sequence by C. botulinum. An alignment of N-termini of WT C3 exoenzyme (Swiss-Prot entry P15879), SEQ ID NO: 10 and SEQ ID NO: 43 wherein the amino acid residues indicated in italics represent the endogenously cleaved signal peptide of WT C3 exoenzyme, while those in bold have been engineered is shown in FIG. 2A. Further, a schematic representation of variants is shown in FIG. 2B.

SEQ ID NO: 10 is more stable than its predecessor SEQ ID NO: 44. Although SEQ ID NO: 44 produced at lab scale showed no evidence of degradation, even after several weeks of storage at 4° C., the same is not true of SEQ ID NO: 44 produced at large scale. Size exclusion HPLC or non-reducing SDS-PAGE revealed that SEQ ID NO: 44 spontaneously formed dimers that were sensitive to the reducing agent dithiothreitol (FIG. 2C). More specifically, a pre-cast 12% gradient gel (non-reducing) showing dimerization of SEQ ID NO: 44 wherein lane 1=Bio-Rad™ low-range molecular weight protein standards, lane 2=lab-scale SEQ ID NO: 44 taken from −80° C. storage, lane 3=lab-scale SEQ ID NO: 44 stored for 5 days at 4° C., lane 4=lab-scale SEQ ID NO: 44 stored for 5 days at 4° C. in the presence of 0.5 mM DTT, is shown in FIG. 2C. These data suggest that intermolecular disulfide bonding is occurring via the single cysteine residue within the N-terminus. While dimerization is never found to influence the functional activity of SEQ ID NO: 44, its elimination would significantly facilitate the process of large-scale purification by removing the need for reducing agents. In addition, following purification of SEQ ID NO: 44 from high density bioreactor fermentations, there is a second major band on SDS-PAGE that is confirmed by mass spectroscopic analysis to be due to an N-terminal cleavage in bacterial lysates (FIG. 2D). More specifically, in the pre-cast 12% gradient gel (reducing), the enhanced stability of SEQ ID NO: 10 is shown, wherein lane 1=Bio. Rad™ low-range molecular weight protein standards, lane 2=lab-scale SEQ ID NO: 44 taken from −80° C. storage, lane 3=lab-scale SEQ ID NO: 44 stored for 8 weeks at 4° C., lane 4=bioreactor-generated SEQ ID NO: 44 stored for 10 weeks at 4° C., lane 5=bioreactor-generated SEQ ID NO: 10 taken from −80° C. storage, and lane 6=bioreactor-generated SEQ ID NO: 10 stored for 2 weeks at 4° C. (FIG. 2D). Thus, an N-terminally truncated variant, SEQ ID NO: 10, was created which showed neither degradation nor dimerization (FIG. 2D) following storage at 2-8° C. Long-term testing confirmed that this variant retains full activity and stability even after more than 18 months of storage at −70° C. and 2-8° C. (data not shown). The purified protein is >95% pure and low in endotoxin (<2 units/mg) (FIG. 2E). A pre-cast 12% gradient gel (reducing) showing representative purification of variant (SEQ ID NO: 44) is shown in FIG. 2E, wherein lane 1=Bio-Rad™ low-range molecular weight protein standards, lane 2=crude cell lysate, lane 3=supernatant following Polymin P treatment, lane 4=resuspended pellet following ammonium sulfate treatment, lane 5=PD-10 desalting column load, lane 6=SP-XL load, lane 7=SP-XL eluate peak, lane 8=Superdex-75 eluate peak, lane 9=HiPrep desalting eluate, lane 10=Q-sepharose eluate and lane 11=final concentrated pool.

SEQ ID NO: 10 manufactured at large scale is functionally interchangeable with its predecessors, SEQ ID NOs: 43 and 44, having the same or better enzymatic and biological activities but fewer impurities such as endotoxin.

Construction of Truncated Variants of SEQ ID NO: 10

Variants of SEQ ID NO: 10 were derived by deleting successive groups of amino acid residues from either the N- or C-terminus, not including the transport peptide sequence. These variants are illustrated in FIG. 3. The variants were created by site-directed mutagenesis, using standard molecular biology methods, to truncate the cDNA encoding SEQ ID NO: 10, either at the N-terminal region or at the C-terminal region, leaving the transport sequence intact. The activity of the truncated variants disclosed herein can be verified using any of the methods described herein, e.g. those described in Examples 9-13 and 18. Without wishing to be bound by theory, it is believed that truncated variants may penetrate into cells more easily, and therefore require lower doses. In one embodiment of the invention therefore, a shorter or truncated fragment of biologically active SEQ ID NO: 10 is administered to a subject in need thereof.

In addition, physical characteristics of SEQ ID NO: 10 variants are disclosed in Table 1.

TABLE 1

Physical characteristics of truncated SEQ ID NO: 10 variants.

| SEQ ID NOs of variants | # of Amino Acids | % Sequence Identity with SEQ ID NO: 43 | Predicted Molecular Weight (kDa)[1] | Theoretical Extinction Coefficient (Abs 0.1% at 280 nm)[2] | Predicted pI[1] |
|---|---|---|---|---|---|
| 10 | 232 | 94 | 25.9 | 0.72 | 9.7 |
| 13 | 222 | 90 | 24.6 | 0.65 | 9.8 |
| 14 | 212 | 86 | 23.6 | 0.44 | 9.8 |
| 15 | 202 | 82 | 22.4 | 0.34 | 9.7 |
| 16 | 192 | 78 | 21.2 | 0.3 | 9.8 |
| 17 | 182 | 74 | 20.2 | 0.32 | 9.7 |
| 18 | 154 | 62 | 17 | 0.38 | 9.5 |
| 19 | 121 | 49 | 13.3 | 0.38 | 9.9 |
| 20 | 203 | 82 | 22.7 | 0.76 | 9.8 |
| 21 | 214 | 87 | 24 | 0.77 | 9.7 |
| 22 | 224 | 91 | 25 | 0.74 | 9.7 |

[1]From Expasy ProtParam web site (http://ca.expasy.org/cgi-bin/protparam);
[2]New algorithm on ProtParam web site changes previously obtained values.

Deletion mutants or variants are prepared by polymerase chain reaction and subcloned into pET9a vector. Two oligonucleotides are designed per variant to delete the desired amino acids by site-directed-mutagenesis using the QuikChange (Stratagene) kit. Polymerase chain reaction is carried out with the appropriate mutant primer set (see Table 2). The cycle program is as follows: 95° C. for 30 sec, 18 cycles of 95° C. for 30 sec., 55° C. for 1 min., and 68° C. for 10 min., and hold at 4° C.

TABLE 2

Primer and sequence information for truncated SEQ ID NO: 10 variants.

| SEQ ID NOs of variants | Primer set | DNA Sequence # | SEQ ID Nos of primers |
|---|---|---|---|
| 10 | — | AJ5858-2 | |
| 13 | MD3-13F/MD3-13R | MD13-2 | 23-24 |
| 14 | MD3-23F/MD3-23R | MD23-1 | 25-26 |
| 15 | MD3-33F/MD3-33R | MD33-1 | 27-28 |
| 16 | MD3-43F/MD3-43R | MD43-3 | 29-30 |
| 17 | MD3-53F/MD3-53R | MD53-2 | 31-32 |
| 18 | MD3-81F/MD3-81R | MD81-1 | 33-34 |
| 19 | MD3-114F/MD3-114R | MD114-1 | 35-36 |
| 20 | MD183-211F/MD183-211R | MD183-1 | 37-38 |
| 21 | MD194-211F/MD194-211R | MD194-1 | 39-40 |
| 22 | MD204-211F/MD204-211R | MD204-1 | 41-42 |

The primers for the truncation mutants were synthesized at Bio S&T and were supplied as lyophilized powder. After resuspension, the concentrations of the primers were verified spectrophotometrically. A mutagenesis reaction was performed using the above primers according to the instructions provided with the QuikChange Kit. Analyses of the reactions on a 0.8% agarose gel verified that the reactions were successful.

DpnI digestion and transformation of XL-1 Blue supercompetent cells with 1 µL of this product is done according to the manufacturer's instructions. Three clones from each transformation are grown overnight for a plasmid miniprep. One DNA sample from each of the SEQ ID NO: 10 truncated mutants was sent for DNA-sequencing. The sequencing data are analyzed by NCBI's Blast2 sequence analyses software and found to align 100% with the predicted C3 variant coding sequences, except for MD43-1.

Each of the verified DNA samples is used to transform BL21 (DE3) competent cells (One-Shot BL21 (DE3), Invitrogen) with plasmid DNA according to the manufacturer's instructions. Three colonies from each clone are transferred into separate LB-media containing 30 µg/ml Kanamycin) for mini-scale induction analyses. The protein gels are run and the Coomassie stained bands are quantified using scanning densitometry.

The best expressing clone from each truncated mutant is inoculated for large scale expression and purification. First, a flask of 0.5 l Luria Broth with glucose is inoculated with 2 vials of research cell bank (RCB) of and grown overnight. The starter culture is diluted 10-fold into 8 flasks each containing 500 ml of growth medium. The flasks are incubated at 37° C. and after 1 hour 20 min, isopropylthio-B-D-galactoside (IPTG) is added to increase the expression of the variant. After a further 4 hours, the cells are harvested by centrifugation and stored at −80° C. until required. A sample of the harvested culture is analyzed for truncated SEQ ID NO: 10 variants content. Next, the cell pellets are thawed and sonicated in extraction buffer. These crude extracts are purified to approximately 90% purity via SP-Sepharose Fast-Flow 1 ml columns (HiTrap SP FF, Pharmacia). The resulting protein solutions are concentrated by ultrafiltration and then passed through a 0.2 micrometer filtration membrane prior to freezing. Aliquots are analyzed by $A_{280}$ to determine the protein concentration and by scanning densitometry of samples run on SDS-polyacrylamide gels stained with Coomassie Blue to determine purity. Biological activity is assessed using both a fluorescence based enzymatic (glycohydrolase) assay and a cell-based neurite outgrowth assay.

The bioactivity of C3 variants can be determined using a glycohydrolase assay which measures the formation of F-ADP-ribose produced as a result of hydrolysis of ϵ-NAD by C3-variants. Glycohydrolase activity of C3-variants converts ϵ-NAD$^+$ into ϵ-ADP-ribose, a molecule with 10 times higher fluorescence intensity at the selected wavelengths. The fluorescence intensity of ϵ-ADP-ribose is used to measure the amount of ϵ-ADP ribose formed by using a standard curve of fluorescence of known concentrations of ϵ-AMP. The fluorescence intensities of ϵ-AMP and ϵ-ADP-ribose are measured by exciting the reaction at 305 nm and recording the emission at 410 nm. A unit of activity is defined as nmoles ADP-ribose formed in 30 min at 37° C. The assay is linear with up to at least 12 µg of C3-variant protein and up to at least 180 min of incubation time. This assay has been found to be precise, accurate and reproducible. This assay has also been found to be useful in measuring decreases in enzymatic activity after incubation at 70° C., and can be considered to be stability-indicating when used in a well-designed stability study. Other methods which can be used to measure the bioactivity of C3 variants are described in the ale (for example, see Winton et al., 2002, J Biol Chem, 277: 32820-32829).

The bioactivity of C3 variants can also be determined using an NG108 cell neurite outgrowth bioassay. The procedure for the bioassay comprises incubation of NG-108 cells for 4 hours with an aliquot of a buffered solution containing C3 variant. A simultaneous and otherwise identical bioassay is run as a positive control, wherein SEQ ID NO: 10 is used in place of C3 variant. The cells are then fixed with paraformaldehyde, stained with cresyl violet, and the percentage of cells in each well that demonstrated neurites greater than one cell body in length is determined by counting under the microscope. Results shown (Table 3) are based on triplicate measurements of at least two separate experiments.

TABLE 3 eNAD glycohydrolase and neurite outgrowth activities of N-and C-terminal truncation mutants of SEQ ID NO: 10.

| Sample | GH (Mean Spec. Act.) | Neurite Outgrowth (Mean Fold Control) |
|---|---|---|
| SEQ ID NO: 10 | 29 | 70 |
| SEQ ID NO: 13 | 26 | 73 |
| SEQ ID NO: 14 | 2 | 35 |
| SEQ ID NO: 15 | 0 | 0 |
| SEQ ID NO: 16 | 0 | — |
| SEQ ID NO: 17 | 25 | 22 |

These data indicate that the demonstrated minimal functional size of N-terminally truncated SEQ ID NO: 10 is 212 amino acids, and that of C-terminally truncated SEQ ID NO: 10 is 224 amino acids. The expected double-deletion of amino acids from both termini would produce a functional variant of just over 204 amino acids. Examples of double deletion variants encompassed by the present invention include, without limitation, SEQ ID NOs: 78 and 79.

PEGylated Variants of SEQ ID NO: 10

SEQ ID NO: 10 molecule is modified by chemically coupling it to polyethylene glycol moieties to enhance the biological residence properties (Table 4). PEGylation is the act of covalently coupling a PEG structure to another larger molecule, for example, a therapeutic protein or polypeptide (which is then referred to as "PEGylated"). As is known in the art, when attached to various proteins or polypeptides, poly (ethylene glycol) can delay clearance of the carried protein from the blood. This may lead to a longer-acting medicinal effect and/or reduce toxicity, and may therefore allow longer dosing intervals. The activity of the PEGylated variants disclosed herein can be verified using any of the methods described herein, e.g. those described in Examples 9-13 and 18.

TABLE 4

PEGylated variants of SEQ ID NO: 10

| Variant | PEG Adduct | Observed MW (kDa) |
|---|---|---|
| SEQ ID NO: 10 | — | 27 |
| BA-220 | Mono-2.4 kDa | 33 |
| BA-225 | Mono-6.3 kDa | 39 |
| BA-230 | Mono-21 kDa | 61 |
| BA-231 | Di-21 kDa | 83 |
| BA-235 | Mono-30 kDa | 64 |
| BA-236 | Di-30 kDa | 112 |
| BA-240 | Mono-40 kDa | 86 |

PEGylation and Purification of SEQ ID NO: 10 Using mPEG-ButyrALD

N-terminal PEGylation of SEQ ID NO: 10 can be carried out using commercially available in PEG-butyraldehyde reagents (Nectar Therapeutics) supplied in pre-weighed, sealed aliquots. A typical reaction begins by diluting SEQ ID NO: 10 (in sodium citrate buffer, pH 6.5) to a final concentration of 3.3 mg/in L in degassed 0.1M sodium citrate-NaOH, 0.5 M EDTA at pH 5.0. Immediately prior to starting the PEGylation reaction, the mPEG-ButyrALD reagents are dissolved in fresh MilliQ water to achieve the desired concentration. The degree of PEGylation is controlled using a combination of reaction time, pH and ratio of mPEG-ButyrALD reagent-to-SEQ ID NO: 10. For example, mono-PEGylation at the N-terminus is favored using a ratio of 1:1 at pH 5.5. Alternatively, di- or multi-PEGylated forms are generated using higher mPEG-ButyrALD reagent-to-SEQ ID NO: 10 ratios (130:1 for 2.4 kDa mPEG-ButyrALD; 20:1 for 6.3 kDa mPEG-ButyrALD; and 2:1 for 21 kDa in PEG-ButyrALD).

An aliquot of the in PEG-ButyrALD solution is added to the SEQ ID NO: 10 solution, mixed gently, and allowed to incubate for one hour at 37° C. with inversion at each 30 min interval. After one hour, and again after two hours, the reactions are supplemented with fresh aliquots of the PEGylation reagent. The reactions were allowed to incubate for a third hour, after which they are quenched by the addition of 85 µL of 1M sodium cyanoborohydride [Na(CN)BH$_3$] and left for an overnight incubation at RT in order to reduce the intermediate Schiff's base to a stable secondary amine linkage. Under optimal conditions, ~25% conversion of SEQ ID NO: 10 to PEGylated SEQ ID NO: 10 can be obtained (see Table 5).

TABLE 5

Yield of Various PEGylated BA -210 variants.

| Sample | Volume (mL) | Concentration (mg/mL) | Yield (mg) | % of Initial SEQ ID NO: 10 |
|---|---|---|---|---|
| BA-230 | 0.82 | 5.80 | 4.76 | 24 |
| BA-231 | 0.08 | 4.54 | 0.36 | 2 |
| BA-235 | 0.51 | 8.22 | 4.19 | 21 |
| BA-236 | 0.16 | 3.55 | 0.57 | 3 |
| BA-240 | 0.72 | 5.46 | 3.89 | 19 |

Figure 5:
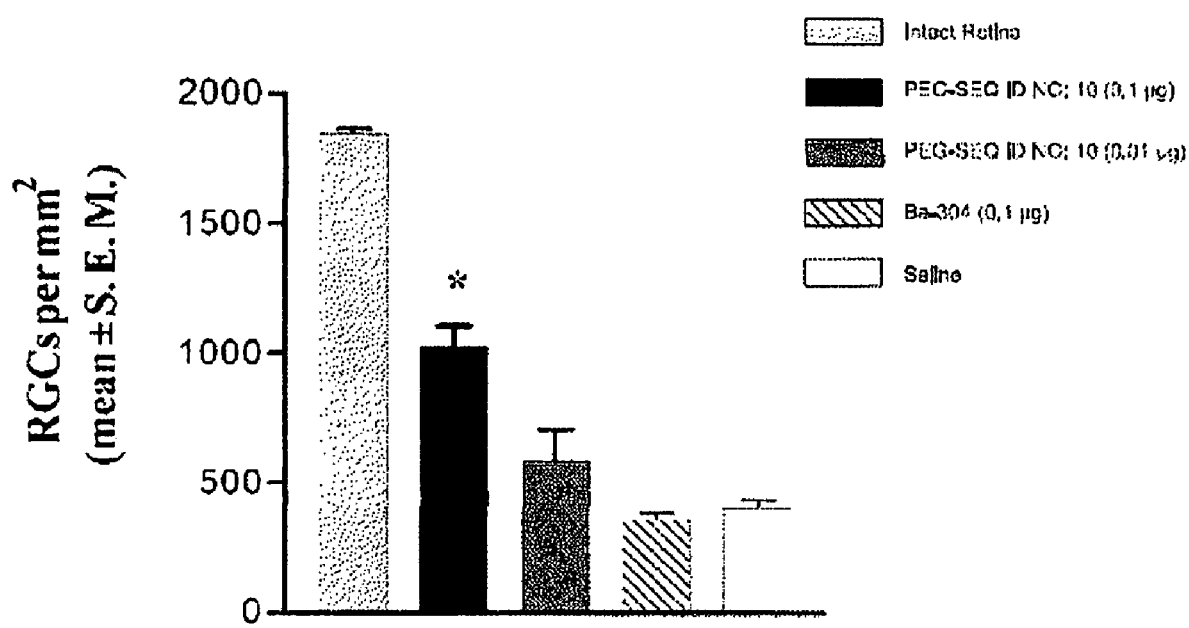
FIG. 5 illustrates Neuroprotective effect of SEQ ID NO: 10 in glaucomatous retinas. *: $P<0.0001$ (ANOVA)

SP-Sepharose Fast-Flow 1 ml (HiTrap SP FF, Pharmacia) cation-exchange columns are used to purify PEGylated SEQ ID NO: 10. Whereas unreacted, non-PEGylated SEQ ID NO: 10 binds tightly to the resin; PEGylated SEQ ID NO: 10 forms (depending on the number of PEG moieties bound) bind less strongly to the resin. The binding buffer consisted of 0.05M HEPES, 0.075M NaCl, 0.5 mM EDTA, pH 7.5. Elution is carried out by the gradual addition of NaCl using a 0-0.16M NaCl linear gradient. FPLC fractions containing the various PEGylated forms are pooled, concentrated using Amicon YM-10s and then dialyzed against 5 mM sodium citrate, pH 6.5, using a Slide-A-Lyser 10 kDa cutoff dialysis cassette. Analyses of Coomassie stained SDS-PAGE gels revealed that some of the purified concentrated samples still contained a small amount of unreacted SEQ ID NO: 10 in all three purifications. Therefore, concentrated samples are re-purified by FPLC using HiTrap SP FF 1 ml columns. The elution profile from re-purification of a 2 kDa PEGylated sample showed semi-resolved peaks while that from a 6 kDa sample showed two well separated peaks (FIGS. 5A and B). The fractions from three purifications are analyzed on NuPAGE gels and pure fractions are pooled.

Anti-Metastatic Properties of a Pharmaceutical Composition Comprising a Fusion Protein of this Invention In another aspect of the present invention, a pharmaceutical composition comprising a fusion protein of this invention can be administered, for example by injection or by a topical application such as by a coating method or other method as described herein to a tissue proximal to or comprising a first tumor in a mammal in need of treatment and can inhibit migration of a metastatic tumor cell in the mammal, the tumor cell originating from a site of the first tumor in the mammal, to a site in healthy or normal tissue of the mammal which is functionally related and proximal to the tissue in which the first tumor resides. For example, a pharmaceutical composition comprising a fusion protein of this invention can be administered to a kidney tissue proximal to or comprising a kidney tumor in a mammal and can inhibit migration of a metastatic kidney tumor cell from the tumor in the kidney to healthy tissue in the same kidney in which the first tumor resides.

In another aspect, a pharmaceutical composition comprising a fusion protein of this invention can be administered, for example by injection or by coating or other method as described herein to a tissue proximal to or comprising a first tumor in a mammal in need of treatment, and can inhibit migration of a metastatic tumor cell in the mammal, the tumor cell originating from a site at the first tumor in the mammal, to a site in a healthy or normal tissue or organ in the mammal that is functionally separate from or remote from the tissue in which the first tumor resides. For example, a pharmaceutical composition comprising a fusion protein of this invention can be administered to a tissue in the brain comprising a brain tumor, and can inhibit migration of a metastatic brain tumor cell into healthy tissues elsewhere in the body such as liver, spleen or lung tissue.

In another aspect, after administration of a pharmaceutical composition comprising a fusion protein of this invention to a patient in need of treatment, metastatic migration of a malignant tumor cell is prevented or inhibited, and can substantially reduce or completely prevent formation of a secondary tumor and can prevent the spread of malignant cancer in a patient.

Demonstration that a Fusion Protein of this Invention Such as SEQ ID NO: 43 can Reduce Cell Motility The therapeutic effectiveness of a pharmaceutical composition comprising a fusion protein of this invention (such as SEQ ID NO: 44) as an anti-metastatic agent can be demonstrated, for example quantitatively, by means of an in vitro two-dimensional cell invasion assay. In one such assay, inhibition of metastatic migration ability of a malignant cell can be measured through the use of purchased Boyden chambers. Boyden chambers have 2 compartments, wherein the upper and lower compartments are separated by a membrane. The extent of cell migration is measured by plating a total number of cells in the upper compartment, and counting the fraction of that total number of cells that migrate to the lower compartment. Growth factors can be added to the lower compartment to enhance cell migration. This model is useful as a model of cancer cell migration in vivo in a mammal. To test the ability of a pharmaceutical composition comprising a fusion protein of this invention (such as SEQ ID NO: 43) in sterile phosphate buffered saline that is isotonic with blood of a mammal) to block migration of tumor cells, the composition comprising SEQ ID NO: 43 is added at different concentrations of SEQ ID NO: 43 to the cancer cells in the upper compartment. The fraction of the total number of cells that migrate to the lower compartment in the presence of fusion protein composition are counted and compared with controls in which the fusion protein is at zero concentration. The number of cancer cells that migrate in a control experiment models such migration in a cancer patient who is not treated with a composition of this invention. The number of cancer cells that migrate in the presence of an aliquot of a composition of this invention models such migration in a cancer patient who is treated with an aliquot of a composition of this invention. The difference between the latter and the control experimental cell migration numbers can be expressed in percent and can range from 100% (i.e., complete inhibition of migration of a metastatic cell) to about 5%, preferably from 100% to about 50%, more preferably from about 100% to about 75%, and most preferably from about 100% to about 90%. A 0% amount can be observed when a first control vehicle is compared with a second control vehicle which may be the same as the first control vehicle. A calculation of this percent is given by solving the expression={(number of cells migrating in the control minus number of cells migrating in the presence of fusion protein) divided by (number of cells migrating in the control)} times 100%.

The therapeutic effectiveness of a pharmaceutical composition comprising a fusion protein of this invention (such as SEQ ID NO: 44) as an anti-metastatic agent can be demonstrated at least qualitatively and in one aspect by means of an in vitro three-dimensional cell invasion assay. In one such assay, inhibition of metastatic migration ability of a malignant cell can be measured by the change in the relative ability of a malignant cell to migrate through a MATRIGEL® matrix after treatment of the cell with a pharmaceutically acceptable formulation of this invention comprising a fusion protein of this invention in a carrier vehicle relative to the ability of the malignant cell to migrate through the MATRIGEL® matrix after treatment with the carrier vehicle as a reference control, the carrier vehicle containing no fusion protein. In one aspect, a fusion protein of this invention can inhibit migration of a metastatic tumor cell in a tissue matrix model to produce an inhibitory change as a reduction in rate of migration of the cell or as a reduction in the distance of migration of the cell in a time period.

The relative change in the distance of migration of a malignant cell through a model matrix is equal to the difference in the distance of migration of a cell in the presence of the fusion protein plus vehicle and the distance of migration of the cell in the presence of a control vehicle in the absence of the fusion protein, the difference divided by the distance of migration of the control vehicle. The relative changes can be expressed in percent and can range from 100% (complete inhibition of migration of a metastatic cell) to about 5%, preferably from 100% to about 50%, more preferably from about 100% to about 75%, and most preferably from about 100% to about 90%. A 0% amount can be observed when a first control vehicle is compared with a second control vehicle which may be the same as the first control vehicle.

In one embodiment, comparison of efficacies of two fusion proteins A and B of this invention, which fusion proteins differ from each other in their amino acid sequence, such as for example in their respective membrane penetration enhancing sequence, may provide different observed percentages of inhibition of migration of a given tumor cell type caused by A and by B. The relative differences (either absolute percentage such as 100% by A versus 80% by B, or qualitative differences such as A is better than B) in inhibition may be the same from tumor type to tumor type or may change from tumor type to tumor type.

In one aspect, a fusion protein of this invention can substantially (100%) inhibit metastatic migration of at least one type of tumor cell.

In another aspect, a fusion protein of this invention can substantially (100%) inhibit metastatic migration of at least two types of tumor cell.

A useful assay is based on the observed ability of an invasive tumor cell to migrate through an artificial basement membrane (MATRIGEL®). In this assay, the change in the ability of different cancer cell types, each with a differing ability to migrate through the MATRIGEL® in the absence of treatment with a composition of this invention, and hence a differing metastatic invasiveness are evaluated by exposure to a concentration or dose range of a fusion protein of this invention from 0.1 µg/ml to 100 µg/ml. A preferred concentration range is about 0.0001 micrograms of fusion protein per cubic centimeter (cc) of tissue to about 100 micrograms per cubic centimeter of tissue.

MATRIGEL® Matrix (BD Biosciences) is a solubulized basement membrane preparation extracted from EHS mouse sarcoma, a tumor rich in ECM proteins. Its major components are laminin, collagen IV, heparan sulfate proteoglycans, and entactin. At room temperature, BD MATRIGEL® Matrix polymerizes to produce biologically active matrix material which can mimic mammalian cellular basement membrane, wherein cells can behave in vitro in a manner similar to in vivo conditions. MATRIGEL® Matrix can provide a physiologically relevant environment for studies of cell morphology, biochemical function, migration or invasion, and gene expression.

Demonstration that a fusion protein of this invention, such as SEQ ID NO: 43, can affect multiple aspects of the phenotypes of malignant cells can be shown by monitoring tritiated thymidine incorporation in proliferating and growing cells, wherein tritiated thymidine added to cell culture medium is taken into the cells and becomes part of the thymidine triphosphate pool therein which is used by each cell to synthesize DNA. Tritiated thymidine becomes covalently incorporated into DNA macromolecules in each of the cells. In cells that are not growing or in cells that are undergoing death by apoptosis or by necrosis, tritiated thymidine is either not taken up into the cell or is released into the cell medium upon lysis of the cell. Tritiated thymidine incorporation can be used as an overall measurement of the effect of a fusion protein of this invention such as SEQ ID NO: 43 on cell growth, cell division, cell stasis, and cell death. Cell lines in which SEQ ID NO: 43 induces a decrease in 3H-thymidin comprise: human endometrial cancer cell line HEC 1B, human colorectal cancer cell line CaCo2, human melanoma cancer cell lie SK-MEL-2, and human CNS cancer cell line A-172.

Data in Table 6 illustrate the effects of changes in dosage amounts of a composition comprising a fusion protein of this invention, SEQ ID NO: 43, administered to each of three representative human cancer cell lines on tritiated thymidine incorporation into the eight human cancer cell lines: HEC 1B, Caco-2, SK-MEL-1, HT1080, MCF7, SW480, 293S, and A172. The dose of SEQ ID NO: 43 administered ranged 50-fold from about 1 micrograms per milliliter to about 10 micrograms per milliliter to about 50 micrograms per milliliter (ug/mL).

TABLE 6

Response data of human tumor cell lines with respect to administration of a fusion protein, BA-07, as measured by incorporation of tritiated thymidine.

| Human Cancer Cell Line | Dose of SEQ ID NO: 43 in micrograms per milliliter | | |
|---|---|---|---|
| | 50 | 10 | 1 |
| | % growth in the presence of a fusion protein relative to that in the presence of a vehicle alone as a control | | |
| HEC 1B | 10 | 13 | 30 |
| Caco-2 | 21 | 17 | 30 |
| SK-MEL-1 | 34 | 30 | 33 |

It is unexpectedly observed that these human tumor cell lines exhibit reduced cell proliferation in the presence of the fusion protein. Table 6 shows the percent of growth compared to a control value of 100%.

Tumor cell lines can be divided into three separate groups with respect to tritiated thymidine incorporation. A composition of the invention comprising SEQ ID NO: 43 exhibits a pronounced effect oil cell proliferation in the HEC 1B cell line, which is an endometrial carcinoma cell line, with an inhibition of proliferation related to a 50% inhibitory concentration ($IC_{50}$) of less than 1 ug/mL. In addition to the inhibition, there is a dose-response effect of increasing inhibition at the higher concentration of SEQ ID NO: 43.

In Caco 2 and SK-MED-1 cell lines, shown in Table 6, a fusion protein exhibits an inhibitory effect on cell proliferation as evidenced by lower level of tritiated thymidine incorporation into the cells of each cell line.

Pharmaceutical Composition

By way of example, the pharmaceutical composition of the present invention can be prepared by mixing the SEQ ID NO: 10 (30 mg/mL stock solution or diluted solution) with a flowable carrier component capable of forming a therapeutically acceptable matrix in vivo, such as for example tissue adhesives, such as for example a fibrin glue or a collagen gel.

In one embodiment, the pharmaceutical composition of the present invention can be prepared by mixing the SEQ ID NO: 10 (30 mg/mL stock solution or diluted solution) with the four components of the Tisseel® (fibrin sealant) kit:
Lyophilized Thrombin;
1 mL $CaCl_2$/Buffer reconstitution solution to reconstitute Thrombin;
Lyophilized Fibrinogen; and
1 mL buffer solution to reconstitute Fibrinogen.

Fibrin sealant has three basic components: fibrinogen concentrate, calcium chloride and thrombin. Other components can be added to affect the properties of the gel formation. Added components may be used to modulate the time it takes for the fibrin gel to form from the soluble components, the size of the protein network that is formed, and the strength of the gel, and protease inhibitors slow down the removal of the gel after it is placed in the body. Several different commercial preparations are available as kits. Non-limiting examples of these include Tissucol/Tisseel (Immuno AG, Vienna, now marketed by Baxter), Beriplast P (Hoechst, West Germany), and Hemaseel (Haemacure Inc., Kirkland, Quebec).

To make a fibrin gel, soluble thrombin and fibrinogen are mixed in the presence of calcium chloride. When the components mix, a fibrin adhesive gel is formed because the fibrinogen molecule is cleaved by thrombin to form fibrin monomers. The fibrin monomers polymerize spontaneously to form a three-dimensional network of fibrin, a reaction that mimics the final common pathway of the clotting cascade, i.e. the conversion of fibrinogen to fibrin sealant. The key to the preparation of commercial preparations is to keep the fibrinogen and thrombin components separate until use, so that the polymerization can be controlled with the desired timing before or after application to the body.

Today such use of fibrin as a biologic adhesive has been widely accepted and has found application in many fields of surgery. Hemaseel or Tisseel VH are used as an adjunct to hemostasis in surgeries involving cardiopulmonary bypass and treatment of splenic injuries due to blunt or penetrating trauma to the abdomen, when control of bleeding by conventional surgical techniques, including suture, ligature and cautery is ineffective or impractical. The action of these fibrin gels is also used to stop bleeding in surgical procedures involving cardiopulmonary bypass and repair of the spleen. Tisseel VH has also been shown to be an effective sealant as an adjunct in the closure of colostomies.

As mentioned hereinabove and in U.S. Pat. No. 7,141,428, the entire contents of which are hereby incorporated by reference, fibrin sealant has three basic components: fibrinogen concentrate, calcium chloride and thrombin. Other components can be added to affect the time of clot formation, and the size of the protein network that is formed. Generally when the components are mixed, a fibrin coagulum is formed in that the fibrinogen molecule is cleaved through the action of thrombin to form fibrin monomers which polymerize spontaneously to form a three-dimensional network of fibrin, largely kept together by hydrogen bonding. This corresponds to the last phase of the natural blood clotting cascade, the coagulation rate being dependent on the concentration of thrombin used. In order to improve the tensile strength, covalent crosslinking between the fibrin chains is provided for by including Factor XIII in the sealant composition. In the presence of calcium ions, thrombin activates Factor XIII to Factor XIIIa. Activated Factor XIIIa together with thrombin catalyzes the cross-linkage of fibrin and increases the strength of the clot. The strength of the fibrin clot is further improved by the addition of fibronectin to the composition, the fibronectin being crosslinked and bound to the fibrin network formed. During wound healing the clot material undergoes gradual lysis and is completely absorbed. To prevent a too early degradation of the fibrin clot by fibrinolysis, the fibrin sealant composition may comprise a plasminogen activator inhibitor or a plasmin inhibitor, such as aprotinin. Such an inhibitor will also reduce the fibrinolytic activity resulting from any residual plasminogen in the fibrinogen composition. Similarly, compositions may include hyaluronic acid (or other polysaccharides), and these may also comprise a hyaluronidase inhibitor such as one or more flavonoids (or corresponding inhibitors for other polysaccharides) in order to prevent degradation (i.e. to prolong the duration) of the hyaluronic acid component by hyaluronidase which is always present in the surrounding tissues. The hyaluronic acid may, as mentioned above, be crosslinked, a commercially available example being Hylan® (available from Biomatrix, Ritchfield, N.Y., USA). The hyaluronic acid compositions may e.g. have the form of gels, solutions, etc.

Fibrin clots may be used for the application of a pharmaceutically active substance. By incorporating a drug, such as an antibiotic, a growth factor, etc. into the tissue adhesive it will be enclosed in the fibrin network formed upon application of the tissue adhesive. It will thereby be ensured that the drug is kept at the site of application while being controllably released from the composition.

Fibrin sealant products prepared from human plasma fibrinogen/Factor XIII are available commercially. One product is a tissue glue called Tisseel Fibrin Sealant (Baxter Hyland Immuno Corporation; Tissucol/Tisseel, Immuno AG, Vienna). Another product is Beriplast P (Hoechst, West Germany). An example of a frozen formulation of a fibrin glue delivered with a 2 syringe system is Evicel™ made by Omrix (New York, U.S.A.).

In one embodiment, the fibrin sealant used to formulate/deliver the pharmaceutical composition of the present invention is TISSEEL VH, Two-Component Fibrin Sealant, Vapor Heated, Kit (TISSEEL VH Fibrin Sealant) manufactured by Baxter Healthcare Corporation. The TISSEEL VH Fibrin Sealant kit contains Fibrinogen (Sealer Protein Concentrate) and Thrombin as the main active ingredients. It also contains Calcium Chloride Solution, and Fibrinolysis Inhibitor Solution (Aprotinin, bovine). The two reconstituted components, the Sealer Protein Solution and Thrombin Solution, are mixed and applied topically. Mixing the Sealer Protein Solution and Thrombin Solution produces a viscous solution that quickly sets into an elastic coagulum. Thrombin is a highly specific protease that transforms the fibrinogen contained in Sealer Protein Concentrate into fibrin. Most of the thrombin is adsorbed by the fibrin so formed. Excess thrombin, if any, is inactivated by protease inhibitors in the blood. Fibrinolysis Inhibitor Solution (Aprotinin) is a polyvalent protease inhibitor which prevents premature degradation of fibrin.

Other fibrin sealants that can be used to formulate/deliver the pharmaceutical composition of the present invention are Cebus™, Ateles™ and Proleus™ (PlasmaSeal); Vivostat® (Vivolution); CryosSeal FS® (Thermogenesis); CoSeal™ (Angiotech); Duraseal® (Confluent Surgical); Poliphase® (Avalon Medical); Bioglue®D (Cryolife Inc.); Avitene Flour™ (Davol); Dermabond™ (Johnson & Johnson); Hemaseel, Hemaseel-HMN and Hemaseel-Thrombin (Haemacure); Beriplast-P® (Aventis); Fibrocaps® (Profibrix); and Crosseal™, Evicel™ Thrombin (Omrix Pharmaceuticals).

Alternatively, other fibrin sealants that can also be used in the methods and compositions of the invention are described in U.S. Pat. Nos. RE39,298; RE39,321; 4,427,650; 4,427,651; 4,414,976; 4,640,834; 5,290,552; 5,607,694; 5,714,370; 5,750,657; 5,773,418; 5,962,405; 5,962,420; 6,117,425; 6,162,241; 6,262,236; 6,780,411; in U.S. patent application publication No 2005/0271646; and in European patent No 0 804 257, all of which are hereby incorporated by reference in their entirety. Tissue adhesive formulations are also described in U.S. Pat. No. 7,141,428, which is hereby incorporated by reference in its entirety.

It should be understood that these tissue adhesives are named by way of example and are not meant to be limiting. It is to be understood that any pharmaceutically acceptable tissue adhesive such as a fibrin or collagen gel may be used in the methods and compositions of the invention.

Components of Tiseel VH

Tisseel VH contains the following substances in four separate vials:

1. Sealer Protein Concentrate (Human), Vapor Heated, freeze-dried;
2. Fibrinolysis Inhibitor Solution (Bovine);
3. Thrombin (Human), Vapor Heated, freeze-dried; and
4. Calcium Chloride Solution.

Sealer Protein Concentrate (Human), Vapor Heated is formulated as a sterile, non-pyrogenic, freeze-dried, vapor-heated powder preparation made from pooled human plasma. Fibrinolysis Inhibitor Solution (Bovine) is formulated as a sterile, non-pyrogenic solution containing 3,000 kallikrein inhibitor units (KIU)/mL of Aprotinin, an inhibitor of proteases including plasmin. After reconstitution of the lyophilized Sealer Protein Concentrate in Fibrinolysis Inhibitor Solution, the resulting Sealer Protein Solution contains:

Total protein: 100-0130 mg/mL;
Fibrinogen: 75-0115 mg/mL;
Fibrinolysis Inhibitor: 2250-3750 KIU/mL; and
Excipients.

Thrombin (Human), Vapor Heated is formulated as a sterile, non-pyrogenic, freeze-dried, vapor-heated powder preparation made from pooled human plasma. Calcium Chloride Solution is formulated as a sterile, non-pyrogenic solution containing 40 µmol/mL $CaCl_2$. After reconstitution of the lyophilized Thrombin in Calcium Chloride Solution, the resulting Thrombin Solution contains:

Thrombin (Human): 400-600 I.U./mL
Calcium Chloride: 36-044 µmol/mL
Excipients: see table 4

The Sealer Protein Solution and Thrombin Solution are then combined by using the DUPLOJECT Preparation and Application System, or equivalent delivery device cleared by FDA for use with TISSEEL VH Fibrin Sealant, to form the Fibrin Sealant. TISSEEL VH Fibrin Sealant is supplied in four different kit sizes of 0.5, 1.0, 2.0 and 5.0 mL, containing the following components disclosed hereinafter.

Source Plasma obtained from US licensed plasma collection centers is used to produce Sealer Protein Concentrate and FEIBA® bulk powder, the starting material of Thrombin. To obtain Sealer Protein Concentrate, the cryoprecipitate derived from Source Plasma is washed, dissolved in buffer solution, filtered and freeze-dried, Fibrinolysis Inhibitor Solution is produced from sterile, non-pyrogenic Aprotinin bulk solution obtained from Bayer. Thrombin is prepared by dissolving FEIBA® bulk powder and incubating the solution with calcium chloride in order to activate prothrombin to thrombin, followed by ultra/diafiltration, sterile filtration and freeze drying. The Calcium Chloride Solution is prepared from calcium chloride complying with the specifications listed in the US Pharmacopeia (USP).

The Sealer Protein Concentrate and Thrombin are made from pooled human plasma. The twostep vapor heat treatment used in their manufacture has been shown to be capable of significant viral reduction. Other fibrin sealants are known in the art and can be used in the present invention. For example, fibrin sealants are described in U.S. application No. RE 39,299, U.S. Pat. Nos. 6,162,241, 6,780,411, 5,773,418, 5,290,552, 5,607,694, 4,414,976, 4,427,650 and 4,427,651, documents being hereby incorporated by reference.

The invention is further illustrated in various embodiments and aspects by the following non-limiting examples.

Example 1

Matrigel Assay Experiment

Data from a typical Matrigel assay experiment, for example relating to the effect of a pharmaceutical composition comprising a fusion protein designated as SEQ ID NO: 8 on length of an angiogenesis-derived capillary network are summarized in Table 7. These data show that the network formation was inhibited by approximately 13% to about 20% under the dose and formulation conditions used versus the inhibition produced by a control vehicle wherein zero inhibition provides 100% growth. This effect on angiogenesis can be enhanced by using higher doses of fusion protein and by preincubation of the HUVEC cells with SEQ ID NO: 8 prior to addition of the cells to Matrigel. The anti-angiogenesis effect of a composition comprising a polypeptide of this invention comprising an amino acid sequence of a transport agent covalently linked to an amino acid sequence of an active agent, wherein the amino acid sequence of the active agent retains an ADP-ribosyl transferase activity can be useful for inhibiting or substantially reducing the rate of subretinal neovascularization and proliferation of neovascular tissue in the eye of a mammalian host when the composition is administered to the mammal according to the methods of this invention.

TABLE 7

Anti-angiogenesis effect of a pharmaceutical composition comprising a fusion protein, SEQ ID NO: 8, on the mean length of a capillary network in a Matrigel matrix assay.

| Mean length of a capillary network associated with angiogenesis | Relative mean length of a capillary network produced in the presence of a vehicle control | Relative mean length of a capillary network produced in the presence of a pharmaceutical composition comprising SEQ ID NO: 8, at a concentration of 10 micrograms per milliliter |
|---|---|---|
| Y1 | 100 | 86.4 |
| Y2 | 100 | 78.2 |
| Y3 | 100 | 86.7 |

Example 2

Preparation of SEQ ID NO: 43 and SEQ ID NO: 10

SEQ ID NO: 43 is prepared by polymerase chain reaction and subcloned into pET9a vector to create SEQ ID NO: 10. Two oligonucleotides are designed to delete amino acids 3-17 by site-directed-mutagenesis using the QuikChange (Stratagene) kit. Polymerase chain reaction is carried out in a thermo cycler using 50 ng of the pET9a-C3-variant, using 42-mer mutant primers: primer 2029F 5'-GGA GAT ATA CAT ATG TC*G GCT TAT TCA AAT ACT TAC CAG GAG-3' (SEQ ID NO: 11); and primer 2029R 5'-CTC CTG GTA AGT ATT TGA ATA AGC C*GA CAT ATG TAT ATC TCC-3'(SEQ ID NO: SEQ ID NO: 12). The symbol (*) indicates the junction where the 45 nucleotide deletion occurred.

DpnI digestion is done according to the manufacturer's instructions and 1 µL of this product was used to transform XL1-Blue Super-competent cells (InVitrogen). These plates are then incubated overnight at 37° C. Clones of putative SEQ ID NO: 10 are selected and their plasmid DNA amplified and purified using the Qiagen Midi-Prep kit. The purified plasmids are analyzed by restriction digestion analyses. The DNA from three candidate clones is sequenced at BioS&T (Lachine, Quebec) using the T7 and T7T primers. Mutant AJC311-2 is confirmed to contain the mutation and the DNA is used to transform BL21 (DE3) (Invitrogen) cells and prepare a research cell bank (RCB).

Purified SEQ ID NO: 10 is prepared from $E.\ coli$. First, a flask of 0.5 L Luria Broth with glucose is inoculated with 2 vials of research cell bank (RCB) and grown overnight. The starter culture is diluted 10-fold into 8 flasks each containing 500 mL growth medium. The flasks are incubated at 37° C. and after 1 hour 20 min, isopropylthio-B-D-galactoside (IPTG) is added to increase the expression of SEQ ID NO: 10. After a further 4 hours, the cells are harvested by centrifugation and stored at −80° C. until use. A sample of the harvested culture is analyzed for SEQ ID NO: 10 content. Next, the cells are thawed and subjected to primary recovery, which in the research scale process for production of SEQ ID NO: 10 is sonication in extraction buffer. The crude extract is treated with positively-charged polymer to remove nucleic acids and with ammonium sulfate to remove some proteins and reduce the volume. Excess salt is removed. The protein is further purified by passing over four chromatography columns. The final purification and isolation steps consisted of concentration of the resulting purified protein solution (ultrafiltration can be used), filtration of the protein solution (e.g., through a 0.2 micrometer filtration membrane which can be useful to sterilize the protein solution), dispensing of the solution into sterile tubes, freezing the protein solution, and lyophilization of the frozen solution to leaving the protein formulated in the form of a powder. After the SEQ ID NO: 10 is purified, the fusion protein is analyzed to determine the amount of protein which is produced, its purity, its potency and its biological activity (e.g., ADP-ribosyl transferase related activity for neurite outgrowth). Purity is measured by scanning densitometry of SDS-polyacrylamide gels stained with Coomassie Blue. The activity of SEQ ID NO: 10 is determined using an NG108 cell 4 hour neurite outgrowth bioassay. The procedure for the bioassay comprises incubation of NG-108 cells for 4 hours with an aliquot of a buffered solution containing SEQ ID NO: 10. A simultaneous and otherwise identical bioassay is run as a positive control, wherein SEQ ID NO: 8 is used in place of SEQ ID NO: 10. The cells are then fixed with paraformaldehyde, stained with cresyl violet, and the percentage of cells in each well that demonstrated neurites greater than one cell body in length is determined by counting under the microscope. Each data point is determined in triplicate.

Example 3

Preparation of SEQ ID NO: 10 Fusion Protein

SEQ ID NO: 10 is derived from the cell-penetrating C3 exoenzyme variant, SEQ ID NO: 44. SEQ ID NO: 44 is transferred from the pGEX-4T vector to the pET9a vector to improve expression and eliminate the GST fusion tag. The resulting variant, SEQ ID NO: 43, is purified by FPLC using an Akta Explorer™ (Amersham Biosciences, Montreal, QC). In order to achieve a robust process for cGMP manufacturing, site-directed mutagenesis is employed to remove vestigial residues at the N-terminus and eliminate protease sensitive residues to obtain SEQ ID NO: 10.

SEQ ID NOs: 44 or 10 are purified using standard techniques known in the art. For example, SEQ ID NOs: 44 or 10 are expressed in *E. coli* BL21 (DE3) cells grown in 4 L flasks. Following induction with IPTG, cells are extracted by sonication and precipitated with polyethyleneimine and ammonium sulfate or filtered to remove the bulk of the nucleic acids. The lysates are passed through an SPXL column at neutral pH. The eluted variant is found to be >85% pure after this step. Further removal of contaminants is achieved via gel filtration (Superdex™ 75, Amersham Biosciences, Montreal, QC) and an anion exchange step (Q Sepharose™, Amersham Biosciences, Montreal, QC). The final purification step consists of membrane ultrafiltration followed by sterile filtration. Purified aliquots are stored at −70° C. Residual endotoxin, assessed by *Limulus* Amebocyte Lysate assay; BioWhittaker QCL-1000 kit, is less than 2 EU/mg. Protein concentration is evaluated using either UV spectroscopy (A280) or the Bradford reaction (Coomassie® Plus reagent, Pierce), while protein integrity and identity are established using Coomassie staining of 4-12% acrylamide gradient gels (NuPAGE Bis-Tris; Invitrogen, Burlington, ON) with or without the addition of reducing agent. Glycohydrolase activity of variants is determined by a fluorescence assay that quantifies the cleavage of NAD into ADP-ribose and nicotinamide (Lasko and McKerracher, 2006, Methods Enzymol., 406: 512-520). Neuritogenic activity is evaluated by a neurite outgrowth assay using NG-108 cells.

Example 4

General Method for Determination of Inhibition of Angiogenesis

Figure 33A:
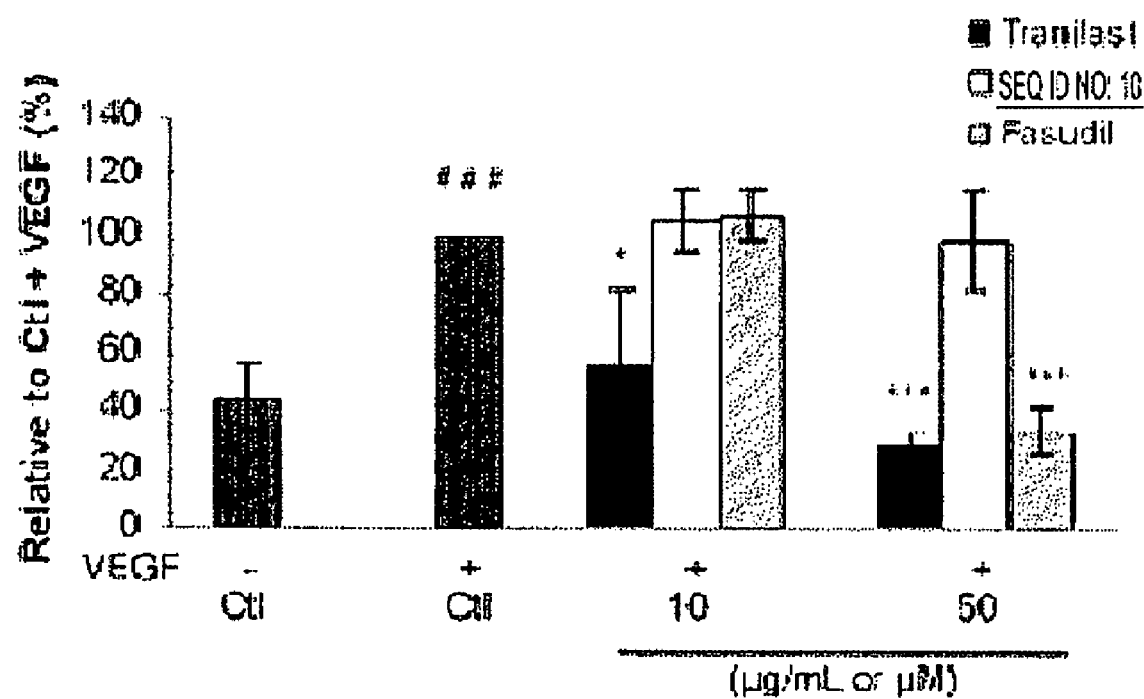
FIG. 33 illustrates that SEQ ID NO: 10 can modify VEGF-dependent HUVEC migration, wherein in (A) HUVEC were seeded into 24-well-fibronectin-coated transwell chambers containing SEQ ID NO: 10, Fasudil or Tranilast, migration was stimulated for 20 hours with 10 ng/mL of VEGF with or without test compound, migrated cells were measured by fluorescence using Calcein-AM as a probe, and in (B) HUVEC were pre-treated for 24 hours with 50 µg/mL of SEQ ID NO: 10 prior to the start of migration (results are expressed as a percentage of that from untreated cells stimulated with VEGF±SEM and represent 4 independent experiments analyzed in duplicate; symbols * and *** represent, respectively, significant (p<0.05) and highly significant (p<0.001) difference from untreated cells+VEGF (Control+VEGF); symbol # # # represents significant difference (p<0.001) from untreated cells−VEGF (Control−VEGF))

Referring to FIG. 33, the formation of new blood vessels can be studied in a cell culture model by growing endothelial cells in the presence of a matrix of basement membrane (Matigel). Human umbilical vein endothelial cells (HUVEC) are harvested from stock cultures by trypinization, and are resuspended in growth medial consisting of EBM-2 (Clonetics), FBS, hydrocortisone, hFGF, VEGF, R3-IGF-1, ascorbic acid, hEGF, GA-1000, heparin. MATRIGEL® (12.5 mg/mL) is thawed at 4° C., and 50 mL of MATRIGEL® is added to each well of a 96 well plate, and allowed to solidify for 10 min. at 37° C. Cells in growth medium at a concentration of 15,000 cells/well are added to each well, and are allowed to adhere for 6 hours. A fusion protein of this invention, e.g., SEQ ID NO: 8, in phosphate buffered saline (PBS) is added to the well at about 10 mg/ml, and in other wells PBS is added as control. The cultures are allowed to grow for a further 6 to 8 hours. The growth of tubes can be visualized by microscopy at a magnification of 50×, and the mean length of the capillary network is quantified using Northern Eclipse software. Treatment of the cells in the Matrigel assay with a fusion protein of this invention (e.g., SEQ ID NO: 8) reduces tube formation (see FIG. 33).

Example 5

A Lyophilized Formulation

A solution comprising a unit dosage amount of a composition of this invention comprising a fusion protein such as SEQ ID NO: 8 dissolved in an pharmaceutically acceptable isotonic aqueous medium comprising a pharmaceutically acceptable buffer salt and/or a readily water-soluble pharmaceutically acceptable carbohydrate (preferably a pharmaceutically acceptable non-reducing sugar or a cyclodextrin) is sterile-filtered (e.g. through a 0.2 micron filter) under aseptic conditions, the filtrate is placed in a sterilized vial, the filtrate is frozen, the frozen aqueous solution is lyophilized aseptically at reduced pressure in a pharmaceutically acceptable lyophilizer to leave a dried matrix comprising the fusion protein in the vial, the vial is returned to atmospheric pressure under a sterile inert atmosphere, the vial is sealed with a sterile stopper (e.g. together with a crimp cap). The sealed vial is labeled with its contents and dosage amount and placed in a kit together with a second sealed sterile vial which contains sterilized water for injection in an amount useful to transfer into the first vial containing the lyophilized fusion protein in order to reconstitute the fusion protein matrix to a solution as a unit dosage form. In another embodiment, the fusion protein can be dissolved in a starting volume of aqueous medium which comprises a hypertonic aqueous medium, the solution sterile filtered, the filtrate filled into a vial, and lyophilized to form a dried matrix. This dried matrix can be dissolved or reconstituted in a larger-than-original volume of sterile water, the larger volume sufficient to form an isotonic solution for injection such as by intravenous injection and/or infusion. Alternatively, a hypertonic solution can be used for administration by infusion into a drip bag containing a larger volume of isotonic aqueous medium such that the hypertonic solution is substantially diluted. Optionally, a vial containing a volume of sterile water in an amount suitable to reconstitute the matrix to a unit dosage form is distributed as a kit with the lyophilized protein. Preferably the reconstituted composition comprises an isotonic solution. The fusion protein can be used for intravenous delivery, and/or infusion, and/or direct injection into tissue of the eye or tissue proximal to the eye with this formulation.

Example 6

General Procedure to Determine the Relative Neuroprotection Ability in the Retina of a Fusion Protein of this Invention In the visual system, retinal ganglion cells die after optic nerve injury. The severity (i.e., the number of cells which die) and rate of cell death depends on the proximity of axonal injury to the eye. To study the effects of inactivation of Rho on RGC survival, two cell-membrane penetrating (i.e., cell-membrane permeable) derivatives of C3 transferase (SEQ ID NO: 8 and SEQ ID NO: 43) are used. Similarly, truncated versions of SEQ ID NO: 10 (FIG. 3) or Pegylated BA-variants (FIGS. 4A and 4B) can be used.

Rats are anaesthetized under 2-3% isoflurane. RGCs are retrogradely labelled from the superior colliculus with Fluorogold (Fluorchrome Inc, Denver, Colo.). The right midbrain of a rat is exposed by making a small circular opening in the bone, followed by aspiration of cortex, and removal of the pia matter overlying the superior colliculi. A small piece of Gelfoam soaked in an aqueous medium comprising 2% fluorgold and 10% DMSO is applied to the surface of the right superior colliculus. Seven days after Fluorogold application, the left optic nerve is transected 1 mm from the eye. The optic nerve is accessed within the orbit by making an incision parasagitally in the skin covering the superior rim of the orbit bone, taking care to leave the supraorbital vein intact. Following partial resection or reflection of the lacrimal gland, the superior extraocular muscles are spread with a small retractor or 6-0 silk suture. The optic nerve is exposed, and the surrounding sheath is cut longitudinally to avoid cutting blood vessels while exposing the optic nerve. The pia mater of the optic nerve is nicked, the optic nerve moved gently to dislodge it, and then scissors are slipped tangentially under the optic nerve to give a clean cut 1 mm from the eye. In animals used for studies on cytokine levels, a microcrush lesion is used. For these studies the pia is left intact, and the optic nerve is lifted out from the sheath and crushed 1 mm from the globe by constriction with a 10.0 suture held for 60 seconds.

Anesthetized animals receive single injections of SEQ ID NO: 8 or SEQ ID NO: 43 in aqueous buffer immediately after the optic nerve is cut, or 4 days later. Intraocular injections are made with a 10 µl syringe attached to a glass micropipette. A hole is made in the superior nasal retina approximately 4 mm from the optic disc with a 30 g needle before introduction of the glass pipette to inject 5 µl of fusion protein (e.g., SEQ ID NO: 43) or buffer control. The needle is withdrawn slowly to allow diffusion of the solution into the vitreous spaces. The sclera is then sealed with tissue adhesive (Indermil, Tyco Heathcare, Mansfield, USA). Care is taken not to damage the lens during injection to avoid cataract formation and consequential increased survival of the RGCs. The skin is closed, and the integrity of the retinal vasculature is evaluated by a postoperative opthalmoscopic examination. Rats with compromised vasculature or rats that developed cataracts are not included in the experimental results.

Fluorogold labeled retinas are prepared for counting 7 or 14 days after axotomy. Animals are perfused with 4% paraformaldehyde (PFA), and their eyes are removed and postfixed in 4% PFA after puncture of the cornea. The eyes are then rinsed with phosphate buffered saline (PBS) for 1 hour. Incisions are made in each eye in the four retinal quadrants, and the retinas are removed and flat-mounted on glass slides. Excess vitreous is blotted away with paper wicks. Coverslips are placed on the slides over the mounted retinas, and RGCs are examined with an ultraviolet filter (365/420). Labeled RGCs are counted under the microscope at 20× magnification with the aid of a rectangle insert in one ocular field of view of the microscope to provide a rectangular field area of 0.375 mm×0.1125 mm. Four standard rectangular areas of retina are counted at 1 and 2 mm from the disc. The number of labeled cells in each area is divided by 0.04125 (rectangular area counted in mm$^2$), and the average density for each retina is calculated as RGCs/mm$^2$. Cells counts are conducted by the same investigator blind to the treatment. After axotomy, Fluorogold is also present in endothelial cells and microglial cells. These cells, identified by morphology are excluded from the counts of RGCs. Statistics are performed with Excel, and results from treated animals are compared with results from controls by T-test.

A single injection of FPLC-purified SEQ ID NO: 8 is neuroprotective and rescue all RGCs at 7 days after axotomy, and a single injection of FPLC-purified SEQ ID NO: 43 is neuroprotective and rescue all RGCs at 7 days after axotomy. To determine if RGC cell survival following SEQ ID NO: 43 injection might be increased because of properties of SEQ ID NO: 43 other than its Rho ribosylation activity, the effect of SEQ ID NO: 6 is tested on RGC cell survival. The mutant protein, SEQ ID NO: 6, is purified by FPLC, and 1 ug is injected immediately after axotomy in the manner used for SEQ ID NO: 43. Cell survival following administration of SEQ ID NO: 6 is not significantly different from cell survival following axotomy alone, and is significantly different from the effect of SEQ ID NO: 43. Therefore, the neuroprotective activity of SEQ ID NO: 43 is due to the presence of ADP-ribosyl transferase in the fusion protein and thus inactivation of Rho, not from other effects (data not shown).

Ischemia can be produced in the retina of the albino Lewis rat by raising intraocular pressure by intraocular injection of saline (Unoki and LaVail, Invest Opthalmol. Vis. Sci. 35:907, 1994). The survival of RGCs can be assessed by counting RGCs retrogradely labeled with Florogold in retinal wholemounts, as described above.

Example 7

Neuroprotection of RGCs in a Glaucoma Model

The efficacy of Rho inactivation as neuroprotective therapy can be tested in a pre-clinical model of glaucoma. For example, an ocular hypertension animal model, which shares many similarities with human glaucoma, can be used, such as the model of ocular hypertension in Brown Norway rats developed by Dr. J. Morrison and collaborators at the Casey Eye Institute (Portland, Oreg.) (Morrison et al., 1997, Exp. Eye Res., 64: 85-96). Intraocular pressure (IOP) is a measurement of the fluid pressure inside the eye. This fluid, called aqueous humor, is circulated and then drained out via specialized outflow pathways. If the drainage system does not function properly, as in prevalent forms of glaucoma, pressure inside the eye builds up. The Morrison model involves injection of hypertonic saline into an episcleral vein, leading to blockade of the aqueous humor outflow pathways. This procedure leads to gradual increase of eye pressure and progressive death of RGCs. Importantly, inner retinal atrophy, optic nerve degeneration, and optic nerve head remodeling observed in this model are similar to that seen in human glaucoma. Thus, the Morrison model is considered the best pre-clinical rodent model of glaucoma (Morrison et al., 2005, Progress in Retinal and Eye Research, 217-240).

The Morrison model can be used to determine if the C3 variants of the invention provide RGC protection in glaucoma. For example, polypeptides of the invention or saline (control) can be injected into the vitreous chamber of the eye subjected to ocular hypertension surgery. The number of surviving RGCs following injection can be counted in order to determine whether the polypeptide confers significant RGC neuroprotection in the ocular hypertension rat model of glaucoma.

Example 8

Procedure to Measure Efficacy to Prevent Photoreceptor Cell Death in Rat Models of Photoreceptor Degeneration Handling of animals was in accordance with guidelines of the Canadian Council of Animal Care. Animals were housed under a 12-h light-dark cycle with free access to water and food. Adult pathogen-free male and female Sprague-Dawley rats (8 weeks) were used. On the day of surgery, animals were randomized to their respective group while the surgical team was blinded to the treatment groups. Postoperative treatments included 0.9% saline subcutaneously for rehydration, Buprenex for pain control and Baytril to prevent infection. Daily inspections included bladder function evaluation and voiding, examination of laminectomy site for evidence of infection and presence of autophagia. None of the animals originally assigned to the studies were excluded from the analyses.

Figure 6:
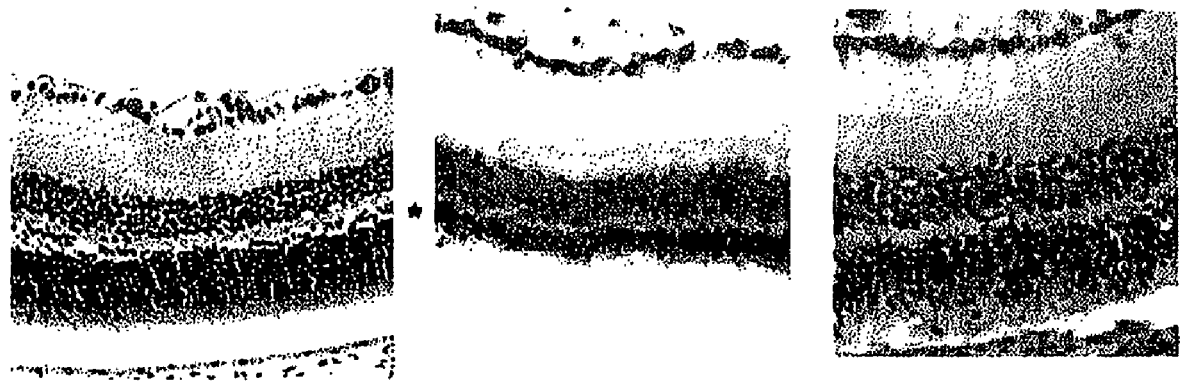
FIG. 6 illustrates photoreceptor survival visualized using H&E staining in adult rat exposed to light for 3 days and survival measured 5 days after exposure in presence of 1 μg of SEQ ID NO: 10.

Rats (Sprague-Dawley) were injected in the posterior chamber of the right eye with 5 ul of saline or the left eye with 5 ul (1 µg) of SEQ ID NO: 10 using a Hamilton syringe/capillary. Following the injections, rats were placed in cages and exposed to constant light (~2000 lux) for 1 or 2 days. Atropine was applied once per day or as necessary for the duration of the light exposure. Rats were then returned to the regular housing facility and kept for an additional 5 or 7 days. Eyes were collected and dissected from connective tissue, fixed in Bouin for 24 hours, and then embedded in paraffin for sectioning. Photoreceptors were visualized using H&E staining (FIG. 6). The photoreceptor-destroying effect of light treatments is apparent in the middle panel as a substantial thinning of the receptor layer (*). The corresponding rescue effect of SEQ ID NO: 10 is evident from the increased number of photoreceptor cells and resulting thicker layer in animals treated with 1 µg of SEQ ID NO: 10 (right-hand panel).

The rescue of photoreceptor cells can be demonstrated in Royal College of Surgeons (RCS) rats, which rats have an inherited retinal degeneration (Faktorovich et al., Nature 347: 83, 1990). Intraocular injections of SEQ ID NO: 8 in aqueous buffer are made with a 10 µl syringe attached to a glass micropipette. A hole is made in the superior nasal retina approximately 4 mm from the optic disc using a 30 g needle before introduction of the glass pipette to inject 5 µl of 1 ug SEQ ID NO: 8 or buffer control. The needle is withdrawn slowly to allow diffusion of the solution into the vitreous spaces, and the sclera is sealed with tissue adhesive. Care is taken not to damage the lens during injection because lens damage can lead to cataract formation and consequent increases in survival of the RGCs. The skin is closed, and the integrity of the retinal vasculature is evaluated by a postoperative opthalmoscopic examination. Rats with compromised vasculature or rats that develop cataracts are not included in the experimental results.

A histological analysis useful to assess photoreceptor survival in therapeutically treated or untreated RCS rats comprises the steps of vascular perfusion of an anesthetized animal, embedding of the animal's eye in paraffin, and staining of 6 micron thick sections with hemotoxyline and eosin or with toluidine blue. In the eyes of untreated RCS rats at 53 days after birth (P53) the outer nuclear layer, which contains the photoreceptor cells, is reduced in thickness to only a few rows of cells (approximately 20% of the thickness found in normal rats at the same age). A therapeutically effective dose of SQ ID NO: 8 administered by intravitreal administration (e.g., a single injection comprising one microgram of protein) can restore the thickness of the outer nuclear layer, and hence rescue photoreceptor cells.

Alternatively, rescue of photoreceptor cells can be demonstrated using 2-to-3 month old male Sprague-Dawley rats in a model of exposure to constant light (115-200 foot-candles) for 1 week following the procedures of LaVail et al. (1992, PNAS USA 89: 11249). An aqueous buffer solution of SEQ ID NO: 8 can be injected (1 ug of protein) into the subretinal space or into the vitreous humor 48 hours prior to the onset of continuous illumination. Histological examination and analysis of retinas following a fixed recovery period (usually 10 days) is used to assess the death or damage to and the rescue or survival of photoreceptor cells.

Retinal detachment also leads to the death of photoreceptor cells. An animal model described by Erickson et al. (1992, J. Struct. Biol., 108: 148), can demonstrate the effect of administration of SEQ ID NO: 8 to enhance survival of retinal cells in vitro relative to administration of buffer control, a protein mutated to eliminate ADP-ribosylation activity, and to untreated controls.

Example 9

Procedure to Measure Efficacy of a Fusion Protein of the Invention to Prevent Photoreceptor Cell Death in Transgenic Mouse Models of Photoreceptor Degeneration As SEQ ID NO: 10 was shown to be neuroprotective towards retinal ganglion cells, its neuroprotective properties were studied on retinal neuron populations using a genetic retinal degeneration mouse model (rd). These models which harbour gene mutations similar to those found in patients with retinitis pigmentosa, display progressive photoreceptor cell loss. Although these rd models do not represent well the multifactoral nature of changes observed in human macular degeneration (e.g. drusen accumulation), these animal models provide insight on photoreceptor survival after treatment. Mice homozygous for the Rd1 mutation have an early-onset retinal degeneration due to a mutation of the Pde6b gene encoding the beta subunit of cGMP-phosphodiesterase expressed in rod photoreceptors. This mutation leads to accumulation of the second messenger cGMP in the cell body, which triggers apoptotic cell death. In Rd1 mice, degeneration starts around postnatal day (P) 7-9, with complete disappearance of the outer nuclear layer in less than 4 weeks (Chang et al., 2002).

Four mice per group were injected twice in the right eye with different doses of SEQ ID NO: 10 (0.001 to 0.1 µg) (at postnatal day 7 and postnatal day 14) and tissues were collected on day 21. All left eyes were injected with saline or BA-304 (nucleotide sequence corresponds to SEQ ID NO: 80; amino acids sequence corresponds to SEQ ID NO: 81) (enzymatically inactive mutant) and served as surgery controls.

Figure 7:
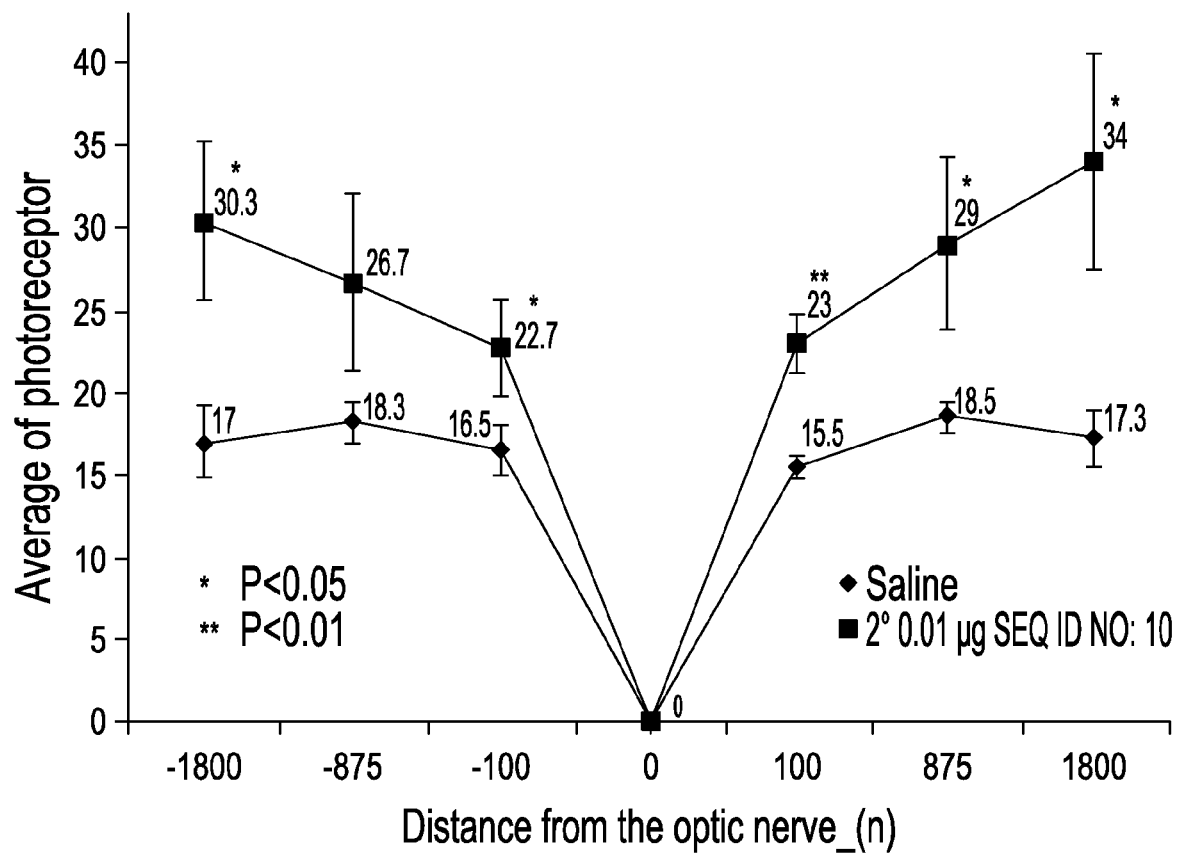
FIG. 7 illustrates that SEQ ID NO: 10 increases photoreceptor survival after 2 injections of 0.01 μg.

Results in FIG. 7 represent cell density (mean counts over 100 micron length) for three regions of the mice retinas (central, mid and peripheral retina) for the 0.01 µg group at 21 days post natal. As expected, Rd1 mice sacrificed 3 weeks after birth, there were very few photoreceptors left. The outer nuclear layer (ONL) was reduced to 1 layer and outer segments had almost disappeared in most animals. Degeneration was very uniform throughout the retina with around 17 photoreceptor nuclei per 100 microns length in the ONL compared with about 200 in a normal mouse. Treatment with 0.01 µg of SEQ ID NO: 10 before onset of apoptosis in Rd1 mice rescued photoreceptors in all regions of the retina. The neuroprotective effect was more dramatic in peripheral retina, with an increase of about 50% in photoreceptor survival. There was no protective effect observed for the lower dose of 0.001 µg and for the enzymatically inactive mutant BA-304 (SEQ ID NO: 81). No additional benefits were obtained with 0.1 µg doses (results not shown).

Figure 8:
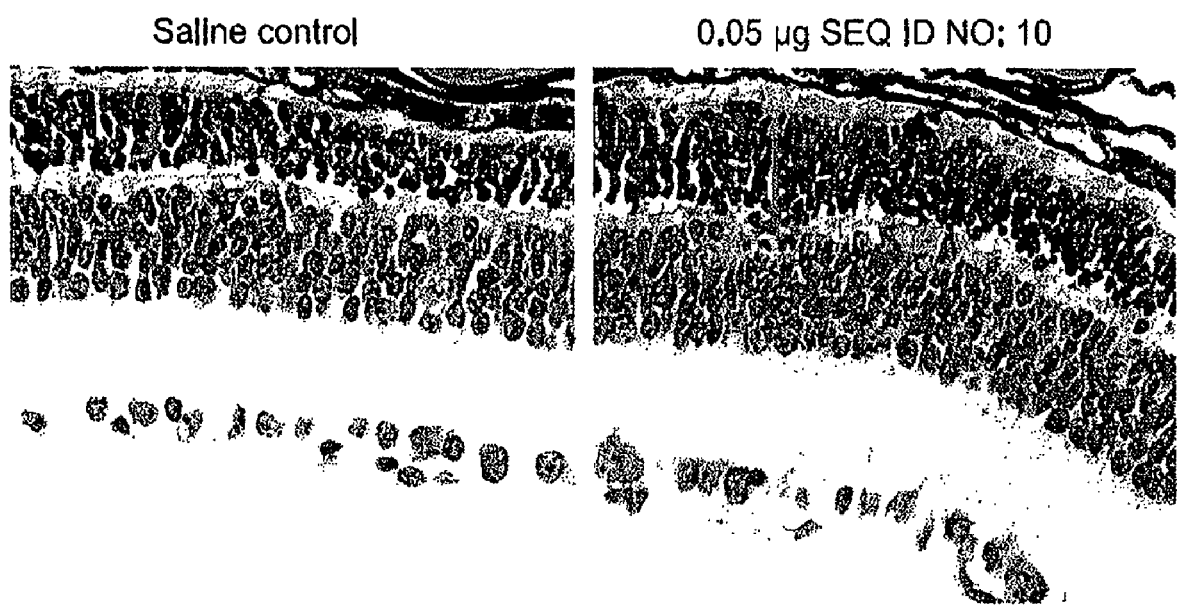
FIG. 8 illustrates that intravitreous injection of SEQ ID NO: 10 protects the outer nuclear layer in Rd1 mice.

The short term protective effect of SEQ ID NO: 10 in the period of active degeneration (P13-16) was also investigated. FIG. 8 shows representative pictures of retinas from the same animal with increased outer nuclear layer (ONL) thickness in the eye that received one injection of 0.05 µg SEQ ID NO: 10.

Figure 9A:
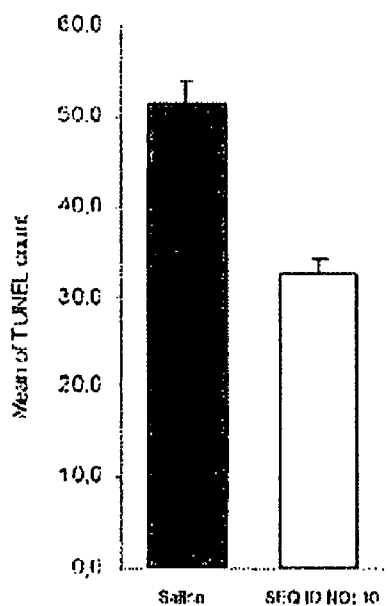

To correlate photoreceptor survival with the extent of apoptosis, slides of the same animals used for photoreceptor counts (FIG. 8) were also stained to assess extent of apoptosis in the ONL. The total number of TUNEL labeled photoreceptors in 100 micron lengths was counted and is presented in FIG. 9A.

Figure 9B:
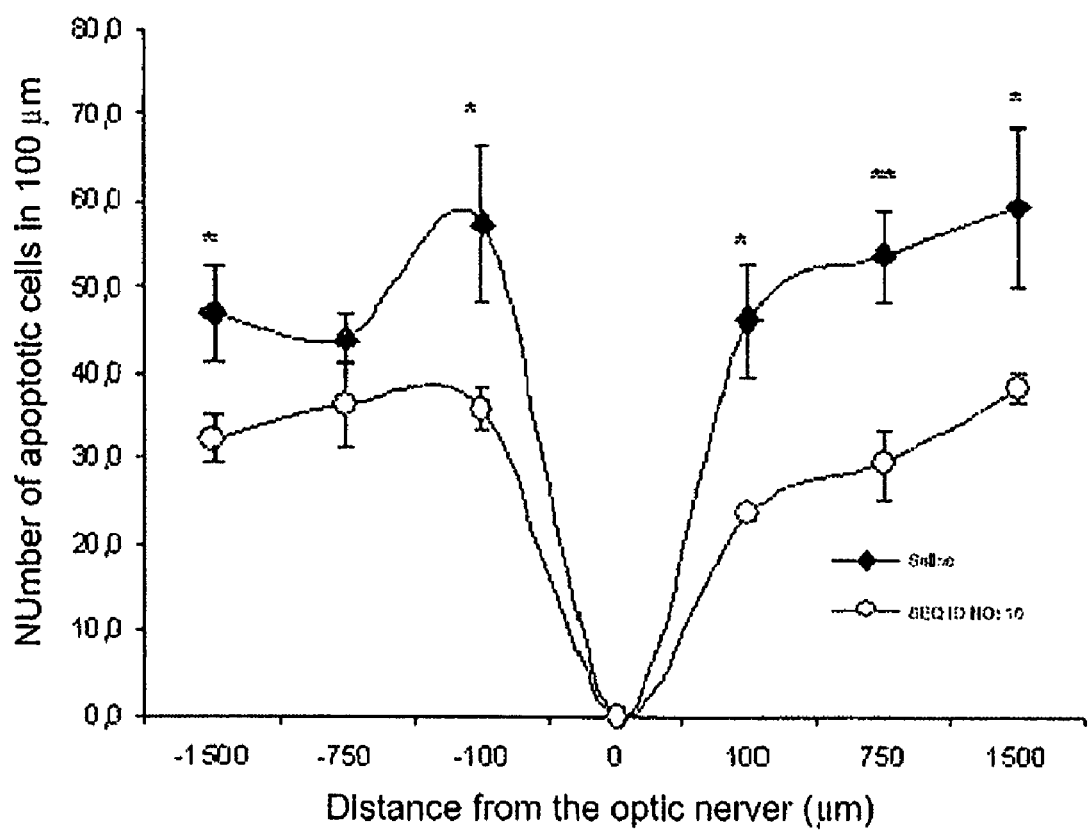
FIG. 9B illustrates that SEQ ID NO: 10 decreases apoptotic photoreceptor cell death in Rd1 mice retinas.

Significant reduction in the number of apoptotic cells in all regions of mouse retinas injected with BA-210 was observed (FIG. 9B).

Results in Rd1 mice are promising and show neuroprotection of photoreceptors associated with anti-apoptotic effects in a severe and fast retinal degeneration animal model. The degeneration time course of the disease is well known with peak of apoptosis around P14. When SEQ ID NO: 10 was injected at this peak period, apoptotic photoreceptor number was reduced by about 40% throughout the retina. In all mice examined 3 days after injection, SEQ ID NO: 10 treated eyes always showed thicker ONLs made up of more rows of photoreceptors when compared to the control eye injected with vehicle (saline). Inactivation of Rho in the active phase of degeneration slowed down apoptotic cell death of photoreceptors in this severe retinal degeneration model.

The results presented here demonstrate that SEQ ID NO: 10 exhibits a number of interesting biological activities. Its potent anti-angiogenic effects combined with inhibition of photoreceptor apoptosis could lead to a prolongation of vision for human patients with macular degeneration.

Several mouse genetic models of photoreceptor degeneration (e.g., rd-mutant of 0 subunit of cGMP phosphodiesterasel rds-mutant of peripherin) can be employed using the modes of administration described above to demonstrate fusion protein-related (e.g., SEQ ID NO: 8-related) photoreceptor cell enhanced survival effects in vivo.

Rd-mutant mice and rds-mutant mice exhibit retinal degeneration within a few weeks after birth. Following intravitreal injection of a fusion protein (e.g., SEQ ID NO: 8) as described above, tissues are analysed by histological methods described above.

Retinal explants from rd-mutant mice cultured in a SEQ ID NO: 8-containing medium can be assayed for thickness of the outer nuclear layer using methods described in Caffe et al. (1993, Curr. Eye Res., 12: 719). Thus, mouse pups are enucleated 48 hours after birth and treated with proteinase K. After this enzyme treatment, the neural retina with the retinal pigmented epithelium (RPE) attached is recovered, placed into a multi-well culture dish, and incubated in 1.2 ml culture medium (e.g., R16) for up to 4 weeks at 37° C. with 5% $CO_2$. Immunocytochemical staining for opsin of fixed (e.g., 4% paraformaldehyde) sections is used to assess the degeneration and rescue of photoreceptor cells. In the rd-mutant mouse the outer nuclear layer (photoreceptor cells) degenerate after 2-to-4 weeks in culture. The media can be supplemented with a dose range of SEQ ID NO: 8 to achieve an effect on retinal cell function, such as rescue of the outer nuclear layer from degeneration. Survival effects can also be shown using the TUNEL method on sections of retina analysed in the models described above.

Example 10

Procedure to Determine Efficacy of a Fusion Protein to Prevent Neovascularization of the Retina To confirm the in vitro angiostatic effect that was observed in cell culture assays, SEQ ID NO: 10 was then tested in different animal models of angiogenesis in the eye. The first model that was investigated was retinal physiological angiogenesis in newborn rats. The rat retina is avascular at birth, leaving an opportunity to assess angiostatic drug potential.

Figure 10:
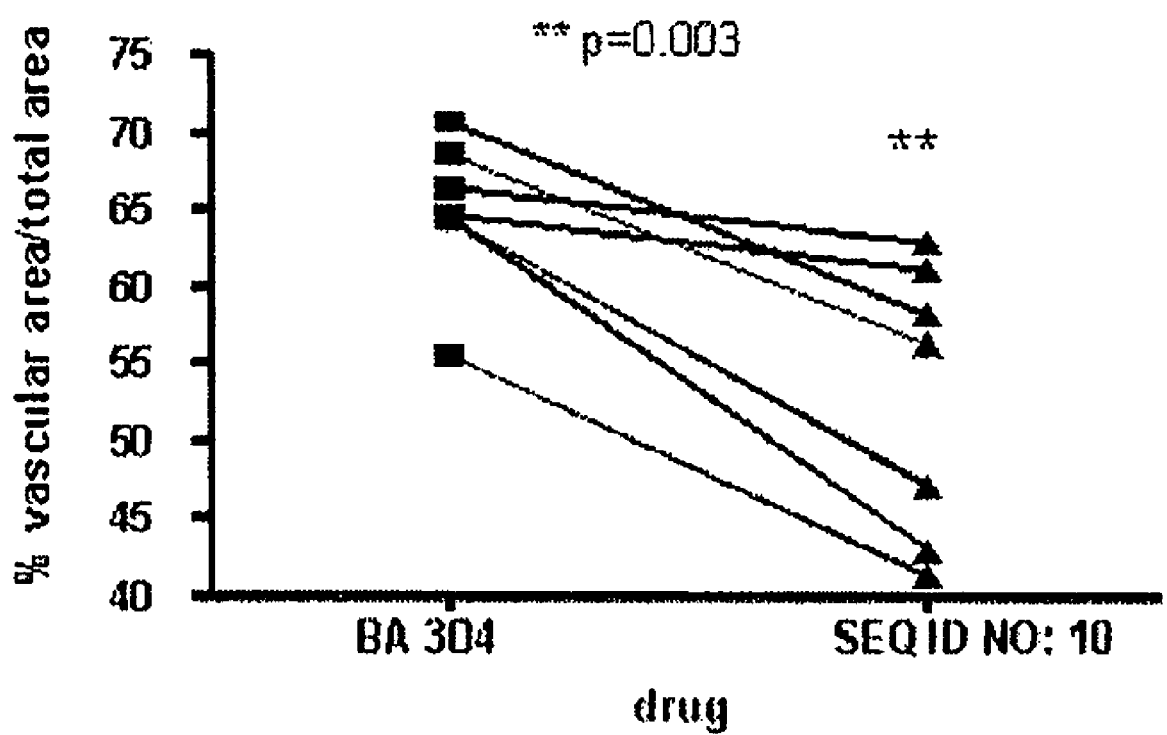
FIG. 10 illustrates that SEQ ID NO: 10 intravitreous injection inhibits physiological angiogenesis in the rat retina.

SEQ ID NO: 10 was injected into one eye while BA-304 (SEQ ID NO: 81), an inactive version of the protein, was injected into the contralateral eye from the same rat at post natal day 4. SEQ ID NO: 10 significantly inhibited physiological angiogenesis in the retina of rat pups after intravitreous injection of 0.1 µg when compared with the eye injected with the inactive protein (FIG. 10). Lower doses did not decrease the extent of vascularization, and pericyte coverage of the retinal vessels was not changed by SEQ ID NO: 10 treatment. (results not shown).

In order to study the effect of Rho inactivation in pathological angiogenesis, corneal neovascularization was induced by an alkaline burn in C57 mice. Animals were dosed by topical application 3 times a day from day 3 to day 8 post-injury with either saline, BA-304 (SEQ ID NO: 81) or SEQ ID NO: 10. Invasion of new blood vessels into the normally avascular cornea occurred in all injured mice (FIG. 11). However, repeated application of SEQ ID NO: 10 at 2 µg/µL significantly decreased the cornea vascularized area. The inactive protein BA-304 (SEQ ID NO: 81) had no effect on vessel growth.

Choroidal neovascularization is a major cause of central vision loss in patients with AMD. In response to an increase of locally produced angiogenic factors, such as VEGF, in a wounded area, vessels grow between Bruch's membrane and the RPE as well as into the subretinal space. To complete the proof of principle for the use of SEQ ID NO: 10 as an inhibitor of angiogenesis in the eye, laser-induced rupture of Bruch's membrane was used. This method provides a very reliable model for neovascularization originating from the choroid. Laser impact was done in both eyes of four mice and, 3 days later, SEQ ID NO: 10 was injected in the right eye while the left received the same dose of inactive protein. Pictures of sections containing the maximal neovascular response were taken for each impact and the area of vascularization was measured 10 days after the injury.

FIG. 12 shows that SEQ ID NO: 10 significantly inhibited subretinal vessel growth induced by laser photocoagulation at the two doses tested (1 and 0.2 µg) as compared with BA-304 (SEQ ID NO: 81) injections in the same animals. Representative pictures of lesions for both eyes in the same animal treated with 1 µg is presented in FIG. 12.

Results from in vitro studies in endothelial cells were thus confirmed in animal models as SEQ ID NO: 10 inhibited angiogenesis in all models (rats and mice) used in preclinical studies. Inhibition of subretinal neovascularization clearly suggests that SEQ ID NO: 10 penetrates through the retina to reach the site of choroidal vessel growth. Moreover, it demonstrates a potent and sustained effect on pathological vessel formation in the eye after a single dose.

Uncontrolled retinal angiogenesis can contribute to the pathology of wet macular degeneration. Vascular endothelial growth factor (VEGF) production is increased by hypoxia in the retina, and neovascularization of the retina is thereby induced.

A mouse model of ischemia-induced retinal neovascularization employs newborn C57BL/6J mice which are exposed to 75% $O_2$ from postnatal day (P) 7 to P12, along with their nursing mothers, followed by a return to room air. To accomplish this, the mice are weighed and placed at day P7 in a plexiglass box which serves as an oxygen chamber together with enough food and water for 5 days to P12. An oxygen flow rate of 1.5 L/min is maintained through the box for 5 days. The flow rate is checked twice daily with a Beckman oxygen analyzer (model D2, Irvine Calif.). The chamber is not opened during the 5 days of hyperoxia. An intraocular injection of a fusion protein (e.g., SEQ ID NO: 8) is performed at day P12 and the mice are removed to ambient air thereby inducing hypoxia. At day P17 the mice are sacrificed by cardiac perfusion with saline followed by 4% paraformaldehyde (PF), and their eyes are removed and fixed in PF overnight. The eyes are then rinsed, brought through a graded alcohol series, and then radial sections 6 um thick are cut. Sections through the optic nerve head are stained with periodic acid/Schiff reagent and hematoxylin. Sections 30 um apart are evaluated for a span of 300 um through the retina. All retinal vascular nuclei anterior to the internal limiting membrane are counted in each section. The mean of 10 counted sections is determined to give the average number of neovascular nuclei per section per eye. No vascular cell nuclei anterior to the limiting membrane are observed in normal, unmanipulated animals. The administration of a fusion protein substantially reduces the number of retinal vascular nuclei relative to the number observed in the absence of fusion protein.

Example 11

Intravitreal Injection of SEQ ID NO: 44 or SEQ ID NO: 43 Stimulates Regeneration in the Optic Nerve To test whether treatment of the RGC cell bodies promotes regeneration in vitro, Rho antagonists can be injected into the vitreous immediately after microlesion of the optic nerve 1 mm behind the optic disc. In a first experiment, SEQ ID NO: 4 (n=4) is used. Control animals receive a PBS injection (n=5) or microlesion alone (n=5). Axon regeneration in the optic nerve is evaluated 14 days later, after an injection of the anterograde tracer CTβ.

Figure 13A:
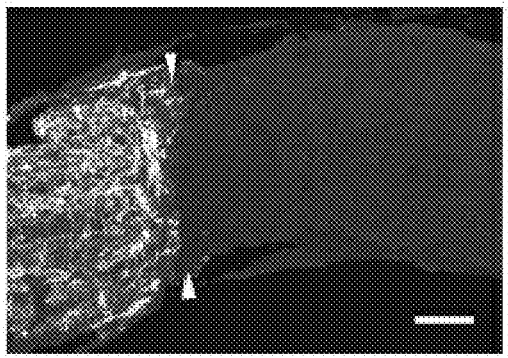
FIG. 13 illustrates in (A-C) photographs of optic nerve sections immunostained with a CTβ antibody to reveal axons regenerating distally to the lesion site (arrowheads) 2 weeks after microlesion in untreated (A), SEQ ID NO: 44-treated (B), or SEQ ID NO: 43-treated (C) animals; and in (D-E) quantification of regeneration 2 weeks after microlesion in SEQ ID NO: 44 (D)- and SEQ ID NO: 43 (E)-treated animals, compared with controls, wherein scale bar: in A-C=100 μm, *$p<0.001$; $p<0.01$, *1)<0.05, Student's t test.
Figure 13B:
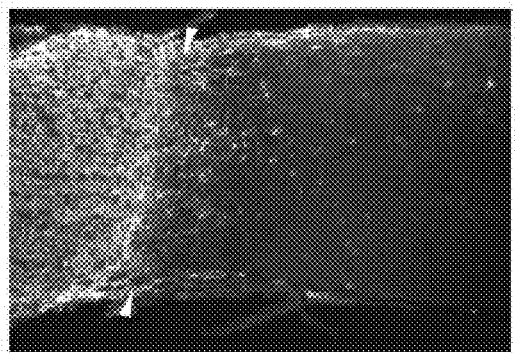
Figure 13C:
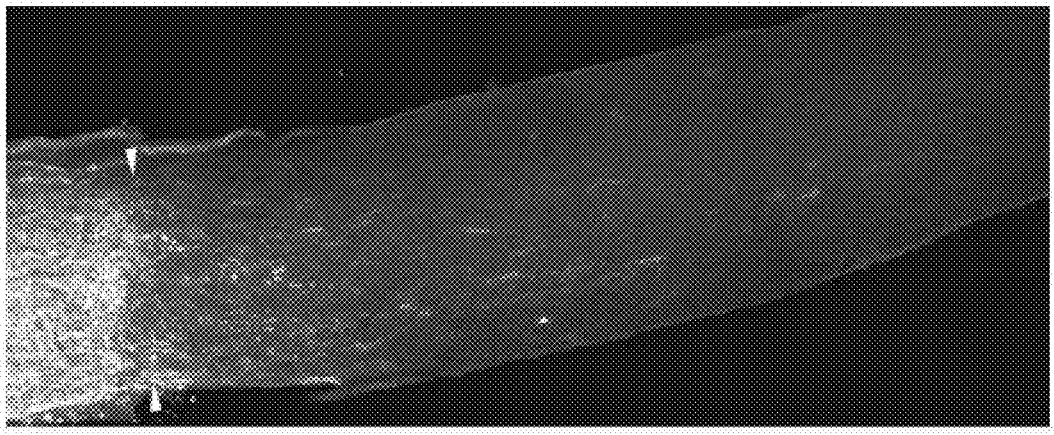
Figure 13D:
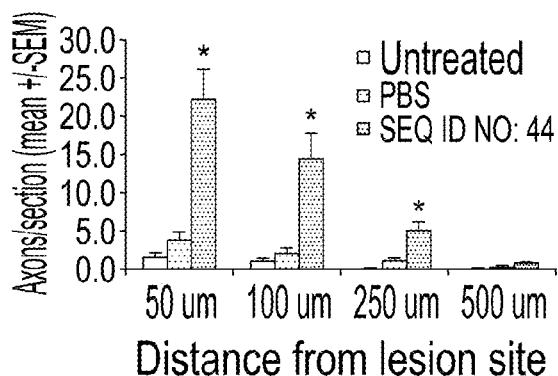
Figure 13E:
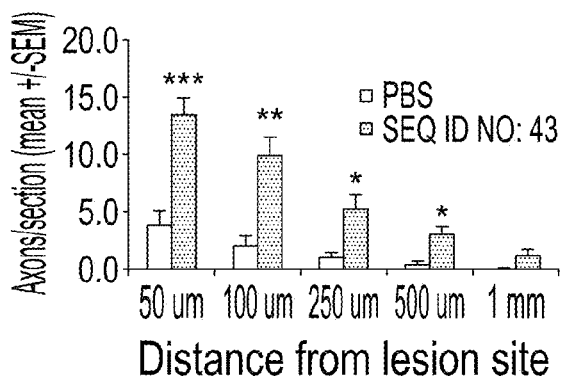

Two weeks after microlesion, virtually no CT-positive axons are detectable in control animals (FIG. 13A), whereas a large number of axons are visible past the lesion site in SEQ ID NO: 44 (FIG. 13B)- and SEQ ID NO: 43-treated rats (FIG. 13C). The microcrush injury model provides a clearly defined lesion site with little or no cavitation, and the lesion site is identified by dark-field microscopy and/or CTβ staining. The number of axons present at various distances past the lesion site is then counted. Animals treated with SEQ ID NO: 44 (FIG. 13D) or SEQ ID NO: 43 (FIG. 13E) have a significantly higher number of regenerating axons per section than controls, at distances of 50, 100, and 250 µm from the lesion site. Regeneration in animals injected with SEQ ID NO: 43 is similar to that of SEQ ID NO: 44-treated animals, but a greater number of longer axons in some animals treated with the more highly purified SEQ ID NO: 43 (FIG. 13C) is observed. SEQ ID NO: 44 is also used to evaluate regeneration 4 weeks after microlesion. The results indicate that application of Rho antagonists SEQ ID NO: 44/43 to RGC cell bodies can promote optic nerve regeneration after microlesion. To examine whether treatment has a sustained effect on axon growth, the average length of the longest axon in treated optic nerves 2 and 4 weeks after axotomy can be compared. No significant differences in axon length are detected at 4 weeks compared with 2 weeks (data not shown), suggesting that a single treatment does not result in sustained long-term growth. To examine the localization of SEQ ID NO: 43 after injection in the eye, 5 µg of SEQ ID NO: 43 in the eye after microlesion of the optic nerve is injected. Retina and optic nerve homogenates are prepared for Western blots 3 days later and probed with an anti-C3 antibody. The specific SEQ ID NO: 43 band is compared with recombinant SEQ ID NO: 43 protein run in a separate lane (data not shown).

Example 12

Figure 14A:
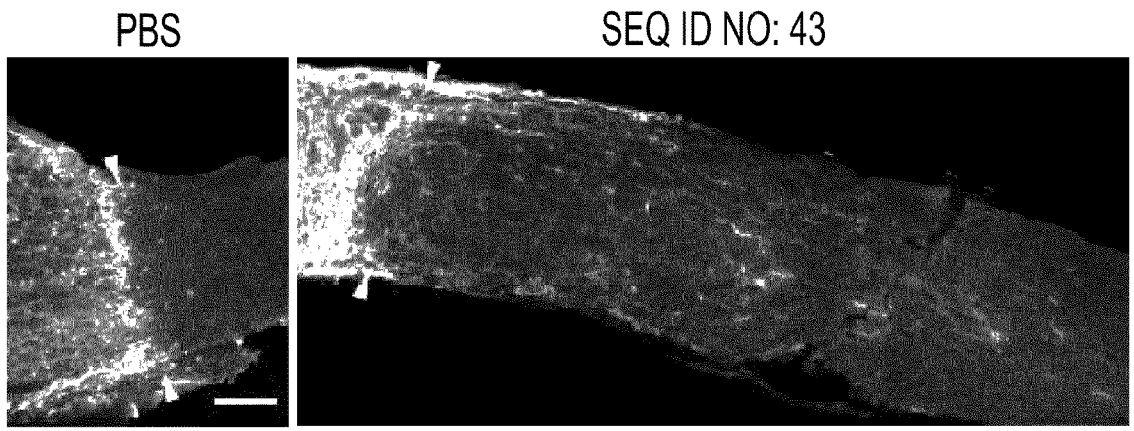
FIG. 14 illustrates in (A) photographs of optic nerve sections immunostained with CTβ antibody to reveal axons regenerating distally to the lesion site (arrowheads) 2 weeks after microlesion in SEQ ID NO: 43-treated animals and PBS controls. SEQ ID NO: 43 or PBS was injected into the vitreous 4 days after optic nerve injury. Scale bar=1100 μm; in (B) a quantification of regeneration in SEQ ID NO: 43-treated animals compared with controls; and in (C) a comparison of average longest axon in each treatment group after an immediate or delayed treatment; wherein **$p<0.01$; *$p<0.05$ and Student's t test.
Figure 14B:
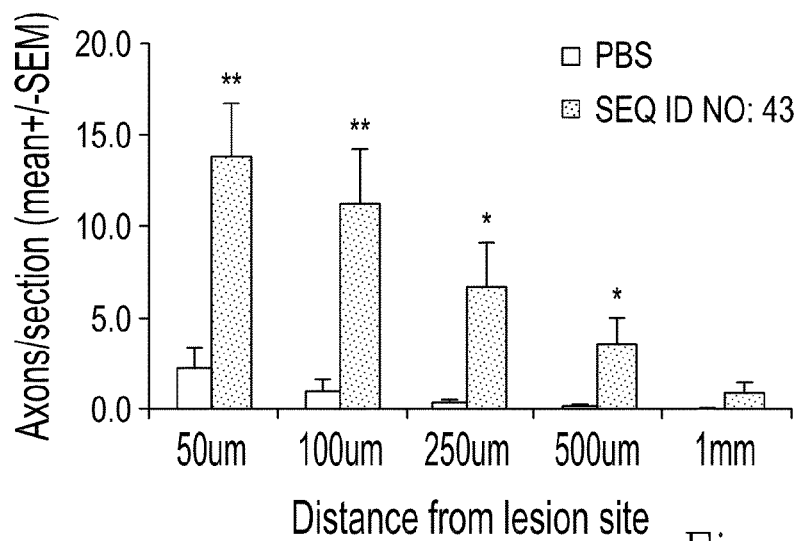
Figure 14C:
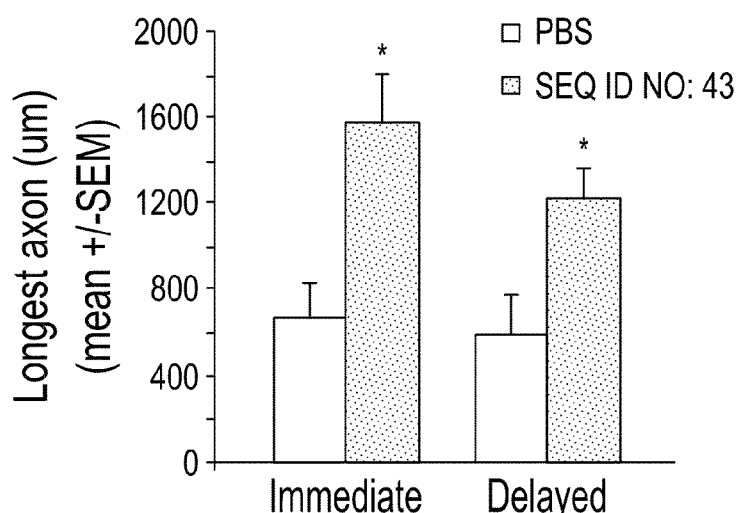

Delayed Treatment with SEQ ID NO: 43 Stimulates Regeneration Through the Lesion Sear To determine whether a delayed treatment with SEQ ID NO: 43 stimulates regeneration of RGCs through the lesion scar, SEQ ID NO: 43 can be injected (n=8) in the vitreous 4 days after microlesion of the optic nerve, and regeneration is examined 10 days later. Control animals are injected with PBS (n=5). A large number of CTβ-positive axons can be seen past the lesion site in treated animals, whereas very few are observed in PBS controls (FIG. 14A). Animals treated with SEQ ID NO: 43 have a significantly higher number of regenerating axons per section than controls, at distances of 50, 100, 250, and 500 µm from the lesion site (FIG. 14B). A comparison of the number of axons per section shows similar numbers of regenerating axons in animals treated with an immediate (FIG. 13D) or delayed (FIG. 14B) injection of SEQ ID NO: 43. The average longest axon is significantly longer in animals receiving either an immediate or a delayed SEQ ID NO: 43 treatment than in PBS controls (FIG. 14C). These results demonstrate the existence of a therapeutic window for a Rho antagonist treatment after optic nerve injury and indicate that inactivation of Rho allows RGC axons to grow across the lesion scar.

Example 13

Intravitreal Injection of SEQ ID NO: 43 Increases RGC Survival

Figure 15:
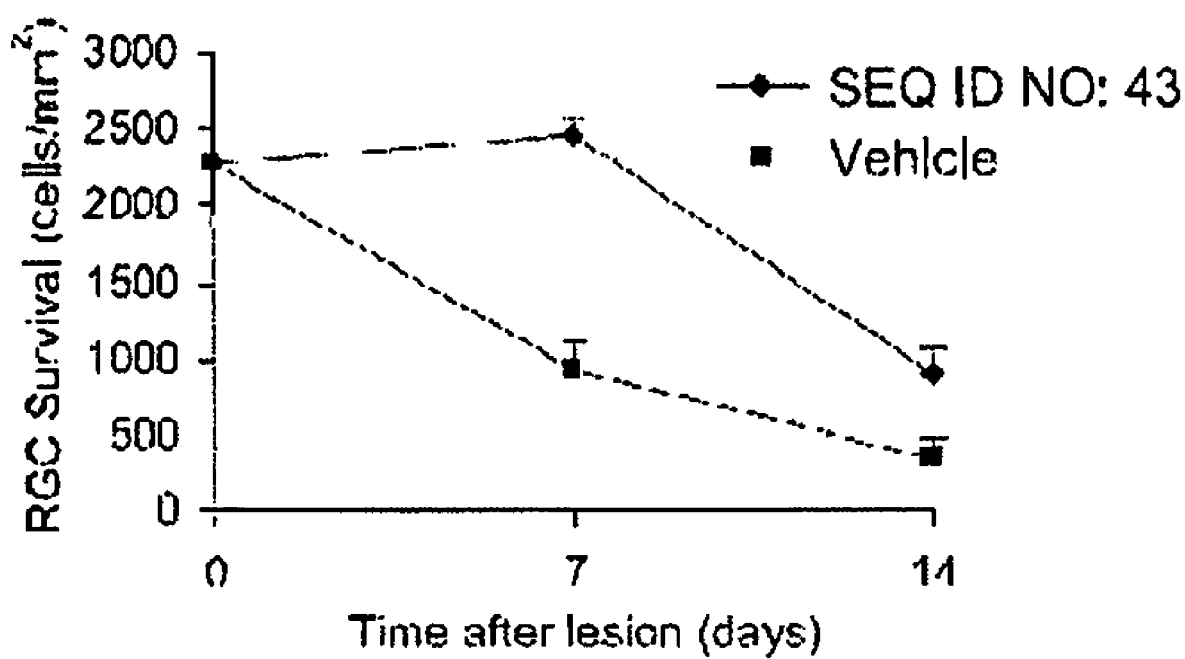
FIG. 15 illustrates RGCs which were retrogradely labeled 1 week before optic nerve injury. SEQ ID NO: 43 or vehicle was injected into the vitreous after optic nerve transection, and retrogradely labeled RGCs were counted in retinal whole mounts prepared 7 or 14 days after axotomy.
Figure 16:
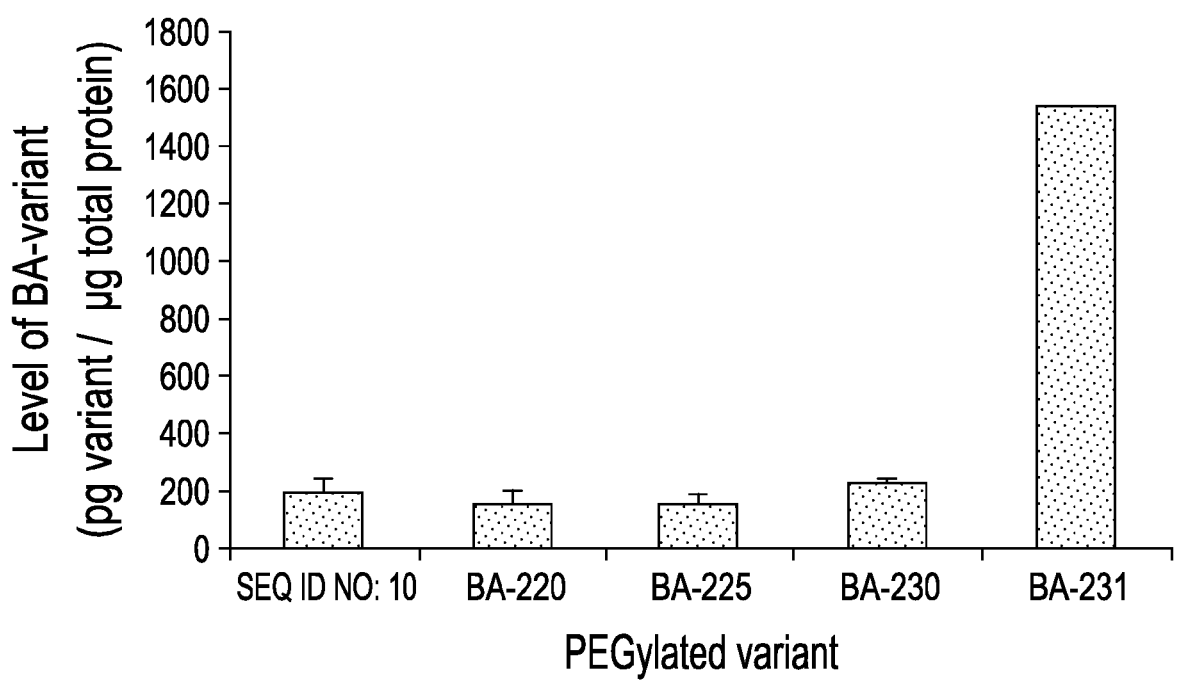
FIG. 16 illustrates the levels of low molecular weight PEG-BA-variants described in FIG. 5 in the retinas of adult rats (ELISA) at 24 hours after intravitreal injection.
Figure 17:
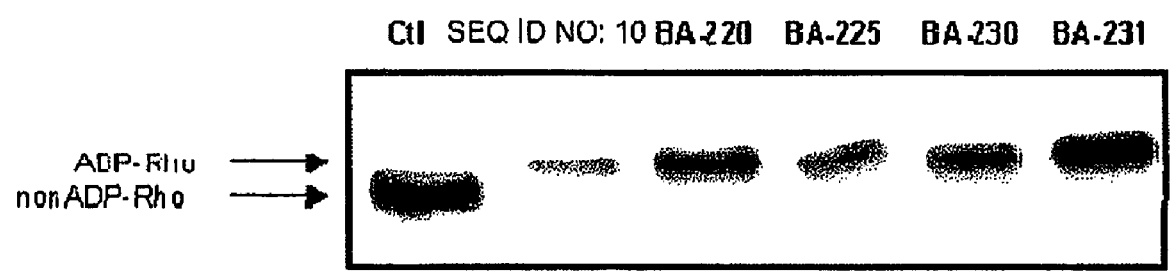
FIG. 17 illustrates RhoA ADP-ribosylation 24 hours after PEG-BA-variant intraocular injection in rats.
Figure 19:
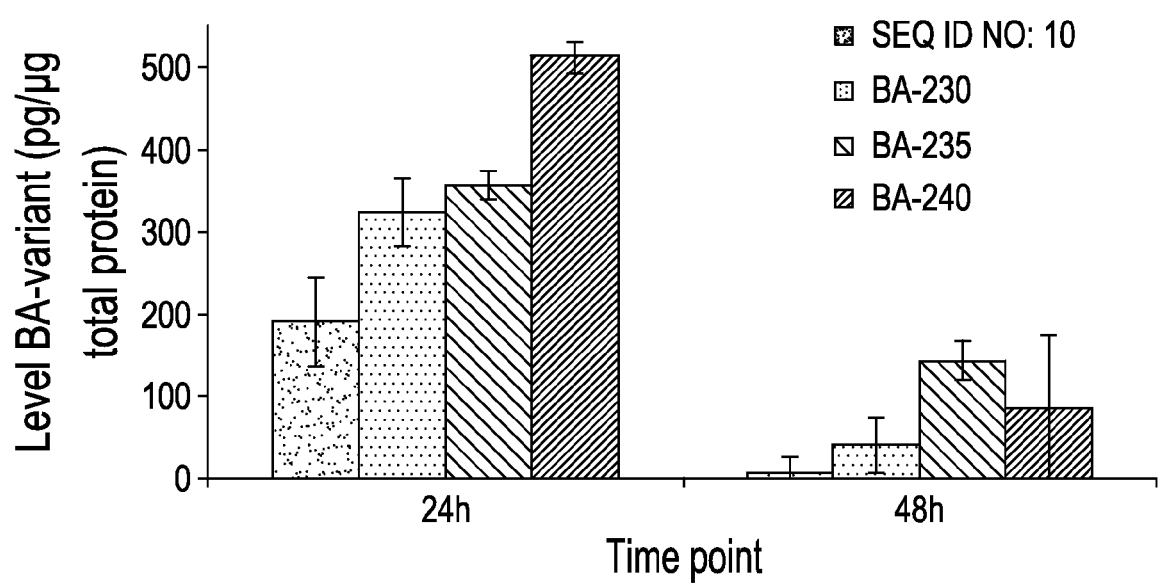
FIG. 19 illustrates the levels of high molecular weight PEG-BA-variant in the retina of adult rats at 24 h and 48 h after intraocular injection.
Figure 20:
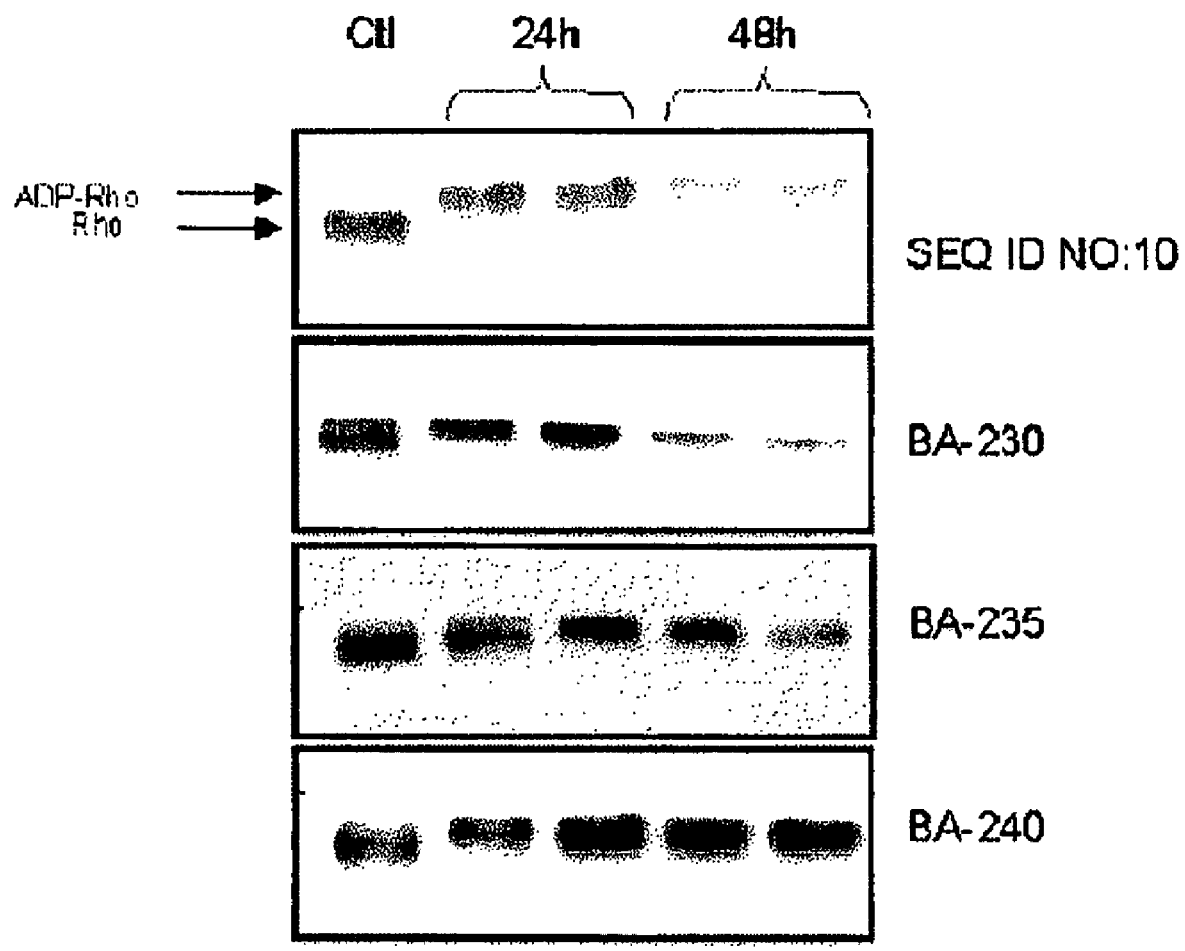
FIG. 20 shows SDS gels that reveal a molecular weight shift that is indicative of RhoA ADP-ribosylation 24 and 48 hours after BA-variants intraocular injection in rats.
Figure 21:
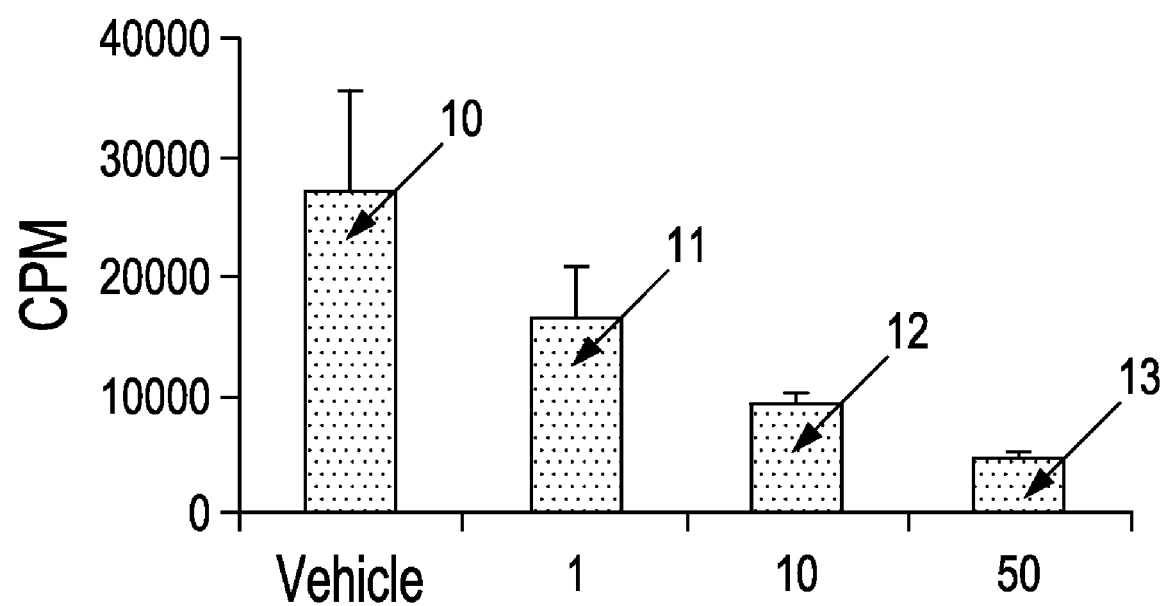
FIG. 21 illustrates the effect of a composition of this invention comprising a fusion protein, SEQ ID NO: 43, on the proliferation of HEC1B human endometrial adenocarcinoma cells as measured by tritiated thymidine incorporation, wherein the vehicle (10) is phosphate buffered saline, and SEQ ID NO: 43 is used at concentrations of 1 µg/ml (11), 10 µg/ml (12) and 50 µg/ml (13), and wherein the cancer cell proliferation is reduced in a dose dependent manner.
Figure 22:
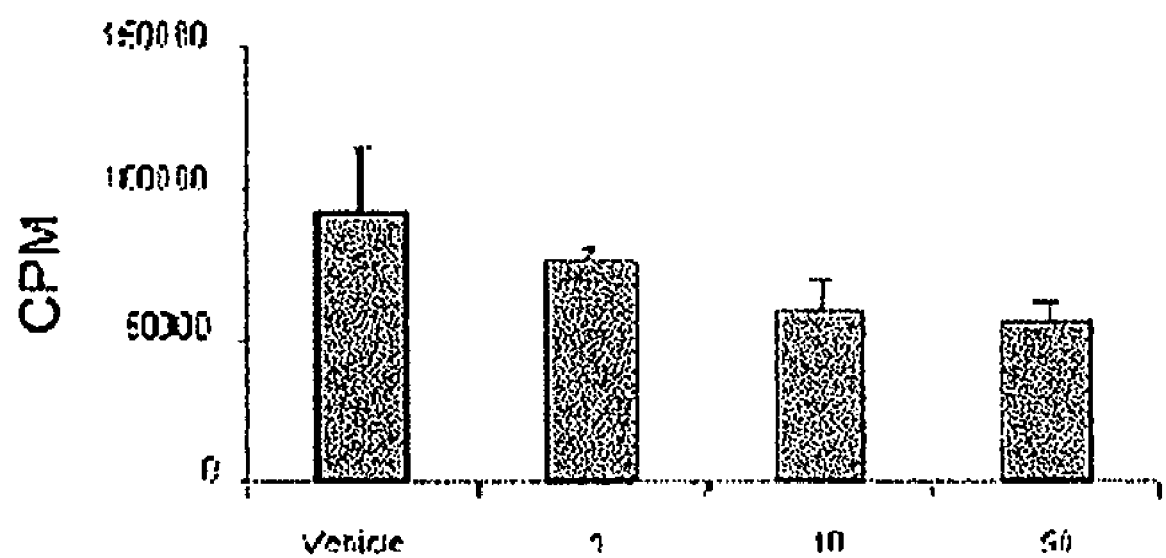
FIG. 22 illustrates the effect of a composition of this invention comprising a fusion protein, SEQ ID NO: 43, on the proliferation of SK-MEL-1 human melanoma cells as measured by tritiated thymidine incorporation; the vehicle is phosphate buffered saline, and SEQ ID NO: 43 is used at concentrations of 1 µg/ml, 10 µg/ml, and 50 µg/ml; cancer cell proliferation is reduced in a dose dependent manner.
Figure 23A:
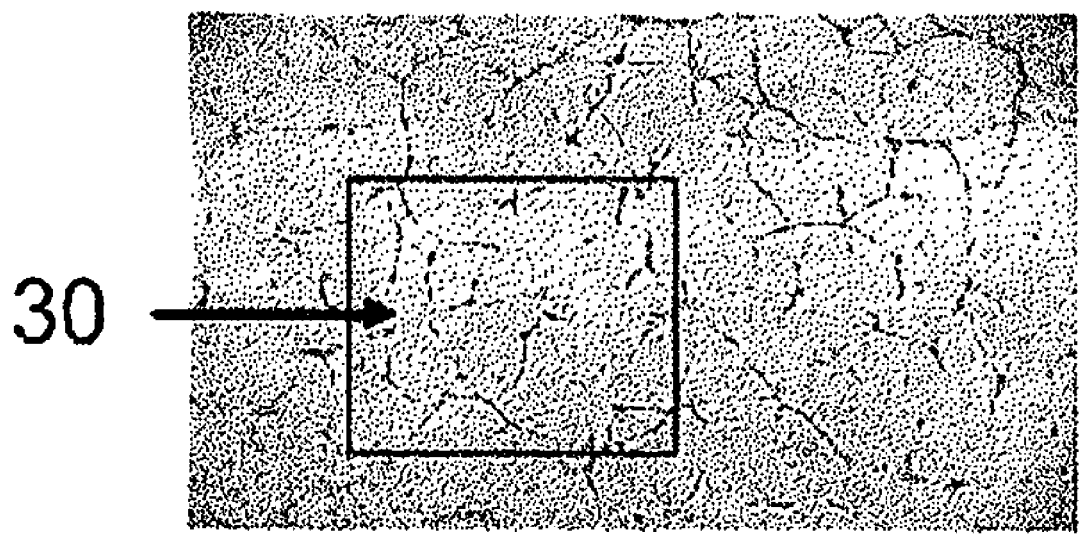
FIG. 23A illustrates tube formation by HUVEC endothelial cells cultured in a MATRIGEL® matrix, wherein this assay is a cell culture assay for antiogenesis and the tube formation can be seen in the control which does not contain a fusion protein of this invention (box 30)
Figure 23B:
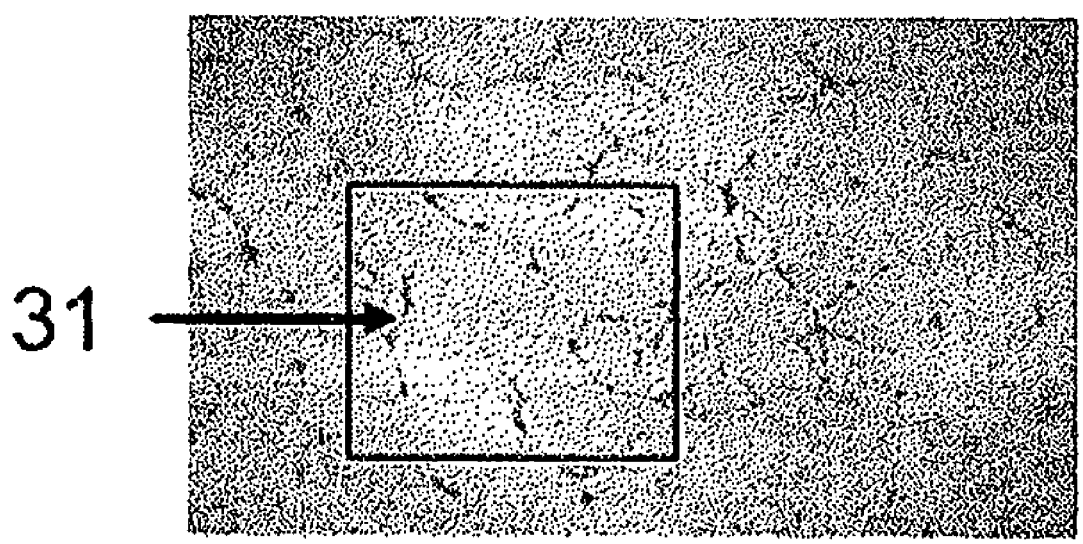
FIG. 23B illustrates a reduction in tube formation of HUVEC endothelial cells cultured in a MATRIGEL® matrix, wherein the cultures treated with a composition of this invention comprising a fusion protein, SEQ ID NO: 43, had fewer tubes demonstrating an inhibition of angiogenesis, as shown in box 31.
Figure 24:
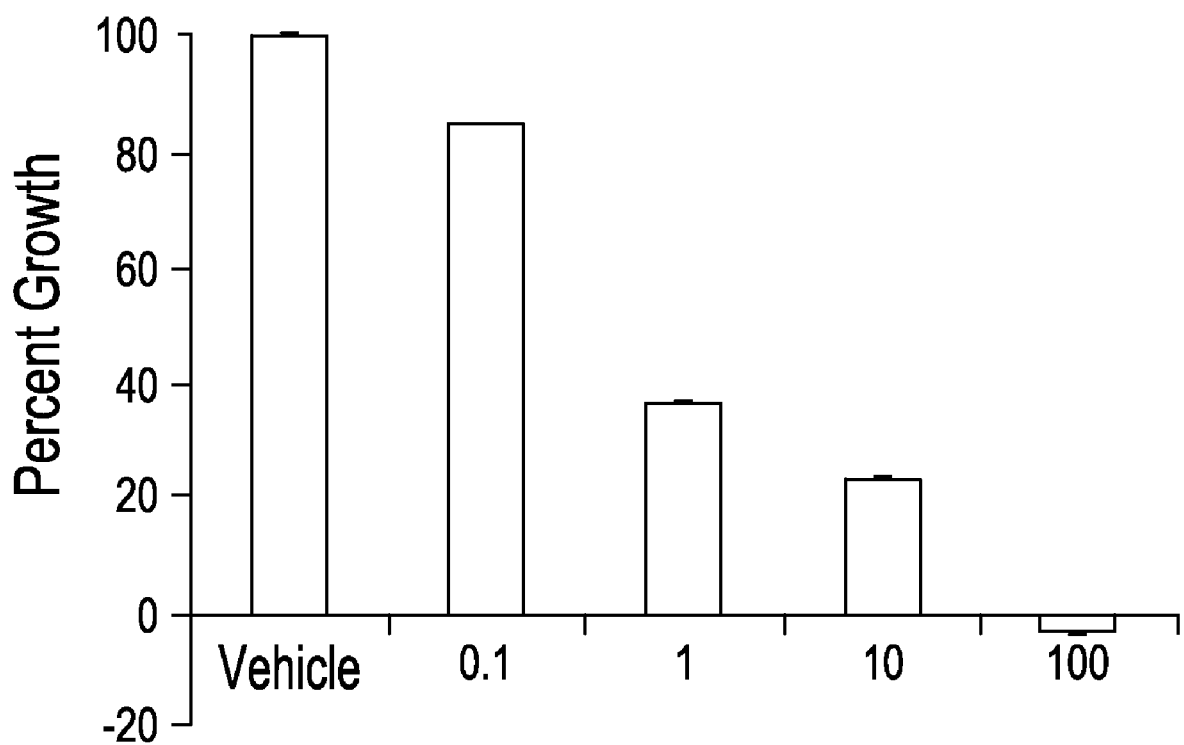
FIG. 24 shows the inhibition of growth of TK-10 human renal carcinoma cells by a composition of this invention comprising a fusion protein, SEQ ID NO: 43, as measured by a sulforhodamine B (SRB) growth inhibition assay, wherein the SEQ ID NO: 43, is used at concentrations of 0.1 µg/ml, 1 µg/ml, 10 µg/ml, and 100 µg/ml, wherein at all concentrations used, cancer cell proliferation is reduced, wherein reduction in cancer cell proliferation is dose dependent and at a concentration of fusion protein of 100 µg/ml, the composition of the invention induced cell death of cancer cells.
Figure 25:
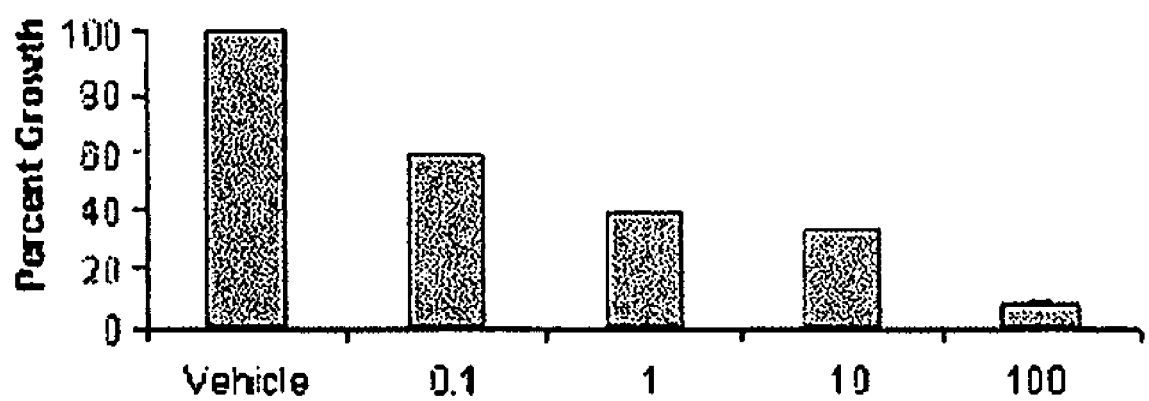
FIG. 25 shows the inhibition of growth of HOP-62 non-small cell lung cancer cells by a composition of this invention comprising SEQ ID NO: 43, as measure by a sulforhodamine B (SRB) growth inhibition assay, wherein the SEQ ID NO: 43, is used at concentrations of 0.1 µg/ml, 1 µg/ml, 10 µg/ml, and 100 µg/ml, and wherein at all concentrations used, cancer cell proliferation is reduced and reduction of cancer cell proliferation is dose dependent.
Figure 26:
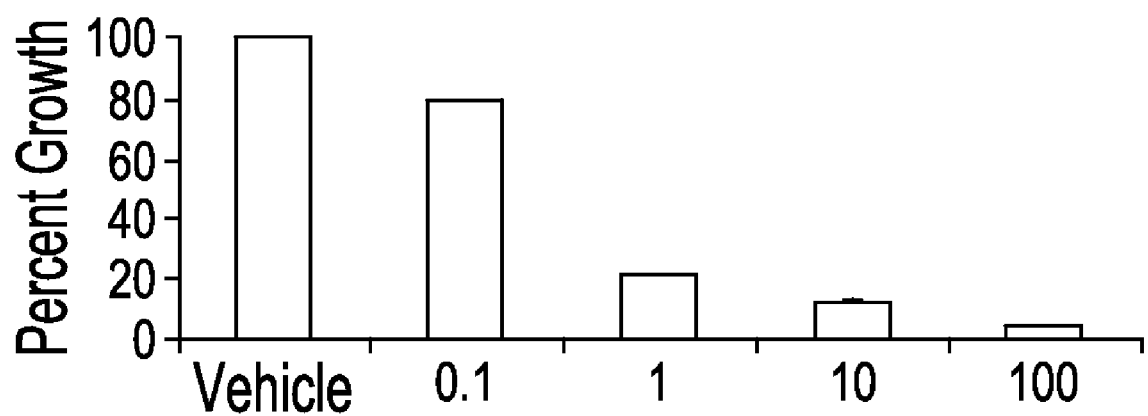
FIG. 26 shows the inhibition of growth of SF-286 CNS cancer cells by a composition of this invention comprising a fusion protein, SEQ ID NO: 43, as measured by a sulforhodamine B (SRB) growth inhibition assay, wherein the SEQ ID NO: 43, is used at concentrations of 0.1 µg/ml, 1 µg/ml, 10 µg/ml, and 100 µg/ml, and wherein at all concentrations used, cancer cell proliferation is reduced and reduction of cancer cell proliferation is dose dependent.
Figure 27:
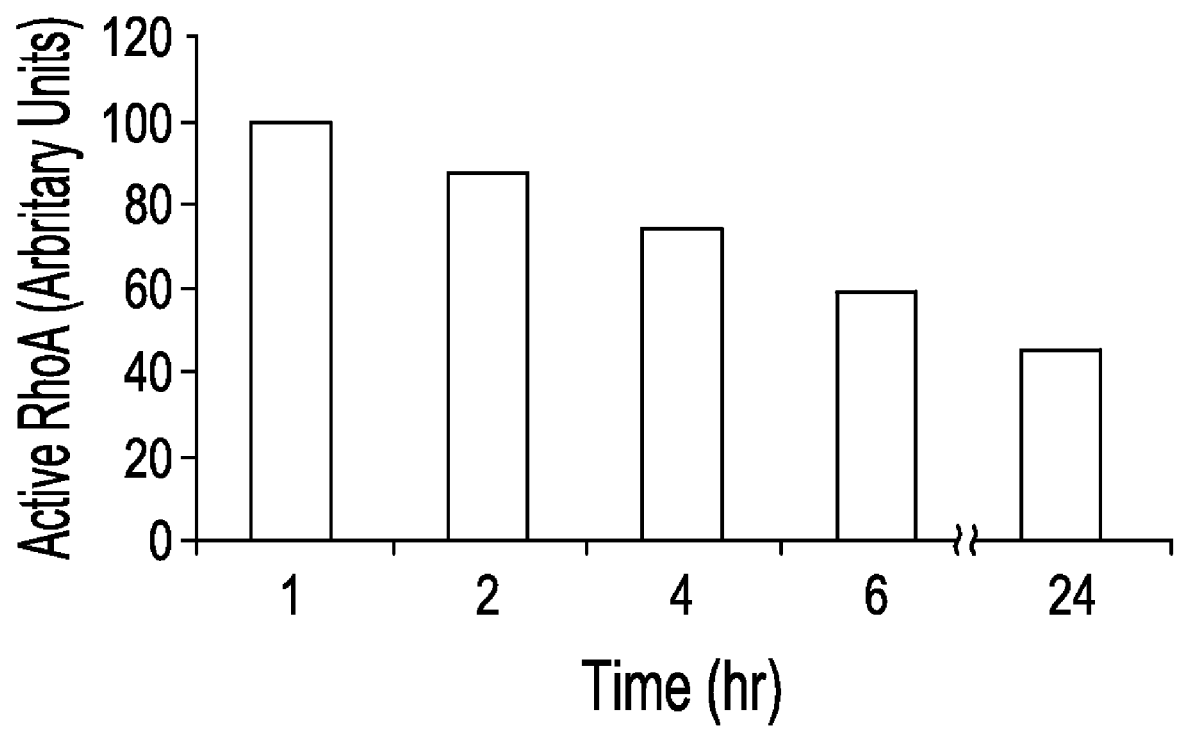
FIG. 27 shows reduction in levels of activated RhoA after incubation with 10 micrograms per milliliter of SEQ ID NO: 10, at 1 hour, 2 hours, 4 hours, 6 hours, and 24 hours after administration of a pharmaceutical composition comprising a fusion protein of this invention and a pharmaceutically acceptable vehicle.
Figure 28:
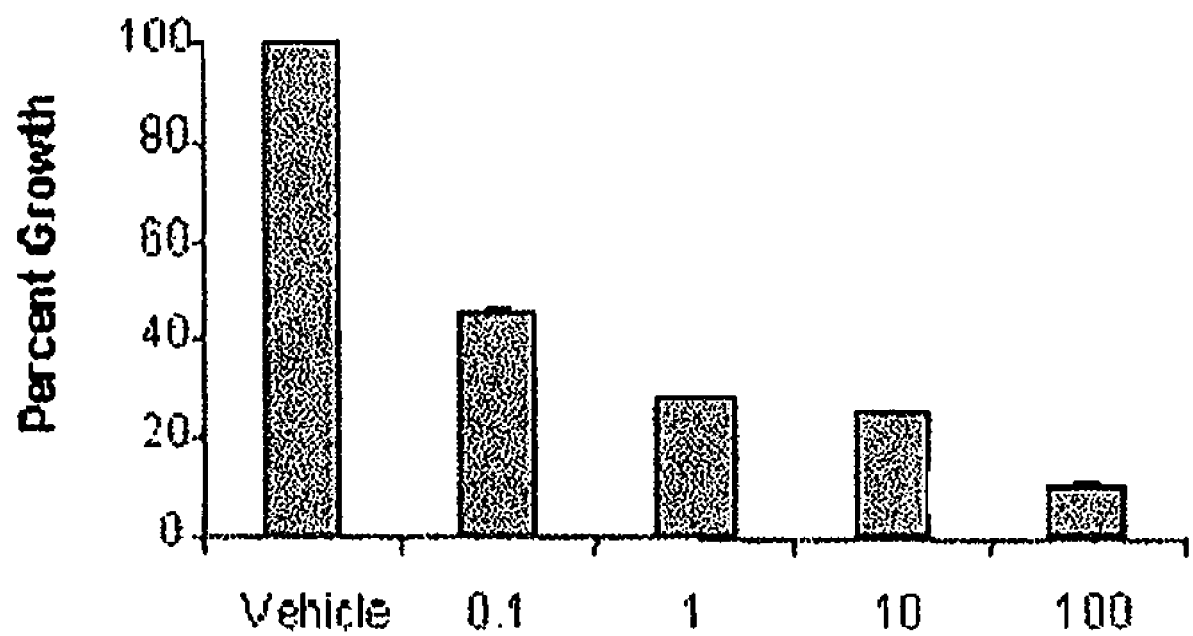
FIG. 28 shows the inhibition of growth (as % growth versus a vehicle control as reference) of Caki-1 renal carcinoma cells by a composition comprising SEQ ID NO: 43, the % growth measured with an SRB assay at relative concentrations of fusion protein of 0.1, 1, 10, and 100.

After injury of the optic nerve, approximately one-half of the RGCs die by apoptosis after 1 week. To determine whether a single intravitreal injection of SEQ ID NO: 43 protects RGC from cell death, RGC survival can be examined in retinal whole mounts. RGCs are retrogradely labeled with Fluorogold 1 week before optic nerve axotomy, and surviving RGCs are counted 7 or 14 days later in animals treated with SEQ ID NO: 43 (n=7 at 7 d; n=5 at 14 d) or vehicle control (n=3 at 7 d; n=4 at 14d). Treatment with SEQ ID NO: 43 completely rescues RGCs 1 week after axotomy, compared with 40% survival in vehicle-injected animals (FIG. 15). RGC survival after a single injection is not sustained, and RGC numbers decrease after 1 week. However, at 14 days, cell survival is still significantly improved with SEQ ID NO: 43 treatment, with more than twice the number of RGCs in treated animals compared with controls.

Example 14

Repeated Delivery of a Rho Antagonist Increases RGC Survival

Densities of RGCs at 2 weeks after axotomy in eyes that receive 1, 2 or 3 injections of 1 µg C3-11 can be quantified. The following SEQ ID NO: 43 treatment regimens can be performed: (i) single injection at the time of optic nerve lesion (day 0); (ii) 2 injections (day 0 and day 5 after nerve injury); and (iii) 3 injections (days 0, 5 and 10). The number of punctures through the sclera is limited to a maximum of 2 by using the same injection site for all injections performed after day 0. This is an important issue because retinal injury such as a cut or puncture through the retina can increase the level of mRNAs for ciliary neurotrophic factor (CNTF), basic fibroblast growth factor (bFGF) and FGF receptor-1 (FGFR-1) in rodents, and both CNTF and bFGF have been shown to promote RGC survival or regeneration following optic nerve lesion.

Example 15

Repeated Delivery of a Rho Antagonist Increases RGC Regeneration

To determine if repeated injections of the Rho inhibitor further enhance axon regeneration, an experimental protocol is established in which multiple injections of SEQ ID NO: 43 (1 μg) are performed over a 2-week period. Microlesion of the optic nerve is performed on day 0 and the treatment groups are as follows: (i) 3 injections (days 0, 5 and 10 after nerve injury); (ii) 2 late injections (days 4 and 10); and (iii) 2 early injections (days 0 and 5). The 2-injection protocol is designed based on an early and late administration schedule because it was previously found that the extent of regeneration is similar when a single injection is performed either on day 0 or on day 4 (Bertrand et al., 2005, J Neurosci, 25: 1113-1121).

Example 16

Activity of BA-Variants

The GH activity of the PEGylated variants was assessed as described above. A semi-quantitative evaluation of Rho ADP-ribosylation ability of SEQ ID NO: 10 PEGylated variants is carried out using cultured PC-12 cells (Table 8). At the molecular level, C3 exoenzyme treatment of cells in vitro results in ADP-ribosylation of RhoA at 41Asn, leading to its irreversible inactivation.

As indicated in Table 3, there is a correlation between a C3 variant's GH activity and its ability to promote neuritogenesis of NG108 cells. This correlation was confirmed using heat-inactivated C3 that had lost its GH and ADP-ribosylating activities and correspondingly failed to promote neuritogenesis. Similar findings apply in vivo, where a mutated variant of C3 that had both its GH and ADP-ribosylation activities removed was unable to provide neuroprotection or neuroregeneration following optic nerve injury.

In order to assess ADP ribosylation, one can take advantage of the fact that the covalently bound ADP-ribose group increases the apparent molecular weight of RhoGTPases on SDS-PAGE and can be readily visualized in western blots using anti-Rho antibodies. The shift in the apparent molecular weight of Rho GTPase confirms the expected addition of an ADP-ribose moiety to the Rho molecules. All of the PEG-SEQ ID NO: 10 variants showed a high molecular weight band of ADP-ribosylated RhoA, indicating that they retained their inherent ADP-ribosylation activity along with their ability to penetrate into PC-12 cells.

TABLE 8

GH activity of the PEGylated variants

| PEG-SEQ ID NO: 10 Variant | GH Specific activity, U | ADP Ribosylation |
|---|---|---|
| SEQ ID NO: 10 | 31.8 | + |
| BA-220 | 26.9 | + |
| BA-225 | 25.9 | + |
| BA-230 | 27.5 | + |
| BA-231 | 27.2 | + |
| BA-235 | 30.4 | + |
| BA-236 | 22.5 | +/− |
| BA-240 | 28.2 | + |

Example 17

In Vivo Applications of Pegylated SEQ ID NO: 10 Variants

SEQ ID NO: 10 provides neuroprotection of retinal cells in several animal models of glaucoma and age-related macular degeneration (AMD). Referring to FIG. 18, ocular pharmacokinetic studies in Sprague Dawley rats demonstrate that intraocularly injected SEQ ID NO: 10 was rapidly distributed in retinal tissue with peak concentrations reached within 1 hour after delivery. By 24 hours, the protein is almost undetectable in the retina. In order to develop viable intraocular injection therapies for diseases that progress slowly over the course of years, long lasting or sustained release formulations will be required. One potential means by which to achieve this could be to prolong the biological residence time of injected proteins via PEGylation. This strategy has already proven successful in the case of Macugen®, a PEGylated therapeutic aptamer that has recently been marketed for wet AMD. With this in mind, PEGylated forms of SEQ ID NO: 10 are tested in rat ocular PK studies to test whether the modifications would lead to an increase in retinal residence times.

For the first set of experiments testing PEGylated SEQ ID NO: 10 variants, retinas are collected 24 hours after intraocular injection (into the vitreous humor of the posterior chamber using a 10 μl Hamilton syringe) of 10 fig of each protein diluted in 5 μl isotonic saline (3 rats per group). Control eyes are injected with the vehicle (isotonic saline). Animals are sacrificed by anaesthetic overdosing, perfused with saline and the eyes are removed and processed for dissection. The retinas are homogenized and proteins are extracted in a solubilisation buffer. Protein concentrations in each extract are determined using a modified Lowry assay. Tissue levels of variants are measured using a sensitive sandwich ELISA. Briefly, a polyclonal capture antibody specific to SEQ ID NO: 10 is adsorbed to a microplate to create the solid phase. After blocking the plate with bovine serum albumin (BSA), test samples, standards, and quality controls are incubated with the coated phase antibody, which captures the variant in solution. After incubation with the same polyclonal antibody conjugated to biotin, detection is performed with streptavidin-HRP and its substrate solution (e.g. tetramethylbenzidine (TMB)/hydrogen peroxide). Color development is proportional to the amount of bound BA-variant and the color intensity is quantified by spectrophotometry.

Measured protein levels for BA-220, and BA-225 are equivalent to those of SEQ ID NO: 10, reflecting similar pharmacokinetic profiles. In contrast, BA-231 demonstrate a decreased tissue clearance and, thus, longer residence time (FIG. 16). This encouraging result led to the synthesis of larger PEG adducts of SEQ ID NO: 10.

Example 18

Pharmacodynamic Profile of SEQ ID NO: 10 and Pegylated Variants

To investigate the pharmacodynamic profile of SEQ ID NO: 10 and PEGylated variants with regard to their biological target Rho, the ADP-ribosylation of retinal RhoA is visualized using the gel shift assay (described above). Referring to FIG. 17, tissues are collected as described above for ELISAs and retinal proteins are extracted by lysis in RIPA buffer containing protease inhibitors. Postnuclear extracts are obtained by centrifugation and resolved (30 μg samples) by SDS-PAGE (Laemmli 1970) on 12.5% polyacrylamide gels. All of the variants tested are able to ADP-ribosylate intracellular Rho, indicating that they retained biological activity plus the ability to penetrate into tissues and cells (FIG. 17).

To compare the pharmacokinetic profiles between the parent protein and the PEGylated variants, 10 μg of each protein is injected in 5 μl saline (3 rats per group) and the retinal tissues collected as described above at predetermined time points for ELISA analyses.

Figure 18:
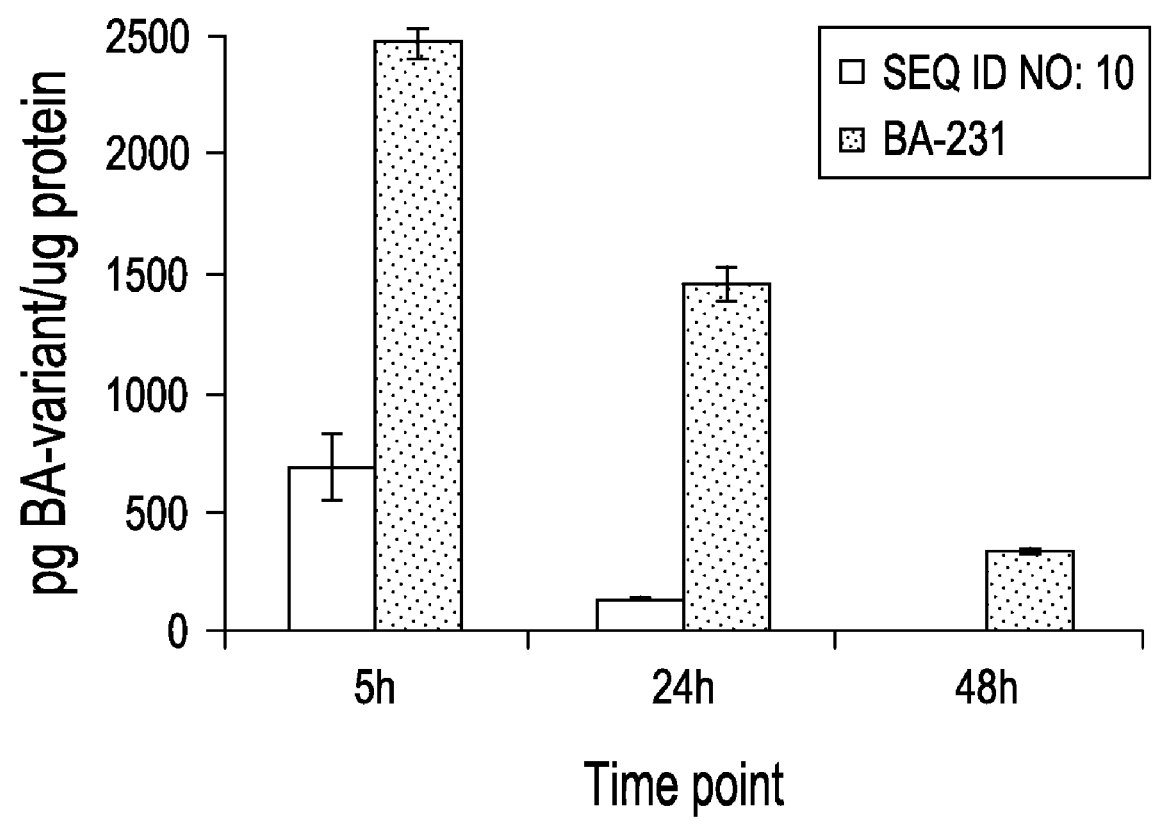

The comparative time courses of retinal clearance are investigated using di-PEG-21 kDa-BA-231. At all of the time points tested, this variant shows higher tissue retention when compared to the parent protein (FIG. 18). Thus, PEGylation significantly increase the total residence time of SEQ ID NO: 10 in the eye, lasting at least until 48 hrs.

The pharmacokinetic profile of several other higher molecular weight adducts can also be investigated as described above (10 μg variant in 5 μl saline in 3 rats per group). The addition of 21, 30 and 40 kDa PEG groups onto SEQ ID NO: 10 significantly increase retinal tissue levels at both 24 and 48 hrs compared to the non-pegylated variant (FIG. 19).

The same tissue samples can also be run on a gel shift assay as described above to confirm the in vivo biological activity of the variants. All tested variants are able to ADP-ribosylate Rho at the two time points tested (FIG. 20).

Example 19

Neuroprotective Ability of BA-231 (Pegylated Variant of SEQ ID NO: 10)

The potential neuroprotective ability of BA-231 can be tested in a mouse strain that is prone to slow retinal degeneration. The rds mouse has an inherited, spontaneous form of retinis pigmentosa that is related to human mutations within the photoreceptor RDS-peripherin gene. Degeneration in this model has an early onset and slow progression, with about 50% of the photoreceptors remaining at 4 months of age. These mice represent a well characterized and reproducible in vivo model to study the neuroprotective potential of BA variants in retinal degeneration model.

0.1 μg of SEQ ID NO: 10 or BA-231 is injected into the right eyes of mice (5 per group) starting at weaning age (3 weeks) and continuing every 2 or 3 weeks until the mice were 4 months old. The left eye receive the same schedule of repeated saline injection to serve as a control. Under isoflurane anesthesia, intraocular injections are performed using a microinjector at a dose volume of 1 μl. Animals are sacrificed by anaesthetic overdosing and the eyes are removed and incubated in Bouin's fixative before paraffin embedding. The eyeballs are cut into 5 μm serial sections and stained with hematoxylin and eosin. Retinal sections taken near the optic nerve are photographed and photoreceptor counts are done in 6 to 8 different pictures/animal for each condition. Counts are made so as to be representative of each hemisphere of the retina in an area of 100×100 μm length (3 to 4 area per hemisphere).

As indicated in the table below (Table 9), the PEGylated variant, compared to unmodified SEQ ID NO: 10, significantly improves the survival of peripheral photoreceptors in the retinas of rds mutant mice (the results are expressed as the percentage of photoreceptor survival between the treated and the control eyes of each mouse). This data supports that PEGylated SEQ ID NO: 10 variant with an increased ocular residence time confers a therapeutic benefic potential for enhanced neuroprotection in a chronic model requiring repeated dosing and continuous drug exposure.

TABLE 9

Neuroprotection of photoreceptors by repeated intraocular injections in a mouse model of progressive retinal degeneration (rds).

| BA-variant | Treatment regimen | % increase in peripheral photoreceptor survival versus vehicle injected eye |
|---|---|---|
| SEQ ID NO: 10 | 0.01 μg every 2 weeks | 0 |
| | 0.01 μg every 3 weeks | 0 |
| BA-231 | 0.01 μg every 2 weeks | 13% ($p < 0.05$) |
| | 0.01 μg every 3 weeks | 15% ($p < 0.05$) |

Example 20

General Method for Tritiated Thymidine Uptake as Measure of Cell Proliferation and Useful to Demonstrate that Fusion Protein SEQ ID NO: 43 Reduces Proliferation of Cancer Cells Cell lines are tested for mycoplasma and found to be negative prior to the initiation of the studies. Cell lines are obtained from ATCC. The line HEC-1B is cultured in E-MEM supplemented with 10% FBS and 1% HEPES. The line Caco-2 is cultured in E-MEM supplemented with 20% FBS, 1% HEPES, 1 mM sodium pyruvate and 0.1 mM of non-essential amino acid. The line SK-MEL-1 is cultured in McCoy's supplemented with 10% FBS and 1% HEPES.

Volumes of 10011 of each 2× working solution of fusion protein, positive and vehicle controls are plated in triplicate in 96-well microtiter plates containing cells ($4\times10^3$/100 μl), yielding a final volume of 200 μl. The plates are placed at 37° C. incubator with 100% humidity and 5% $CO_2$. After about 54 hours of incubation, a volume of 20 μl of tritiated thymidine (3H-thymidine) (ICN, Montreal, Canada), containing 1.0 μCi, is added to each well. The $^3$H-thymidine is prepared in RPMI-1640 supplemented with 10% FBS. The cultures are incubated in the same conditions as stated above, for a further 18 hours. At the end of the incubation, the cells are harvested with an automated cell harvester (Tomtec), and the incorporated Counts per minute (cpm) of $^3$H-thymidine are measured with a microplate scintillation counter (TopCount NXT, Packard).

Demonstration that a fusion protein of this invention, such as SEQ ID NO: 43, can affect multiple aspects of the phenotypes of malignant cells can be shown by monitoring tritiated thymidine incorporation in proliferating and growing cells, wherein tritiated thymidine added to cell culture medium is taken into the cells and becomes part of the thymidine triphosphate pool therein which is used by each cell to synthesize DNA. Tritiated thymidine becomes covalently incorporated into DNA macromolecules in each of the cells. In cells that are not growing or in cells that are undergoing death by apoptosis or by necrosis, tritiated thymidine is either not taken up into the cell or is released into the cell medium upon lysis of the cell. Tritiated thymidine incorporation can be used as an overall measurement of the effect of a fusion protein of this invention such as SEQ ID NO: 43 on cell growth, cell division, cell stasis, and cell death. Cell lines in which SEQ ID NO: 43 induces a decrease in 3H-thymidin comprise: human endometrial cancer cell line HEC 1B, human colorectal cancer cell line CaCo2, human melanoma cancer cell line SK-MEL-2, and human CNS cancer cell line A-172 (see FIG. 21 to 28).

Example 21

SEQ ID NO: 10 ADP-Ribosylates RhoA

Figure 30:
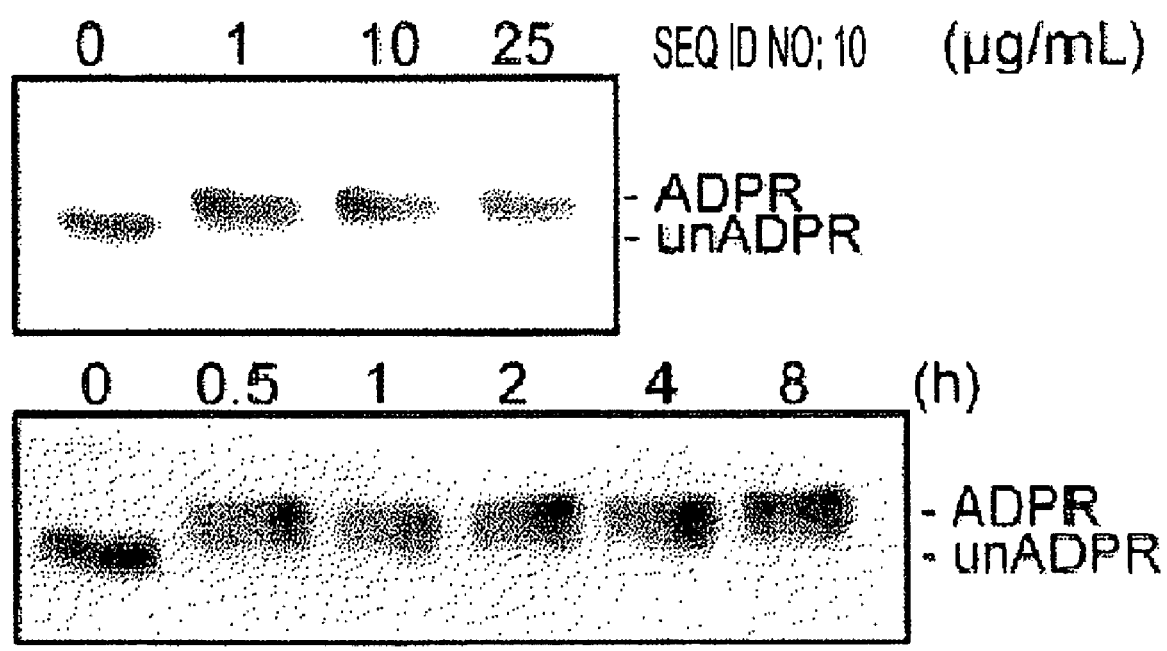
FIG. 30 illustrates that SEQ ID NO: 10 ADP-ribosylates RhoA, wherein sub-confluent HUVEC were treated during 24 hours with different concentrations of SEQ ID NO: 10 (0-25 µg/mL, upper panel) or with 10 µg/mL of SEQ ID NO: 10 for varying time (0.5-8 h, bottom panel) and RhoA ADP-ribosylation was analyzed by western blot using RhoA

C3 exoenzyme treatment of cells in vitro results in ADP-ribosylation of RhoA, B and C at $^{41}$Asn, leading to their subsequent inactivation. The covalently bound ADP-ribose group increases the apparent molecular weight of RhoGTPases on SDS-PAGE and can be readily visualized in western blots using anti-Rho antibodies. The shift in the apparent molecular weight of Rho GTPase in the anti-RhoA western blots of HUVEC treated with SEQ ID NO: 10 (FIG. 30) indicates the expected addition of an ADP-ribose moiety to the Rho molecules. Even concentrations of SEQ ID NO: 10 as low as 1 µg/mL, and treatment durations of 30 min, are sufficient to produce complete ADP-ribosylation of RhoA. These findings clearly demonstrate that relatively low doses of SEQ ID NO: 10 are sufficient to efficiently penetrate into the cytoplasm of cultured HUVEC.

Example 22

SEQ ID NO: 10 Decreases In Vitro Tube Formation by HUVEC

Figure 31A:
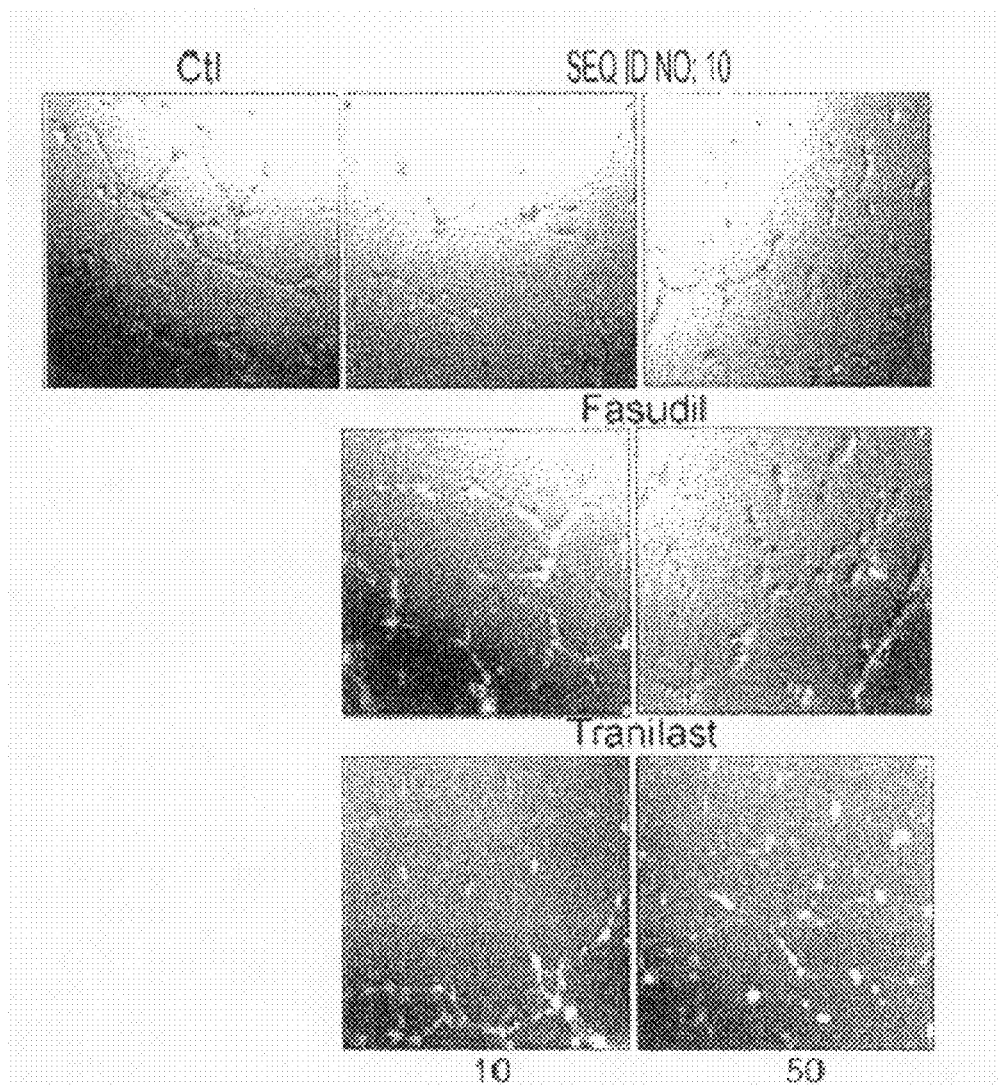
FIG. 31 illustrates that SEQ ID NO: 10 decreases tube formation in HUVEC, wherein HUVEC were seeded on solidified ECmatrix™ without (Control) or with 10 µg/mL or 50 µg/mL of SEQ ID NO: 10 or the angiogenesis inhibitor Tranilast, cells were also incubated with 10 µM or 50 µM of the ROCK inhibitor Fasudil, capillary-like structures were visualized between 6 h to 20 h incubation, and wherein in (A) photographs were taken under phase contrast inverted microscope at 40× magnification and (B) quantification of tube length was reported as percentage of the length from untreated cells SEM (photographs and quantification are representative of at least 2 independent experiments analyzed in triplicate; symbols * and ** represent respectively significant (p<0.05) and highly significant (p<0.01) difference from untreated cells)
Figure 31B:
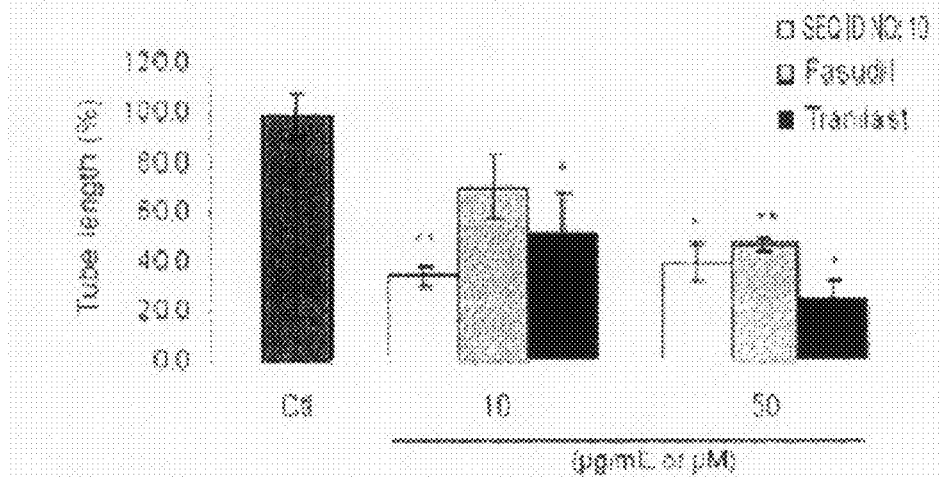

Referring to FIG. 31, to evaluate the importance of the signalling pathway Rho-Rock in angiogenesis, Transilat (10 µg/ml and 50 µg/ml) is used as a positive control. Transilat is known to block one of the principal angiogenesis routes i.e. the VEGF pathway. The binding of VEGF to VEGF-R stimulates tyrosine auto-phosphorylation of one of the receptors which initiates a signalling pathway, in part through PKC. Tranilast acts by inhibiting VEGF dependent PKC activation. FIG. 31A shows that untreated HUVEC (Ctl) formed thick and well closed capillary-like structures. SEQ ID NO: 10 at both concentrations tested produced immature tubes that are thin and not completely closed compared to those found in control cells (FIG. 31A). A similar morphology was obtained with the ROCK inhibitor Fasudil at both concentrations tested. Tranilast as expected produced at both concentrations used a decrease in tube formation characterized also by immature capillary structures and many colonies without elongation. The measurement of capillary length revealed that SEQ ID NO: 10 and Tranilast decreased significantly ($p<0.05$ or $p<0.01$) by at least 51% the length of tubes depending on the concentration, while Fasudil significantly decreased ($p<0.05$) tube formation by 58% but only at a high dose (50 µM) (FIG. 31B).

All the results presented hereinabove suggest that Rho can act on angiogenesis through its ability to regulate the cytoskeleton to a greater extent than its effects on proliferation and migration.

Example 23

SEQ ID NO: 10 Decreases Angiogenesis in Rat Aortic Rings

Figure 29A:
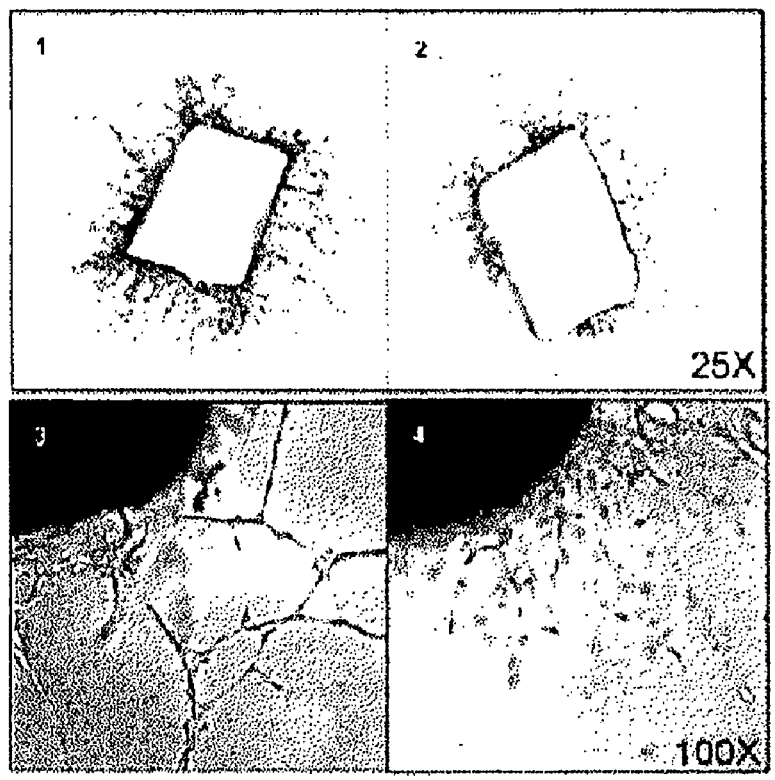
FIG. 29 illustrates SEQ ID NO: 10 decreases angiogenesis in rat aortic rings, wherein a Rat aorta was cut into small rings of 1 mm, aortic rings enrobed with solidified ECmatrix™ (matrigel) were incubated without (control) or with 10 µg/mL of SEQ ID NO: 10 from day 0 to day 7-8, a replenish of media containing (panels 2 and 4) or not (panels 1 and 3) SEQ ID NO: 10 was done at day 4, wherein in (A) angiogenesis from the rings was observed under phase contrast inverted microscope at 25× (upper panel) or 100× (lower panel) magnification and in (B) the length of vessels was measured and reported as mean±SEM (results are representative of 3 independent experiments analyzed at least in triplicate and the symbol * represents significant difference (p<0.05) from control rings)

Rat (Sprague-Dawley) thoracic aorta were cut into small rings of 1 mm thickness, enrobed with solidified ECmatrix™ (matrigel) and then incubated without (Ctl) or with 10 µg/mL of SEQ ID NO: 10 from day 0 to day 7-8 in endothelial basal-2 media (EBM-2) supplemented with hEGF, GA-1000, VEGF, hFGF-B, r$^3$-IGF-1, ascorbic acid and heparin (corresponding to EGM-2 minus FBS and hydrocortisone). A replenishment of the media (without or with SEQ ID NO: 10) was done at day 4. Angiogenesis from the rings was observed via phase contrast inverted microscope at 25× (upper panel) or 100× (lower panel) magnification. Images were taken at indicated magnifications using Northern Eclipse software. Low magnification (25×) phase contrast microscopic analyses revealed extensive cellular outgrowths from control rings (FIG. 29A, panel 1). At higher magnification (100×), well formed capillary-like structures consisting of chains and cords of conjoined elongated cells were clearly visible (FIG. 29A, panel 3). In contrast, a low magnification view of SEQ ID NO: 10 treated rings revealed considerably fewer cellular outgrowths (FIG. 29A, panel 2) compared to control rings. At higher magnification, the capillary network was seriously disrupted, comprising much shorter and thinner tubules (FIG. 29A, panel 4) compared to those of control rings.

Figure 29B:
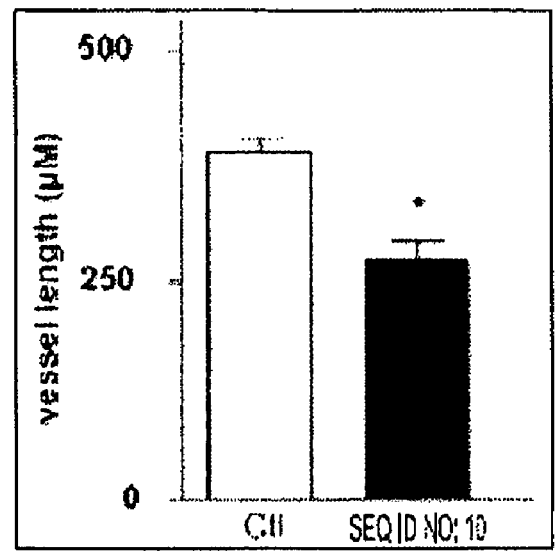

The length of tubules was measured and reported as the mean±SEM (FIG. 29B). Results are representative of 3 independent experiments analyzed at least in triplicate. The symbol * indicates a significant difference ($p<0.05$) from control rings. These quantitative analyses of tubule length indicated a 30% decrease ($p<0.05$) in vessel length caused by SEQ ID NO: 10 treatment. Collectively, these data clearly demonstrate that SEQ ID NO: 10 can mediate inhibition of angiogenesis in a robust ex vivo model.

Example 24

SEQ ID NO: 10 has Minimal Effects on HUVEC Proliferation and Migration

Figure 32:
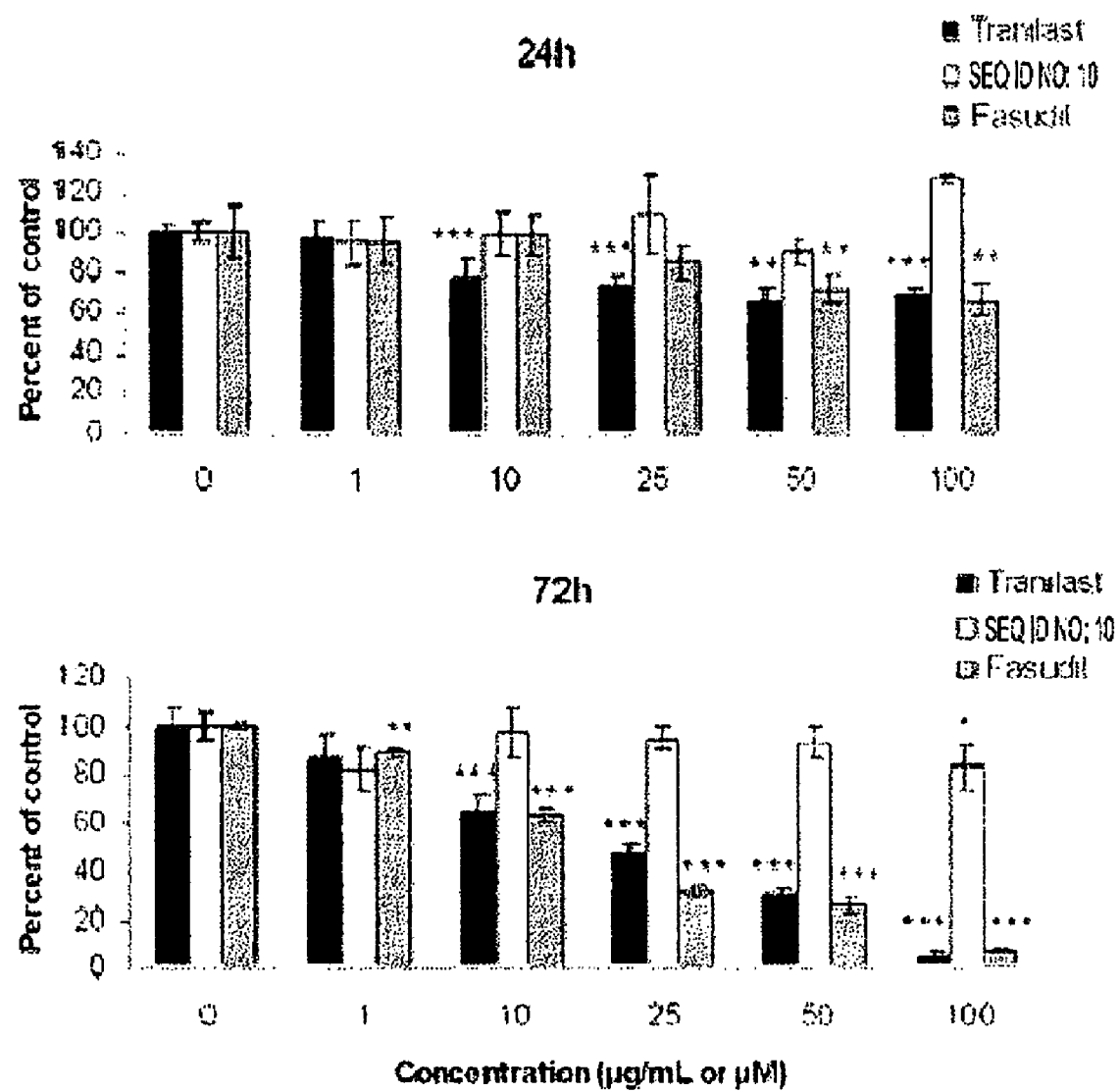
FIG. 32 illustrates that SEQ ID NO: 10 affects HUVEC proliferation at high concentration, wherein HUVEC were plated in 96 wells (collagen 1-coated) and incubated during 24 h or 72 with 0 to 100 µg/mL (or µM) of SEQ ID NO: 10, Fasudil or Tranilast, cells from 4 h and 24 h were washed out and replenished with fresh media containing no test compounds and left until 72 hours, and at the end of treatment (72 hours) Alamar blue was added, incubated for 4 hours and fluorescence was measured. Proliferation is represented in a graph as a percentage of that from untreated cells (0 µg/mL) ±S.D. and represents 2 independent studies analyzed in triplicate.

In HUVEC cultures seeded onto collagen coated wells, SEQ ID NO: 10, even at very high doses (up to 100 µg/mL for 72 hr) has no discernible effect on the proliferation rate as assessed by Alamar Blue staining (FIG. 32). By comparison, both the Rho kinase inhibitor Fasudil, as well as Tranilast, produce significant ($p<0.01$) reductions in HUVEC cell proliferation at either 24 hr or 72 hr. Given that SEQ ID NO: 10 efficiently ribosylates RhoA and therefore inhibits its activity under these conditions, it appears that the proliferation of HUVEC in this system, along with this part of the angiogenic sequence, proceeds independently of RhoA activity. In contrast, HUVEC proliferation seems to depend on Rho kinase activity as well as on the activity of those targets, possibly including protein kinase C, blocked by Tranilast.

Figure 33B:
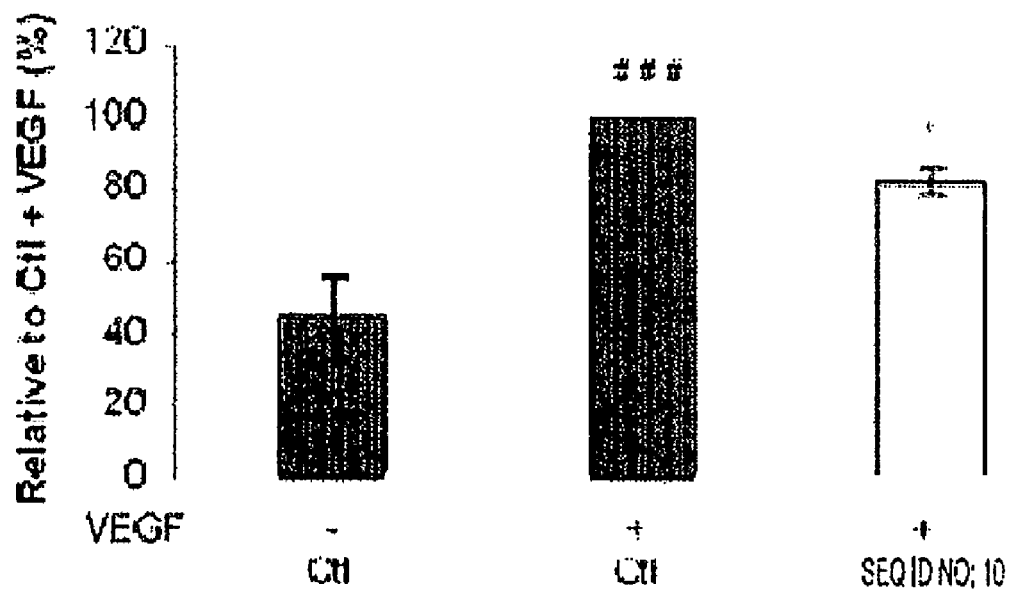

Another cellular function and part of the angiogenic process that is known to be perturbed by Rho GTPase inhibition is endothelial cell migration. In order to evaluate the effect of SEQ ID NO: 10 on HUVEC migration, cells are seeded in the upper side of a transwell insert along with the desired test compounds, and migration is then induced with 10 ng/mL of VEGF at the bottom side of the insert. After 20 hours of migration, cells that pass through the membrane of the insert are labeled with calcein AM probe and detected via fluorescence. As expected, 10 ng/mL of VEGF significantly ($p<0.001$) stimulates HUVEC migration by 2.2 fold (FIG. 33A) compared to untreated control cells. Tranilast, a positive control known to inhibit VEGF-induced migration, significantly decreases HUVEC migration at 10 (45%, $p<0.05$) and 50 (72%, $p<0.001$) µg/mL. SEQ ID NO: 10 barely decreases the migration of HUVEC at both concentrations tested, while 50 µM Fasudil decreases migration by 66% ($p<0.001$). Only after a 24 hour pretreatment with 50 µg/mL of SEQ ID NO: 10 is a decrease (17%, $p<0.05$) in VEGF-dependent HUVEC migration observed (FIG. 33B). The noteworthy differences between inhibiting either Rho GTPases or Rho kinase with respect to both proliferation and migration of HUVEC suggest that there are distinct cellular pathways involved.

Combined, these results involving Rho inactivation with SEQ ID NO: 10 suggest that proliferation and VEGF-dependent migration of endothelial cells are not the main events regulating the decrease in HUVEC tube formation in vitro. Presumably, other steps of the angiogenesis process must be affected following the inhibition of Rho GTPase or Rho kinase.

Example 25

General Method to Demonstrate the Effect of a Fusion Protein on Inhibition of Proliferation of Cancer Cells A sulforhodamine B (SRB, available from Molecular Probes) protein staining assay for the in vitro measurement of cellular protein content was developed and subsequently adopted for routine use in the NCI in vitro antitumor screening (Skehan et al., 1990). The SRB binds to basic amino acids of cellular protein and colorimetric evaluation provides an estimate of total protein mass which is related to cell number. This assay is based on the assumption that dead cells either lyse and are removed during the procedure, or otherwise do not contribute to the calorimetric end point. The SRB assay might overestimate the surviving fraction of cells.

Protocol for SRB Assay

These tests are conducted on a NCI 60 cell line panel. Cells are grown in RMPI-L 640 media supplemented with 5% fetal bovine serum and L-glutamine according to ATCC recommendations for each cell line. Cells in logarithmic growth are trypsinized and counted. Cells are inoculated in a 96-well microplate depending oil the doubling time of individual cell lines in 100 µL of growth media. The microplates are incubated at 37° C., 5% $CO_2$ and 100% relative humidity for 24 h to resume exponential growth. After 24 h, two plates of each cell line are fixed in situ with TCA to represent a measurement of the cell population for each cell line at the time of test article addition ($T_0$). The TCA is removed and the plates are incubated at room temperature for at least 24 h to dry.

A fusion protein of this invention is prepared and stored frozen as a lyophilized powder. It can be reconstituted with sterile water to form a pharmaceutical composition at about 4.42 microgram of fusion protein per microliter in 10 mM sodium phosphate, buffer pH 7.4. For each dose point, serial dilutions of the stock solution are prepared with complete medium containing 50 µg/mL gentamicin to provide fusion protein at 200 µg/mL, 20 µg/mL, 2 µg/mL, 0.2 µg/mL, and 0.02 µg/mL. Aliquots of 100 µL of those test article dilutions are added to the appropriate well already containing 100 µL of medium to achieve the final log dilution series doses for the fusion protein.

After fusion protein (i.e., drug) addition, the microplates are incubated for an additional period at 37° C., 5% $CO_2$ and 100% relative humidity. The assay is terminated by fixing the protein in the cells to the bottom of the wells using trichloroacetic acid (TCA). The plates are dried, and then 100 µL of SRB solution at 0.4% (w/v) in 1% acetic acid is added to each well. The plates are incubated with the protein-binding stain for 10 min at room temperature.

After staining, unbound dye is removed by washing 1% acetic acid, and the plates are dried. Bound stain is solubilized by adding 200 µL of 10 mM Trizma base while the plates are gently mixed. The amount of dye is measured by reading the optical density with a microplate reader at a wavelength of 515 nm.

Data is analyzed in an Excel spreadsheet.

$T_0$=Mean absorbance at the time of fusion protein addition (time 0);

C=Mean absorbance for control (no test article containing drug);

$T_i$=Mean absorbance for fusion protein article (different dose points in dilution series);

GI=Growth inhibition;

TGI=total growth inhibition;

$LC_{50}$=lethal concentration (lethal to 50% of total population);

A percentage growth is calculated for each of the test article concentrations:

$$\% \text{ Growth} = \left[\frac{(Ti - To)}{(C - To)}\right] \times 100 \text{ for concentrations where } T_i > T_0$$

% Growth inhibition=

$$\left[\frac{(Ti - To)}{(To)}\right] \times 100 \text{ for concentrations where } T_i < T_0.$$

The % growth inhibition can be used to prepare a chart to compare the effect at different doses. The percentage growth plots are plotted, and the points where the dose response curves crossed the PG values of +50, 0, and −50 are used to calculate the $GI_{50}$, TGI and $LC_{50}$. $GI_{50}$, or concentration required to inhibit growth 50% is the relevant parameter for the fusion protein.

Example 26

Specific Use of SRB Assay to Demonstrate Inhibition of Cell Growth of Human Cancer Cell Lines

TABLE 10

GI50 (concentration for 50% inhibition of cell growth) following fusion protein treatment measured by SRB assay

| Cell line | Type of Cancer | GI50 (µg/mL) |
|---|---|---|
| Caki-1 | Renal | 0.054 |
| TK-10 | Renal | 0.52 |
| SF-268 | CNS | 0.326 |
| HOP-62 | Non-SCLC | 0.269 |
| NCI-H226 | Non-SCLC | 48.2 |
| HS 578T | Breast | 36.6 |

One fusion protein of this invention, SEQ ID NO: 43 has an effect on 4 of 6 human tumor cell lines tested with $^3$H-thymidine and an effect on about 10% of the cell lines of the NCI screen. In the SRB test, it appears to have cytostatic properties; growth is inhibited compared to controls but the overall amount of protein does not decrease compared to the amount measured at time zero (Tz). These results agree with in vivo data showing that C3 transferase is not highly toxic to animals. The observed $GI_{50}$ values are in the nanomolar to micromolar range, given a molecular weight of about 27 kDa for the fusion protein (Table 10).

Example 27

Detection of Activated Rho by Pull-Down Assay

NG108 cells are grown in cell culture in the presence of 5% fetal bovine serum (FBS), 1% penicillin-streptomycin (P/S). After the cells settle (3-6 hours at 37° C.), BA-05 is added to the cultures. To lyse the cells, they are washed with ice cold Tris buffered saline (TBS) and are lysed in modified RIPA buffer (50 mM Tris pH 7.2, 1% Triton X-100, 0.5% sodium deoxycholate, 0.1% SDS, 500 mM NaCl, 10 mM $MgCl_2$, 10 µg/ml leupeptin, 10 µl/ml aprotinin, 1 mM phenylmethyl-sulfonyl fluoride (PMSF)). Cell lysates are clarified by centrifugation at 13,000 g for 10 minutes at 4° C. and kept at –80° C.

Purification of GST-Rho Binding Domain (GST-RBD) is performed with the cell lysates, which are thawed and resuspended in 500 uL of RIPA buffer per 1 million cells. To make the GST-Rho Binding Domain (GST-RBD), bacteria expressing GST-RBD in a PGEX vector are grown in L-broth (LB) with 100 µl/ml ampicillin. Overnight cultures are diluted 1:10 into 3600 ml LB and incubated in a shaking bacterial incubator at 37° C. for 2 hours. Isopropyl-β-D-thiogalactopyranoside (0.5 mM) is then added to the incubating cultures for 2 hours. Bacteria are then collected by centrifugation at 5,000 g for 15 minutes. The pellets are then resuspended in 40 ml lysis buffer (50 mM Tris pH 7.5, 1% Triton-X, 150 mM NaCl, 5 mM $MgCl_2$, 1 mM DTT, 10 µg/ml leupeptin, 10 µg/ml aprotinin, 1 mM PMSF). After sonication, the lysates are spun at 14,000 rpm for 30 minutes at 4° C.

Frozen cell culture is homogenized in RIPA buffer (50 mM Tris pH 7.2, 1% Triton X-100, 0.5% sodium deoxycholate, 0.1% SDS, 500 mM NaCl, 10 mM $MgCl_2$, 10 µg/ml leupeptin, 10 µg/ml aprotinin, 1 mM PMSF). The homogenates and cell lysates are clarified by two 10-minute centrifugations at 13,000 g at 4° C. They are then incubated for 50 minutes at 4° C. with GST-RBD coupled to glutathinon agarose beads (Sigma, Oakville, Canada). The beads are then washed 4 times and eluted in sample buffer. GTP-bound Rho and total Rho present in tissue homogenates are detected by western blot. The proteins are transferred to nitrocellulose and are probed using a monoclonal RhoA antibody (Santa Cruz, Santa Cruz, Calif.). Bands are visualized with peroxidase-linked secondary antibodies (Promega, Madison, Wyo.) and an HRP based chemiluminescence reaction (Pierce, Rockford, Ill.). Densitometry analysis is performed to quantitate the signal in each band.

Example 28

Use of Rho Pull-Down Assay as a Diagnostic to Diagnose or Determine which Tumours can Best Respond to Protein Fusion Therapy Using SEQ ID NO: 43 as an Example Biopsy samples of tumours are taken by surgical removal from a tissue in a mammal (e.g., a human patient) to leave residual tissue in the margin of the excised tumor when all of a tumor is removed. The samples are frozen on dry ice or in liquid nitrogen. Samples of excised tissue of approximately 5 $mm^2$ are homogenized in 500 uL RIPA buffer (50 mM Tris pH 7.2, 1% Triton X-100, 0.5% sodium deoxycholate, 0.1% SDS, 500 mM NaCl, 10 mM $MgCl_2$, 10 mg/ml leupeptin, 10 mg/ml aprotinin, 1 mM PMSF). The homogenates are clarified by two 10-minute centrifugations at 13,000 g at 4° C. to provide samples for further analysis. The samples are then incubated for 50 minutes at 4° C. with GST-RBD coupled to glutathione agarose beads. GTP-bound Rho and total Rho present in the tissue homogenates are detected by western blot.

To detect which cells in the biopsy sample have activated Rho, cryostat sections can be prepared. Bacterial lysates of RBD-GST are clarified by centrifugation at 14,000 rpm for 30 minutes at 4° C. Activated Rho is detected by incubating the section with bacterial lysate containing RBD-GST. Biopsy sample cryosections (about 16 µm thickness) are incubated, after post fixation with 4% PFA, with the bacterial lysate overnight at 4° C. The sections are then washed 3 times is TBS, blocked in 3% BSA for 1 hr at room temperature and incubated with anti-GST antibody (Cell signalling, New England Biolabs, Mississauga, Canada) and with cell-type specific antibodies. In the case of a brain tumour neuron-specific antibody (NeuN) or astrocyte-specific antibody (GFAP) can be used to detect the cell type with activated Rho to aid in tumour diagnosis. Sections are washed in TBS and incubated for 2 hr at room temperature with FITC, Texas Red or Rhodamine conjugated secondary antibodies (Jackson ImmunoResearch, Mississauga, Canada).

Example 29

General Method to Detect Reduction in Metalloproteinase (MMP) Activity

Metalloproteinase activity is detected by zymography whereby proteolytic activity of enzymes is separated in polyacrylamide gels under non-reducing conditions. To detect metalloproteinase activity the gelatinolytic activity in culture media from growth of Caki-1 colon carcinoma cells is detected by gelatin zymography. The Caki-1 cells are incubated with SEQ ID NO: 43 at 0.1, 1.0 or 10 µg/ml or buffer as control for 24 hr. An aliquot (25 µL) of the culture media is subjected to SDS/PAGE with 7.5% polyacrylamide containing 1 mg/ml gelatin, and the polypeptides are separated under non-reducing conditions. To assess MMP activity, SDS is removed by incubation for 30 min at room temperature in 2.5% (v/v) Triton X-100. This step is repeated, followed by five rinses with $ddH_2O$, Next, the gel is incubated for 20 h at 37° C. in a buffer containing 50 mM Tris-HCl, pH 7.6, 0.2 M NaCl, 5 mM $CaCl_2$, and 0.02% (v/v) Brij-35. The gel is stained with Coomassie Brilliant Blue R-250, and destained. Enzyme activity on the gelatin substrate is detectable as transparent bands in a blue background. The identity of the MMP enzyme with gelatinase activity is assessed with a positive control such as, in these experiments, HT-1080.

Example 30

General Method to Treat an Excised Tumor Margin

A composition of the invention comprising a fusion protein, such as SEQ ID NO: 43, formulated in a pharmaceutically acceptable cream can be used to treat an excision site from the skin. An example is the treatment of malignant melanoma, where such a cream is put on the skin surrounding the excision site of the tumor. In one aspect, such a formulation of a cream containing the fusion protein such as SEQ ID NO: 43 can be administered to the skin prior to excision of the tumor and used to treat the tumor between the period of first biopsy and before positive histological diagnosis. The cream when applied to the tumor site can prevent the spread and metastasis of the tumor.

Example 31

Prevention of a Second Tumour Growing in a Tumour Margin

A composition of this invention comprising a fusion protein, such as SEQ ID NO: 43, for example such as an aqueous solution as described above or such as formulated in a surgical adhesive gel, such as a fibrin adhesive or a hydrogel, can be used to treat the area of a surgical resection of a tumor. An example is the treatment of a healthy colon after colonectomy for a colon cancer. The healthy colon tissue that otherwise surrounded the tumor region prior to excision of the tumor can be treated with a fusion protein composition such as SEQ ID NO: 43, after removal of the tumor and associated tissue, in a surgical gel such as a fibrin sealant, and will be useful to prevent formation of additional lesions in the residual tissue.

Example 32

General Method to Demonstrate Preclinical Efficacy in a Mammal

A melanoma cell line is implanted subcutaneously in a first group of nude mice (Charles River Laboratories). Tumors are grown mice of the first group of mice, harvested, and transplanted individually into each mouse (one tumor per mouse) of a second group of mice. A daily injection of a pharmaceutical composition of this invention comprising an effective dose of a fusion protein such as SEQ ID NO: 43, which is estimated to be in the range of 10-100 ug/mL of tumor volume, in a pharmaceutically acceptable vehicle is administered to each mouse in the second group of mice. Control animals are injected with vehicle as a control. Tumor growth is measured, and histology performed to measure markers from malignant keratinocytes such as gamma immuno protein 10 (IP10). The composition comprising the fusion protein prevents or substantially inhibits the growth of tumors in the second mice.

Example 33

Use of a Composition Comprising a Fusion Protein Applied to the Surface of an Implanted Breast Device in the Prevention of Recurrence of Breast Cancer A therapeutically effective amount of a pharmaceutical composition of this invention comprising a fusion protein is coated onto the surface of a pharmaceutically acceptable breast implant. A tumor is excised from the tissue of a breast in a patient, optionally with co-administration (pre and/or post operative) of a pharmaceutical composition of this invention as described hereinabove. The void created by the excision of the tumor is filled at least in part with the breast implant coated with a pharmaceutical composition comprising a fusion protein, and the wound created by the excision and/or implantation is closed. Growth of a second tumor in the residual tumor margin tissue is substantially inhibited or prevented.

Example 34

Preparation of a Pharmaceutical Composition for Administration in Patient

A pharmaceutical composition of the present invention can be prepared by mixing the SEQ ID NO: 10 (30 mg/mL stock solution or diluted solution) with the four components of the Tisseel® (fibrin sealant) kit:
Lyophilized Thrombin;
1 mL $CaCl_2$/Buffer reconstitution solution to reconstitute Thrombin;
Lyophilized Fibrinogen; and
1 mL buffer solution to reconstitute Fibrinogen.

The stock solution of SEQ ID NO: 10 is stored at −20° C. and kept frozen until 1 hour before use. The stock solution of SEQ ID NO: 10 is thawed by placing the vial in the palm of the hands for a few minutes. 0.3 mL of the SEQ ID NO: 10 stock solution using a 1 mL syringe is drawned and injected into an empty vial. 0.15 mL of sterile water using a sterile syringe is added. Mixing is then performed by swirling gently. Using a 1 mL syringe, 0.3 mL of the $CaCl_2$ solution (from the Tisseel® kit) is drawned and discarded. Using the same syringe, 0.3 mL from the appropriate SEQ ID NO: 10 working solution is drawned and injected into the $CaCl_2$ vial, and mixed by swirling gently. The full volume of the $CaCl_2$/SEQ ID NO: 10 vial with a 1 mL syringe is drawned and injected into the thrombin reconstituted vial. The Thrombin solution is kept at 37° C. until use. The Tisseel® Sealer Protein Concentrate should be prepared and reconstituted according to the manufacturer's instructions prior to use. The Thrombin/SEQ ID NO: 10 and the Tisseel® Sealer Protein solutions with their respective Duploject syringes are drawned and the Tisseel® application is followed for clot formation.

Example 35

Distribution of SEQ ID NO: 10 Following Extramural Application

Referring to FIG. 34, the distribution of SEQ ID NO: 10 can be characterized in the normal and injured rat spinal cords. Penetration and distribution of SEQ ID NO: 10 in spinal cord tissues are evaluated using Western blotting for tissue obtained from individual rats (n=3-5 rats for each experiment). For all blots, 50 μg of protein is loaded into each lane. After separation on 12% SDS-PAGE, the proteins are transferred to nitrocellulose, blocked and probed using a polyclonal anti-SEQ ID NO: 10 antibody. Bands are visualized with peroxidase-linked secondary antibodies (Promega) and an HRP-based chemiluminescence reaction (Pierce Chemical Co.). Blots are scanned for densitometry using a laser Personal Densitometer SI (Molecular Dynamics) and the band images are then analyzed with the ImageQuant software version 5.0 (Molecular Dynamics). The software measures the pixel density in the band image after background subtraction, and the densitometry value is in arbitrary units.

For immunohistochemistry, spinal cords embedded in OCT are processed in 10 μm sections onto Super Frost glass slides and post fixed in 4% PFA. After a one hour incubation in blocking solution (5% normal goat serum, 3% BSA in PBS), SEQ ID NO: 10 is detected using a monoclonal antibody and visualized following a one hour incubation with FITC-conjugated goat anti-mouse secondary antibody (Jackson ImmunoResearch Laboratories). Slides are examined with Zeiss Axioskop 2 fluorescence microscope. Images of the tissue sections are taken using Northern Eclipse software. Rats, to which only PBS in Tisseel are applied, are used as controls in this experiment to assess antibody specificity and background interference.

Figure 34A:
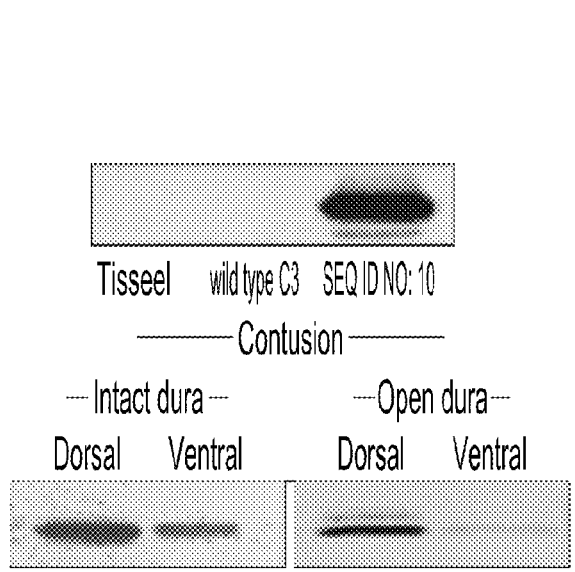
FIG. 34 illustrates penetration and distribution profile of a cell permeable C3 in rat spinal cord; wherein in (A) it is disclosed the comparison of penetration of SEQ ID NO: 10 with wild type C3 (SEQ ID NO: 1) into the spinal cord of rat, wherein SEQ ID NO: 10 was detected by Western blot after contusion both in intact dura and open dura by surgery (B) SEQ ID NO: 10 distribution pattern along the spinal cord is disclosed, and (C) (immunohistochemical detection of SEQ ID NO: 10 (50 ug) penetration 24 hrs after application on contused spinal cord is also disclosed.

In time course experiments, the ability of SEQ ID NO: 10 (50 µg) to penetrate spinal cord tissue is verified in combination with Tisseel® when applied onto the dura in uninjured laminectomized rats. The dura is left intact and 1 cm of tissue at the application site is collected one hour after the surgery. As opposed to wild type C3 lacking the transport sequence, SEQ ID NO: 10 is found to rapidly penetrate into the spinal cord (FIG. 34A). Bolus delivery from the Tisseel matrix gave maximal and constant spinal cord levels in the first 2 hours after application followed by a slow release phase with residual levels still detected at 7 days.

Rho is a ubiquitous protein and important in normal cell function. Its systemic inhibition could bear important side effects. It is therefore preferable that SEQ ID NO: 10 delivery is locally restricted to the injured spinal cord in order to limit systemic exposure. Following extradural application, low levels of SEQ ID NO: 10 are detected in tissues close to the application site such as skin and back muscle (less than 5% of initial dose). However, when administered topically with Tisseel®, SEQ ID NO: 10 (up to 50 µg) has no demonstrable effects on wound healing at the doses used. Limited exposure is found in the systemic circulation (about 0.5% of initial dose, Cmax at 1 hour) and the protein is not found to concentrate itself in any organ systems (data not shown). In a further experiment, kidney is found to be responsible for elimination (1% of initial dose detected in the tissue at 1 hour) and the protein is detected in urine in the first hours after application. SEQ ID NO: 10 is also detected in the liver shortly after dosing though in smaller amounts than the one found in the kidney.

Figure 34C:
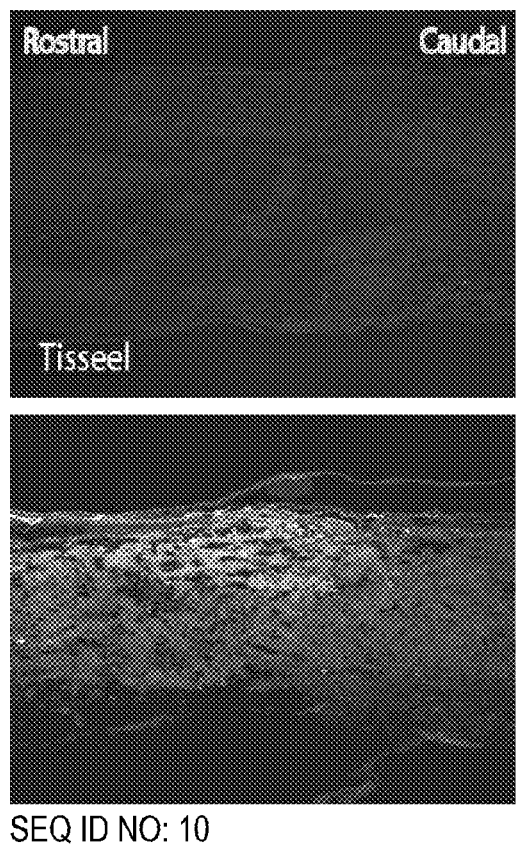
Figure 34B:
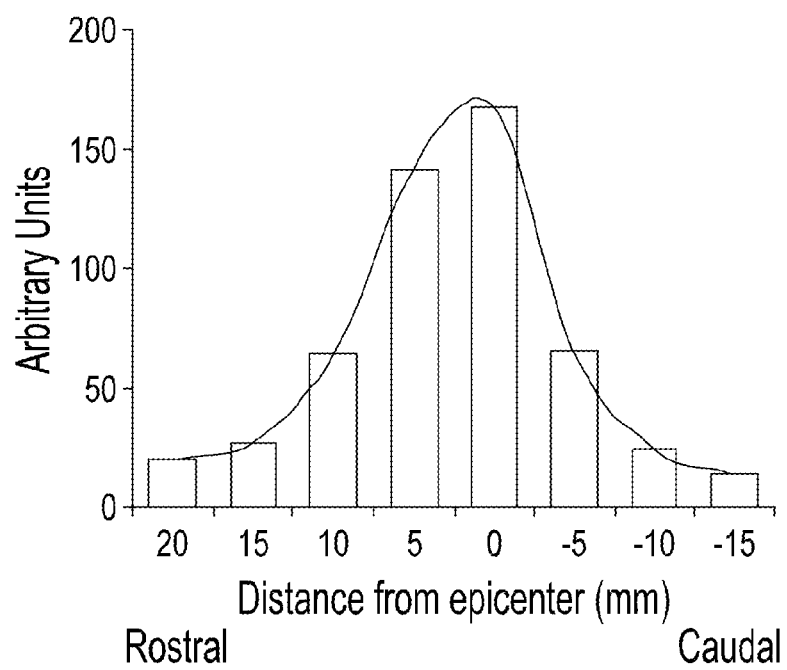

The dorso-ventral and rostro-caudal distribution of SEQ ID NO: 10 is also assessed. Twenty-four hours after delivery, the protein is detected in both dorsal and ventral contused spinal cord of treated rats either with an intact or open dura (FIG. 34A). Spinal cord trauma is found not to affect the distribution of SEQ ID NO: 10 under our experimental conditions. At two hours after application of 50 µg SEQ ID NO: 10 in laminectomized normal spinal cord, diffusion is found both caudally and rostrally from the site of application with distance covering approximately 2 cm (FIG. 34B). Immunohistochemistry confirmed that at 24 hours after its application on contused spinal cord, exogenously-delivered SEQ ID NO: 10 has been absorbed and distributed within the grey and white matter of the spinal cord. Immunostaining is mostly detectable dorsally, within the dura mater and is intense at the injury epicenter. Spinal cord sections, collected from vehicle treated animals, faile to exhibit any labeling (FIG. 34C).

Example 36

Time and Dose Dependent Rho Inactivation by SEQ ID NO: 10 Treatment

Figure 35A:
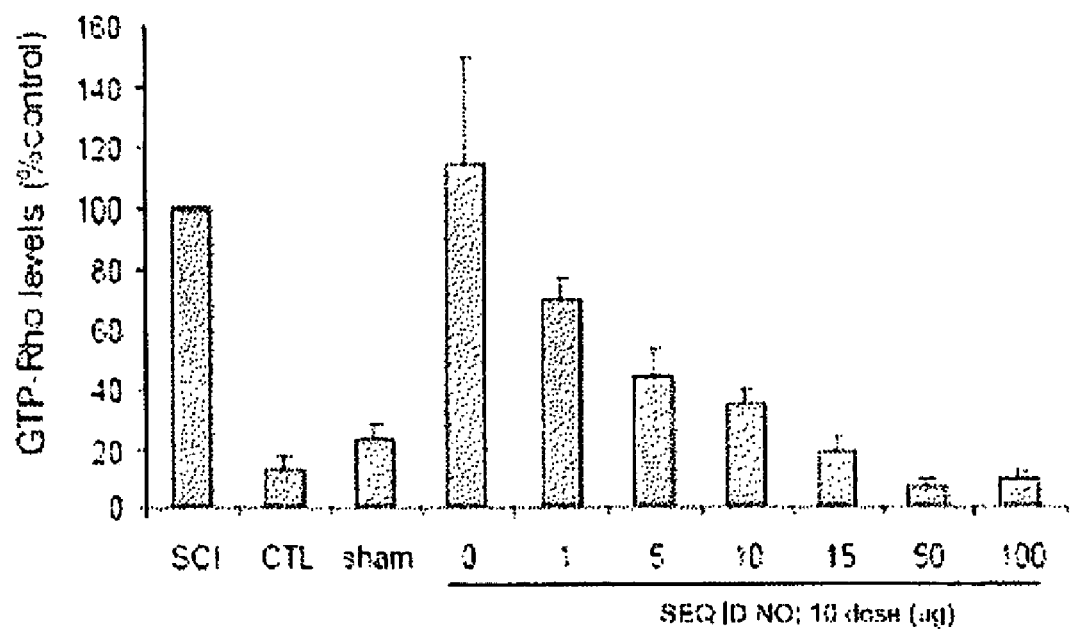
FIG. 35 shows the time and dose dependent Rho inactivation by SEQ ID NO: 10 treatment after contusion in rats, wherein in (A) different doses of SEQ ID NO: 10 were applied extramurally in Tisseel® immediately following moderate spinal cord contusion in adult female rats (10 g×25 mm) and active Rho levels were measured 24 hrs post-SCI; and in (B) Spinal cords were injured at different times after 50 µg of SEQ ID NO: 10 application in Tisseel® (2 hr to 7 days) and tissues were collected 3 hrs post injury to measure active Rho levels.

Referring to FIG. 35, the therapeutic benefit of SEQ ID NO: 10 depends on its ability to block the activation of Rho that occurs following SCI. Therefore, after establishing the distribution of SEQ ID NO: 10 in spinal cord following extradural application, active Rho levels can be measured in contused spinal cord tissue using affinity precipitation with RhoA-binding domain of the effector protein rhotekin followed by Western blot detection of RhoA. Active Rho levels are determined more specifically using pull-down assays and immunoblotting. The pixel density of active Rho levels in tissues from contused spinal cord is used to calculate the normalized active Rho levels of treated spinal cord samples. For dose-response and reversibility studies, the results are averaged for 3 to 9 rats per group.

A dose response curve for Rho inactivation is obtained to determine the minimal effective dose of SEQ ID NO: 10. Doses of SEQ ID NO: 10 are applied in Tisseel® onto the spinal cord of rats immediately following SCI induced by moderate contusion (10 g weight dropped from a height of 25 mm) and active Rho levels (GTP-bound state) are determined at 24 hours after injury.

As shown hereinabove, contusion injury produces a robust Rho activation in all rats. This level of activation is used to normalize active Rho levels observed under different conditions. The level of GTP bound Rho in normal rat spinal cord is found to be around 15% of that seen in contused rats. Sham surgery (laminectomy) is not significantly inducing Rho activation. SEQ ID NO: 10 application in Tisseel® blocks Rho activation caused by the contusion injury to the basal levels found in normal uninjured or laminectomized rat spinal cord. This inhibition of Rho activation is maximal using a single dose of 15 µg SEQ ID NO: 10. The 15 µg dose is selected for the efficacy studies as it consistently give a robust and reproducible Rho inactivation. Regression analysis of the dose response curve ($\mu 2=0.97$) show that the dose necessary for 50% Rho inactivation in the rat spinal cord is around 2 µg.

Figure 35B:
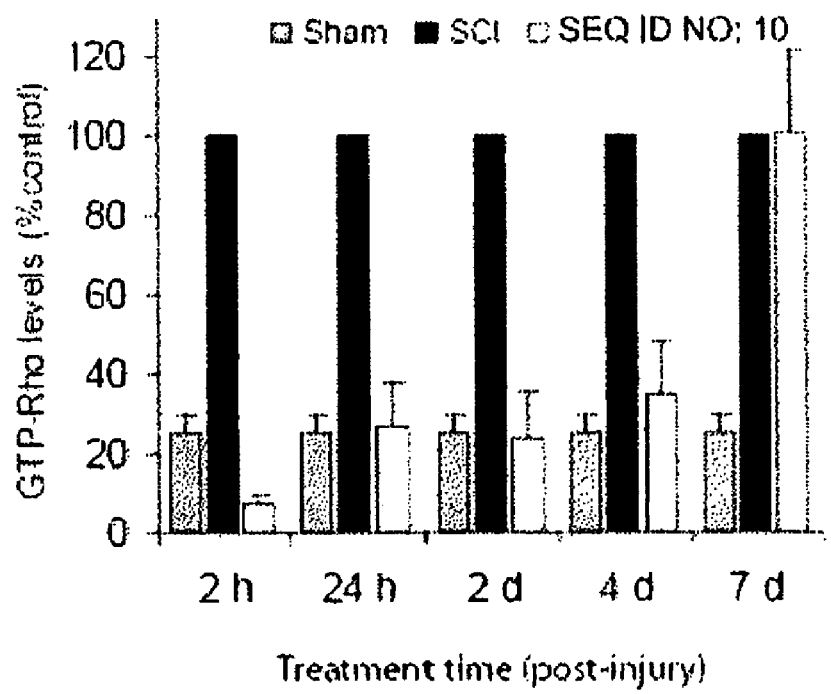

To determine how long the drug remained at therapeutic levels in vivo, SEQ ID NO: (50 µg) is applied to the dura without spinal cord injury. The wound is re-opened and the spinal cord is injured by hemisection at the site of SEQ ID NO: 10 delivery at different times after SEQ ID NO: 10 application (2 hours, 24 hours, 2 days, 4 days and 7 days). Animals are then sacrificed 4 hours later. Pretreatment with SEQ ID NO: 10 up to 4 days before SCI is able to prevent Rho activation following extradural application (FIG. 35B). The inhibition is evident in the 2 hour pretreatment group underlining the fast absorption of SEQ ID NO: 10 into the spinal cord after application in Tisseel®. Therapeutic SEQ ID NO: 10 levels are maintained for at least 4 days after delivery while 7 days after application, SEQ ID NO: 10 pretreatment do not prevent the activation of Rho following SCI. While Rho ADP-ribosylation catalyzed by SEQ ID NO: 10 is irreversible, the normal protein turn-over of Rho in cells can explain the reversibility observed.

Example 37

Delayed SEQ ID NO: 10 Treatment Improves Functional Recovery in Mice

Referring to FIG. 36, after the cell permeable SEQ ID NO: 10 is optimized, experiments are repeated in the hemisection mice model and it is demonstrated that 1 µg is sufficient in promoting functional recovery. SCI patients usually undergo surgery to decompress and stabilize or fix the spinal cord up to a few days post-injury. Therefore, it is important to understand the time window for therapeutic intervention. Because of the faster functional recovery in mice and ease of manipulation, the time window for SEQ ID NO: 10 delivery after SCI is studied in this model. Behavioral recovery is evaluated by scoring hind limb movements for 2 weeks on a modified BBB scale (Dergham et al., 2002, J Neurosci, 22: 6570-6577). SEQ ID NO: 10 impact on locomotor function after immediate or delayed delivery is compared using a dose of 1 µg delivered in Tisseel®. More specifically, motor function of animals is assessed using the Basso, Beattie, and Bresnahan (BBB)

Open Field Locomotor Rating Scale for 11 rats treated with 15 ug SEQ ID NO: 10, and 12 control rats. BBB score is evaluated by two observers for 4 minutes and locomotion is taped using a video camera by another observer. The scores for both hind limbs are averaged to obtain the score of each session. The BBB score is registered blinded every time using separate sheets. Locomotor recovery of hindlimb movement in mice is measured using modified BBB scoring for 4 to 6 mice per treatment group. As opposed to rats, mice do not show foot drag and the BBB scale has been modified from the 21 point rat scale to a 17 point scale.

Each treatment group has its own control to account for variability in the second, delayed surgery requires to give the treatment at 24 or 72 hrs. The initial spinal cord injury was considered day 0.

Figure 36A:
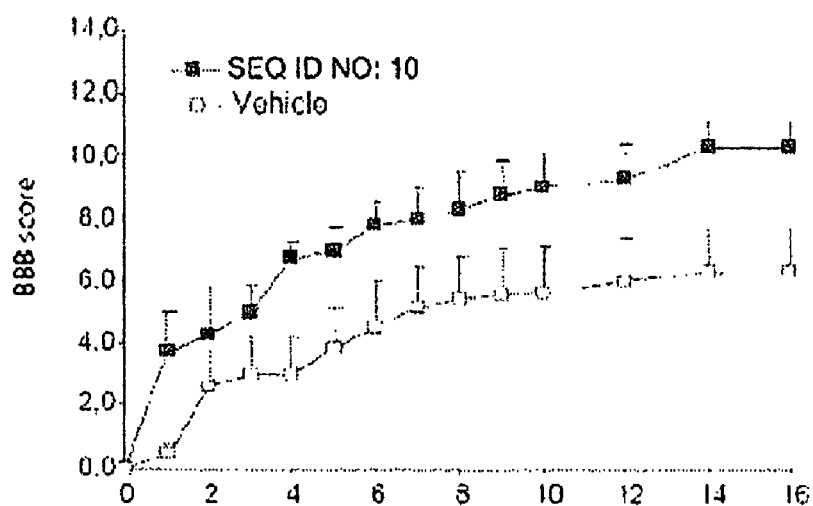
FIG. 36 shows delayed treatment with SEQ ID NO: 10 that promotes functional recovery in mice, wherein in (A) it is disclosed that after laminectomy and SC hemisection in adult female BAlb/c mice, 1 µg of SEQ ID NO: 10 in Tisseel® was immediately applied on the spinal cord, (B) treatment was delayed by 24 hrs after SCI, and (C) treatment was delayed for 72 hrs after SCI; wherein each treatment group had its own control (Tisseel® only) to account for variability in the second, delayed surgery required to give the treatment at 24 or 72 hrs (arrows represent treatment application); wherein the initial spinal cord injury was considered day 0; and wherein the locomotor recovery was measured for 16 days using the modified 17 points "Beattie-Bresnahan-Basso" scale for mice (BBB scale)

The group of animals with immediate delivery receives only one surgery and is treated with either SEQ ID NO: 10 or PBS in Tisseel®. There is a rapid improvement during the early posttraumatic stages of recovery in the treated group, within 24 hours, likely because of the neuroprotective effect of SEQ ID NO: 10. Sixteen days post-injury, treated animals reach frequent plantar stepping with weight support (BBB of 10) compared to sweeping with movements of 2-3 joints (BBB of 6) in the control mice (FIG. 36A).

Figure 36B:
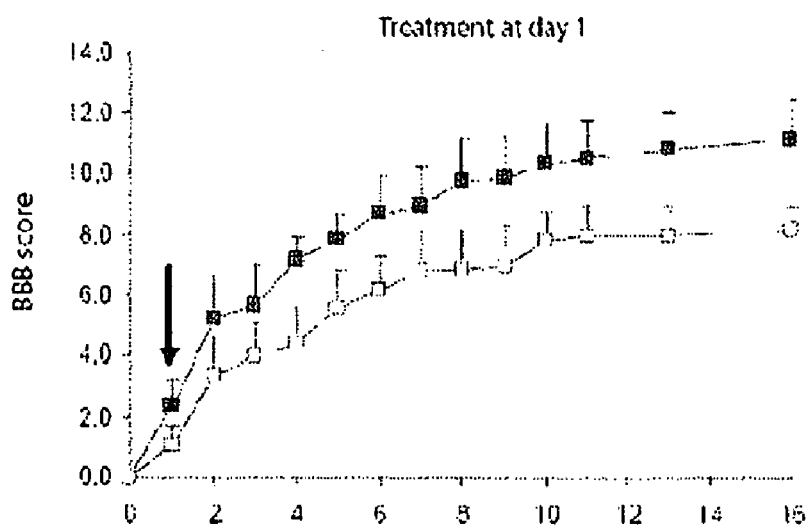

Animals treated 24 hours post injury are re-anaesthetized, the skin and muscles re-opened, and the treatment is applied on the injured surface of the spinal cord. When treatment is delayed by 24 hours, improved functional recovery is still observed in the treated mice (FIG. 36B). SEQ ID NO: 10 treated mice demonstrate a significant 3 points improvement over control mice at 16 days. As observed in the immediate treatment group, those animals can also reached consistent weight supported plantar stepping. However, in this experiment, the early recovery phase is not as marked as in the immediate treatment group. This effect can be masked by the fact that mice underwent two general anesthesias within 24 hours.

Figure 36C:
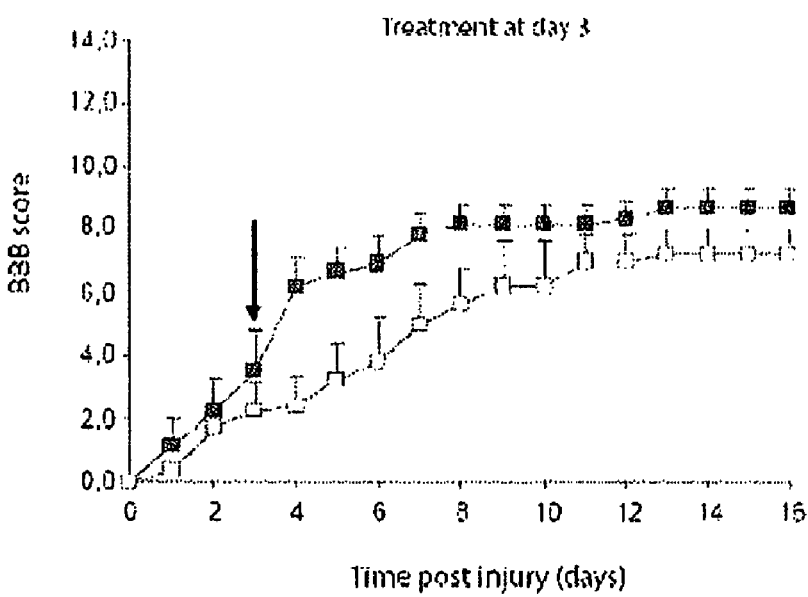

Animals that received SEQ ID NO: 10 seventy two hours after spinal cord hemisection show a transient significant improvement up to 3 days after the delayed delivery and an overall trend to better recovery (FIG. 36C). However, after this initial improvement, the slope of recovery lessened and the final average scores are not significantly different from the control mice after 16 days (FIG. 36C).

Example 38

Extradural Treatment with the Rho Antagonist SEQ ID NO: 10 is Well Tolerated

Figure 37A:
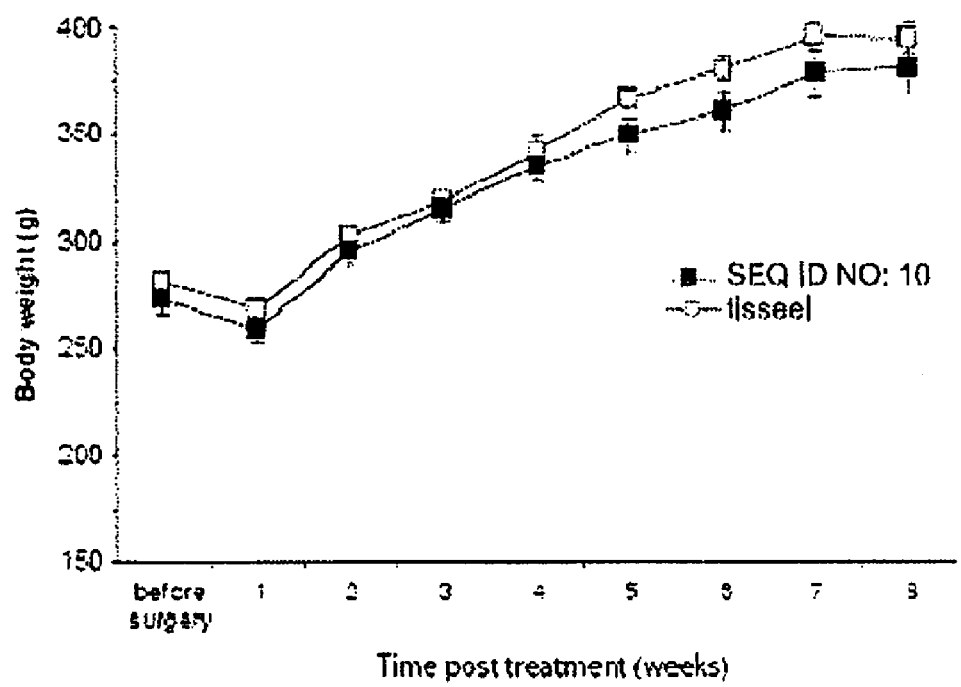
FIG. 37 illustrates that SEQ ID NO: 10 is well tolerated when applied locally on the rat spinal cord; wherein (A) shows the body weight of each rat (SEQ ID NO: 10 or vehicle) was measured right before surgery and every week for 8 weeks; (B) and (C) show the morphology of rat spinal cord 3 months after laminectomy and treatment; wherein in (B) it is disclosed spinal cord longitudinal section of a vehicle (Tisseel®) treated rat; wherein in (C) the spinal cord is a longitudinal section of a 50 µg of SEQ ID NO: 10 treated rat; and wherein the laminectomy was performed but dura were kept intact; rostral was in left side and bar indicates 400 µm.

Referring to FIG. 37, experiments in rats can be carried our to assess the safety and functional recovery after treatment with SEQ ID NO: 10 or with the variants described in FIGS. 3 and 4. In order to assess functional recovery after spinal cord contusion in rats, a total of 25 male animals are operated and randomly assign to the two treatment groups, vehicle (PBS in Tisseel®) or 15 µg of SEQ ID NO: 10 in Tisseel®. After the surgery, postoperative care is undertaken, including manual expression of bladders twice daily until bladder function returned. All rats recover autonomous bladder function by day 10 to 15 independently of treatment group. Analysis of the body weight shows that all groups (SEQ ID NO: 10 and vehicle treated) of animals gain weight normally (FIG. 37A). There are no significant differences between groups. In another set of experiments, rats treated with a 50 µg dose also present normal weight gain over a 1.5 month observation period.

Figures 37B, 37C:
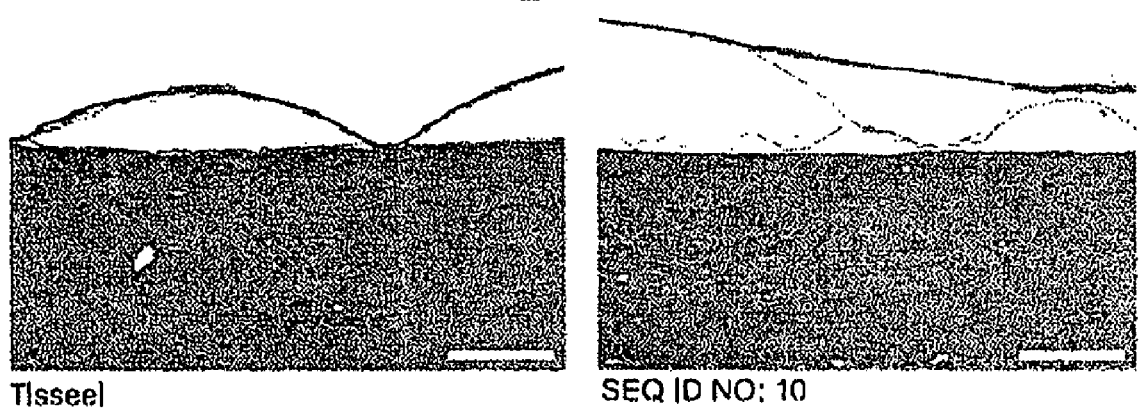

Using a separate set of rats, the long tens safety of extradural application of SEQ ID NO: 10 in Tisseel® on spinal cord is verified on rats following a vertebral laminectomy similar to the procedure that can be required in humans. Tissue is collected 3 months after a single application of 10 or 50 µg. Extensive histological analysis of the spinal cords treated with SEQ ID NO: 10/Tisseel® do not present any in morphology or cellular changes (normal spinal cords, sham operated control, vehicle control and SEQ ID NO: 10 treated with either opened or intact dura mater). FIGS. 37B and 37C show a representative longitudinal section of rat spinal cord following surgery and treatment for a vehicle and a 50 µg of SEQ ID NO: 10 treated animal at 3 months post-injury.

Example 39

Treatment with SEQ ID NO: 10 Improves Locomotor Recovery in Rats

Figure 38A:
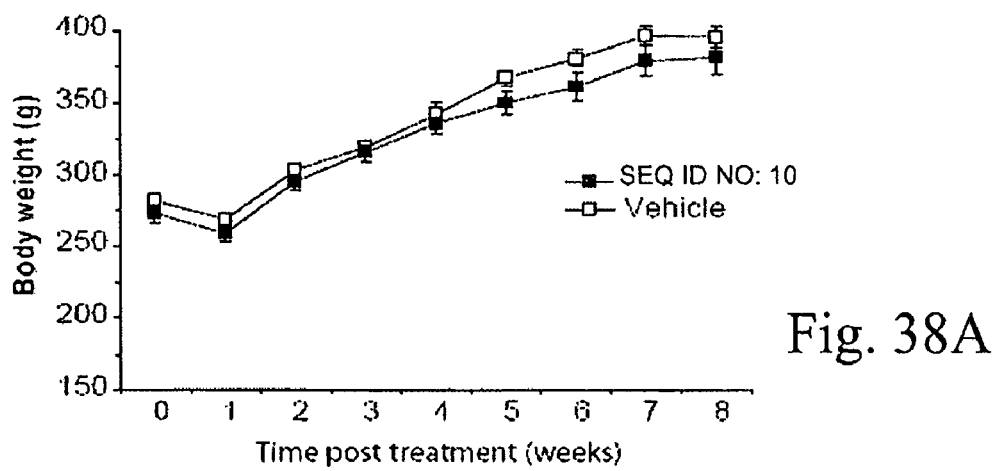
FIG. 38 illustrates that SEQ ID NO: 10 improves locomotor function after spinal cord contusion in rats; wherein in (A) the body weight of each rat (SEQ ID NO: 10, n=1 or vehicle, n=12) was measured before surgery and every week for 8 weeks; (B), adult male rats underwent laminectomy and moderate spinal cord contusion (NYU impactor, 10 g weight dropped from a 50 mm height), SEQ ID NO: 10 (15 µg) or vehicle was applied in Tisseel® on the spinal cord dura immediately after SCI. BBB score of vehicle and SEQ ID NO: 10 treated rats were measured each week for 8 weeks by two blinded independent observers; and wherein in (C) percentage of rats reaching weight supported plantar placement or stepping (BBB score of 9 to 11) in vehicle versus SEQ ID NO: 10 treated group over time are disclosed.
Figure 38B:
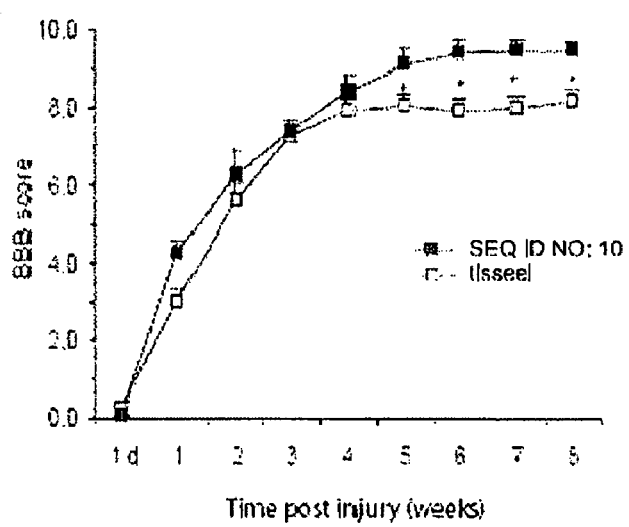

Referring to FIG. 38, experiments in rats can be carried out to assess the functional recovery after treatment with SEQ ID NO: 10 or with the variant sequences described in FIGS. 3 and 4. The compression depth in the spinal cord is monitored as a measure of the reproducibility of the contusion injury. No differences in the compression depth are observed between SEQ ID NO: 10 and control groups.

Animals are operated and randomly assigned to the two treatment groups, vehicle (PBS) (n=12 rats) or 15 µg SEQ ID NO: 10 (n=11 rats). All treatments are applied in a fibrin sealant. Animals are subjected to postoperative care, including manual expression of bladders twice daily until bladder function returned. All rats recover autonomous bladder function by day 10 to 15 independently of treatment group. One day after the contusion, all rats demonstrate flaccid paralysis of the hind limbs associated with a BBB score of less than 1.

Analysis of the body weight showed that the two treatment groups (SEQ ID NO: 10 and vehicle treated) gained weight normally (FIG. 38A). There are no significant differences in weight gain over the 8 week study between groups (P=0.98, repeated measures two-way ANOVA). In another set of experiments, rats treated with a 50 µg dose of SEQ ID NO: 10 also present normal weight gain over a 1.5 month observation period.

Figure 38C:
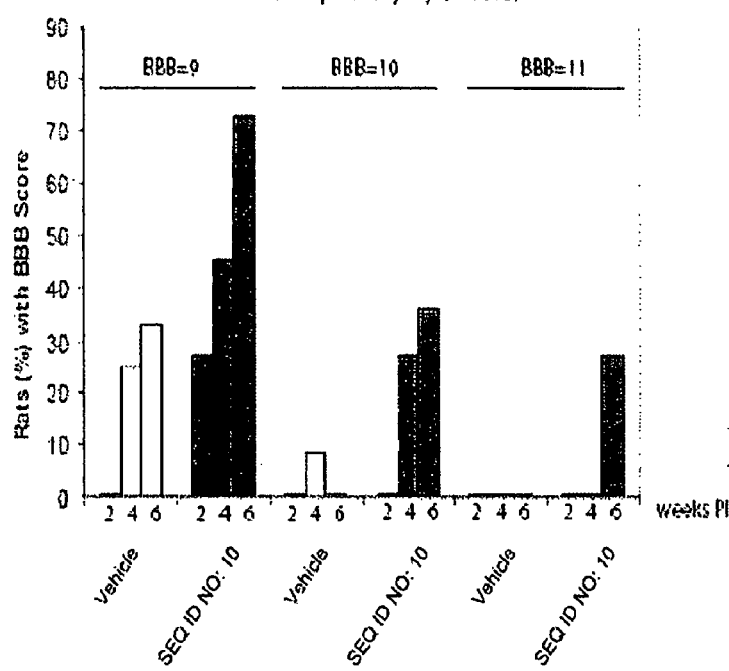

There is a significant improvement in the locomotion scores in SEQ ID NO: 10 treated rats compared to vehicle/PBS treated animals. The recovery is typically faster in SEQ ID NO: 10 treated rats. One week post-injury, treated animals have a BBB score >4 associated with movements in all 3 joints of hip, knee and ankle. In comparison, BBB score are between 2 and 3 in control animals as only two joints movement are observed. Control animal BBB score plateau at week 4 while treated rats still continue to improve. After 5 to 6 weeks post-injury, maximum improvement of locomotor function is reached in all rats. FIG. 38C gives an overview of the progression rate and final scores obtained by treated versus control rats. Overall, treated rats progress faster and regain some functional use of their hind limbs. The percentage of rats reaching body weight supported plantar placement by 6 weeks with BBB score >9 is 75% of treated rats compared with 35% of controls. Moreover, at 6 weeks post-injury, treated rats are able to perform occasional (BBB=10) or consistent (BBB=11) weight-supported plantar steps compared to none of the control rats. In contrast, the majority of control animals show only 3 joint movements and move with sweeping motions without weight support (BBB <9) (FIG. 38C)

Example 40

SCI and Delivery of Rho Antagonist in Fibrin Matrix

Handling of animals was in accordance with guidelines of the Canadian Council of Animal Care. Animals were housed under a 12-h light-dark cycle with free access to water and food. Female Balb-c mice (4 weeks) were used.

Female Balb-C mice are anesthetized with 0.4 mL/kg hypnorm and 5 mg/kg diazepam. After laminectomy, dorsal overhemisection is performed at T7 using spring scissors. A single bolus dose of SEQ ID NO: 10 (1 µg in 4 µL) or vehicle (PBS) is administered on the exposed cord in fibrin sealant by mixing 15 µL of thrombin to 15 µL of fibrinogen (Tisseel® kit VH, Baxter Corporation, Ontario). The solution is left to polymerize for a few minutes before skin and muscle are sutured.

Under isoflurane anesthesia (3-5%), rats are subjected to laminectomy at the level of T9. SCI is induced by dropping a 10-g weight rod from 25 mm height onto the exposed spinal cord using a NYU contusion impactor. In Rho inactivation experiments, some rats are injured by dorsal over-hemisection. The rod velocity and compression from the impactor are recorded. This technique causes paralysis of hind-limbs in a reproducible and graded manner. Laminectomy alone is performed as a sham operation. SEQ ID NO: 10 (at different concentrations) or control vehicle (PBS) in the same volume of 5 µL is mixed with 15 µL of thrombin and 15 µL of fibrinogen (Tisseel® kit VH, Baxter Corporation, Ontario). After test compound application, the overlaying muscle and skin are sutured.

For the morphological evaluation, rats from the behavioral study groups are sacrificed with an overdose of anesthetics and are cardially perfused with 0.9% saline, followed by phosphate buffered 4% paraformaldehyde (PFA). The spinal cord tissue centered at T9 is removed from the column and post-fixed in 4% PFA overnight. Ten segments of 1 mm spinal cord, in both rostral and caudal sides, are embedded in paraffin blocks and sectioned transversally on a microtome for use in spared tissue area measurements. Spinal cord tissues are also collected and paraffin embedded to obtain longitudinal sections stained with Hematoxylin and Eosin in another set of experiments. For immunohistochemistry experiments on cryostat sections, 1 cm spinal cord (epicenter) is post-fixed in 4% PFA and transferred into a 30% sucrose solution. The next day, tissues are snapped-frozen in cold isopentane and embedded into O.C.T.

For Western blots and pull-down assays, the animals are sacrificed with an overdose of anesthetics and perfused with 0.9% saline only. The spinal cord tissue is separated into dorsal and ventral parts, or different segments from rostral to caudal parts. Tissues are washed in saline and the dura mater is removed. For pull down assays, the 8 mm spinal cord tissue is frozen in situ by pouring liquid nitrogen onto the laminectomy site. The frozen spinal cord samples are homogenized using a Vari-Mix III homogenizer (Dentsply Caulk, Toronto, Canada) and solubilized in ice cold NP-40 lysis buffer for Western blot.

Example 41

SEQ ID NO: 10 Reduces the Lesion Volume in the Contused Rat Spinal Cord

Referring to FIG. 39, histological analysis of spinal cord injured tissue treated with SEQ ID NO: 10 or variant proteins can be used to measure neuroprotection.

Rats subjected to open field evaluations are sacrificed and the tissue prepared for histology. The spared area of gray, white matter and whole sectional area of spinal cord are measured using three 5 µm thick transverse sections per level. Multiple levels are sampled at 1 mm intervals along a 2 cm region centered around the epicenter. The images are captured using an Axioskop plus light microscope (Carl Zeiss, Germany) and a QICAM digital camera (Qimaging, BC, Canada) and analyzed using Northern Eclipse software (Empix, ON, Canada). The spared tissue area of gray and white matter is determined by the equation $S_{sp}\% = (G_{sp} + W_{sp})/T_s * 100$, where ($G_{sp}$) and ($W_{sp}$) are the area of spared gray and white matter, respectively, and ($T_s$) is total area of spinal section. The analysis is performed blinded to treatment group.

Figure 39A:
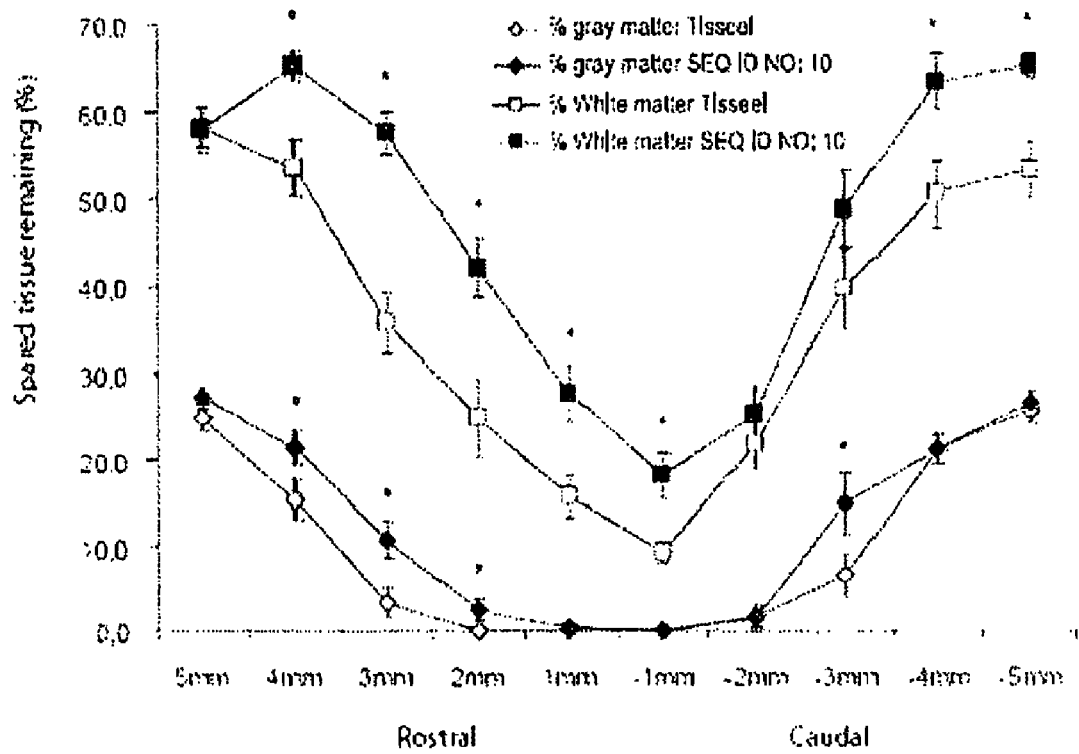
FIG. 39 shows that SEQ ID NO: 10 provides neuroprotection to the contused rat spinal cord; wherein in (A) spared gray and white matter in the 1 cm lesion were measured in spinal cord transverse sections stained with Luxol fast blue using a computerized system, where analysis was performed 8 weeks after injury and treatment; and wherein in (B) the total lesion areas were calculated for each rat using area under the curve generated from % spared tissue on 2 cm of spinal cord.
Figure 39B:
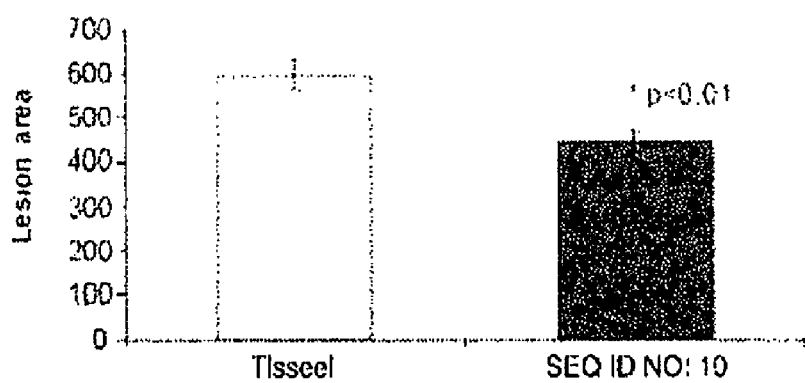

A massive loss of tissue follows spinal cord injury as signaling cascades trigger apoptotic cell death that target neuron and glia. The extent of tissue loss through this process takes place within days of the injury and dictates largely the extent of the functional recovery post injury. For that reason, whether SEQ ID NO: 10 possesses neuroprotective properties is assessed and the size of the lesion at the site of the contusion is verified. The percentage of remaining gray and white matter is analyzed 2 months post-injury by image analysis on sections taken at 1 mm intervals along the caudal and rostral spinal cord on a total length of 2 cm covering the 1 cm lesion site. All rats from the functional recovery groups are included in the analysis (n=23). There is a significant difference in the total lesion area between groups where SEQ ID NO: 10 treated animals presented a 25% decrease in loss tissue versus control group. This difference is most notable rostral to the epicenter (FIG. 39A; 25%) while the changes caudal to the impact site are less pronounced (10%). Two months after the contusion, much of the T9 spinal cord of control animals is occupied by a large cystic cavity with no gray matter evident and less than 10% of white matter remaining at epicenter (FIG. 39A). In contrast, spinal cord at the epicenter of treated rats have an average of 10% increase in residual white matter consisting of a peripheral rim. This increase white matter sparing in treated rats reached 22% in the first 4 mm rostral to the epicenter. Gray matter is also significantly preserved in treated rats at 2 to 4 mm from the injury epicenter. An overall significant difference was observed in the extent of spinal cord tissue remaining at the lesion site for both white (P<0.0001) and grey matter (P=0.038) between treated and control rats using a two way repeated measures ANOVA. The extent of tissue spared is characterized further by calculating areas under the curve for each rat to represent the total lesion area. FIG. 39B demonstrates that treated rats showed a 25% decrease in the area occupied by the lesion. Similar to humans, the formation of cystic cavity at the lesion site after SCI in rats is a common occurrence. Luxol fast blue staining demonstrated that treated rats showed more abundant compact myelin in a smaller cavitation than the control animals. This is also reflected by a decreased longitudinal lesion length in treated rats (10.3±0.7 mm for controls vs 7.8±0.7 mm for treated, P<0.01, unpaired Student's T test) (data not shown). Finally, linear regression analysis (Deming) shows that there is a significant correlation between total lesion area and final BBB scores in SEQ ID NO: 10 treated rats (P=0.02) (data not shown).

Example 42

SEQ ID NO: 10 Treatment Had No Impact on Allodynia in Rats

Figure 40:
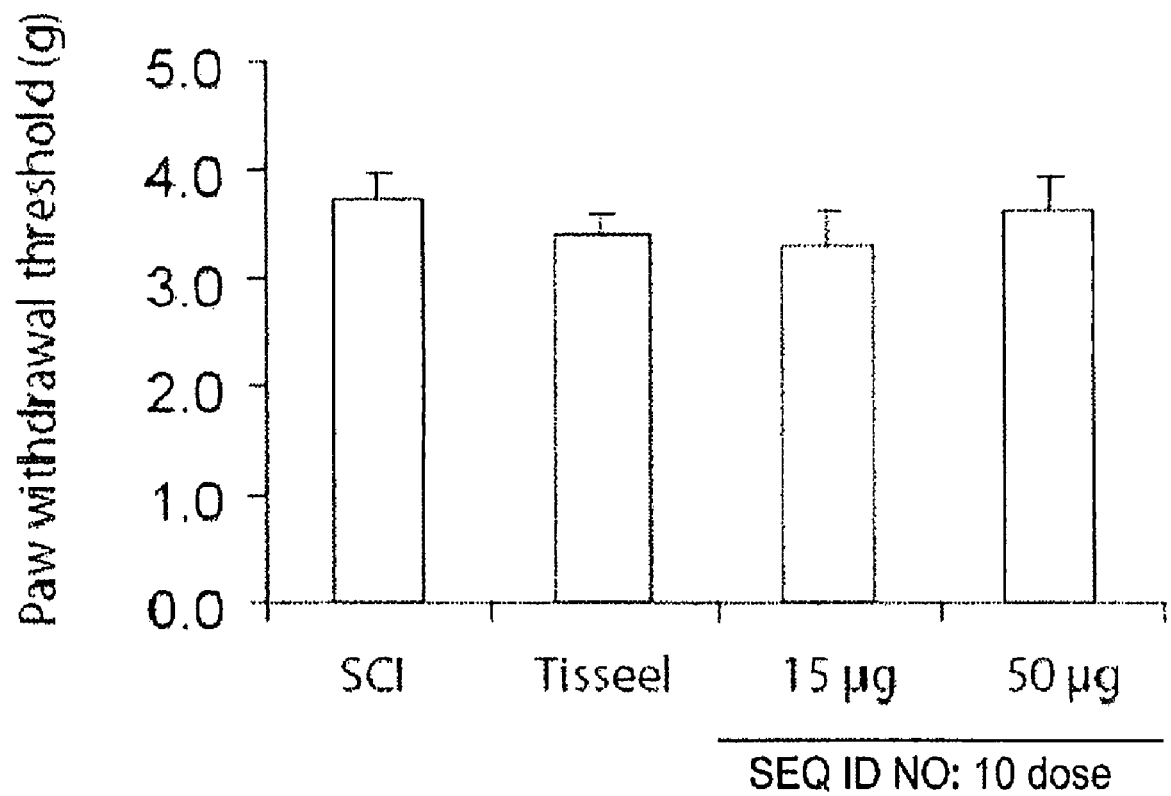
FIG. 40 illustrates that SEQ ID NO: 10 had no impact on allodynia development after contusion in rats, wherein the Von Frey test of paw withdrawal was performed 6 weeks after SEQ ID NO: 10 or vehicle treatment in female rats with severe contusion.

Referring to FIG. 40, SEQ ID NO: 10 or variant proteins can be tested in an animal model of neuropathic pain to test for unwanted side effects. Aberrant axonal sprouting is known to lead to the development of neuropathic pain after spinal cord trauma. Limb withdrawal in response to Von Frey filaments of increasing diameter is used to test sensitivity to mechanical stimuli. Rats are placed inside a Plexiglas box on an elevated, fine metal screen and acclimated for 60 min prior to testing. The filament is applied to the plantar surface for each hind limb. Von Frey filament threshold (grams amount of force) is recorded as the force necessary to elicit a withdrawal three to four out of four times. Data for left and right hindlimbs are averaged. Observers are blinded to treatment group. For each treatment group, 5 to 7 rats are evaluated.

The effect of SEQ ID NO: 10 on sensory outcome in injured rats can be examined. The Von Frey test is used to verify if there is any difference in sensitivity to mechanical stimulation after the animals have reached their plateau of locomotor recovery 6 weeks after a severe contusion. The foot withdrawal response to sensory stimulation is measured for both hind limbs with calibrated probes. The same level of tactile allodynia develops in all injured rats independently of their treatment group. Vehicle or SEQ ID NO: 10 treatments at 15 or 50 μg have no effect on paw withdrawal threshold six weeks after the injury (FIG. 40).

Those skilled in the alt will recognize, or be able to ascertain using no more than routine experimentation, numerous equivalents to the specific procedures described herein. Such equivalents are considered to be within the scope of this invention and are covered by the following claims.

The contents of all publications cited herein are hereby incorporated by reference.

---

What is claimed is:

1. An isolated polypeptide selected from the group consisting of SEQ ID NO:4, SEQ ID NO:6, SEQ ID NO:14, SEQ ID NO:18, and SEQ ID NO:20.

2. The isolated polypeptide of claim 1, wherein the polypeptide selected from the group consisting of SEQ ID NO:6, SEQ ID NO:14, SEQ ID NO:18, and SEQ ID NO:20 is truncated by 20 amino acids at its N-terminus.

3. The isolated polypeptide of claim 1, wherein the polypeptide selected from the group consisting of SEQ ID NO:4, SEQ ID NO:6, SEQ ID NO:14, SEQ ID NO:18, and SEQ ID NO:20 is truncated by 10 amino acids at its C-terminus.

4. The isolated polypeptide of claim 1, wherein the polypeptide selected from the group consisting of SEQ ID NO:6, SEQ ID NO:14, SEQ ID NO:18, and SEQ ID NO:20 is truncated by 20 amino acids at its N-terminus and 10 amino acids at its C-terminus.

5. The isolated polypeptide of claim 1, wherein said polypeptide is PEGylated.

6. A pharmaceutical composition comprising (a) an isolated polypeptide selected from the group consisting of SEQ ID NO:4, SEQ ID NO:6, SEQ ID NO:14, SEQ ID NO:18, and SEQ ID NO:20 and (b) a pharmaceutically acceptable carrier.

7. The pharmaceutical composition of claim 6, wherein the polypeptide selected from the group consisting of SEQ ID NO:6, SEQ ID NO:14, SEQ ID NO:18, and SEQ ID NO:20 is truncated by 20 amino acids at its N-terminus.

8. The pharmaceutical composition of claim 6, wherein the polypeptide selected from the group consisting of SEQ ID NO:4, SEQ ID NO:6, SEQ ID NO:14, SEQ ID NO:18, and SEQ ID NO:20 is truncated by 10 amino acids at its C-terminus.

9. The pharmaceutical composition of claim 6, wherein the polypeptide selected from the group consisting of SEQ ID NO:6, SEQ ID NO:14, SEQ ID NO:18, and SEQ ID NO:20 is truncated by 20 amino acids at its N-terminus and 10 amino acids at its C-terminus.

10. The pharmaceutical composition of claim 6, wherein the polypeptide is PEGylated.

11. The pharmaceutical composition of claim 6, wherein the pharmaceutical composition is sterile, sterilizable or sterilized.

12. The pharmaceutical composition of claim 6, wherein the pharmaceutical composition is in a vial in a unit dosage amount or in an integral multiple of a unit dosage amount.

13. The pharmaceutical composition of claim 6, wherein the pharmaceutical composition is dried or comprises a dehydrated matrix.

14. The pharmaceutical composition of claim 6, wherein the pharmaceutical composition comprises a fusion protein and wherein the fusion protein comprises the isolated polypeptide selected from the group consisting of SEQ ID NO:4, SEQ ID NO:6, SEQ ID NO:14, SEQ ID NO:18, and SEQ ID NO:20 in a lyophilized matrix.

15. An isolated polypeptide consisting of SEQ ID NO: 10.

16. The isolated polypeptide of claim 15, wherein the polypeptide consisting of SEQ ID NO:10 is truncated by 20 amino acids at its N-terminus.

17. The isolated polypeptide of claim 15, wherein the polypeptide consisting of SEQ ID NO:10 is truncated by 10 amino acids at its C-terminus.

18. The isolated polypeptide of claim 15, wherein the polypeptide consisting of SEQ ID NO:10 is truncated by 20 amino acids at its N-terminus and 10 amino acids at its C-terminus.

19. The isolated polypeptide of claim 15, wherein said polypeptide is PEGylated.

20. A pharmaceutical composition comprising (a) an isolated polypeptide consisting of SEQ ID NO:10 and (b) a pharmaceutically acceptable carrier.

21. The pharmaceutical composition of claim 20, wherein the polypeptide consisting of SEQ ID NO:10 is truncated by 20 amino acids at its N-terminus.

22. The pharmaceutical composition of claim 20, wherein the polypeptide consisting of SEQ ID NO:10 is truncated by 10 amino acids at its C-terminus.

23. The pharmaceutical composition of claim 20, wherein the polypeptide consisting of SEQ ID NO:10 is truncated by 20 amino acids at its N-terminus and 10 amino acids at its C-terminus.

24. The pharmaceutical composition of claim 20, wherein said polypeptide is PEGylated.

25. The pharmaceutical composition of claim 20, wherein the pharmaceutical composition is sterile, sterilizable, or sterilized.

26. The pharmaceutical composition of claim 20, wherein the pharmaceutical composition is in a vial in a unit dosage amount or in an integral multiple of a unit dosage amount.

27. The pharmaceutical composition of claim 20, wherein the pharmaceutical composition is dried or comprises a dehydrated matrix.

28. The pharmaceutical composition of claim 20, wherein the pharmaceutical composition comprises a fusion protein and wherein the fusion protein comprises the isolated polypeptide consisting of SEQ ID NO:10 in a lyophilized matrix.

29. An isolated nucleic acid selected from the group consisting of SEQ ID NO: 25, SEQ ID NO: 30, SEQ ID NO: 35, and SEQ ID NO: 37.

* * * * *

SEQUENCE LISTING

```
<160> NUMBER OF SEQ ID NOS: 81

<210> SEQ ID NO 1
<211> LENGTH: 470
<212> TYPE: PRT
<213> ORGANISM: Artificial Sequence
<220> FEATURE:
<223> OTHER INFORMATION: Includes GST sequences, ADP-ribosyl
      transferase C3 (C. botulinum) sequence and a random basic
      amino acid sequence.

<400> SEQUENCE: 1

Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190
```

```
Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Ser Arg Val Asp Leu Gln Ala Cys Asn Ala Tyr Ser Ile Asn
225                 230                 235                 240

Gln Lys Ala Tyr Ser Asn Thr Tyr Gln Glu Phe Thr Asn Ile Asp Gln
                245                 250                 255

Ala Lys Ala Trp Gly Asn Ala Gln Tyr Lys Tyr Gly Leu Ser Lys
        260                 265                 270

Ser Glu Lys Glu Ala Ile Val Ser Tyr Thr Lys Ser Ala Ser Glu Ile
        275                 280                 285

Asn Gly Lys Leu Arg Gln Asn Lys Gly Val Ile Asn Gly Phe Pro Ser
        290                 295                 300

Asn Leu Ile Lys Gln Val Glu Leu Leu Asp Lys Ser Phe Asn Lys Met
305                 310                 315                 320

Lys Thr Pro Glu Asn Ile Met Leu Phe Arg Gly Asp Pro Ala Tyr
                325                 330                 335

Leu Gly Thr Glu Phe Gln Asn Thr Leu Leu Asn Ser Asn Gly Thr Ile
        340                 345                 350

Asn Lys Thr Ala Phe Glu Lys Ala Lys Ala Lys Phe Leu Asn Lys Asp
        355                 360                 365

Arg Leu Glu Tyr Gly Tyr Ile Ser Thr Ser Leu Met Asn Val Ser Gln
        370                 375                 380

Phe Ala Gly Arg Pro Ile Ile Thr Lys Phe Lys Val Ala Lys Gly Ser
385                 390                 395                 400

Lys Ala Gly Tyr Ile Asp Pro Ile Ser Ala Phe Gln Gly Gln Leu Glu
                405                 410                 415

Met Leu Leu Pro Arg His Ser Thr Tyr His Ile Asp Asp Met Arg Leu
                420                 425                 430

Ser Ser Asp Gly Lys Gln Ile Ile Thr Ala Thr Met Met Gly Thr
        435                 440                 445

Ala Ile Asn Pro Lys Glu Phe Arg Arg Lys Gln Arg Lys Arg Arg
        450                 455                 460

Leu Gln Ala Ala Ala Ser
465                 470

<210> SEQ ID NO 2
<211> LENGTH: 17
<212> TYPE: PRT
<213> ORGANISM: Artificial Sequence
<220> FEATURE:
<223> OTHER INFORMATION: Amino acid sequence of the proline rich region
      of C3APLT

<400> SEQUENCE: 2

Val Met Asn Pro Ala Asn Ala Gln Gly Arg His Thr Pro Gly Thr Arg
 1               5                  10                  15

Leu

<210> SEQ ID NO 3
<211> LENGTH: 12
<212> TYPE: PRT
<213> ORGANISM: Artificial Sequence
<220> FEATURE:
<223> OTHER INFORMATION: transport peptide rich in Proline

<400> SEQUENCE: 3
```

```
Ala Ala Val Leu Leu Pro Val Leu Leu Ala Ala Pro
 1               5                  10
```

<210> SEQ ID NO 4
<211> LENGTH: 24
<212> TYPE: PRT
<213> ORGANISM: Artificial Sequence
<220> FEATURE:
<223> OTHER INFORMATION: Sperm fertiline alpha peptide

<400> SEQUENCE: 4

```
His Pro Ile Gln Ile Ala Ala Phe Leu Ala Arg Ile Pro Pro Ile Ser
 1               5                  10                  15

Ser Ile Gly Thr Cys Ile Leu Lys
            20
```

<210> SEQ ID NO 5
<211> LENGTH: 744
<212> TYPE: DNA
<213> ORGANISM: Artificial Sequence
<220> FEATURE:
<223> OTHER INFORMATION: Sequence of C3-07Q189A

<400> SEQUENCE: 5

```
atgtctagag tcgacctgca ggcatgcaat gcttattcca ttaatcaaaa ggcttattca     60
aatacttacc aggagtttac taatattgat caagcaaaag cttggggtaa tgctcagtat    120
aaaaagtatg gactaagcaa atcagaaaaa gaagctatag tatcatatac taaaagcgct    180
agtgaaataa atggaaagct aagacaaaat aagggagtta tcaatggatt tccttcaaat    240
ttaataaaac aagttgaact tttagataaa tctttaata aaatgaagac ccctgaaaat     300
attatgttat ttagaggcga cgaccctgct tatttaggaa cagaatttca aaacactctt    360
cttaattcaa atggtacaat taataaaacg gcttttgaaa aggctaaagc taagttttta    420
aataaagata gacttgaata tggatatatt agtacttcat taatgaatgt ttctcaattt    480
gcaggaagac caattattac aaaatttaaa gtagcaaaag gctcaaaggc aggatatatt    540
gaccctatta gtgcttttgc aggagcactt gaaatgttgc ttcctagaca tagtacttat    600
catatagacg atatgagatt gtcttctgat ggtaaacaaa taataattac agcaacaatg    660
atgggcacag ctatcaatcc taagaattc gtgatgaatc ccgcaaacgc gcaaggcaga    720
catacacccg gtaccagact ctag                                           744
```

<210> SEQ ID NO 6
<211> LENGTH: 247
<212> TYPE: PRT
<213> ORGANISM: Artificial Sequence
<220> FEATURE:
<223> OTHER INFORMATION: Amino acid sequence of C3-07Q189A

<400> SEQUENCE: 6

```
Met Ser Arg Val Asp Leu Gln Ala Cys Asn Ala Tyr Ser Ile Asn Gln
 1               5                  10                  15

Lys Ala Tyr Ser Asn Thr Tyr Gln Glu Phe Thr Asn Ile Asp Gln Ala
            20                  25                  30

Lys Ala Trp Gly Asn Ala Gln Tyr Lys Lys Tyr Gly Leu Ser Lys Ser
        35                  40                  45

Glu Lys Glu Ala Ile Val Ser Tyr Thr Lys Ser Ala Ser Glu Ile Asn
    50                  55                  60

Gly Lys Leu Arg Gln Asn Lys Gly Val Ile Asn Gly Phe Pro Ser Asn
```

```
                65                  70                  75                  80
Leu Ile Lys Gln Val Glu Leu Leu Asp Lys Ser Phe Asn Lys Met Lys
                    85                  90                  95

Thr Pro Glu Asn Ile Met Leu Phe Arg Gly Asp Asp Pro Ala Tyr Leu
                100                 105                 110

Gly Thr Glu Phe Gln Asn Thr Leu Leu Asn Ser Asn Gly Thr Ile Asn
                115                 120                 125

Lys Thr Ala Phe Glu Lys Ala Lys Ala Lys Phe Leu Asn Lys Asp Arg
            130                 135                 140

Leu Glu Tyr Gly Tyr Ile Ser Thr Ser Leu Met Asn Val Ser Gln Phe
145                 150                 155                 160

Ala Gly Arg Pro Ile Ile Thr Gln Phe Lys Val Ala Lys Gly Ser Lys
                165                 170                 175

Ala Gly Tyr Ile Asp Pro Ile Ser Ala Phe Gln Gly Ala Leu Glu Met
                180                 185                 190

Leu Leu Pro Arg His Ser Thr Tyr His Ile Asp Asp Met Arg Leu Ser
                195                 200                 205

Ser Asp Gly Lys Gln Ile Ile Ile Thr Ala Thr Met Met Gly Thr Ala
            210                 215                 220

Ile Asn Pro Lys Glu Phe Val Met Asn Pro Ala Asn Ala Gln Gly Arg
225                 230                 235                 240

His Thr Pro Gly Thr Arg Leu
                245

<210> SEQ ID NO 7
<211> LENGTH: 887
<212> TYPE: DNA
<213> ORGANISM: Artificial Sequence
<220> FEATURE:
<223> OTHER INFORMATION: Sequence of C3APLT: includes sequences from
      ADP-ribosyl transferase C3 (Clostridium botulinum)
      and a sequence encoding a proline  rich region.

<400> SEQUENCE: 7
ggatcctcta gagtcgacct gcaggcatgc aatgcttatt ccattaatca aaaggcttat       60
tcaaatactt accaggagtt tactaatatt gatcaagcaa agcttgggg taatgctcag      120 tataaaaagt atggactaag caaatcagaa aaagaagcta tagtatcata tactaaaagc      180
gctagtgaaa taaatggaaa gctaagacaa ataagggag ttatcaatgg atttccttca      240
aatttaataa acaagttga acttttagat aaatctttta ataaaatgaa accccctgaa      300
aatattatgt tatttagagg cgacgaccct gcttatttag gaacagaatt tcaaaacact      360
cttcttaatt caaatggtac aattaataaa acggcttttg aaaaggctaa agctaagttt      420
ttaaataaag atagacttga atatggatat attagtactt cattaatgaa tgtttctcaa      480
tttgcaggaa gaccaattat tacaaaattt aaagtagcaa aaggctcaaa ggcaggatat      540 attgaccctattagtgcttt tcaggacaac ttgaaatgt tgcttcctag acatagtact      600
tatcatatag acgatatgag attgtcttct gatggtaaac aaataataat tacagcaaca      660
atgatgggca cagctatcaa tcctaaagaa ttcgtgatga atcccgcaaa cgcgcaaggc      720
agacatacac ccggtaccag actctagagc tagagaagga gtttcacttc aatcgctact      780
tgacccgtcg gcgaaggatc gagatcgccc acgccctgtg cctcacggag cgccagataa      840
agatttggtt ccagaatcgg cgcatgaagt ggaagaagga gaactga                   887

<210> SEQ ID NO 8
```

-continued

```
<211> LENGTH: 248
<212> TYPE: PRT
<213> ORGANISM: Artificial Sequence
<220> FEATURE:
<223> OTHER INFORMATION: Sequence of C3APLT: includes sequences from
      ADP-ribosyl transferase C3 (Clostridium botulinum)
      and a sequence encoding a proline rich region.

<400> SEQUENCE: 8

Gly Ser Ser Arg Val Asp Leu Gln Ala Cys Asn Ala Tyr Ser Ile Asn
 1               5                  10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Lys Phe Lys Val Ala Lys Gly Ser
                165                 170                 175

Lys Ala Gly Tyr Ile Asp Pro Ile Ser Ala Phe Ala Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Ile Thr Ala Thr Met Met Gly Thr
    210                 215                 220

Ala Ile Asn Pro Lys Glu Phe Val Met Asn Pro Ala Asn Ala Gln Gly
225                 230                 235                 240

Arg His Thr Pro Gly Thr Arg Leu
                245

<210> SEQ ID NO 9
<211> LENGTH: 699
<212> TYPE: DNA
<213> ORGANISM: Artificial Sequence
<220> FEATURE:
<223> OTHER INFORMATION: Nucleotide sequence of BA-210

<400> SEQUENCE: 9
atgtcggctt attcaaatac ttaccaggag tttactaata ttgatcaagc aaaagcttgg      60
ggtaatgctc agtataaaaa gtatggacta agcaaatcag aaaaagaagc tatagtatca     120
tatactaaaa gcgctagtga aataaatgga aagctaagac aaaataaggg agttatcaat     180
ggatttcctt caaatttaat aaaacaagtt gaactttag ataaatcttt taataaaatg      240
aagacccctg aaaatattat gttatttaga ggcgacgacc ctgcttattt aggaacagaa     300
tttcaaaaca ctcttcttaa ttcaaatggt acaattaata aaacggcttt tgaaaaggct     360
```

```
aaagctaagt ttttaaataa agatagactt gaatatggat atattagtac ttcattaatg    420
aatgtttctc aatttgcagg aagaccaatt attacaaaat ttaaagtagc aaaaggctca    480
aaggcaggat atattgaccc tattagtgct tttgcaggac aacttgaaat gttgcttcct    540
agacatagta cttatcatat agacgatatg agattgtctt ctgatggtaa acaaataata    600
attacagcaa caatgatggg cacagctatc aatcctaaag aattcgtgat gaatcccgca    660
aacgcgcaag gcagacatac acccggtacc agactctag                           699
```

<210> SEQ ID NO 10
<211> LENGTH: 232
<212> TYPE: PRT
<213> ORGANISM: Artificial Sequence
<220> FEATURE:
<223> OTHER INFORMATION: Protein sequence of BA-210

<400> SEQUENCE: 10

```
Met Ser Ala Tyr Ser Asn Thr Tyr Gln Glu Phe Thr Asn Ile Asp Gln
 1               5                  10                  15

Ala Lys Ala Trp Gly Asn Ala Gln Tyr Lys Lys Tyr Gly Leu Ser Lys
            20                  25                  30

Ser Glu Lys Glu Ala Ile Val Ser Tyr Thr Lys Ser Ala Ser Glu Ile
        35                  40                  45

Asn Gly Lys Leu Arg Gln Asn Lys Gly Val Ile Asn Gly Phe Pro Ser
    50                  55                  60

Asn Leu Ile Lys Gln Val Glu Leu Leu Asp Lys Ser Phe Asn Lys Met
65                  70                  75                  80

Lys Thr Pro Glu Asn Ile Met Leu Phe Arg Gly Asp Asp Pro Ala Tyr
                85                  90                  95

Leu Gly Thr Glu Phe Gln Asn Thr Leu Leu Asn Ser Asn Gly Thr Ile
           100                 105                 110

Asn Lys Thr Ala Phe Glu Lys Ala Lys Ala Lys Phe Leu Asn Lys Asp
       115                 120                 125

Arg Leu Glu Tyr Gly Tyr Ile Ser Thr Ser Leu Met Asn Val Ser Gln
   130                 135                 140

Phe Ala Gly Arg Pro Ile Ile Thr Lys Phe Lys Val Ala Lys Gly Ser
145                 150                 155                 160

Lys Ala Gly Tyr Ile Asp Pro Ile Ser Ala Phe Ala Gly Gln Leu Glu
               165                 170                 175

Met Leu Leu Pro Arg His Ser Thr Tyr His Ile Asp Asp Met Arg Leu
           180                 185                 190

Ser Ser Asp Gly Lys Gln Ile Ile Ile Thr Ala Thr Met Met Gly Thr
       195                 200                 205

Ala Ile Asn Pro Lys Glu Phe Val Met Asn Pro Ala Asn Ala Gln Gly
   210                 215                 220

Arg His Thr Pro Gly Thr Arg Leu
225                 230
```

<210> SEQ ID NO 11
<211> LENGTH: 42
<212> TYPE: DNA
<213> ORGANISM: Artificial Sequence
<220> FEATURE:
<223> OTHER INFORMATION: Sequence of primer 2029F

<400> SEQUENCE: 11

```
ggagatatac atatgtcggc ttattcaaat acttaccagg ag                        42
```

-continued

<210> SEQ ID NO 12
<211> LENGTH: 42
<212> TYPE: DNA
<213> ORGANISM: Artificial Sequence
<220> FEATURE:
<223> OTHER INFORMATION: Sequence of primer 2029R

<400> SEQUENCE: 12
ctcctggtaa gtatttgaat aagccgacat atgtatatct cc                          42

<210> SEQ ID NO 13
<211> LENGTH: 222
<212> TYPE: PRT
<213> ORGANISM: Artificial Sequence
<220> FEATURE:
<223> OTHER INFORMATION: Sequence of BA-350

<400> SEQUENCE: 13

Met Ser Ala Ile Asp Gln Ala Lys Ala Trp Gly Asn Ala Gln Tyr Lys
 1               5                  10                  15

Lys Tyr Gly Leu Ser Lys Ser Glu Lys Glu Ala Ile Val Ser Tyr Thr
            20                  25                  30

Lys Ser Ala Ser Glu Ile Asn Gly Lys Leu Arg Gln Asn Lys Gly Val
        35                  40                  45

Ile Asn Gly Phe Pro Ser Asn Leu Ile Lys Gln Val Glu Leu Leu Asp
    50                  55                  60

Lys Ser Phe Asn Lys Met Lys Thr Pro Glu Asn Ile Met Leu Phe Arg
65                  70                  75                  80

Gly Asp Asp Pro Ala Tyr Leu Gly Thr Glu Phe Gln Asn Thr Leu Leu
                85                  90                  95

Asn Ser Asn Gly Thr Ile Asn Lys Thr Ala Phe Glu Lys Ala Lys Ala
            100                 105                 110

Lys Phe Leu Asn Lys Asp Arg Leu Glu Tyr Gly Tyr Ile Ser Thr Ser
        115                 120                 125

Leu Met Asn Val Ser Gln Phe Ala Gly Arg Pro Ile Ile Thr Lys Phe
    130                 135                 140

Lys Val Ala Lys Gly Ser Lys Ala Gly Tyr Ile Asp Pro Ile Ser Ala
145                 150                 155                 160

Phe Ala Gly Gln Leu Glu Met Leu Leu Pro Arg His Ser Thr Tyr His
                165                 170                 175

Ile Asp Asp Met Arg Leu Ser Ser Asp Gly Lys Gln Ile Ile Ile Thr
            180                 185                 190

Ala Thr Met Met Gly Thr Ala Ile Asn Pro Lys Glu Phe Val Met Asn
        195                 200                 205

Pro Ala Asn Ala Gln Gly Arg His Thr Pro Gly Thr Arg Leu
    210                 215                 220

<210> SEQ ID NO 14
<211> LENGTH: 212
<212> TYPE: PRT
<213> ORGANISM: Artificial Sequence
<220> FEATURE:
<223> OTHER INFORMATION: Sequence of BA-351

<400> SEQUENCE: 14

Met Ser Ala Gln Tyr Lys Lys Tyr Gly Leu Ser Lys Ser Glu Lys Glu
 1               5                  10                  15

Ala Ile Val Ser Tyr Thr Lys Ser Ala Ser Glu Ile Asn Gly Lys Leu

-continued

```
                 20                  25                  30
Arg Gln Asn Lys Gly Val Ile Asn Gly Phe Pro Ser Asn Leu Ile Lys
             35                  40                  45

Gln Val Glu Leu Leu Asp Lys Ser Phe Asn Lys Met Lys Thr Pro Glu
         50                  55                  60

Asn Ile Met Leu Phe Arg Gly Asp Asp Pro Ala Tyr Leu Gly Thr Glu
 65                  70                  75                  80

Phe Gln Asn Thr Leu Leu Asn Ser Asn Gly Thr Ile Asn Lys Thr Ala
                 85                  90                  95

Phe Glu Lys Ala Lys Ala Lys Phe Leu Asn Lys Asp Arg Leu Glu Tyr
            100                 105                 110

Gly Tyr Ile Ser Thr Ser Leu Met Asn Val Ser Gln Phe Ala Gly Arg
            115                 120                 125

Pro Ile Ile Thr Lys Phe Lys Val Ala Lys Gly Ser Lys Ala Gly Tyr
            130                 135                 140

Ile Asp Pro Ile Ser Ala Phe Ala Gly Gln Leu Glu Met Leu Leu Pro
145                 150                 155                 160

Arg His Ser Thr Tyr His Ile Asp Asp Met Arg Leu Ser Ser Asp Gly
                165                 170                 175

Lys Gln Ile Ile Ile Thr Ala Thr Met Met Gly Thr Ala Ile Asn Pro
            180                 185                 190

Lys Glu Phe Val Met Asn Pro Ala Asn Ala Gln Gly Arg His Thr Pro
            195                 200                 205

Gly Thr Arg Leu
            210

<210> SEQ ID NO 15
<211> LENGTH: 202
<212> TYPE: PRT
<213> ORGANISM: Artificial Sequence
<220> FEATURE:
<223> OTHER INFORMATION: Sequence of BA-352

<400> SEQUENCE: 15

Met Ser Ala Glu Lys Glu Ala Ile Val Ser Tyr Thr Lys Ser Ala Ser
  1               5                  10                  15

Glu Ile Asn Gly Lys Leu Arg Gln Asn Lys Gly Val Ile Asn Gly Phe
             20                  25                  30

Pro Ser Asn Leu Ile Lys Gln Val Glu Leu Leu Asp Lys Ser Phe Asn
         35                  40                  45

Lys Met Lys Thr Pro Glu Asn Ile Met Leu Phe Arg Gly Asp Asp Pro
     50                  55                  60

Ala Tyr Leu Gly Thr Glu Phe Gln Asn Thr Leu Leu Asn Ser Asn Gly
 65                  70                  75                  80

Thr Ile Asn Lys Thr Ala Phe Glu Lys Ala Lys Ala Lys Phe Leu Asn
                 85                  90                  95

Lys Asp Arg Leu Glu Tyr Gly Tyr Ile Ser Thr Ser Leu Met Asn Val
            100                 105                 110

Ser Gln Phe Ala Gly Arg Pro Ile Ile Thr Lys Phe Lys Val Ala Lys
            115                 120                 125

Gly Ser Lys Ala Gly Tyr Ile Asp Pro Ile Ser Ala Phe Ala Gly Gln
            130                 135                 140

Leu Glu Met Leu Leu Pro Arg His Ser Thr Tyr His Ile Asp Asp Met
145                 150                 155                 160

Arg Leu Ser Ser Asp Gly Lys Gln Ile Ile Ile Thr Ala Thr Met Met
```

165                 170                 175
Gly Thr Ala Ile Asn Pro Lys Glu Phe Val Met Asn Pro Ala Asn Ala
                180                 185                 190

Gln Gly Arg His Thr Pro Gly Thr Arg Leu
            195                 200

<210> SEQ ID NO 16
<211> LENGTH: 192
<212> TYPE: PRT
<213> ORGANISM: Artificial Sequence
<220> FEATURE:
<223> OTHER INFORMATION: Sequence of BA-353

<400> SEQUENCE: 16

Met Ser Ala Ser Ala Ser Glu Ile Asn Gly Lys Leu Arg Gln Asn Lys
 1               5                  10                  15

Gly Val Ile Asn Gly Phe Pro Ser Asn Leu Ile Lys Gln Val Glu Leu
                20                  25                  30

Leu Asp Lys Ser Phe Asn Lys Met Lys Thr Pro Glu Asn Ile Met Leu
            35                  40                  45

Phe Arg Gly Asp Asp Pro Ala Tyr Leu Gly Thr Glu Phe Gln Asn Thr
        50                  55                  60

Leu Leu Asn Ser Asn Gly Thr Ile Asn Lys Thr Ala Phe Glu Lys Ala
65                  70                  75                  80

Lys Ala Lys Phe Leu Asn Lys Asp Arg Leu Glu Tyr Gly Tyr Ile Ser
                85                  90                  95

Thr Ser Leu Met Asn Val Ser Gln Phe Ala Gly Arg Pro Ile Ile Thr
                100                 105                 110

Lys Phe Lys Val Ala Lys Gly Ser Lys Ala Gly Tyr Ile Asp Pro Ile
            115                 120                 125

Ser Ala Phe Ala Gly Gln Leu Glu Met Leu Leu Pro Arg His Ser Thr
        130                 135                 140

Tyr His Ile Asp Asp Met Arg Leu Ser Ser Asp Gly Lys Gln Ile Ile
145                 150                 155                 160

Ile Thr Ala Thr Met Met Gly Thr Ala Ile Asn Pro Lys Glu Phe Val
                165                 170                 175

Met Asn Pro Ala Asn Ala Gln Gly Arg His Thr Pro Gly Thr Arg Leu
            180                 185                 190

<210> SEQ ID NO 17
<211> LENGTH: 182
<212> TYPE: PRT
<213> ORGANISM: Artificial Sequence
<220> FEATURE:
<223> OTHER INFORMATION: Sequence of BA-354

<400> SEQUENCE: 17

Met Ser Ala Gln Asn Lys Gly Val Ile Asn Gly Phe Pro Ser Asn Leu
 1               5                  10                  15

Ile Lys Gln Val Glu Leu Leu Asp Lys Ser Phe Asn Lys Met Lys Thr
                20                  25                  30

Pro Glu Asn Ile Met Leu Phe Arg Gly Asp Asp Pro Ala Tyr Leu Gly
            35                  40                  45

Thr Glu Phe Gln Asn Thr Leu Leu Asn Ser Asn Gly Thr Ile Asn Lys
        50                  55                  60

Thr Ala Phe Glu Lys Ala Lys Ala Lys Phe Leu Asn Lys Asp Arg Leu
65                  70                  75                  80

```
Glu Tyr Gly Tyr Ile Ser Thr Ser Leu Met Asn Val Ser Gln Phe Ala
                85                  90                  95

Gly Arg Pro Ile Ile Thr Lys Phe Lys Val Ala Lys Gly Ser Lys Ala
            100                 105                 110

Gly Tyr Ile Asp Pro Ile Ser Ala Phe Ala Gly Gln Leu Glu Met Leu
        115                 120                 125

Leu Pro Arg His Ser Thr Tyr His Ile Asp Asp Met Arg Leu Ser Ser
130                 135                 140

Asp Gly Lys Gln Ile Ile Ile Thr Ala Thr Met Met Gly Thr Ala Ile
145                 150                 155                 160

Asn Pro Lys Glu Phe Val Met Asn Pro Ala Asn Ala Gln Gly Arg His
            165                 170                 175

Thr Pro Gly Thr Arg Leu
            180

<210> SEQ ID NO 18
<211> LENGTH: 154
<212> TYPE: PRT
<213> ORGANISM: Artificial Sequence
<220> FEATURE:
<223> OTHER INFORMATION: Sequence of BA-355

<400> SEQUENCE: 18

Met Ser Ala Thr Pro Glu Asn Ile Met Leu Phe Arg Gly Asp Asp Pro
1               5                   10                  15

Ala Tyr Leu Gly Thr Glu Phe Gln Asn Thr Leu Leu Asn Ser Asn Gly
            20                  25                  30

Thr Ile Asn Lys Thr Ala Phe Glu Lys Ala Lys Ala Lys Phe Leu Asn
        35                  40                  45

Lys Asp Arg Leu Glu Tyr Gly Tyr Ile Ser Thr Ser Leu Met Asn Val
    50                  55                  60

Ser Gln Phe Ala Gly Arg Pro Ile Ile Thr Lys Phe Lys Val Ala Lys
65                  70                  75                  80

Gly Ser Lys Ala Gly Tyr Ile Asp Pro Ile Ser Ala Phe Ala Gly Gln
                85                  90                  95

Leu Glu Met Leu Leu Pro Arg His Ser Thr Tyr His Ile Asp Asp Met
            100                 105                 110

Arg Leu Ser Ser Asp Gly Lys Gln Ile Ile Ile Thr Ala Thr Met Met
        115                 120                 125

Gly Thr Ala Ile Asn Pro Lys Glu Phe Val Met Asn Pro Ala Asn Ala
    130                 135                 140

Gln Gly Arg His Thr Pro Gly Thr Arg Leu
145                 150

<210> SEQ ID NO 19
<211> LENGTH: 121
<212> TYPE: PRT
<213> ORGANISM: Artificial Sequence
<220> FEATURE:
<223> OTHER INFORMATION: Sequence of BA-356

<400> SEQUENCE: 19

Met Ser Ala Thr Ala Phe Glu Lys Ala Lys Ala Lys Phe Leu Asn Lys
1               5                   10                  15

Asp Arg Leu Glu Tyr Gly Tyr Ile Ser Thr Ser Leu Met Asn Val Ser
            20                  25                  30

Gln Phe Ala Gly Arg Pro Ile Ile Thr Lys Phe Lys Val Ala Lys Gly
        35                  40                  45
```

```
Ser Lys Ala Gly Tyr Ile Asp Pro Ile Ser Ala Phe Ala Gly Gln Leu
    50                  55                  60

Glu Met Leu Leu Pro Arg His Ser Thr Tyr His Ile Asp Asp Met Arg
 65                  70                  75                  80

Leu Ser Ser Asp Gly Lys Gln Ile Ile Ile Thr Ala Thr Met Met Gly
                 85                  90                  95

Thr Ala Ile Asn Pro Lys Glu Phe Val Met Asn Pro Asn Ala Gln
                100                 105                 110

Gly Arg His Thr Pro Gly Thr Arg Leu
            115                 120

<210> SEQ ID NO 20
<211> LENGTH: 203
<212> TYPE: PRT
<213> ORGANISM: Artificial Sequence
<220> FEATURE:
<223> OTHER INFORMATION: Sequence of BA-357

<400> SEQUENCE: 20

Met Ser Ala Tyr Ser Asn Thr Tyr Gln Glu Phe Thr Asn Ile Asp Gln
  1               5                  10                  15

Ala Lys Ala Trp Gly Asn Ala Gln Tyr Lys Lys Tyr Gly Leu Ser Lys
                 20                  25                  30

Ser Glu Lys Glu Ala Ile Val Ser Tyr Thr Lys Ser Ala Ser Glu Ile
             35                  40                  45

Asn Gly Lys Leu Arg Gln Asn Lys Gly Val Ile Asn Gly Phe Pro Ser
    50                  55                  60

Asn Leu Ile Lys Gln Val Glu Leu Leu Asp Lys Ser Phe Asn Lys Met
 65                  70                  75                  80

Lys Thr Pro Glu Asn Ile Met Leu Phe Arg Gly Asp Asp Pro Ala Tyr
                 85                  90                  95

Leu Gly Thr Glu Phe Gln Asn Thr Leu Leu Asn Ser Asn Gly Thr Ile
                100                 105                 110

Asn Lys Thr Ala Phe Glu Lys Ala Lys Ala Lys Phe Leu Asn Lys Asp
            115                 120                 125

Arg Leu Glu Tyr Gly Tyr Ile Ser Thr Ser Leu Met Asn Val Ser Gln
130                 135                 140

Phe Ala Gly Arg Pro Ile Ile Thr Lys Phe Lys Val Ala Lys Gly Ser
145                 150                 155                 160

Lys Ala Gly Tyr Ile Asp Pro Ile Ser Ala Phe Ala Gly Gln Leu Glu
                165                 170                 175

Met Leu Leu Pro Arg His Pro Lys Glu Phe Val Met Asn Pro Ala Asn
            180                 185                 190

Ala Gln Gly Arg His Thr Pro Gly Thr Arg Leu
        195                 200

<210> SEQ ID NO 21
<211> LENGTH: 214
<212> TYPE: PRT
<213> ORGANISM: Artificial Sequence
<220> FEATURE:
<223> OTHER INFORMATION: Sequence of BA-358

<400> SEQUENCE: 21

Met Ser Ala Tyr Ser Asn Thr Tyr Gln Glu Phe Thr Asn Ile Asp Gln
  1               5                  10                  15

Ala Lys Ala Trp Gly Asn Ala Gln Tyr Lys Lys Tyr Gly Leu Ser Lys
```

```
                    20                  25                  30
Ser Glu Lys Glu Ala Ile Val Ser Tyr Thr Lys Ser Ala Ser Glu Ile
                35                  40                  45

Asn Gly Lys Leu Arg Gln Asn Lys Gly Val Ile Asn Gly Phe Pro Ser
         50                  55                  60

Asn Leu Ile Lys Gln Val Glu Leu Leu Asp Lys Ser Phe Asn Lys Met
 65                  70                  75                  80

Lys Thr Pro Glu Asn Ile Met Leu Phe Arg Gly Asp Asp Pro Ala Tyr
                 85                  90                  95

Leu Gly Thr Glu Phe Gln Asn Thr Leu Leu Asn Ser Asn Gly Thr Ile
                100                 105                 110

Asn Lys Thr Ala Phe Glu Lys Ala Lys Ala Lys Phe Leu Asn Lys Asp
                115                 120                 125

Arg Leu Glu Tyr Gly Tyr Ile Ser Thr Ser Leu Met Asn Val Ser Gln
                130                 135                 140

Phe Ala Gly Arg Pro Ile Ile Thr Lys Phe Lys Val Ala Lys Gly Ser
145                 150                 155                 160

Lys Ala Gly Tyr Ile Asp Pro Ile Ser Ala Phe Ala Gly Gln Leu Glu
                165                 170                 175

Met Leu Leu Pro Arg His Ser Thr Tyr His Ile Asp Asp Met Arg Leu
                180                 185                 190

Ser Pro Lys Glu Phe Val Met Asn Pro Ala Asn Ala Gln Gly Arg His
                195                 200                 205

Thr Pro Gly Thr Arg Leu
                210

<210> SEQ ID NO 22
<211> LENGTH: 224
<212> TYPE: PRT
<213> ORGANISM: Artificial Sequence
<220> FEATURE:
<223> OTHER INFORMATION: Sequence of BA-359

<400> SEQUENCE: 22

Met Ser Ala Tyr Ser Asn Thr Tyr Gln Glu Phe Thr Asn Ile Asp Gln
 1               5                  10                  15

Ala Lys Ala Trp Gly Asn Ala Gln Tyr Lys Lys Tyr Gly Leu Ser Lys
                20                  25                  30

Ser Glu Lys Glu Ala Ile Val Ser Tyr Thr Lys Ser Ala Ser Glu Ile
                35                  40                  45

Asn Gly Lys Leu Arg Gln Asn Lys Gly Val Ile Asn Gly Phe Pro Ser
         50                  55                  60

Asn Leu Ile Lys Gln Val Glu Leu Leu Asp Lys Ser Phe Asn Lys Met
 65                  70                  75                  80

Lys Thr Pro Glu Asn Ile Met Leu Phe Arg Gly Asp Asp Pro Ala Tyr
                 85                  90                  95

Leu Gly Thr Glu Phe Gln Asn Thr Leu Leu Asn Ser Asn Gly Thr Ile
                100                 105                 110

Asn Lys Thr Ala Phe Glu Lys Ala Lys Ala Lys Phe Leu Asn Lys Asp
                115                 120                 125

Arg Leu Glu Tyr Gly Tyr Ile Ser Thr Ser Leu Met Asn Val Ser Gln
                130                 135                 140

Phe Ala Gly Arg Pro Ile Ile Thr Lys Phe Lys Val Ala Lys Gly Ser
145                 150                 155                 160

Lys Ala Gly Tyr Ile Asp Pro Ile Ser Ala Phe Ala Gly Gln Leu Glu
```

```
                        165                 170                 175
Met Leu Leu Pro Arg His Ser Thr Tyr His Ile Asp Asp Met Arg Leu
            180                 185                 190

Ser Ser Asp Gly Lys Gln Ile Ile Ile Thr Ala Pro Lys Glu Phe Val
        195                 200                 205

Met Asn Pro Ala Asn Ala Gln Gly Arg His Thr Pro Gly Thr Arg Leu
    210                 215                 220

<210> SEQ ID NO 23
<211> LENGTH: 47
<212> TYPE: DNA
<213> ORGANISM: Artificial Sequence
<220> FEATURE:
<223> OTHER INFORMATION: Sequence of primer MD3-13F

<400> SEQUENCE: 23
gaaggagata tacatatgtc ggctattgat caagcaaaag cttgggg            47

<210> SEQ ID NO 24
<211> LENGTH: 47
<212> TYPE: DNA
<213> ORGANISM: Artificial Sequence
<220> FEATURE:
<223> OTHER INFORMATION: Sequence of primer MD3-13R

<400> SEQUENCE: 24
ccccaagctt ttgcttgatc aatagccgac atatgtatat ctccttc            47

<210> SEQ ID NO 25
<211> LENGTH: 43
<212> TYPE: DNA
<213> ORGANISM: Artificial Sequence
<220> FEATURE:
<223> OTHER INFORMATION: Sequence of primer MD3-23F

<400> SEQUENCE: 25
gaaggagata tacatatgtc ggctcagtat aaaaagtatg gac                43

<210> SEQ ID NO 26
<211> LENGTH: 43
<212> TYPE: DNA
<213> ORGANISM: Artificial Sequence
<220> FEATURE:
<223> OTHER INFORMATION: Sequence of primer MD3-23R

<400> SEQUENCE: 26
gtccatactt tttatactga gccgacatat gtatatctcc ttc                43

<210> SEQ ID NO 27
<211> LENGTH: 44
<212> TYPE: DNA
<213> ORGANISM: Artificial Sequence
<220> FEATURE:
<223> OTHER INFORMATION: Sequence of primer MD3-33F

<400> SEQUENCE: 27
gaaggagata tacatatgtc ggctgaaaaa gaagctatag tatc               44

<210> SEQ ID NO 28
<211> LENGTH: 44
<212> TYPE: DNA
<213> ORGANISM: Artificial Sequence
<220> FEATURE:
<223> OTHER INFORMATION: Sequence of primer MD3-33R
```

<400> SEQUENCE: 28
gatactatag cttcttttc agccgacata tgtatatctc cttc            44

<210> SEQ ID NO 29
<211> LENGTH: 44
<212> TYPE: DNA
<213> ORGANISM: Artificial Sequence
<220> FEATURE:
<223> OTHER INFORMATION: Sequence of primer MD3-43F

<400> SEQUENCE: 29
gaaggagata tacatatgtc ggctagcgct agtgaaataa atgg            44

<210> SEQ ID NO 30
<211> LENGTH: 44
<212> TYPE: DNA
<213> ORGANISM: Artificial Sequence
<220> FEATURE:
<223> OTHER INFORMATION: Sequence of primer MD3-43R

<400> SEQUENCE: 30
ccatttattt cactagcgct agccgacata tgtatatctc cttc            44

<210> SEQ ID NO 31
<211> LENGTH: 42
<212> TYPE: DNA
<213> ORGANISM: Artificial Sequence
<220> FEATURE:
<223> OTHER INFORMATION: Sequence of primer MD3-53F

<400> SEQUENCE: 31
gaaggagata tacatatgtc ggctcaaaat aagggagtta tc            42

<210> SEQ ID NO 32
<211> LENGTH: 42
<212> TYPE: DNA
<213> ORGANISM: Artificial Sequence
<220> FEATURE:
<223> OTHER INFORMATION: Sequence of primer MD3-53R

<400> SEQUENCE: 32
gataactccc ttattttgag ccgacatatg tatatctcct tc            42

<210> SEQ ID NO 33
<211> LENGTH: 42
<212> TYPE: DNA
<213> ORGANISM: Artificial Sequence
<220> FEATURE:
<223> OTHER INFORMATION: Sequence of primer MD3-81F

<400> SEQUENCE: 33
gaaggagata tacatatgtc ggctacccct gaaaatatta tg            42

<210> SEQ ID NO 34
<211> LENGTH: 42
<212> TYPE: DNA
<213> ORGANISM: Artificial Sequence
<220> FEATURE:
<223> OTHER INFORMATION: Sequence of primer MD3-81R

<400> SEQUENCE: 34
cataatattt tcaggggtag ccgacatatg tatatctcct tc            42

<210> SEQ ID NO 35
<211> LENGTH: 41

-continued

<210> SEQ ID NO 35
<211> LENGTH: 41
<212> TYPE: DNA
<213> ORGANISM: Artificial Sequence
<220> FEATURE:
<223> OTHER INFORMATION: Sequence of primer MD3-114F

<400> SEQUENCE: 35
gaaggagata tacatatgtc ggctacggct tttgaaaagg c          41

<210> SEQ ID NO 36
<211> LENGTH: 41
<212> TYPE: DNA
<213> ORGANISM: Artificial Sequence
<220> FEATURE:
<223> OTHER INFORMATION: Sequence of primer MD3-114R

<400> SEQUENCE: 36
gccttttcaa aagccgtagc cgacatatgt atatctcctt c          41

<210> SEQ ID NO 37
<211> LENGTH: 50
<212> TYPE: DNA
<213> ORGANISM: Artificial Sequence
<220> FEATURE:
<223> OTHER INFORMATION: Sequence of primer MD183-211F

<400> SEQUENCE: 37
cttgaaatgt tgcttcctag acatcctaaa gaattcgtga tgaatcccgc          50

<210> SEQ ID NO 38
<211> LENGTH: 50
<212> TYPE: DNA
<213> ORGANISM: Artificial Sequence
<220> FEATURE:
<223> OTHER INFORMATION: Sequence of primer MD183-211R

<400> SEQUENCE: 38
gcgggattca tcacgaattc tttaggatgt ctaggaagca acatttcaag          50

<210> SEQ ID NO 39
<211> LENGTH: 50
<212> TYPE: DNA
<213> ORGANISM: Artificial Sequence
<220> FEATURE:
<223> OTHER INFORMATION: Seqeunce of primer MD194-211F

<400> SEQUENCE: 39
catatagacg atatgagatt gtctcctaaa gaattcgtga tgaatcccgc          50

<210> SEQ ID NO 40
<211> LENGTH: 50
<212> TYPE: DNA
<213> ORGANISM: Artificial Sequence
<220> FEATURE:
<223> OTHER INFORMATION: Sequence of primer MD194-211R

<400> SEQUENCE: 40
gcgggattca tcacgaattc tttaggagac aatctcatat cgtctatatg          50

<210> SEQ ID NO 41
<211> LENGTH: 55
<212> TYPE: DNA
<213> ORGANISM: Artificial Sequence
<220> FEATURE:
<223> OTHER INFORMATION: Sequence of primer MD204-211F

<400> SEQUENCE: 41

-continued

```
ctgatggtaa acaaataata attacagcac ctaaagaatt cgtgatgaat cccgc        55
```

<210> SEQ ID NO 42
<211> LENGTH: 55
<212> TYPE: DNA
<213> ORGANISM: Artificial Sequence
<220> FEATURE:
<223> OTHER INFORMATION: Sequence of primer MD204-211R

<400> SEQUENCE: 42

```
gcgggattca tcacgaattc tttaggtgct gtaattatta tttgtttacc atcag        55
```

<210> SEQ ID NO 43
<211> LENGTH: 247
<212> TYPE: PRT
<213> ORGANISM: Artificial Sequence
<220> FEATURE:
<223> OTHER INFORMATION: pET9a-BA-07 fusion protein

<400> SEQUENCE: 43

```
Met Ser Arg Val Ala Leu Gln Ala Cys Asn Ala Tyr Ser Ile Asn Gln
  1               5                  10                  15

Lys Ala Tyr Ser Asn Thr Tyr Gln Glu Phe Thr Asn Ile Asp Gln Ala
             20                  25                  30

Lys Ala Trp Gly Asn Ala Gln Tyr Lys Lys Tyr Gly Leu Ser Lys Ser
         35                  40                  45

Glu Lys Glu Ala Ile Val Ser Tyr Thr Lys Ser Ala Ser Glu Ile Asn
     50                  55                  60

Gly Lys Leu Arg Gln Asn Lys Gly Val Ile Asn Gly Phe Pro Ser Asn
 65                  70                  75                  80

Leu Ile Lys Gln Val Glu Leu Leu Asp Lys Ser Phe Asn Lys Met Lys
                 85                  90                  95

Thr Pro Glu Asn Ile Met Leu Phe Arg Gly Asp Asp Pro Ala Tyr Leu
            100                 105                 110

Gly Thr Glu Phe Gln Asn Thr Leu Leu Asn Ser Asn Gly Thr Ile Asn
        115                 120                 125

Lys Thr Ala Phe Glu Lys Ala Lys Ala Lys Phe Leu Asn Lys Asp Arg
    130                 135                 140

Leu Glu Tyr Gly Tyr Ile Ser Thr Ser Leu Met Asn Val Ser Gln Phe
145                 150                 155                 160

Ala Gly Arg Pro Ile Ile Thr Lys Phe Lys Val Ala Lys Gly Ser Lys
                165                 170                 175

Ala Gly Tyr Ile Asp Pro Ile Ser Ala Phe Ala Gly Gln Leu Glu Met
            180                 185                 190

Leu Leu Pro Arg His Ser Thr Tyr His Ile Asp Met Arg Leu Ser
        195                 200                 205

Ser Asp Gly Lys Gln Ile Ile Ile Thr Ala Thr Met Met Gly Thr Ala
    210                 215                 220

Ile Asn Pro Lys Glu Phe Val Met Asn Pro Ala Asn Ala Gln Gly Arg
225                 230                 235                 240

His Thr Pro Gly Thr Arg Leu
                245
```

<210> SEQ ID NO 44
<211> LENGTH: 248
<212> TYPE: PRT
<213> ORGANISM: Artificial Sequence
<220> FEATURE:
<223> OTHER INFORMATION: pGEX-4TBA-05 protein sequence for BA-05

```
<400> SEQUENCE: 44

Gly Ser Ser Arg Val Asp Leu Gln Ala Cys Asn Ala Tyr Ser Ile Asn
1               5                   10                  15

Gln Lys Ala Tyr Ser Asn Thr Tyr Gln Glu Phe Thr Asn Ile Asp Gln
            20                  25                  30

Ala Lys Ala Trp Gly Asn Ala Gln Tyr Lys Lys Tyr Gly Leu Ser Lys
        35                  40                  45

Ser Glu Lys Glu Ala Ile Val Ser Tyr Thr Lys Ser Ala Ser Glu Ile
    50                  55                  60

Asn Gly Lys Leu Arg Gln Asn Lys Gly Val Ile Asn Gly Phe Pro Ser
65                  70                  75                  80

Asn Leu Ile Lys Gln Val Glu Leu Leu Asp Lys Ser Phe Asn Lys Met
                85                  90                  95

Lys Thr Pro Glu Asn Ile Met Leu Phe Arg Gly Asp Pro Ala Tyr
            100                 105                 110

Leu Gly Thr Glu Phe Gln Asn Thr Leu Leu Asn Ser Asn Gly Thr Ile
        115                 120                 125

Asn Lys Thr Ala Phe Glu Lys Ala Lys Ala Lys Phe Leu Asn Lys Asp
    130                 135                 140

Arg Leu Glu Tyr Gly Tyr Ile Ser Thr Ser Leu Met Asn Val Ser Gln
145                 150                 155                 160

Phe Ala Gly Arg Pro Ile Ile Thr Lys Phe Lys Val Ala Lys Gly Ser
                165                 170                 175

Lys Ala Gly Tyr Ile Asp Pro Ile Ser Ala Phe Ala Gly Gln Leu Glu
            180                 185                 190

Met Leu Leu Pro Arg His Ser Thr Tyr His Ile Asp Asp Met Arg Leu
        195                 200                 205

Ser Ser Asp Gly Lys Gln Ile Ile Thr Ala Thr Met Met Gly Thr
    210                 215                 220

Ala Ile Asn Pro Lys Glu Phe Val Met Asn Pro Ala Asn Ala Gln Gly
225                 230                 235                 240

Arg His Thr Pro Gly Thr Arg Leu
                245

<210> SEQ ID NO 45
<211> LENGTH: 16
<212> TYPE: PRT
<213> ORGANISM: Artificial Sequence
<220> FEATURE:
<223> OTHER INFORMATION: Random basic amino acid sequence of C3Basic1

<400> SEQUENCE: 45

Lys Arg Arg Arg Arg Pro Lys Lys Arg Arg Ala Lys Arg Arg
1               5                   10                  15

<210> SEQ ID NO 46
<211> LENGTH: 13
<212> TYPE: PRT
<213> ORGANISM: Artificial Sequence
<220> FEATURE:
<223> OTHER INFORMATION: Random amino acid sequence of C3Basic2

<400> SEQUENCE: 46

Lys Arg Arg Arg Arg Lys Lys Arg Gln Arg Arg Arg
1               5                   10

<210> SEQ ID NO 47
```

```
<211> LENGTH: 9
<212> TYPE: PRT
<213> ORGANISM: Artificial Sequence
<220> FEATURE:
<223> OTHER INFORMATION: Reverse HIV-1 Tat amino acid sequence of
      C3Basic3

<400> SEQUENCE: 47

Arg Arg Lys Gln Arg Arg Lys Arg Arg
 1               5

<210> SEQ ID NO 48
<211> LENGTH: 64
<212> TYPE: PRT
<213> ORGANISM: Artificial Sequence
<220> FEATURE:
<223> OTHER INFORMATION: Amino acid sequence of Antennapedia from C3APL

<400> SEQUENCE: 48

Val Met Glu Ser Arg Lys Arg Ala Arg Gln Thr Tyr Thr Arg Tyr Gln
 1               5                  10                  15

Thr Leu Glu Leu Glu Lys Glu Phe His Phe Asn Arg Tyr Leu Thr Arg
                20                  25                  30

Arg Arg Arg Ile Glu Ile Ala His Ala Leu Cys Leu Thr Glu Arg Gln
            35                  40                  45

Ile Lys Ile Trp Phe Gln Asn Arg Arg Met Lys Trp Lys Lys Glu Asn
        50                  55                  60

<210> SEQ ID NO 49
<211> LENGTH: 19
<212> TYPE: PRT
<213> ORGANISM: Artificial Sequence
<220> FEATURE:
<223> OTHER INFORMATION: Amino acid sequence of Antennapedia from C3APS

<400> SEQUENCE: 49

Arg Gln Ile Lys Ile Trp Phe Gln Asn Arg Arg Met Lys Trp Lys Lys
 1               5                  10                  15

Val Asp Ser

<210> SEQ ID NO 50
<211> LENGTH: 60
<212> TYPE: PRT
<213> ORGANISM: Artificial Sequence
<220> FEATURE:
<223> OTHER INFORMATION: Amino acid sequence of HIV-1 Tat from C3-TL

<400> SEQUENCE: 50

Lys His Pro Gly Ser Gln Pro Lys Thr Ala Cys Thr Asn Cys Tyr Cys
 1               5                  10                  15

Lys Lys Cys Cys Phe His Cys Gln Val Cys Phe Ile Thr Lys Ala Leu
                20                  25                  30

Gly Ile Ser Tyr Gly Arg Lys Arg Arg Gln Arg Arg Arg Ala His Gln
            35                  40                  45

Asn Ser Gln Thr His Gln Ala Ser Leu Ser Lys Gln
        50                  55                  60

<210> SEQ ID NO 51
<211> LENGTH: 20
<212> TYPE: PRT
<213> ORGANISM: Artificial Sequence
<220> FEATURE:
<223> OTHER INFORMATION: Amino acid sequence of HIV-1 Tat from C3-TS
```

-continued

```
<400> SEQUENCE: 51

Tyr Gly Ala Lys Lys Arg Arg Gln Arg Arg Val Asp Ser Ser Gly
1               5                   10                  15

Pro His Arg Asp
            20

<210> SEQ ID NO 52
<211> LENGTH: 16
<212> TYPE: PRT
<213> ORGANISM: Artificial Sequence
<220> FEATURE:
<223> OTHER INFORMATION: Antennapedia (Penetratin)

<400> SEQUENCE: 52

Arg Gln Ile Lys Ile Trp Phe Gln Asn Arg Arg Met Lys Trp Lys Lys
1               5                   10                  15

<210> SEQ ID NO 53
<211> LENGTH: 13
<212> TYPE: PRT
<213> ORGANISM: Artificial Sequence
<220> FEATURE:
<223> OTHER INFORMATION: Sequence of TAT

<400> SEQUENCE: 53

Gly Arg Lys Lys Arg Arg Gln Arg Arg Arg Pro Pro Gln
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Sequence of Polyarginine

<400> SEQUENCE: 54

Arg Arg Arg Arg Arg Arg Arg Arg Arg Arg Arg
1               5                   10

<210> SEQ ID NO 55
<211> LENGTH: 27
<212> TYPE: PRT
<213> ORGANISM: Artificial Sequence
<220> FEATURE:
<223> OTHER INFORMATION: Transportan

<400> SEQUENCE: 55

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 56
<211> LENGTH: 21
<212> TYPE: PRT
<213> ORGANISM: Artificial Sequence
<220> FEATURE:
<223> OTHER INFORMATION: Transportan

<400> SEQUENCE: 56

Ala Gly Tyr Leu Leu Gly Lys Ile Asn Leu Lys Ala Leu Ala Ala Leu
1               5                   10                  15

Ala Lys Lys Ile Leu
            20
```

```
<210> SEQ ID NO 57
<211> LENGTH: 22
<212> TYPE: PRT
<213> ORGANISM: Artificial Sequence
<220> FEATURE:
<223> OTHER INFORMATION: Pep-1

<400> SEQUENCE: 57

Lys Glu Thr Trp Trp Glu Thr Trp Trp Thr Glu Trp Ser Gln Pro Lys
 1               5                  10                  15

Lys Lys Arg Lys Val Cys
            20

<210> SEQ ID NO 58
<211> LENGTH: 20
<212> TYPE: PRT
<213> ORGANISM: Artificial Sequence
<220> FEATURE:
<223> OTHER INFORMATION: S413-PV

<400> SEQUENCE: 58

Ala Leu Trp Lys Thr Leu Leu Lys Lys Val Leu Lys Ala Pro Lys Lys
 1               5                  10                  15

Lys Arg Lys Val
            20

<210> SEQ ID NO 59
<211> LENGTH: 18
<212> TYPE: PRT
<213> ORGANISM: Artificial Sequence
<220> FEATURE:
<223> OTHER INFORMATION: MAP (Model sunthtic peptide)

<400> SEQUENCE: 59

Lys Leu Ala Leu Lys Leu Ala Leu Lys Ala Leu Lys Ala Ala Leu Lys
 1               5                  10                  15

Leu Ala

<210> SEQ ID NO 60
<211> LENGTH: 18
<212> TYPE: PRT
<213> ORGANISM: Artificial Sequence
<220> FEATURE:
<223> OTHER INFORMATION: SynB1

<400> SEQUENCE: 60

Arg Gly Gly Arg Leu Ser Tyr Ser Arg Arg Arg Phe Ser Thr Ser Thr
 1               5                  10                  15

Gly Arg

<210> SEQ ID NO 61
<211> LENGTH: 10
<212> TYPE: PRT
<213> ORGANISM: Artificial Sequence
<220> FEATURE:
<223> OTHER INFORMATION: SynB3

<400> SEQUENCE: 61

Arg Arg Leu Ser Tyr Ser Arg Arg Arg Phe
 1               5                  10

<210> SEQ ID NO 62
<211> LENGTH: 17
<212> TYPE: PRT
```

<213> ORGANISM: Artificial Sequence
<220> FEATURE:
<223> OTHER INFORMATION: SynB5

<400> SEQUENCE: 62

Arg Gly Gly Arg Leu Ala Tyr Leu Arg Arg Arg Trp Ala Val Leu Gly
1               5                   10                  15

Arg

<210> SEQ ID NO 63
<211> LENGTH: 20
<212> TYPE: PRT
<213> ORGANISM: Artificial Sequence
<220> FEATURE:
<223> OTHER INFORMATION: FGF-4 signal sequence

<400> SEQUENCE: 63

Ala Ala Ala Ala Ala Ala Ala Ala Ala Ala Ala Ala Ala Ala Ala Ala
1               5                   10                  15

Ala Ala Ala Ala
            20

<210> SEQ ID NO 64
<211> LENGTH: 18
<212> TYPE: PRT
<213> ORGANISM: Artificial Sequence
<220> FEATURE:
<223> OTHER INFORMATION: pVEC (VE-Cad)

<400> SEQUENCE: 64

Ala Ala Ala Ala Ala Ala Ala Ala Ala Ala Ala Ala Ala Ala Ala Ala
1               5                   10                  15

Ala Ala

<210> SEQ ID NO 65
<211> LENGTH: 16
<212> TYPE: PRT
<213> ORGANISM: Artificial Sequence
<220> FEATURE:
<223> OTHER INFORMATION: Sequence of bPrPp

<400> SEQUENCE: 65

Asn Asn Asn Asn Asn Asn Asn Asn Asn Asn Lys Lys Arg Pro Lys Pro
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Unknown CPP

<400> SEQUENCE: 66

Arg Asp Leu Trp Glu Met Met Met Val Ser Leu Ala Cys Gln Tyr
1               5                   10                  15

<210> SEQ ID NO 67
<211> LENGTH: 17
<212> TYPE: PRT
<213> ORGANISM: Artificial Sequence
<220> FEATURE:
<223> OTHER INFORMATION: C105Y (359-374 of alpha1-antitrypsin)

<400> SEQUENCE: 67

Cys Ser Ile Pro Pro Glu Val Lys Phe Asn Lys Pro Phe Val Tyr Leu

```
<210> SEQ ID NO 68
<211> LENGTH: 16
<212> TYPE: PRT
<213> ORGANISM: Artificial Sequence
<220> FEATURE:
<223> OTHER INFORMATION: DPV3

<400> SEQUENCE: 68

Arg Lys Lys Arg Arg Arg Glu Ser Arg Lys Lys Arg Arg Arg Glu Ser
 1               5                  10                  15

<210> SEQ ID NO 69
<211> LENGTH: 17
<212> TYPE: PRT
<213> ORGANISM: Artificial Sequence
<220> FEATURE:
<223> OTHER INFORMATION: DPV6

<400> SEQUENCE: 69

Gly Arg Pro Arg Glu Ser Gly Lys Lys Arg Lys Arg Lys Arg Leu Lys
 1               5                  10                  15

Pro

<210> SEQ ID NO 70
<211> LENGTH: 15
<212> TYPE: PRT
<213> ORGANISM: Artificial Sequence
<220> FEATURE:
<223> OTHER INFORMATION: DPV7

<400> SEQUENCE: 70

Gly Lys Arg Lys Lys Lys Gly Lys Leu Gly Lys Lys Arg Asp Pro
 1               5                  10                  15

<210> SEQ ID NO 71
<211> LENGTH: 17
<212> TYPE: PRT
<213> ORGANISM: Artificial Sequence
<220> FEATURE:
<223> OTHER INFORMATION: DPV7b

<400> SEQUENCE: 71

Gly Lys Arg Lys Lys Lys Gly Lys Leu Gly Lys Lys Arg Pro Arg Ser
 1               5                  10                  15

Arg

<210> SEQ ID NO 72
<211> LENGTH: 18
<212> TYPE: PRT
<213> ORGANISM: Artificial Sequence
<220> FEATURE:
<223> OTHER INFORMATION: DPV3/10

<400> SEQUENCE: 72

Arg Lys Lys Arg Arg Arg Glu Ser Arg Arg Ala Arg Arg Ser Pro Arg
 1               5                  10                  15

His Leu

<210> SEQ ID NO 73
<211> LENGTH: 19
<212> TYPE: PRT
```

```
<213> ORGANISM: Artificial Sequence
<220> FEATURE:
<223> OTHER INFORMATION: DPV10/6

<400> SEQUENCE: 73

Ser Arg Arg Ala Arg Arg Ser Pro Arg Glu Ser Gly Lys Lys Arg Lys
 1               5                  10                  15

Arg Lys Arg

<210> SEQ ID NO 74
<211> LENGTH: 19
<212> TYPE: PRT
<213> ORGANISM: Artificial Sequence
<220> FEATURE:
<223> OTHER INFORMATION: DPV1047

<400> SEQUENCE: 74

Val Lys Arg Gly Leu Lys Leu Arg His Val Arg Pro Arg Val Thr Arg
 1               5                  10                  15

Met Asp Val

<210> SEQ ID NO 75
<211> LENGTH: 14
<212> TYPE: PRT
<213> ORGANISM: Artificial Sequence
<220> FEATURE:
<223> OTHER INFORMATION: DPV10

<400> SEQUENCE: 75

Ser Arg Arg Ala Arg Arg Ser Pro Arg His Leu Gly Ser Gly
 1               5                  10

<210> SEQ ID NO 76
<211> LENGTH: 16
<212> TYPE: PRT
<213> ORGANISM: Artificial Sequence
<220> FEATURE:
<223> OTHER INFORMATION: DPV15

<400> SEQUENCE: 76

Leu Arg Arg Glu Arg Gln Ser Arg Leu Arg Arg Glu Arg Gln Ser Arg
 1               5                  10                  15

<210> SEQ ID NO 77
<211> LENGTH: 22
<212> TYPE: PRT
<213> ORGANISM: Artificial Sequence
<220> FEATURE:
<223> OTHER INFORMATION: DPV15b

<400> SEQUENCE: 77

Gly Ala Tyr Asp Leu Arg Arg Arg Glu Arg Gln Ser Arg Leu Arg Arg
 1               5                  10                  15

Arg Glu Arg Gln Ser Arg

<210> SEQ ID NO 78
<211> LENGTH: 214
<212> TYPE: PRT
<213> ORGANISM: Artificial Sequence
<220> FEATURE:
<223> OTHER INFORMATION: Double deletion mutant BA-368

<400> SEQUENCE: 78

Met Ser Ala Ile Asp Gln Ala Lys Ala Trp Gly Asn Ala Gln Tyr Lys
 1               5                  10                  15
```

-continued

Lys Tyr Gly Leu Ser Lys Ser Glu Lys Glu Ala Ile Val Ser Tyr Thr
            20                  25                  30

Lys Ser Ala Ser Glu Ile Asn Gly Lys Leu Arg Gln Asn Lys Gly Val
            35                  40                  45

Ile Asn Gly Phe Pro Ser Asn Leu Ile Lys Gln Val Glu Leu Leu Asp
 50                  55                  60

Lys Ser Phe Asn Lys Met Lys Thr Pro Glu Asn Ile Met Leu Phe Arg
 65                  70                  75                  80

Gly Asp Asp Pro Ala Tyr Leu Gly Thr Glu Phe Gln Asn Thr Leu Leu
                85                  90                  95

Asn Ser Asn Gly Thr Ile Asn Lys Thr Ala Phe Glu Lys Ala Lys Ala
            100                 105                 110

Lys Phe Leu Asn Lys Asp Arg Leu Glu Tyr Gly Tyr Ile Ser Thr Ser
            115                 120                 125

Leu Met Asn Val Ser Gln Phe Ala Gly Arg Pro Ile Ile Thr Lys Phe
            130                 135                 140

Lys Val Ala Lys Gly Ser Lys Ala Gly Tyr Ile Asp Pro Ile Ser Ala
145                 150                 155                 160

Phe Ala Gly Gln Leu Glu Met Leu Leu Pro Arg His Ser Thr Tyr His
                165                 170                 175

Ile Asp Asp Met Arg Leu Ser Ser Asp Gly Lys Gln Ile Ile Ile Thr
            180                 185                 190

Ala Pro Lys Glu Phe Val Met Asn Pro Ala Asn Ala Gln Gly Arg His
            195                 200                 205

Thr Pro Gly Thr Arg Leu
    210

<210> SEQ ID NO 79
<211> LENGTH: 204
<212> TYPE: PRT
<213> ORGANISM: Artificial Sequence
<220> FEATURE:
<223> OTHER INFORMATION: Double deletion mutant BA-369

<400> SEQUENCE: 79

Met Ser Ala Gln Tyr Lys Lys Tyr Gly Leu Ser Lys Ser Glu Lys Glu
 1               5                  10                  15

Ala Ile Val Ser Tyr Thr Lys Ser Ala Ser Glu Ile Asn Gly Lys Leu
            20                  25                  30

Arg Gln Asn Lys Gly Val Ile Asn Gly Phe Pro Ser Asn Leu Ile Lys
            35                  40                  45

Gln Val Glu Leu Leu Asp Lys Ser Phe Asn Lys Met Lys Thr Pro Glu
 50                  55                  60

Asn Ile Met Leu Phe Arg Gly Asp Asp Pro Ala Tyr Leu Gly Thr Glu
65                  70                  75                  80

Phe Gln Asn Thr Leu Leu Asn Ser Asn Gly Thr Ile Asn Lys Thr Ala
                85                  90                  95

Phe Glu Lys Ala Lys Ala Lys Phe Leu Asn Lys Asp Arg Leu Glu Tyr
            100                 105                 110

Gly Tyr Ile Ser Thr Ser Leu Met Asn Val Ser Gln Phe Ala Gly Arg
            115                 120                 125

Pro Ile Ile Thr Lys Phe Lys Val Ala Lys Gly Ser Lys Ala Gly Tyr
            130                 135                 140

Ile Asp Pro Ile Ser Ala Phe Ala Gly Gln Leu Glu Met Leu Leu Pro
145                 150                 155                 160

Arg His Ser Thr Tyr His Ile Asp Asp Met Arg Leu Ser Ser Asp Gly
            165                      170                    175

Lys Gln Ile Ile Ile Thr Ala Pro Lys Glu Phe Val Met Asn Pro Ala
            180                      185                    190

Asn Ala Gln Gly Arg His Thr Pro Gly Thr Arg Leu
            195                      200

<210> SEQ ID NO 80
<211> LENGTH: 699
<212> TYPE: DNA
<213> ORGANISM: Artificial Sequence
<220> FEATURE:
<223> OTHER INFORMATION: Sequence of BA-304

<400> SEQUENCE: 80

```
atgtcggctt attcaaatac ttaccaggag tttactaata ttgatcaagc aaaagcttgg      60
ggtaatgctc agtataaaaa gtatggacta agcaaatcag aaaaagaagc tatagtatca     120
tatactaaaa gcgctagtga ataaatgga aagctaagac aaaataaggg agttatcaat      180
ggatttcctt caaatttaat aaaacaagtt gaacttttag ataaatcttt taataaaatg     240
aagacccctg aaaatattat gttatttaga ggcgacgacc ctgcttattt aggaacagaa     300
tttcaaaaca ctcttcttaa ttcaaatggt acaattaata aacggctttt gaaaaggct      360
aaagctaagt ttttaaataa agatagactt gaatatggat atattagtac ttcattaatg     420
aatgtttctc aatttgcagg aagaccaatt attacaaaat ttaaagtagc aaaaggctca     480
aaggcaggat atattgaccc tattagtgct tttgcaggac aacttcaaat gttgcttcct     540
agacatagta cttatcatat agacgatatg agattgtctt ctgatggtaa acaaataata     600
attacagcaa caatgatggg cacagctatc aatcctaaag aattcgtgat gaatcccgca     660
aacgcgcaag gcagacatac acccggtacc agactctag                           699
```

<210> SEQ ID NO 81
<211> LENGTH: 232
<212> TYPE: PRT
<213> ORGANISM: Artificial Sequence
<220> FEATURE:
<223> OTHER INFORMATION: Sequence of BA-304

<400> SEQUENCE: 81

Met Ser Ala Tyr Ser Asn Thr Tyr Gln Glu Phe Thr Asn Ile Asp Gln
 1            5                  10                  15

Ala Lys Ala Trp Gly Asn Ala Gln Tyr Lys Lys Tyr Gly Leu Ser Lys
            20                      25                    30

Ser Glu Lys Glu Ala Ile Val Ser Tyr Thr Lys Ser Ala Ser Glu Ile
            35                      40                    45

Asn Gly Lys Leu Arg Gln Asn Lys Gly Val Ile Asn Gly Phe Pro Ser
            50                      55                    60

Asn Leu Ile Lys Gln Val Glu Leu Leu Asp Lys Ser Phe Asn Lys Met
65                  70                      75                    80

Lys Thr Pro Glu Asn Ile Met Leu Phe Arg Gly Asp Asp Pro Ala Tyr
                  85                      90                    95

Leu Gly Thr Glu Phe Gln Asn Thr Leu Leu Asn Ser Asn Gly Thr Ile
            100                    105                  110

Asn Lys Thr Ala Phe Glu Lys Ala Lys Ala Lys Phe Leu Asn Lys Asp
            115                    120                  125

Arg Leu Glu Tyr Gly Tyr Ile Ser Thr Ser Leu Met Asn Val Ser Gln

-continued

```
            130                 135                 140
Phe Ala Gly Arg Pro Ile Ile Thr Lys Phe Lys Val Ala Lys Gly Ser
145                 150                 155                 160

Lys Ala Gly Tyr Ile Asp Pro Ile Ser Ala Phe Ala Gly Gln Leu Gln
                165                 170                 175

Met Leu Leu Pro Arg His Ser Thr Tyr His Ile Asp Asp Met Arg Leu
                180                 185                 190

Ser Ser Asp Gly Lys Gln Ile Ile Ile Thr Ala Thr Met Met Gly Thr
            195                 200                 205

Ala Ile Asn Pro Lys Glu Phe Val Met Asn Pro Ala Asn Ala Gln Gly
            210                 215                 220

Arg His Thr Pro Gly Thr Arg Leu
225                 230
```